US012758565B2

(12) United States Patent
Lowe et al.

(10) Patent No.: US 12,758,565 B2
(45) Date of Patent: Oct. 13, 2026

(54) METHODS OF TREATING p53 MUTANT CANCERS USING OGDH INHIBITORS

(71) Applicant: MEMORIAL SLOAN KETTERING CANCER CENTER, New York, NY (US)

(72) Inventors: Scott Lowe, New York, NY (US); John P. Morris, IV, New York, NY (US); Scott E. Millman, New York, NY (US); Lydia Finley, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 896 days.

(21) Appl. No.: 17/634,775

(22) PCT Filed: Aug. 13, 2020

(86) PCT No.: PCT/US2020/046255
§ 371 (c)(1),
(2) Date: Feb. 11, 2022

(87) PCT Pub. No.: WO2021/030642
PCT Pub. Date: Feb. 18, 2021

(65) Prior Publication Data
US 2022/0280538 A1 Sep. 8, 2022

Related U.S. Application Data

(60) Provisional application No. 62/886,720, filed on Aug. 14, 2019.

(51) Int. Cl.

| | |
|---|---|
| ***A61K 31/655*** | (2006.01) |
| ***A61K 31/198*** | (2006.01) |
| ***A61K 31/282*** | (2006.01) |
| ***A61K 31/47*** | (2006.01) |
| ***A61K 31/4745*** | (2006.01) |
| ***A61K 31/506*** | (2006.01) |
| ***A61K 31/513*** | (2006.01) |
| ***A61K 31/517*** | (2006.01) |
| ***A61K 31/519*** | (2006.01) |
| ***A61K 31/573*** | (2006.01) |
| ***A61K 31/662*** | (2006.01) |
| ***A61K 31/704*** | (2006.01) |
| ***A61K 31/7068*** | (2006.01) |
| ***A61K 39/395*** | (2006.01) |
| ***A61P 35/00*** | (2006.01) |
| ***C12N 15/113*** | (2010.01) |

(52) U.S. Cl.
CPC .......... *A61K 31/655* (2013.01); *A61K 31/198* (2013.01); *A61K 31/282* (2013.01); *A61K 31/47* (2013.01); *A61K 31/4745* (2013.01); *A61K 31/506* (2013.01); *A61K 31/513* (2013.01); *A61K 31/517* (2013.01); *A61K 31/519* (2013.01); *A61K 31/573* (2013.01); *A61K 31/662* (2013.01); *A61K 31/704* (2013.01); *A61K 31/7068* (2013.01); *A61K 39/3955* (2013.01); *A61P 35/00* (2018.01); *C12N 15/1137* (2013.01); *C12N 2310/11* (2013.01); *C12N 2310/14* (2013.01); *C12N 2310/531* (2013.01)

(58) Field of Classification Search
CPC .. A61K 31/655; A61K 31/198; A61K 31/282; A61K 31/47; A61K 31/4745; A61K 31/506; A61K 31/513; A61K 31/517; A61K 31/519; A61K 31/573; A61K 31/662; A61K 31/704; A61K 31/7068; A61K 39/3955; A61P 35/00; C12N 15/1137; C12N 2310/11; C12N 2310/14; C12N 2310/531
See application file for complete search history.

(56) References Cited

PUBLICATIONS

"Can Acute Myeloid Leukemia (AML) Be Prevented?"American Cancer Society, Revised: Aug. 21, 2018, https://www.cancer.org/cancer/types/acute-myeloid-leukemia/causes-risks-prevention/prevention.htm (Year: 2018).*

Saxena et al. "An expert overview of emerging therapies for acute myeloid leukemia: novel small molecules targeting apoptosis, p53, transcriptional regulation and metabolism." Expert Opinion on Investigational Drugs 29, No. 9 (2020): 973-988. (Year: 2020).*

DiNardo et al. "Mutations in AML: prognostic and therapeutic implications." Hematology 2014, the American Society of Hematology Education Program Book 2016, No. 1 (2016): 348-355) (Year: 2016).*

Duffy et al. "Targeting p53 for the treatment of cancer." In Seminars in cancer biology, vol. 79, pp. 58-67. Academic Press, 2022) (Year: 2022).*

Bubnova, X., Hope, L., & Wheadon, H. (2025). Evaluation of current mouse in vivo models and advanced in vitro models for leukaemia research. Blood Reviews, 101318. (Year: 2025).*

Allen et al. 2016. Differential aspartate usage identifies a subset of cancer cells particularly dependent on OGDH. Cell reports, 17(3), pp. 876-890 (Year: 2016).*

(Continued)

*Primary Examiner* — James H Alstrum-Acevedo
*Assistant Examiner* — Carolyn L. Ladd
(74) *Attorney, Agent, or Firm* — Foley & Lardner LLP

(57) ABSTRACT

The present technology relates generally to methods and compositions for treating, preventing, and/or ameliorating p53-mutant cancers in a subject in need thereof, including acute myeloid leukemia (AML), pancreatic cancer, and liver cancer, by administration of a therapeutically effective amount of a 2-oxoglutarate dehydrogenase (OGDH) inhibitor.

6 Claims, 89 Drawing Sheets

Specification includes a Sequence Listing.

(56) References Cited

PUBLICATIONS

Millman et al. 2025. α-Ketoglutarate dehydrogenase is a therapeutic vulnerability in acute myeloid leukemia. Blood, 145(13), pp. 1422-1436 (Year: 2025).*

Allen et al., "Differential Aspartate Usage Identifies a Subset of Cancer Cells Particularly Dependent on OGDH", Cell Reports. Oct. 11, 2016, vol. 17, No. 3, pp. 876-890; especially abstract; p. 877, col. 1, para 1-3; p. 877, col. 2, para 3-p. 878, col. 1, para 1; p. 880, col. 2; para 2 Figure 3.

Atlante et al., "a-ketoglutarate dehydrogenase inhibition counteracts breast cancer-associated lung metastasis", Cell Death and Disease. Jul. 9, 2018, vol. 9, No. 756, pp. 1-18; especially abstract.

International Search Report and Written Opinion dated Jan. 22, 2021.

Lu et al., "Evaluation of K-ras and p53 expression in pancreatic adenocarcinoma using the cancer genome atlas", PLoS ONE. Jul. 25, 2017, vol. 12, No. 7, pp. 1-9; especially abstract; p. 3, para 5.

Wake Forest University Health Sciences et al., "CPI-613 and Combination 1-3., Chemotherapy in Treating Patients With Metastatic Pancreatic Cancer. NCT 01835041"; pp. 1-6; Jun. 11, 2019 (Jun. 11, 2019) (Note. the publication date is listed on p. 2. Study Status > last Update Posted: Jun. 11, 2019 [Actual]) [online]. [Retrieved on Oct. 28, 2020]. Retrieved from the internet <URL: https://clinicaltrials.gov/ct2/history/NCT01835041 ?A=19&B=19&C=merged#StudyPageTop>. Retrieved on Dec. 12, 2020).

Weisberg et al. "Inhibition of wild type p53-expressing AML by novel small molecule HDM2 inhibitor, CGM097," Mol Cancer Ther., Oct. 2015, vol. 14, No. 10, pp. 2249-2259 (Author Manuscript pp. 1-21) p. 7, para 2.

Alistar Angela et al: "Safety and tolerability of the first-in-class agent CPI-613 in combination with modified FOLFIRINOX in patients with metastatic pancreatic cancer: a single-centre, open-label, dose-escalation, phase 1 trial", The Lancet Oncology, Elsevier, Amsterdam, NL, vol. 18, No. 6, May 8, 2017 (May 8, 2017), pp. 770-778, XP085066695, ISSN: 1470-2045, DOI: 10.1016/S1470-2045(17)30314-5.

Allen Eric I. et al: "Differential Aspartate Usage Identifies a Subset of Cancer Cells Particularly Dependent on OGDH Supplemental Information", Cell Reports, vol. 17, No. 3, Oct. 11, 2016 (Oct. 11, 2016), pp. 876-890, XP093057120, US ISSN: 2211-1247, DOI: 10.1016/j.celrep.2016.09.052.

Bunik Victoria I. et al: "Inhibition of mitochondrial 2-oxoglutarate dehydrogenase impairs viability of cancer cells in a cell-specific metabolism-dependent manner", Oncotarget, vol. 7, No. 18, Mar. 26, 2016 (Mar. 26, 2016), pp. 26400-26421, XP093056770, DOI: 10.18632/oncotarget.8387.

Li Wu et al: "Oxidative phosphorylation activation is an important characteristic of DOX resistance in hepatocellular carcinoma cells", Cell Communication and Signaling, vol. 16, No. 1, Feb. 5, 2018 (Feb. 5, 2018), XP055558455, DOI: 10.1186/s12964-018-0217-2.

Muller et al: "Drug-induced Apoptosis in Hepatoma Cells Is Mediated by the CD95 (APO-1/Fas) Receptor/Ligand System and Involves Activation of Wild-type p53", J. Clin. Invest, vol. 99, No. 99, Feb. 1, 1997 (Feb. 1, 1997), pp. 403-413, XP055338392, DOI: 10.1172/JCI119174.

Pardee Timothy S. et al: "A Phase I Study of CPI-613 in Combination with High-Dose Cytarabine and Mitoxantrone for Relapsed or Refractory Acute Myeloid Leukemia", Clinical Cancer Research, vol. 24, No. 9, May 1, 2018 (May 1, 2018), pp. 2060-2073, XP055938372, US ISSN: 1078-0432, DOI: 10.1158/1078-0432.CCR-17-2282.

* cited by examiner

Thiamine diphosphate (TDP)

3-deaza-Thiamine diphosphate (deaza-TDP)

Deaza-Thiamine (deaza-T)

SEQUENCE LISTING

```
<160> NUMBER OF SEQ ID NOS: 98

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ttacacatgt acttgtagtg g                                              21


<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

tagataagca ttataattcc t                                              21


<210> SEQ ID NO 3
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 3
tagataagca ttataattcc t 21

<210> SEQ ID NO 4
<211> LENGTH: 4226
<212> TYPE: DNA
<213> ORGANISM: Homo sapiens

<400> SEQUENCE: 4
attcgggtgg agctgagccg gagacaggca gttgtgaaaa acttcaggac aaaaatgttt 60
catttaagga cttgtgctgc taagttgagg ccattgacgg cttcccagac tgttaagaca 120
ttttcacaaa acagaccagc agcagctagg acatttcaac agattcggtg ctattctgca 180
cctgttgctg ctgagccctt tctcagtggg actagttcga actatgtgga ggagatgtac 240
tgtgcttggc tggaaaaccc caaaagtgta cataagtcat gggacatttt ttttcgcaac 300
acgaatgccg gagccccacc gggcactgcc taccagagtc cccttcccct gagccgaggc 360
tccctggctg ctgtggccca tgcacagtcc ctggtagaag cacagcccaa cgtggacaag 420
ctcgtggagg accacctggc agtgcagtcg ctcatcaggg catatcaggt caggggtcac 480
cacattgcaa aacttgatcc tctcggaatt agttgtgtaa attttgatga tgctccagta 540
actgtttctt caaacgtgga tcttgcagtt ttcaaggaac gacttcgaat gctaacagta 600
ggagggttct atggcctgga tgagtctgac ctcgacaagg tcttccactt gcccaccacc 660
actttcatcg gggacagga atcagcactt cctctgcggg agatcatccg tcggctggag 720
atggcctact gccagcatat tggggtggag ttcatgttca tcaatgacct ggagcagtgc 780
cagtggatcc ggcagaagtt tgagacccct gggatcatgc agttcacaaa tgaggagaaa 840
cggaccctgc tggccaggct tgtgcggtcc accaggtttg aggagttcct acagcggaag 900
tggtcctctg agaagcgctt tggtctagaa ggctgcgagg tactgatccc tgccctcaag 960
accatcattg acaagtctag tgagaatggc gtggactacg tgatcatggg catgccacac 1020
agagggcggc tgaacgtgct tgcaaatgtc atcaggaagg agctggaaca gatcttctgt 1080
caattcgatt caaagctgga ggcagctgat gagggctccg gagatgtgaa gtaccacctg 1140
ggcatgtatc accgcaggat caatcgtgtc accgacagga acattacctt gtccttggtg 1200
gccaaccctt cccaccttga ggccgctgac cccgtggtga tgggcaagac caaagccgaa 1260
cagttttact gtggcgacac tgaagggaaa aaggtcatgt ccatcctgtt gcatgggggat 1320 gctgcatttg ctggccaggg cattgtgtac gagaccttcc acctcagcga cctgccatcc 1380
tacacaactc atggcaccgt gcacgtggtc gtcaacaacc agatcggctt caccaccgac 1440
cctcggatgg cccgctcctc cccctacccc actgacgtgg cccgagtggt gaatgccccc 1500
attttccacg tgaactcaga tgaccccgag gctgtcatgt acgtgtgcaa agtggcggcc 1560
gagtggagga gcaccttcca caaggacgtg gttgtcgatt tggtgtgtta ccggcgcaac 1620
ggccacaacg agatggatga gcccatgttc acgcagccgc tcatgtacaa gcagatccgc 1680
aagcagaagc ctgtgttaca gaagtacgct gagctgctgg tgtcgcaggg tgtggtcaac 1740
cagcctgagt atgaggagga aatttccaag tatgataaga tctgtgagga agcttttgcc 1800
agatctaaag atgagaagat cttgcacatt aagcactggc tggactctcc ctggcctggc 1860
ttcttcaccc tggacgggca gcccaggagc atgtcctgcc cctccacggg tctgacggag 1920

-continued

```
gatattctga cacacatcgg gaatgtggct agttctgtgc ctgtggaaaa ctttactatt   1980

catggagggc tgagccggat cttgaagact cgtggggaaa tggtgaagaa ccggactgtg   2040

gactgggctc tagcggagta catggcgttt ggctcgctcc tgaaggaggg catccacatt   2100

cggctgagcg gccaggacgt ggagcggggc acattcagcc accgccacca tgtgctccat   2160

gaccagaatg tggacaagag aacctgcatc cccatgaacc atctctggcc caatcaggcc   2220

ccctatactg tgtgcaacag ctcactgtct gagtacggcg tgctgggctt tgagctgggc   2280

ttcgccatgg ccagtcctaa tgccctggtc ctctgggaag cccaatttgg tgacttccac   2340

aacacggccc agtgtatcat cgaccagttc atctgcccgg gacaagccaa gtgggtgcgg   2400

cagaatggca tcgtgttgct gctgccccat ggcatggagg gcatgggtcc agaacattcc   2460

tccgcccgcc cagagcggtt cttgcagatg tgcaacgatg acccagatgt cctgccagac   2520

cttaaagaag ccaacttcga catcaatcag ctatatgact gcaattgggt tgttgtcaac   2580

tgctccactc ctggcaactt cttccacgtg ctacgacgcc agatcctgct gccattccgg   2640

aagccgttaa ttatcttcac ccccaaatcc ctgttgcgcc accccgaggc cagatccagc   2700

tttgatgaga tgcttccagg aacccacttc cagcgggtga tcccagaaga tggccctgca   2760

gctcagaacc cagaaaatgt caaaaggctt ctcttctgca ccggcaaagt gtattatgac   2820

ctcacccggg agcgcaaagc acgcgacatg gtggggcagg tggccatcac aaggattgag   2880

cagctgtcgc cattcccctt tgacctcctg ctgaaggagg tgcagaagta ccccaatgct   2940

gagctggcct ggtgccagga ggagcacaag aaccaaggct actatgacta cgtgaagcca   3000

agacttcgga ccaccatcag ccgcgccaag cccgtctggt atgccggccg ggacccagcg   3060

gctgctccag ccaccggcaa caagaagacc cacctgacgg agctgcagcg cctcctggac   3120

acggccttcg acctggacgt cttcaagaac ttctcgtaga tgctgcctag ggttgcttgg   3180

gccactgccc tctccacacc catgactgcc ccttgcttct caactaaaga atagtgcctc   3240

agcgctgccc acaccaccgc cctcctcgct gtgccaccac ccctccctct gctctcatag   3300

gagttaggct gtcgtccccc tccagtgctt ggctgcccca caggccacac gctgcccagg   3360

ctctgctgac ttctgagcag ttttccagga ggccgggggg agcaggagga ggaaaggtag   3420

cccccgaggg atgtccttgg ggaggggtca gctctggcca caatcctccc caccagtctc   3480

acccactagg ataggaactg ggccttgtgt gctggcttcc gctgtcaccc agcaaggcac   3540

aggctcctgt atttgagact aggatagctt catcttgagc ctgagcctta gaatctgtag   3600

aggagcctgg agtcggatct agccatggct ggcagaggtt tctagggtgg gccccagccg   3660

tggcgtgaac tgaggatgac ccggggcagc tggcaggaga gagccttggc ctgacctggc   3720

acagaaaggg cagcttcagt ctctgcagtg tccattatct gctgttcctt cgagggttcc   3780

aggctgtgtg tggggcccaa gcatgcccca cccacccctc ctgggcccag gcagcacctg   3840

gagcccacag agtctgtgtg tagccaggaa gccccgctca ggtagccacc accggggcac   3900

tggctgctct gtcttggtcc tgttaaccct ccacctcctc tcttggactc cctccccacc   3960

ccaaccactc tttctttctc ctttaaccca atggagactt tctgatgcat cgttttcttt   4020

gctgtgccaa agcaggtcag aagagggaga ggaggggctg gggtgaggg gccaggccat    4080

ggccaagggg ccagctgccc ctcatttatc actctgacct tcacagggac agatctgatt   4140

tatttatttt ggttaaaaaa aaaaaaaagg aacagaaaca actttgcatt gcattggctt   4200

gacccataaa ctaagttata tccgtg                                         4226
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
atgttcacga aagccagagc g 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
aacacaaaga gcacccagcg g 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tttaagtttg gagactggga g 21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ttaattgaag gaactttatc tc 22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
ttcataaccg attcttctcc ag 22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
tctgatgttc ttatacttcc at 22

<210> SEQ ID NO 11

<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ttcaattgac ttatcctggt tg 22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
ttgtatttct ttatagcctc tg 22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
taaatgaaac attttgtcct g 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
tagcaattct gcatacttct g 21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
cctacgggaa gcgaccataa 20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gacaccggcg ccgagtttt 19

<210> SEQ ID NO 17
<211> LENGTH: 20

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
gggagaaagc aatatcttcg 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
tgcgacggcg gtggactgcg 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
ctgggatcaa gaccagtgtc 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ccgggccccc tcatggcctg 20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
tggactgcaa gcatagtgga a 21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
gtgaaatcca tacgggctcc t 21

<210> SEQ ID NO 23
<211> LENGTH: 19
<212> TYPE: DNA

<213> ORGANISM: Artificial Sequence
<220> FEATURE:
<223> OTHER INFORMATION: Description of Artificial Sequence: Synthetic
primer

<400> SEQUENCE: 23
caggccgacc tgtatgacg 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
gtcccctgca tggtgtagg 19

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
acactccagc caataagtac agc 23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
ggtaggaacg tccaaaccca 20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
ccctggtgct aaaagattga tgc 23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
tgaactggct tgcgacactg 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
atcgccttcg acatcatcgc 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
ccccatgcgt actccatgag 20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
aggggttcag cttttcggat t 21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
agtgttatca ttctccgggg tag 23

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
cggtgtcaga gtctagggga 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
atcaccagga ttggacatgg 20

<210> SEQ ID NO 35
<211> LENGTH: 20
<212> TYPE: DNA
<213> ORGANISM: Artificial Sequence
<220> FEATURE:

<223> OTHER INFORMATION: Description of Artificial Sequence: Synthetic
primer

<400> SEQUENCE: 35
ctagcattca ggccctcatc 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
tccgactgtg actcctccat 20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
tgtctgtgtc taccgagggt g 21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
tccaacggac tttaacaact tca 23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
atgcaaggag atgaaatgac acg 23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
gcatcacgat tctctatgcc taa 23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
ggccaaggaa aatggtgtag 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
cttccacctt gtctcccatc 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ggtggaagca caacctaacg 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
catggtgccc tcgtatctga 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
gaagctgcac cctgtgactg 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
gacagcagcc acacttggtc 20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
aagctgatgg aaaatgcaag c 21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
gctgaaggtg cctctggagt 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
tcacagcctg catggacttc 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
acgcagcgat tgtcttcctt 20

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
gctccaagca gatgcagca 19

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
ccggatgtga ggcagcag 18

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
caagctgtct gatccttctc c 21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
acagaggtgg catccagaac 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ccggaaaacc gaagcaatta 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
tcgccagcta agagaggttc 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
acaccaagtg gcaatcttcc 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
gctgctttta ccgtggtttc 20

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
gcagaaggaa gcaagatgg 19

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
aaggccgaga gaaagagagg 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gcctccttcc ctacttccac 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
cctggacctg gatttcttga 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ttcaggtctc cccagtccta 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
cccaatagct gctccagttc 20

<210> SEQ ID NO 65
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
aatgatacgg cgaccaccga gatctacact cgtcggcagc gtcagatgtg 50

<210> SEQ ID NO 66
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
caagcagaag acggcatacg agattcgcct tagtctcgtg ggctcggaga tgt 53

<210> SEQ ID NO 67
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
caagcagaag acggcatacg agatctagta cggtctcgtg ggctcggaga tgt 53

<210> SEQ ID NO 68
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
caagcagaag acggcatacg agatttctgc ctgtctcgtg ggctcggaga tgt 53

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
caagcagaag acggcatacg agatgctcag gagtctcgtg ggctcggaga tgt 53

<210> SEQ ID NO 70
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
caagcagaag acggcatacg agataggagt ccgtctcgtg ggctcggaga tgt 53

<210> SEQ ID NO 71
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
caagcagaag acggcatacg agatcatgcc tagtctcgtg ggctcggaga tgt 53

<210> SEQ ID NO 72
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
caagcagaag acggcatacg agatgtagag aggtctcgtg ggctcggaga tgt 53

<210> SEQ ID NO 73
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
caagcagaag acggcatacg agatcctctc tggtctcgtg ggctcggaga tgt 53

<210> SEQ ID NO 74
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
caagcagaag acggcatacg agatagcgta gcgtctcgtg ggctcggaga tgt 53

<210> SEQ ID NO 75
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
caagcagaag acggcatacg agatcagcct cggtctcgtg ggctcggaga tgt 53

<210> SEQ ID NO 76
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
caagcagaag acggcatacg agattgcctc ttgtctcgtg ggctcggaga tgt 53

<210> SEQ ID NO 77
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
caagcagaag acggcatacg agattcctct acgtctcgtg ggctcggaga tgt 53

<210> SEQ ID NO 78
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
caagcagaag acggcatacg agatatcacg acgtctcgtg ggctcggaga tgt 53

<210> SEQ ID NO 79
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
caagcagaag acggcatacg agatacagtg gtgtctcgtg ggctcggaga tgt 53

<210> SEQ ID NO 80
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
caagcagaag acggcatacg agatcagatc cagtctcgtg ggctcggaga tgt 53

<210> SEQ ID NO 81
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
caagcagaag acggcatacg agatacaaac gggtctcgtg ggctcggaga tgt 53

<210> SEQ ID NO 82
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
caagcagaag acggcatacg agatacccag cagtctcgtg ggctcggaga tgt 53

<210> SEQ ID NO 83
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
caagcagaag acggcatacg agataacccc tcgtctcgtg ggctcggaga tgt 53

<210> SEQ ID NO 84
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
caagcagaag acggcatacg agatcccaac ctgtctcgtg ggctcggaga tgt 53

<210> SEQ ID NO 85
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
caagcagaag acggcatacg agatcaccac acgtctcgtg ggctcggaga tgt 53

<210> SEQ ID NO 86
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
caagcagaag acggcatacg agatgaaacc cagtctcgtg ggctcggaga tgt 53

<210> SEQ ID NO 87
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 87
caagcagaag acggcatacg agattgtgac cagtctcgtg ggctcggaga tgt 53

<210> SEQ ID NO 88
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 88
caagcagaag acggcatacg agatagggtc aagtctcgtg ggctcggaga tgt 53

<210> SEQ ID NO 89
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 89
caagcagaag acggcatacg agataggagt gggtctcgtg ggctcggaga tgt 53

<210> SEQ ID NO 90

<211> LENGTH: 4193
<212> TYPE: DNA
<213> ORGANISM: Homo sapiens

<400> SEQUENCE: 90
attcgggtgg agctgagccg gagacaggca gttgtgaaaa acttcaggac aaaaatgttt 60
catttaagga cttgtgctgc taagttgagg ccattgacgg cttcccagac tgttaagaca 120
ttttcacaaa acagaccagc agcagctagg acatttcaac agattcggtg ctattctgca 180
cctgttgctg ctgagccctt tctcagtggg actagttcga actatgtgga ggagatgtac 240
tgtgcttggc tggaaaaccc caaaagtgta cataagtcat gggacatttt ttttcgcaac 300
acgaatgccg gagccccacc gggcactgcc taccagagtc cccttcccct gagccgaggc 360
tccctggctg ctgtggccca tgcacagtcc ctggtagaag cacagcccaa cgtggacaag 420
ctcgtggagg accacctggc agtgcagtcg ctcatcaggg catatcagat acgagggcac 480
catgtagcac agctggaccc cctggggatt ttggatgctg atctggactc ctccgtgccc 540
gctgacatta tctcatccac agacaaactt gggttctatg gcctggatga gtctgacctc 600
gacaaggtct tccacttgcc caccaccact ttcatcgggg gacaggaatc agcacttcct 660
ctgcgggaga tcatccgtcg gctggagatg gcctactgcc agcatattgg ggtggagttc 720
atgttcatca atgacctgga gcagtgccag tggatccggc agaagtttga gacccctggg 780
atcatgcagt tcacaaatga ggagaaacgg accctgctgg ccaggcttgt gcggtccacc 840
aggtttgagg agttcctaca gcggaagtgg tcctctgaga agcgctttgg tctagaaggc 900
tgcgaggtac tgatccctgc cctcaagacc atcattgaca agtctagtga gaatggcgtg 960
gactacgtga tcatgggcat gccacacaga gggcggctga acgtgcttgc aaatgtcatc 1020
aggaaggagc tggaacagat cttctgtcaa ttcgattcaa agctggaggc agctgatgag 1080
ggctccggag atgtgaagta ccacctgggc atgtatcacc gcaggatcaa tcgtgtcacc 1140
gacaggaaca ttaccttgtc cttggtggcc aacccttccc accttgaggc cgctgacccc 1200
gtggtgatgg gcaagaccaa agccgaacag ttttactgtg gcgacactga agggaaaaag 1260
gtcatgtcca tcctgttgca tggggatgct gcatttgctg gccagggcat tgtgtacgag 1320
accttccacc tcagcgacct gccatcctac acaactcatg gcaccgtgca cgtggtcgtc 1380
aacaaccaga tcggcttcac caccgaccct cggatggccc gctcctcccc ctaccccact 1440
gacgtggccc gagtggtgaa tgcccccatt ttccacgtga actcagatga ccccgaggct 1500
gtcatgtacg tgtgcaaagt ggcggccgag tggaggagca ccttccacaa ggacgtggtt 1560
gtcgatttgg tgtgttaccg gcgcaacggc cacaacgaga tggatgagcc catgttcacg 1620
cagccgctca tgtacaagca gatccgcaag cagaagcctg tgttacagaa gtacgctgag 1680
ctgctggtgt cgcagggtgt ggtcaaccag cctgagtatg aggaggaaat ttccaagtat 1740
gataagatct gtgaggaagc ttttgccaga tctaaagatg agaagatctt gcacattaag 1800
cactggctgg actctccctg gcctggcttc ttcaccctgg acgggcagcc caggagcatg 1860
tcctgcccct ccacgggtct gacggaggat attctgacac acatcgggaa tgtggctagt 1920
tctgtgcctg tggaaaactt tactattcat ggagggctga gccggatctt gaagactcgt 1980
ggggaaatgg tgaagaaccg gactgtggac tgggctctag cggagtacat ggcgtttggc 2040
tcgctcctga aggagggcat ccacattcgg ctgagcggcc aggacgtgga gcggggcaca 2100
ttcagccacc gccaccatgt gctccatgac cagaatgtgg acaagagaac ctgcatcccc 2160
atgaaccatc tctggcccaa tcaggccccc tatactgtgt gcaacagctc actgtctgag 2220

```
tacggcgtgc tgggctttga gctgggcttc gccatggcca gtcctaatgc cctggtcctc   2280
tgggaagccc aatttggtga cttccacaac acggcccagt gtatcatcga ccagttcatc   2340
tgcccgggac aagccaagtg ggtgcggcag aatggcatcg tgttgctgct gccccatggc   2400
atggagggca tgggtccaga acattcctcc gcccgcccag agcggttctt gcagatgtgc   2460
aacgatgacc cagatgtcct gccagacctt aaagaagcca acttcgacat caatcagcta   2520
tatgactgca attgggttgt tgtcaactgc tccactcctg gcaacttctt ccacgtgcta   2580
cgacgccaga tcctgctgcc attccggaag ccgttaatta tcttcacccc caaatccctg   2640
ttgcgccacc ccgaggccag atccagcttt gatgagatgc ttccaggaac ccacttccag   2700
cgggtgatcc cagaagatgg ccctgcagct cagaacccag aaaatgtcaa aaggcttctc   2760
ttctgcaccg gcaaagtgta ttatgacctc acccgggagc gcaaagcacg cgacatggtg   2820
gggcaggtgg ccatcacaag gattgagcag ctgtcgccat tcccctttga cctcctgctg   2880
aaggaggtgc agaagtaccc caatgctgag ctggcctggt gccaggagga gcacaagaac   2940
caaggctact atgactacgt gaagccaaga cttcggacca ccatcagccg cgccaagccc   3000
gtctggtatg ccggccggga cccagcggct gctccagcca ccggcaacaa gaagacccac   3060
ctgacggagc tgcagcgcct cctggacacg gccttcgacc tggacgtctt caagaacttc   3120
tcgtagatgc tgcctagggt tgcttgggcc actgccctct ccacacccat gactgcccct   3180
tgcttctcaa ctaaagaata gtgcctcagc gctgcccaca ccaccgccct cctcgctgtg   3240
ccaccacccc tccctctgct ctcataggag ttaggctgtc gtccccctcc agtgcttggc   3300
tgccccacag gccacacgct gcccaggctc tgctgacttc tgagcagttt tccaggaggc   3360
cggggggagc aggaggagga aaggtagccc ccgagggatg tccttgggga ggggtcagct   3420
ctggccacaa tcctccccac cagtctcacc cactaggata ggaactgggc cttgtgtgct   3480
ggcttccgct gtcacccagc aaggcacagg ctcctgtatt tgagactagg atagcttcat   3540
cttgagcctg agccttagaa tctgtagagg agcctggagt cggatctagc catggctggc   3600
agaggtttct agggtgggcc ccagccgtgg cgtgaactga ggatgacccg gggcagctgg   3660
caggagagag ccttggcctg acctggcaca gaaagggcag cttcagtctc tgcagtgtcc   3720
attatctgct gttccttcga gggttccagg ctgtgtgtgg ggcccaagca tgccccaccc   3780
acccctcctg ggcccaggca gcacctggag cccacagagt ctgtgtgtag ccaggaagcc   3840
ccgctcaggt agccaccacc ggggcactgg ctgctctgtc ttggtcctgt taaccctcca   3900
cctcctctct tggactccct ccccacccca accactcttt ctttctcctt taacccaatg   3960
gagactttct gatgcatcgt tttctttgct gtgccaaagc aggtcagaag agggagagga   4020
ggggctgggg gtgaggggcc aggccatggc caaggggcca gctgcccctc atttatcact   4080
ctgaccttca cagggacaga tctgatttat ttattttggt taaaaaaaaa aaaaaggaac   4140
agaaacaact ttgcattgca ttggcttgac ccataaacta agttatatcc gtg          4193
```

<210> SEQ ID NO 91
<211> LENGTH: 1693
<212> TYPE: DNA
<213> ORGANISM: Homo sapiens

<400> SEQUENCE: 91

```
attcgggtgg agctgagccg gagacaggca gttgtgaaaa acttcaggac aaaaatgttt     60
catttaagga cttgtgctgc taagttgagg ccattgacgg cttcccagac tgttaagaca    120
```

```
ttttcacaaa acagaccagc agcagctagg acatttcaac agattcggtg ctattctgca    180

cctgttgctg ctgagccctt tctcagtggg actagttcga actatgtgga ggagatgtac    240

tgtgcttggc tggaaaaccc caaaagtgta cataagtcat gggacatttt ttttcgcaac    300

acgaatgccg gagccccacc gggcactgcc taccagagtc cccttcccct gagccgaggc    360

tccctggctg ctgtggccca tgcacagtcc ctggtagaag cacagcccaa cgtggacaag    420

ctcgtggagg accacctggc agtgcagtcg ctcatcaggg catatcagat acgagggcac    480

catgtagcac agctggaccc cctggggatt ttggatgctg atctggactc ctccgtgccc    540

gctgacatta tctcatccac agacaaactt gggttctatg gcctggatga gtctgacctc    600

gacaaggtct tccacttgcc caccaccact ttcatcgggg gacaggaatc agcacttcct    660

ctgcgggaga tcatccgtcg gctggagatg gcctactgcc agcatattgg ggtggagttc    720

atgttcatca atgacctgga gcagtgccag tggatccggc agaagtttga gacccctggg    780

atcatgcagt tcacaaatga ggagaaacgg accctgctgg ccaggcttgt gcggtccacc    840

aggtttgagg agttcctaca gcggaagtgg tcctctgaga agcgctttgg tctagaaggc    900

tgcgaggtac tgatccctgc cctcaagacc atcattgaca agtctagtga gaatggcgtg    960

gactacgtga tcatgggcat gccacacaga gggcggctga acgtgcttgc aaatgtcatc   1020

aggaaggagc tggaacagat cttctgtcaa ttcgattcaa agctggaggc agctgatgag   1080

ggctccggag atgtgaagta ccacctgggc atgtatcacc gcaggatcaa tcgtgtcacc   1140

gacaggaaca ttaccttgtc cttggtggcc aacccttccc accttgaggc cgctgacccc   1200

gtggtgatgg gcaagaccaa agccgaacag ttttactgtg gcgacactga agggaaaaag   1260

gtaaggccca gagagaggcg tgcaaggcag atcgtcaagg ccccatgttc cagcatggag   1320

ttccgctcac caacataacc cagagccctg ggtgcatcta gactttaaaa aaatatttaa   1380

agtcggccgg gcgcagtgtc tcacgcctgt aatcccagca ctttgggagg ccgaggtggg   1440

cagatcacct gagttcggga gttggagacc agcctgacca acatggagaa actccatctc   1500

tactaaaaat acaaaattag ctgggcgtgg tggcgcgcgc ctgtaatccc agctactcag   1560

gaggctgagg caggagaatc gcttgaaccc gggaggtgga ggttgcagtg agccgagatt   1620

acgccattgc actccagcct gggccaacaa gagcgaaact ctgtctcaaa gaaaaaaata   1680

aataaataaa aaa                                                      1693
```

<210> SEQ ID NO 92
<211> LENGTH: 4181
<212> TYPE: DNA
<213> ORGANISM: Homo sapiens

<400> SEQUENCE: 92

```
attcgggtgg agctgagccg gagacaggca gttgtgaaaa acttcaggac aaaaatgttt     60

catttaagga cttgtgctgc taagttgagg ccattgacgg cttcccagac tgttaagaca    120

ttttcacaaa acagaccagc agcagctagg acatttcaac agattcggtg ctattctgca    180

cctgttgctg ctgagccctt tctcagtggg actagttcga actatgtgga ggagatgtac    240

tgtgcttggc tggaaaaccc caaaagtgta cataagtcat gggacatttt ttttcgcaac    300

acgaatgccg gagccccacc gggcactgcc taccagagtc cccttcccct gagccgaggc    360

tccctggctg ctgtggccca tgcacagtcc ctggtagaag cacagcccaa cgtggacaag    420

ctcgtggagg accacctggc agtgcagtcg ctcatcaggg catatcaggt caggggtcac    480

cacattgcaa aacttgatcc tctcggaatt agttgtgtaa attttgatga tgctccagta    540
```

```
actgtttctt caaacgtggg gttctatggc ctggatgagt ctgacctcga caaggtcttc    600
cacttgccca ccaccacttt catcgggga caggaatcag cacttcctct gcgggagatc    660
atccgtcggc tggagatggc ctactgccag catattgggg tggagttcat gttcatcaat    720
gacctggagc agtgccagtg gatccggcag aagtttgaga cccctgggat catgcagttc    780
acaaatgagg agaaacggac cctgctggcc aggcttgtgc ggtccaccag gtttgaggag    840
ttcctacagc ggaagtggtc ctctgagaag cgctttggtc tagaaggctg cgaggtactg    900
atccctgccc tcaagaccat cattgacaag tctagtgaga atggcgtgga ctacgtgatc    960
atgggcatgc cacacagagg gcggctgaac gtgcttgcaa atgtcatcag gaaggagctg   1020
gaacagatct tctgtcaatt cgattcaaag ctggaggcag ctgatgaggg ctccggagat   1080
gtgaagtacc acctgggcat gtatcaccgc aggatcaatc gtgtcaccga caggaacatt   1140
accttgtcct tggtggccaa cccttcccac cttgaggccg ctgaccccgt ggtgatgggc   1200
aagaccaaag ccgaacagtt ttactgtggc gacactgaag ggaaaaaggt catgtccatc   1260
ctgttgcatg ggatgctgc atttgctggc cagggcattg tgtacgagac cttccacctc   1320
agcgacctgc catcctacac aactcatggc accgtgcacg tggtcgtcaa caaccagatc   1380
ggcttcacca ccgaccctcg gatggcccgc tcctccccct accccactga cgtggcccga   1440
gtggtgaatg cccccatttt ccacgtgaac tcagatgacc ccgaggctgt catgtacgtg   1500
tgcaaagtgg cggccgagtg gaggagcacc ttccacaagg acgtggttgt cgatttggtg   1560
tgttaccggc gcaacggcca caacgagatg gatgagccca tgttcacgca gccgctcatg   1620
tacaagcaga tccgcaagca gaagcctgtg ttacagaagt acgctgagct gctggtgtcg   1680
cagggtgtgg tcaaccagcc tgagtatgag gaggaaattt ccaagtatga taagatctgt   1740
gaggaagctt ttgccagatc taaagatgag aagatcttgc acattaagca ctggctggac   1800
tctccctggc ctggcttctt caccctggac gggcagccca ggagcatgtc ctgcccctcc   1860
acgggtctga cggaggatat tctgacacac atcgggaatg tggctagttc tgtgcctgtg   1920
gaaaacttta ctattcatgg agggctgagc cggatcttga agactcgtgg ggaaatggtg   1980
aagaaccgga ctgtggactg ggctctagcg gagtacatgg cgtttggctc gctcctgaag   2040
gagggcatcc acattcggct gagcggccag gacgtggagc ggggcacatt cagccaccgc   2100
caccatgtgc tccatgacca gaatgtggac aagagaacct gcatccccat gaaccatctc   2160
tggcccaatc aggcccccta tactgtgtgc aacagctcac tgtctgagta cggcgtgctg   2220
ggctttgagc tgggcttcgc catggccagt cctaatgccc tggtcctctg ggaagcccaa   2280
tttggtgact tccacaacac ggcccagtgt atcatcgacc agttcatctg cccgggacaa   2340
gccaagtggg tgcggcagaa tggcatcgtg ttgctgctgc cccatggcat ggagggcatg   2400
ggtccagaac attcctccgc ccgcccagag cggttcttgc agatgtgcaa cgatgaccca   2460
gatgtcctgc cagaccttaa agaagccaac ttcgacatca atcagctata tgactgcaat   2520
tgggttgttg tcaactgctc cactcctggc aacttcttcc acgtgctacg acgccagatc   2580
ctgctgccat tccggaagcc gttaattatc ttcacccca aatccctgtt gcgccacccc   2640
gaggccagat ccagctttga tgagatgctt ccaggaaccc acttccagcg ggtgatccca   2700
gaagatggcc ctgcagctca gaacccagaa aatgtcaaaa ggcttctctt ctgcaccggc   2760
aaagtgtatt atgacctcac ccgggagcgc aaagcacgcg acatggtggg gcaggtggcc   2820
atcacaagga ttgagcagct gtcgccattc ccctttgacc tcctgctgaa ggaggtgcag   2880
```

aagtacccca atgctgagct ggcctggtgc caggaggagc acaagaacca aggctactat 2940
gactacgtga agccaagact tcggaccacc atcagccgcg ccaagcccgt ctggtatgcc 3000
ggccgggacc cagcggctgc tccagccacc ggcaacaaga agacccacct gacggagctg 3060
cagcgcctcc tggacacggc cttcgacctg gacgtcttca agaacttctc gtagatgctg 3120
cctagggttg cttgggccac tgccctctcc acacccatga ctgccccttg cttctcaact 3180
aaagaatagt gcctcagcgc tgcccacacc accgccctcc tcgctgtgcc accacccctc 3240
cctctgctct cataggagtt aggctgtcgt ccccctccag tgcttggctg ccccacaggc 3300
cacacgctgc ccaggctctg ctgacttctg agcagttttc caggaggccg gggggagcag 3360
gaggaggaaa ggtagccccc gagggatgtc cttggggagg ggtcagctct ggccacaatc 3420
ctccccacca gtctcaccca ctaggatagg aactgggcct tgtgtgctgg cttccgctgt 3480
cacccagcaa ggcacaggct cctgtatttg agactaggat agcttcatct tgagcctgag 3540
ccttagaatc tgtagaggag cctggagtcg gatctagcca tggctggcag aggtttctag 3600
ggtgggcccc agccgtggcg tgaactgagg atgacccggg gcagctggca ggagagagcc 3660
ttggcctgac ctggcacaga aagggcagct tcagtctctg cagtgtccat tatctgctgt 3720
tccttcgagg gttccaggct gtgtgtgggg cccaagcatg ccccacccac ccctcctggg 3780
cccaggcagc acctggagcc cacagagtct gtgtgtagcc aggaagcccc gctcaggtag 3840
ccaccaccgg ggcactggct gctctgtctt ggtcctgtta accctccacc tcctctcttg 3900
gactccctcc ccaccccaac cactctttct ttctccttta acccaatgga gactttctga 3960
tgcatcgttt tctttgctgt gccaaagcag gtcagaagag ggagaggagg ggctgggggt 4020
gaggggccag gccatggcca aggggccagc tgcccctcat ttatcactct gaccttcaca 4080
gggacagatc tgatttattt attttggtta aaaaaaaaaa aaaggaacag aaacaacttt 4140
gcattgcatt ggcttgaccc ataaactaag ttatatccgt g 4181

<210> SEQ ID NO 93
<211> LENGTH: 137
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 93
nnnnnnnnnn nnnnnnnnnn gtttttgtac tctcaagatt tagaaataaa tcttgcagaa 60
gctacaaaga taaggcttca tgccgaaatc aacaccctgt cattttatgg cagggtgttt 120
tcgttattta atttttt 137

<210> SEQ ID NO 94
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)

```
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 94

nnnnnnnnnn nnnnnnnnnn gtttttgtac tctcagaaat gcagaagcta caaagataag     60

gcttcatgcc gaaatcaaca ccctgtcatt ttatggcagg gtgttttcgt tatttaattt    120

ttt                                                                  123


<210> SEQ ID NO 95
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 95

nnnnnnnnnn nnnnnnnnnn gtttttgtac tctcagaaat gcagaagcta caaagataag     60

gcttcatgcc gaaatcaaca ccctgtcatt ttatggcagg gtgttttttt               110


<210> SEQ ID NO 96
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 96

nnnnnnnnnn nnnnnnnnnn gttttagagc tagaaatagc aagttaaaat aaggctagtc     60

cgttatcaac ttgaaaaagt ggcaccgagt cggtgctttt tt                       102


<210> SEQ ID NO 97
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 97

nnnnnnnnnn nnnnnnnnnn gttttagagc tagaaatagc aagttaaaat aaggctagtc     60

cgttatcaac ttgaaaaagt gttttttt                                        88
```

```
<210> SEQ ID NO 98
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 98

nnnnnnnnnn nnnnnnnnnn gttttagagc tagaaatagc aagttaaaat aaggctagtc     60

cgttatcatt tttttt                                                     76
```

METHODS OF TREATING p53 MUTANT CANCERS USING OGDH INHIBITORS

CROSS-REFERENCE TO RELATED APPLICATIONS

This application is a U.S. National Stage Application under 35 U.S.C. § 371 of International Patent Application No. PCT/US2020/046255, filed on Aug. 13, 2020, which claims the benefit of and priority to U.S. Provisional Patent Application No. 62/886,720, filed Aug. 14, 2019, the entire contents of which are incorporated herein by reference.

STATEMENT OF GOVERNMENT INTEREST

This invention was made with government support under CA087497, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 18, 2020, is named 115872-0676 SL.txt and is 42,607 bytes in size.

TECHNICAL FIELD

The present technology relates generally to methods and compositions for treating, preventing, and/or ameliorating p53-mutant cancers in a subject in need thereof, including acute myeloid leukemia (AML), pancreatic cancer, and liver cancer, by administration of a therapeutically effective amount of an OGDH inhibitor.

BACKGROUND

The following description of the background of the present technology is provided simply as an aid in understanding the present technology and is not admitted to describe or constitute prior art to the present technology.

The tumor suppressor TP53 is mutated in the majority of human cancers, including over 70% of pancreatic ductal adenocarcinoma (PDAC). Wild-type p53 accumulates in response to cellular stress and regulates gene expression to alter cell fate and prevent tumor development. Wild-type p53 also modulates cellular metabolic pathways, though p53 dependent metabolic alterations that constrain cancer progression remain poorly understood.

Acute myeloid leukemia (AML) represents a group of related hematopoietic cancers characterized by a clonal proliferation of myeloid precursor cells within the bone marrow. Acute myeloid leukemia (AML) is characterized by the rapid growth of abnormal cells that build up in the bone marrow and blood and interfere with normal blood cells. Symptoms may include feeling tired, shortness of breath, easy bruising and bleeding, and increased risk of infection. AML progresses rapidly and is typically fatal within weeks or months if left untreated. The underlying reason for mortality and morbidity involves replacement of normal bone marrow with leukemia cells, which results in a drop in red blood cells, platelets, and normal white blood cells. This disease accounts for approximately 80% of acute leukemias, with an estimated 20,000 new cases and 11,000 deaths expected in the United States yearly. In 2015, AML affected about one million people and resulted in 147,000 deaths globally. Acute Myeloid leukemia (AML) accounts for 25% of pediatric leukemia but more than half of childhood leukemia deaths. In contrast to acute lymphoid leukemia that is curable in >80% of children, pediatric AML has the worst 5-year survival among childhood cancers. Among adults, in those patients diagnosed before 60 years of age, AML is curable in 35-40% of cases, whereas only 5-15% of those presenting later in life can be cured. AML accounts for roughly 1.8% of cancer deaths in the United States. Complex karyotype (CK) AML, defined as leukemia harboring three or more chromosomal abnormalities, portends a particularly unfavorable prognosis, with overall survival at 5 years at less than 20%. Probability of survival is further decreased in ~70% of CK AML cases harboring TP53 tumor suppressor gene mutations, with most patients dying within 1 year of diagnosis. The adverse outcomes in CK AML are due to a combination of factors, including poor chemotherapy response and an absence of conventionally targetable mutations.

SUMMARY OF THE PRESENT TECHNOLOGY

In one aspect, the present disclosure provides a method for treating or preventing a p53 mutant cancer in a subject in need thereof comprising administering to the subject an effective amount of an OGDH inhibitor, wherein the p53 mutant cancer is liver cancer or acute myeloid leukemia (AML). The OGDH inhibitor may be a small molecule, an OGDH-specific inhibitory nucleic acid, or an anti-OGDH neutralizing antibody. In certain embodiments, the small molecule is succinyl phosphonate, (S)-2-[(2,6-dichlorobenzoyl) amino] succinic acid (AA6), KGD09, KGD02, or an azide-alkyne cyclized derivative thereof. The OGDH-specific inhibitory nucleic acid may be a siRNA, a shRNA, an antisense oligonucleotide, or a sgRNA. In some embodiments, the OGDH-specific inhibitory nucleic acid comprises a nucleic acid sequence of any one of SEQ ID NOs: 13, 14, 43, 44, or a complement thereof. Additionally or alternatively, in some embodiments, the subject is human.

In another aspect, the present disclosure provides a method for treating or preventing pancreatic cancer in a subject in need thereof comprising administering to the subject an effective amount of an OGDH inhibitor selected from the group consisting of succinyl phosphonate, (S)-2-[(2,6-dichlorobenzoyl) amino] succinic acid (AA6), KGD09, KGD02, or an azide-alkyne cyclized derivative thereof. In some embodiments, the subject is human and/or harbors a TP53 mutation. Additionally or alternatively, in some embodiments, the pancreatic cancer is pancreatic ductal adenocarcinoma (PDAC).

In any and all embodiments of the methods disclosed herein, the OGDH inhibitor is administered orally, topically, intranasally, systemically, intravenously, subcutaneously, intraperitoneally, intradermally, intraocularly, iontophoretically, transmucosally, or intramuscularly.

Additionally or alternatively, in some embodiments, the methods of the present technology further comprise separately, sequentially or simultaneously administering one or more additional therapeutic agents to the subject. Examples of the one or more additional therapeutic agents include, but are not limited to, Capecitabine, Erlotinib, Fluorouracil (5-FU), Gemcitabine, Ifinotecan, Leucovorin, Nab-paclitaxel, Nanoliposomal irinotecan, Oxaliplatin, Larotrectinib, pembrolizumab, Cabozantinib-S-Malate, Ramucirumab, Lenvatinib Mesylate, Sorafenib Tosylate, Nivolumab, Ramucirumab, Regorafenib, Regorafenib, cisplatin, Doxorubicin, Mitoxantrone, Arsenic Trioxide, Daunorubicin, Cyclophosphamide, Cytarabine, Glasdegib Maleate, Dexamethasone, Doxorubicin, Enasidenib Mesylate, Gemtuzumab Ozogamicin, Gilteritinib Fumarate, Idarubicin, Ivosidenib, Midostaurin, Thioguanine, Venetoclax, and Vincristine Sulfate.

In one aspect, the present disclosure provides a method for monitoring the therapeutic efficacy of an OGDH inhibitor in a subject suffering from or diagnosed with a p53-mutant cancer comprising: (a) detecting OGDH expression levels in a test sample obtained from the subject after the subject has been administered the OGDH inhibitor; and (b) determining that the OGDH inhibitor is effective when the OGDH expression levels in the test sample are reduced compared to that observed in a control sample obtained from the subject prior to administration of the OGDH inhibitor, wherein the OGDH inhibitor is selected from the group consisting of succinyl phosphonate, (S)-2-[(2,6-dichlorobenzoyl) amino] succinic acid (AA6), KGD09, KGD02, or an azide-alkyne cyclized derivative thereof. In some embodiments, the p53-mutant cancer is pancreatic cancer, liver cancer, or AML. Additionally or alternatively, in some embodiments, the expression levels of OGDH are detected via RT-PCR, Northern Blotting, RNA-Seq, microarray analysis, High-performance liquid chromatography (HPLC), mass spectrometry, immunohistochemistry (IHC), fluorescence in situ hybridization (FISH), Western Blotting, immunoprecipitation, flow cytometry, Immuno-electron microscopy, immunoelectrophoresis, enzyme-linked immunosorbent assays (ELISA), or multiplex ELISA antibody arrays.

Also disclosed herein are kits comprising at least one OGDH inhibitor of the present technology and instructions for using the at least one OGDH inhibitor to treat or prevent AML. The OGDH inhibitor may be a small molecule, an OGDH-specific inhibitory nucleic acid, or an anti-OGDH neutralizing antibody. In some embodiments, the small molecule is succinyl phosphonate, (S)-2-[(2,6-dichlorobenzoyl) amino] succinic acid (AA6), KGD09, KGD02, or an azide-alkyne cyclized derivative thereof. Additionally or alternatively, in some embodiments of the kits, the OGDH-specific inhibitory nucleic acid is a siRNA, a shRNA, an antisense oligonucleotide, or a sgRNA.

Data in FIGS. 13A-13F are presented as mean±SD of triplicate wells of a representative experiment with individual data points shown. Significance was assessed by Student's t-test. *, $p<0.001$; **, $p<0.0001$.

Figure 14A:
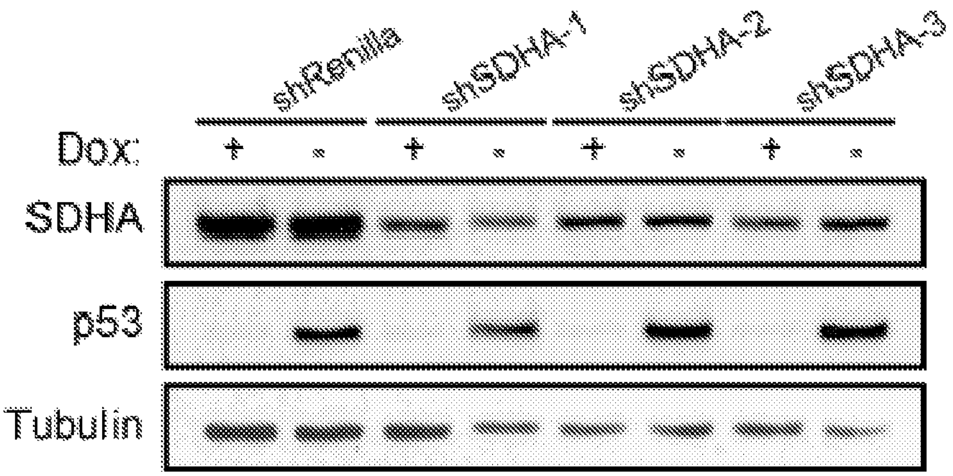

FIG. 14A shows the Sdha and p53 western blot in $KP^{sh}$-2 cells expressing constitutive shRNAs targeting Sdha or *Renilla* grown with or without dox for 8 days.

Figure 14B:
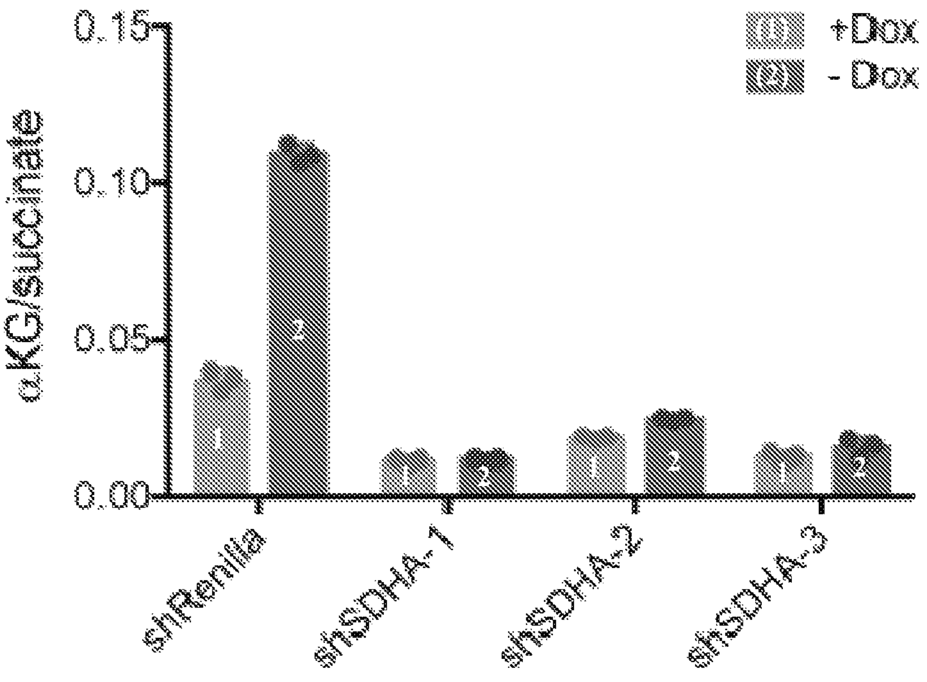

FIG. 14B shows the αKG/succinate ratio of $KP^{sh}$-2 cells expressing constitutive shRNAs targeting Sdha or *Renilla* grown with or without dox for 8 days.

Figure 14C:
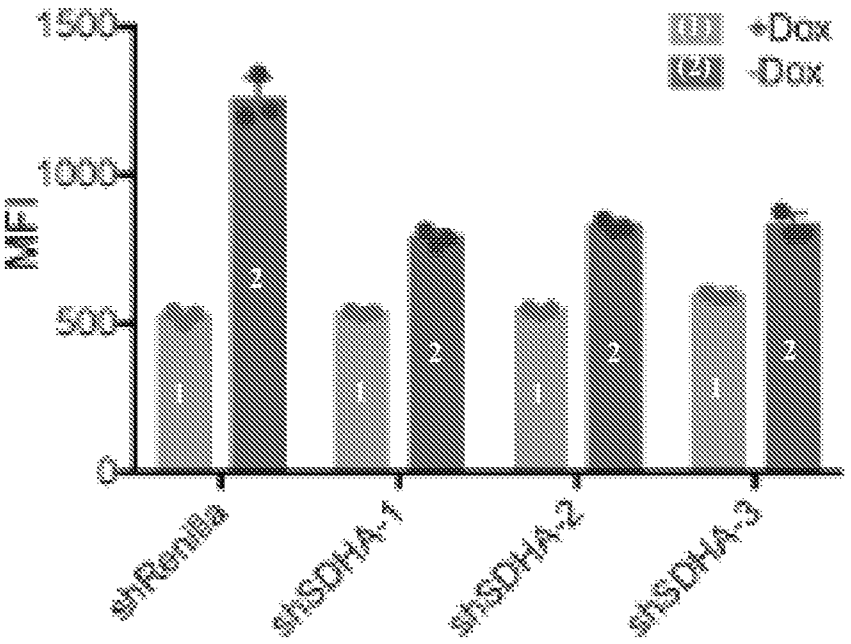

FIG. 14C shows the median fluorescence intensity of 5hmC of $KP^{sh}$-2 cells expressing constitutive shRNAs targeting Sdha or *Renilla* grown with or without dox for 8 days.

Figure 14D:
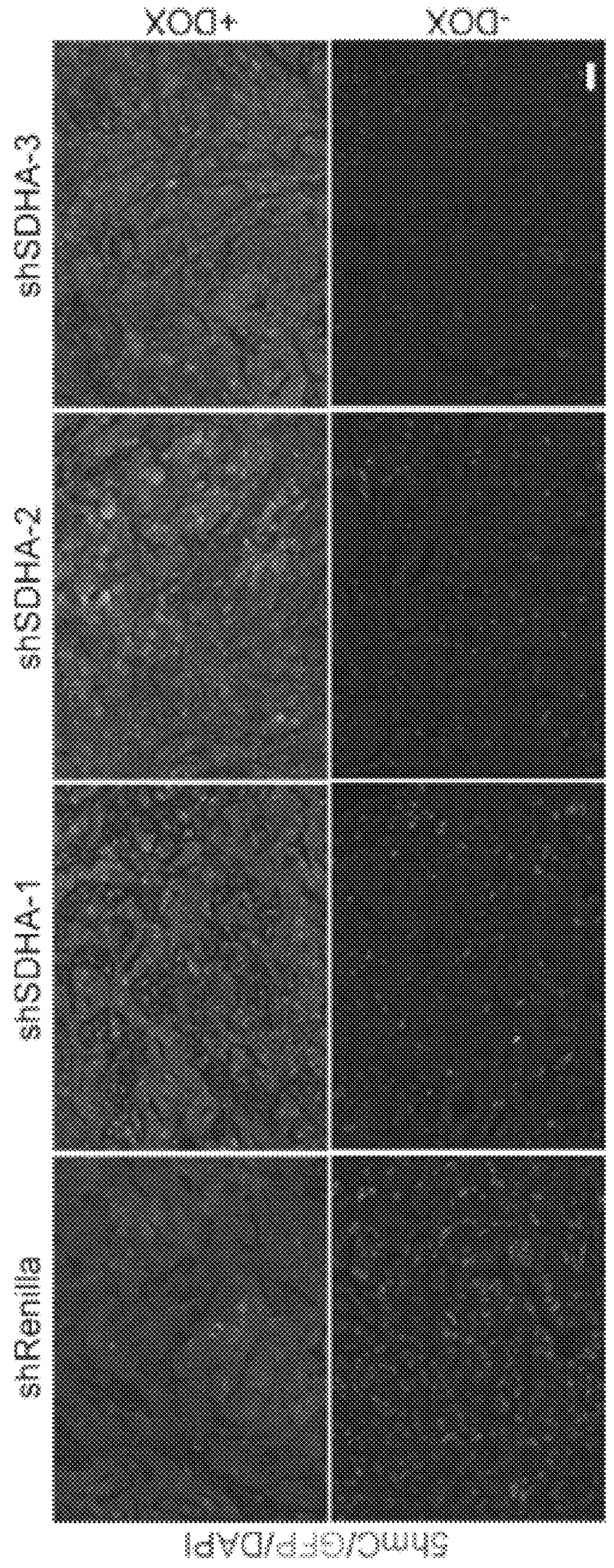

FIG. 14D shows the representative fluorescence microscopy images of 5hmC staining in $KP^{sh}$-2 cells expressing constitutive shRNAs targeting Sdha or *Renilla* grown with or without dox for 8 days.

Figure 14E:
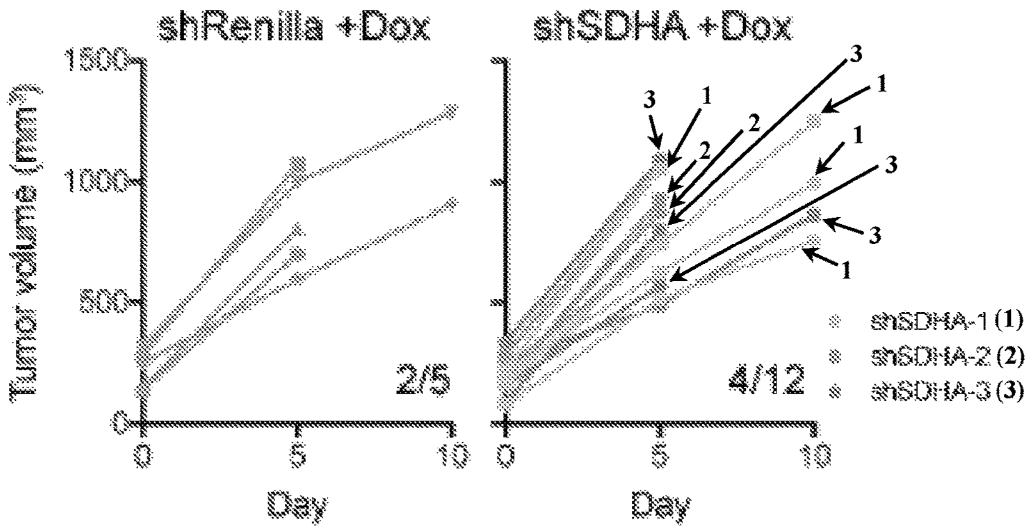

FIG. 14E shows the small animal ultrasound measurement of tumors derived from $KP^{sh}$-2 cells expressing constitutive shRNAs targeting *Renilla* (left) or Sdha (right) orthotopically injected into dox-fed mice maintained on dox diet for 2 weeks. After two weeks (D0), tumor size was measured and mice were randomized into off and on dox chow groups. Subsequent tumor size and mouse survival were monitored up to 10 days.

Figure 14F:
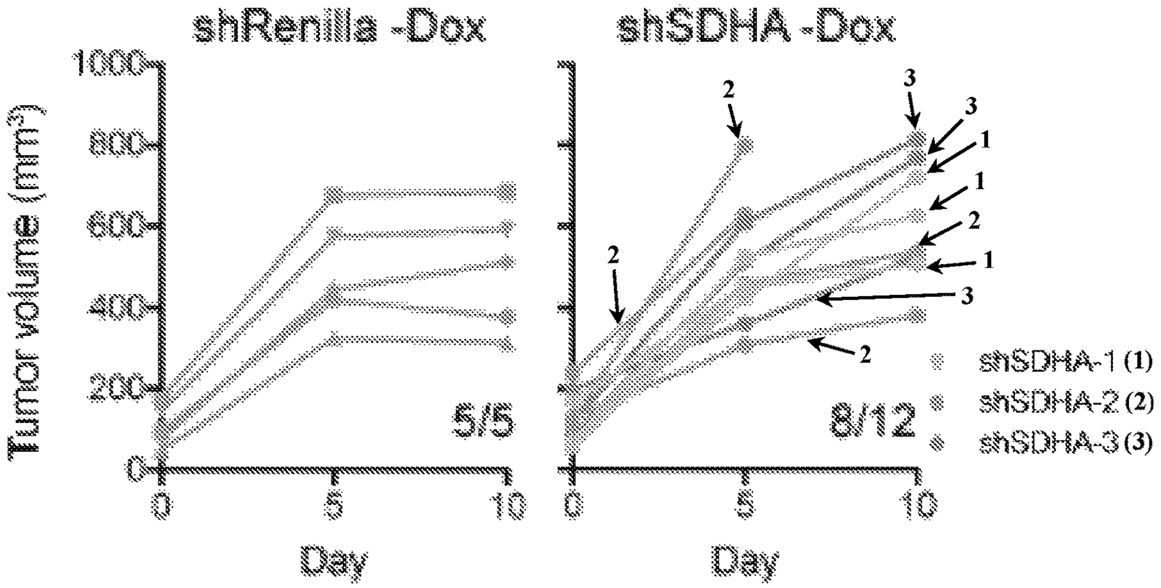

FIG. 14F shows the small animal ultrasound measurement of tumors derived from $KP^{sh}$-2 cells expressing constitutive shRNAs targeting *Renilla* (left) or Sdha (right) orthotopically injected into dox-fed mice maintained on dox diet for 2 weeks. After two weeks (D0), tumor size was measured and mice were randomized into off and on dox chow groups. Subsequent tumor size and mouse survival were monitored for 10 days after dox withdrawal.

Figure 14G:
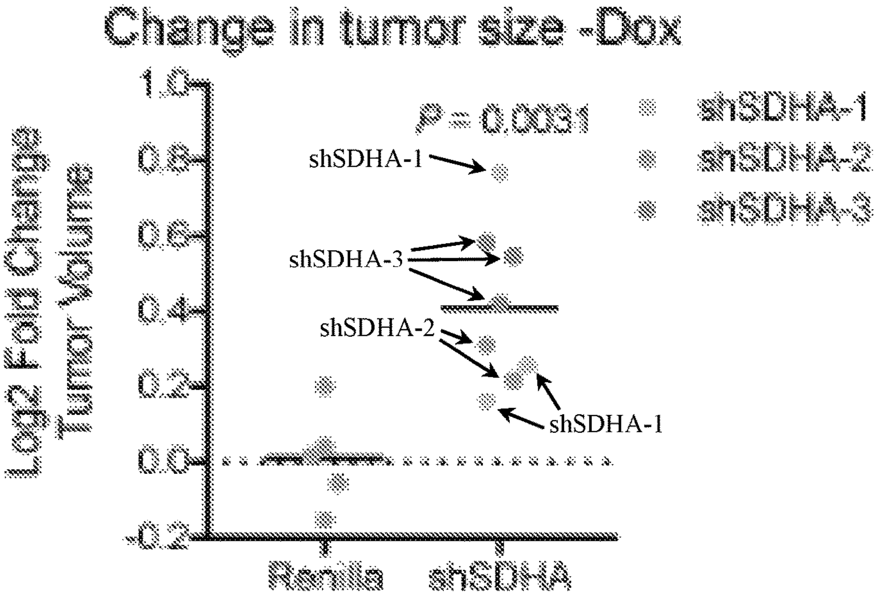
Figure 14H:
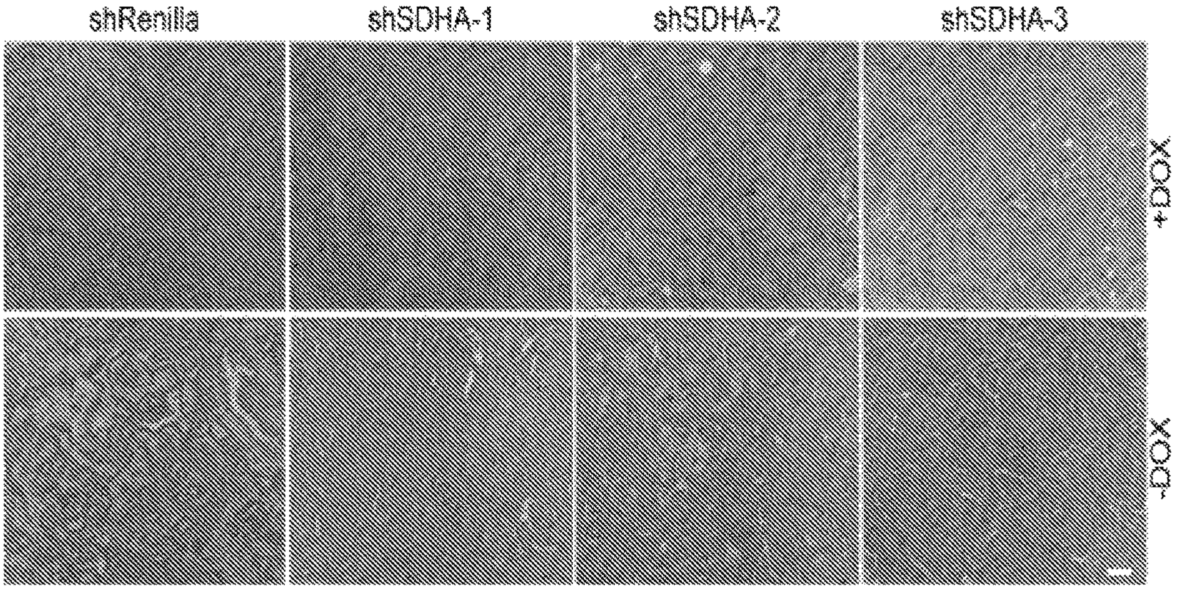
Figure 15A:
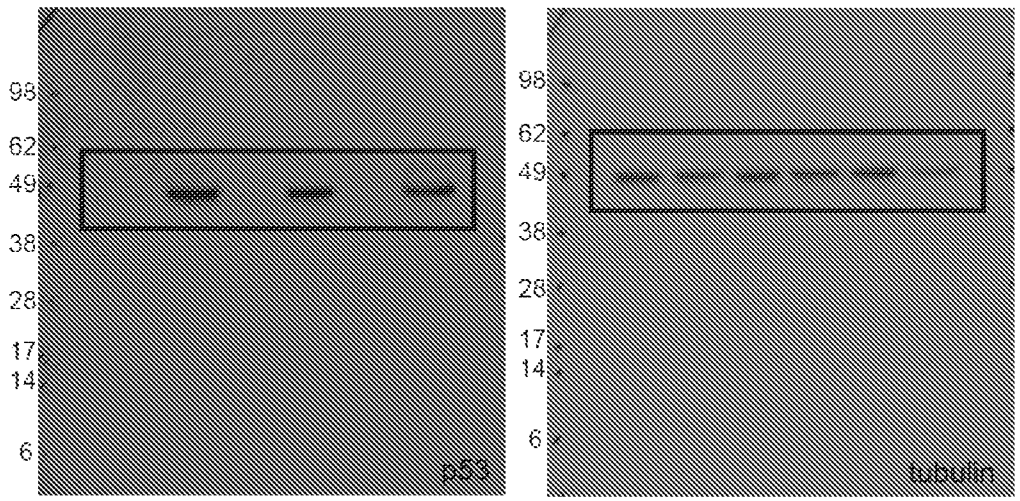
Figure 15B:
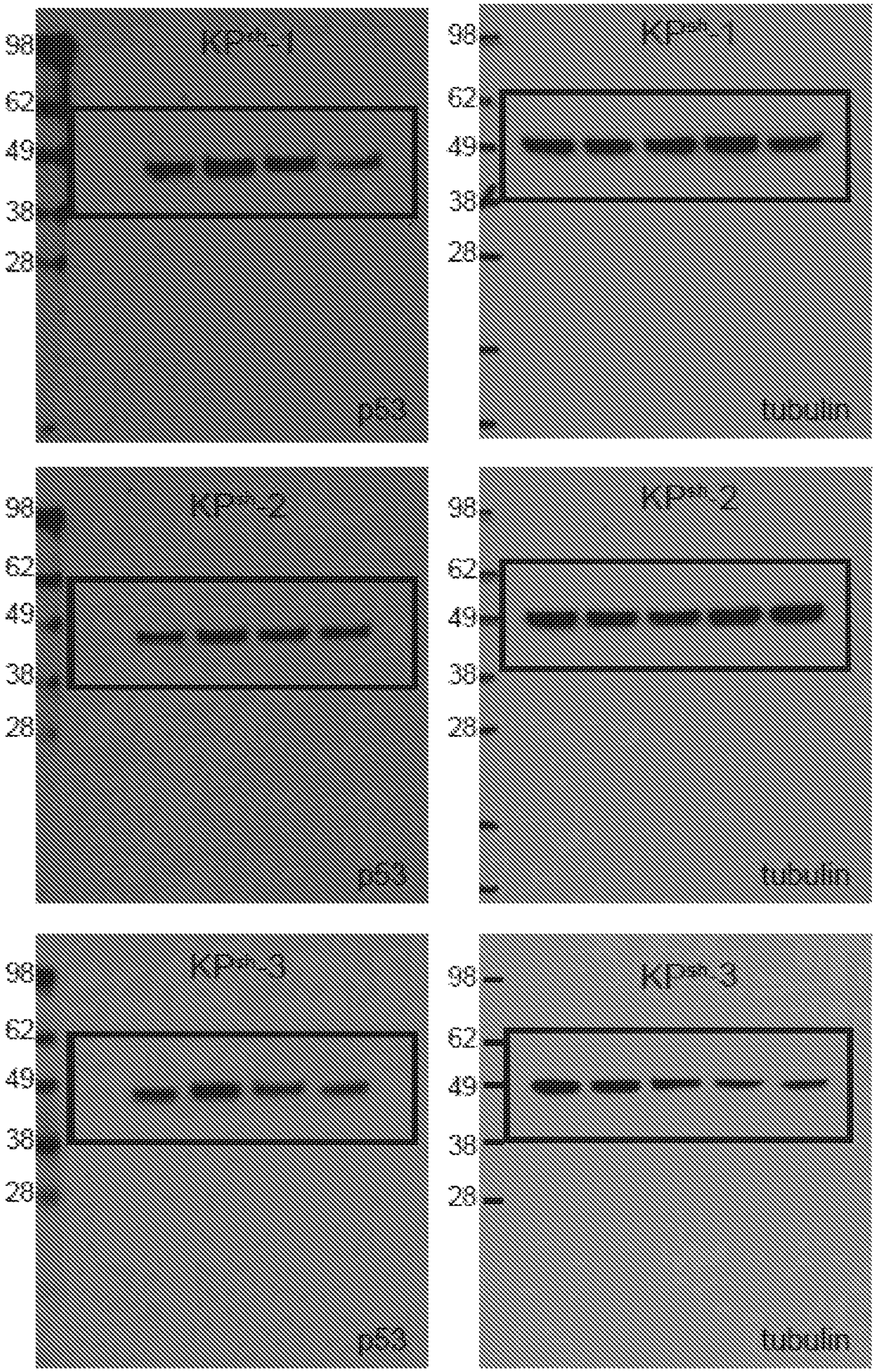
Figure 15C:
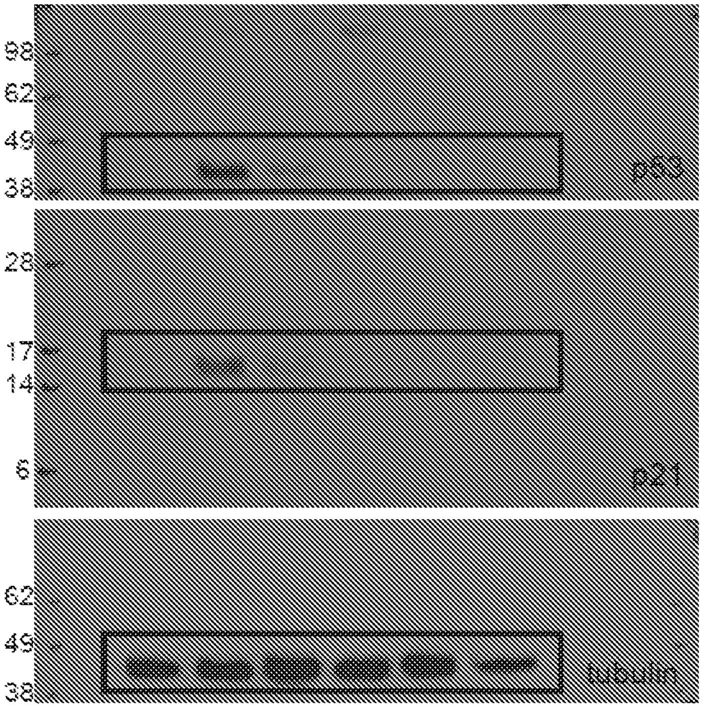
Figure 15D:
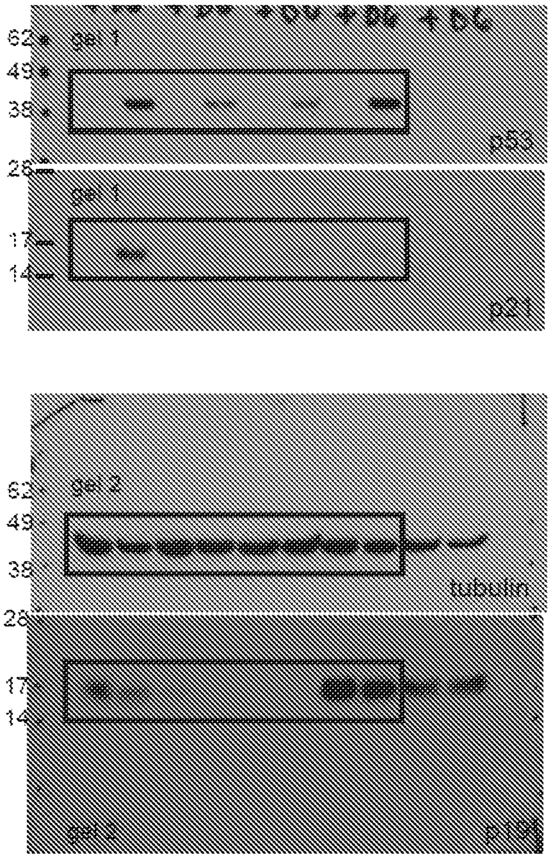
Figure 15E:
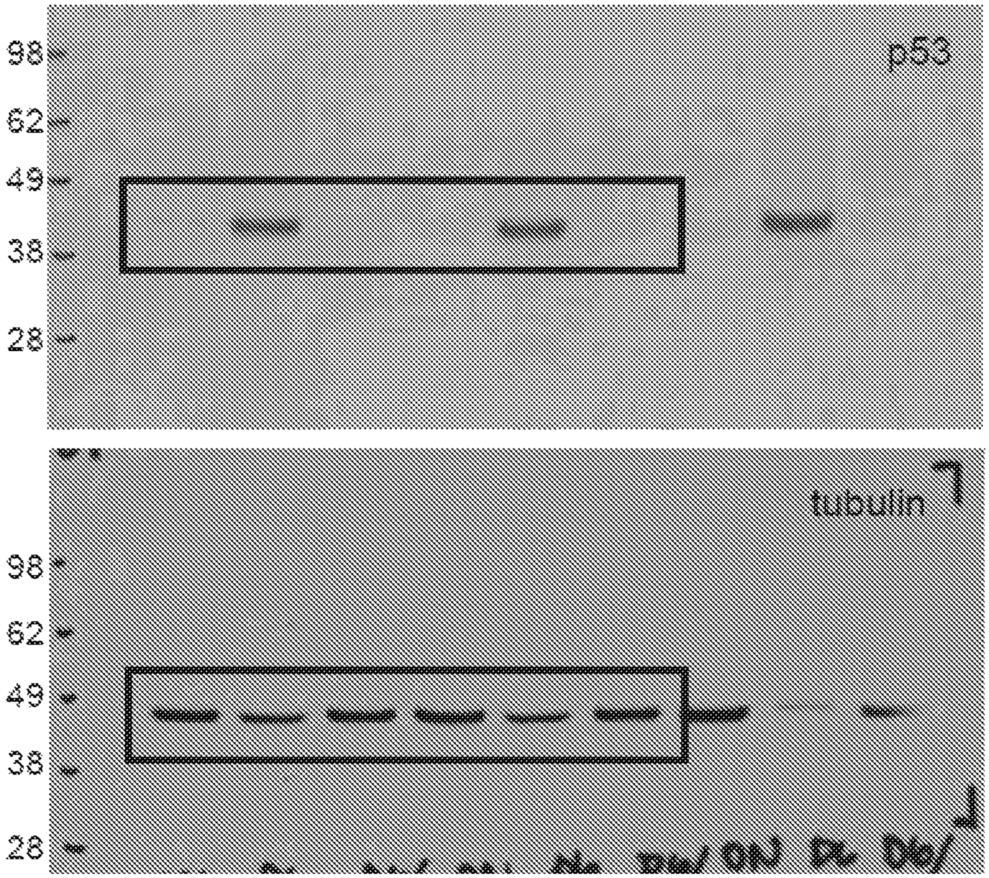
Figure 15F:
Figure 15G:
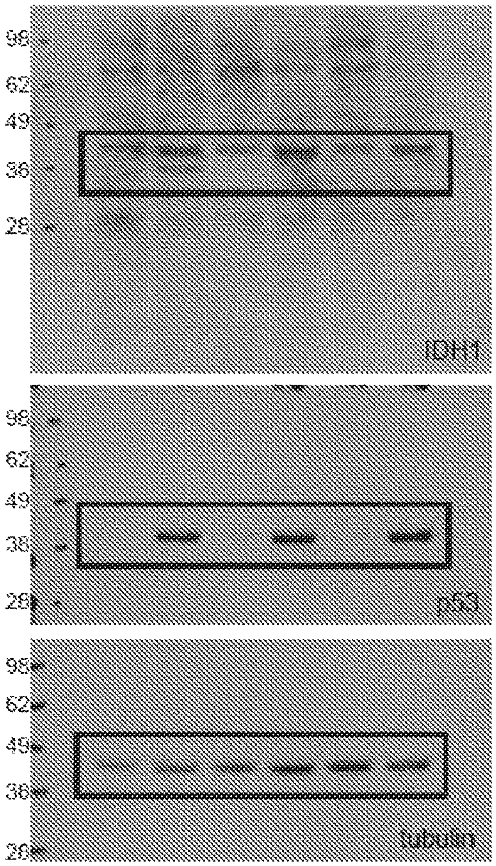
Figure 15H:
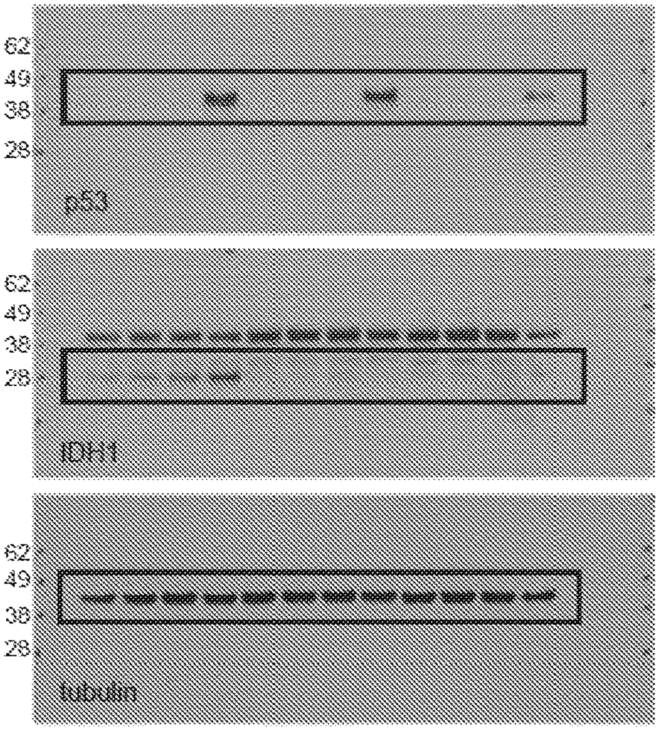
Figure 15I:
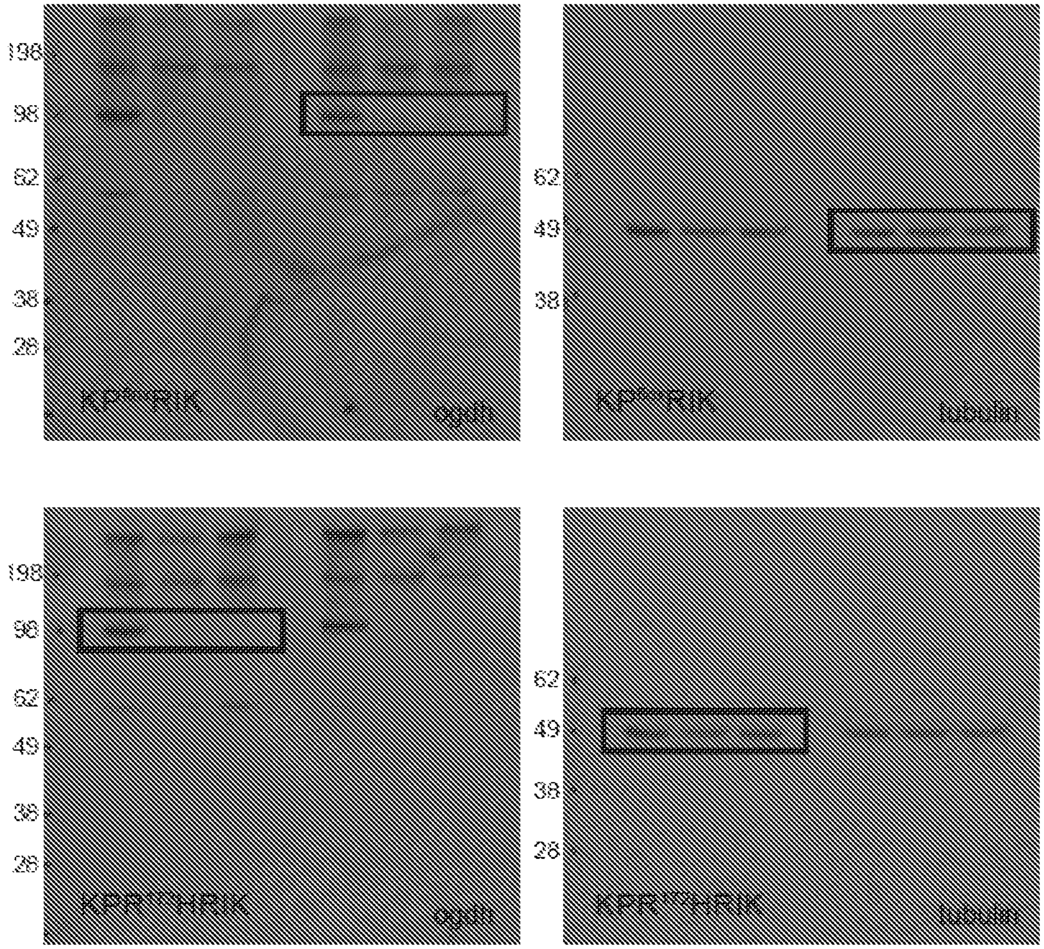
Figure 15J:
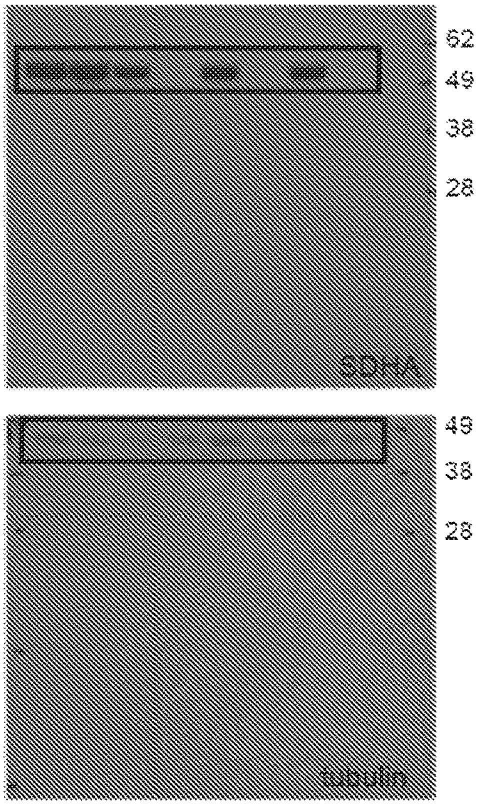
Figure 15K:
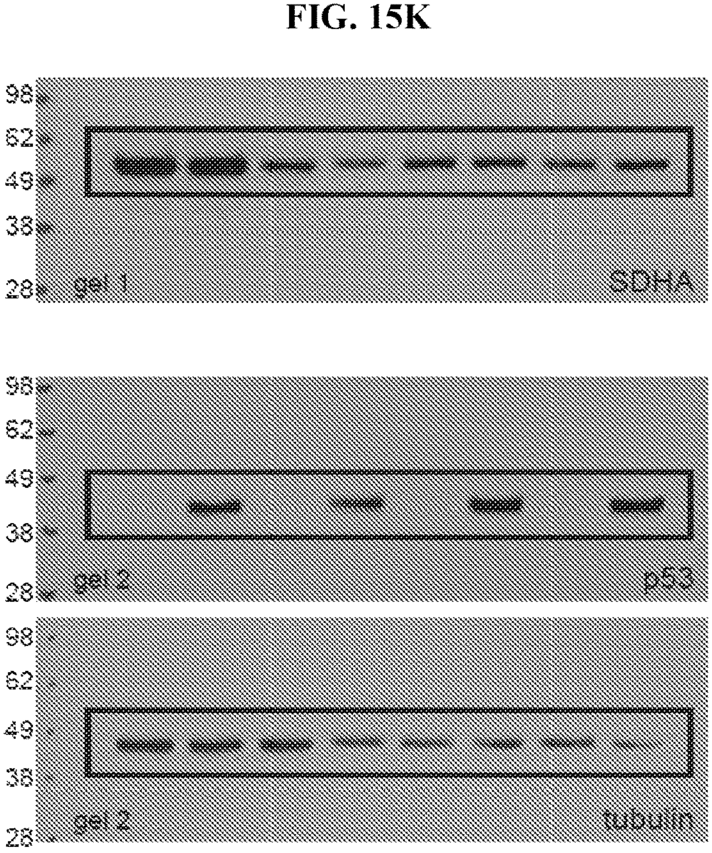

FIG. 14G shows the fold change in tumor size 5-10 days following withdrawal of dox chow from mice bearing orthotopic tumors derived from $KP^{sh}$-2 cells expressing constitutive shRNAs targeting Sdha or *Renilla.*

FIG. 1411 shows the representative H&E staining of orthotopic tumors derived from $KP^{sh}$-2 cells expressing constitutive shRNAs targeting Sdha or *Renilla* maintained on dox or 10 days following dox withdrawal. Scale bar 50 μM. Data in FIGS. 14B, 14C and 14G are presented as mean±SD of triplicate wells of a representative experiment with individual data points shown or as a single point per mouse. Significance was assessed by two-tailed, unpaired t-test.

FIGS. 15A to 15K show the uncropped scans of source data for immunoblots from FIGS. 1A, 5C, 6E, 6I, 7B, 8A, 8J, 8I, 10E, 11G, 14A, respectively.

Figure 16A:
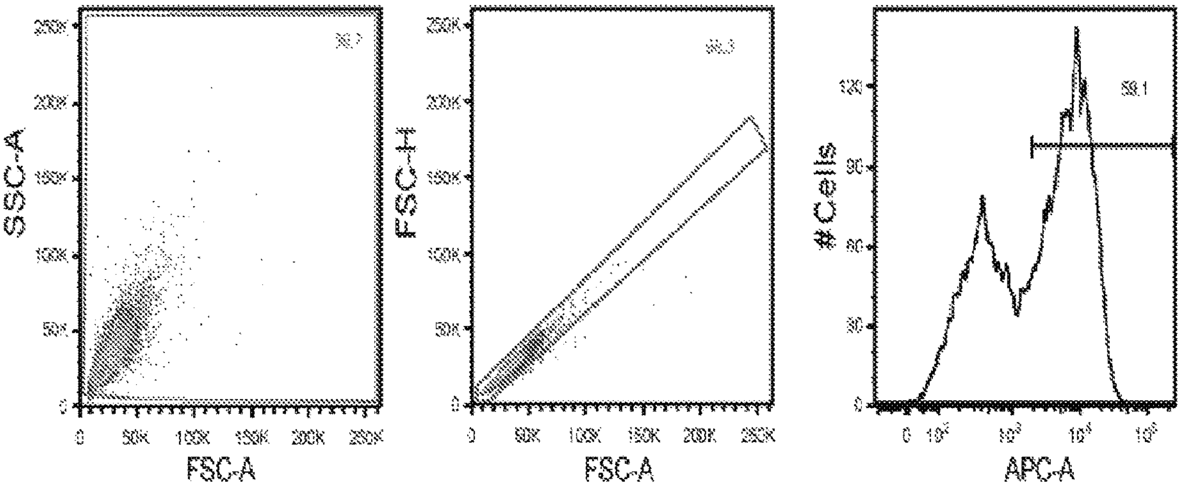

FIG. 16A shows the gating strategy for the BrdU experiments disclosed herein. Left, cells were identified by forward and side scatter. Middle, forward scatter area and forward scatter height used to discriminate doublets. Right, histogram indicating BrdU positive cells.

Figure 16B:
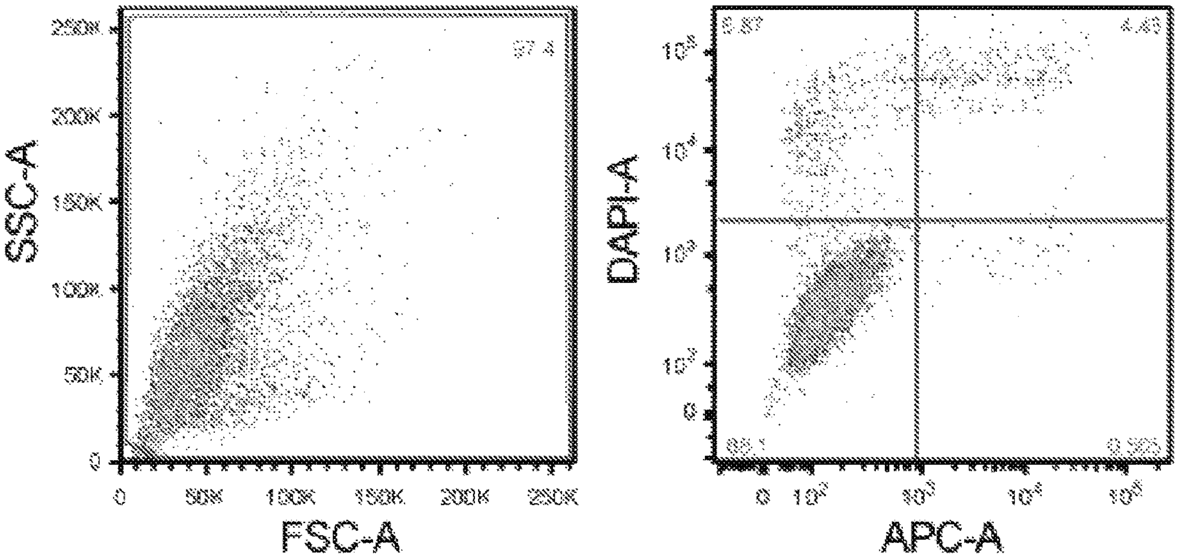

FIG. 16B shows the gating strategy for the Annexin-V experiments disclosed herein. Left, cells were identified by forward and side scatter. Right, Annexin-V and DAPI staining. Percentage of AnnexinV+ DAPI+ and Annexin V+ DAPI− cells were added to report Annexin V percentage in all experiments.

Figure 16C:
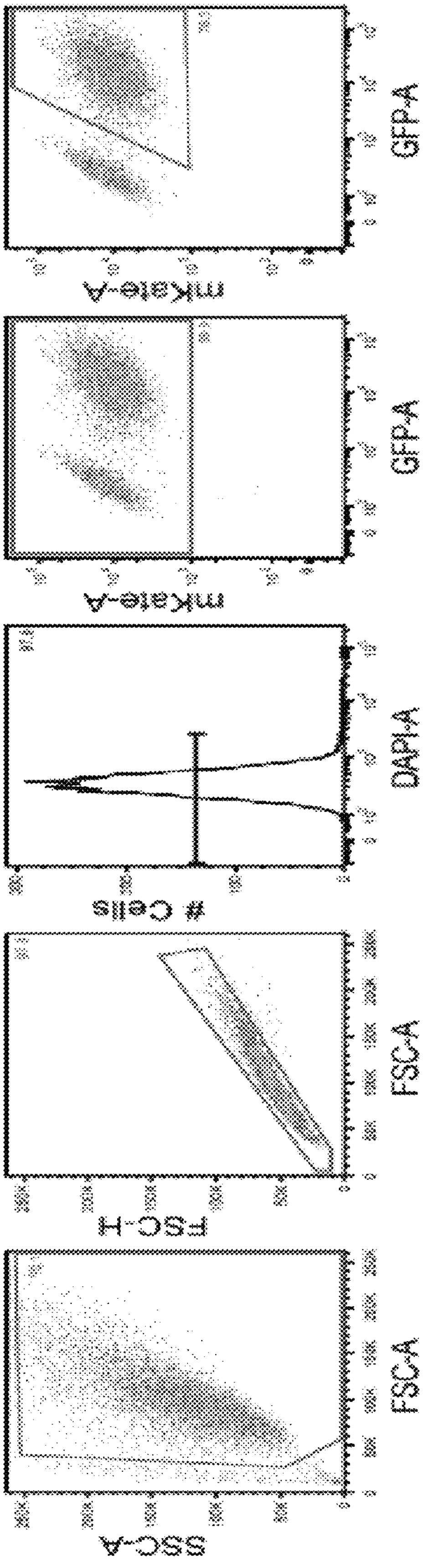
Figure 16D:
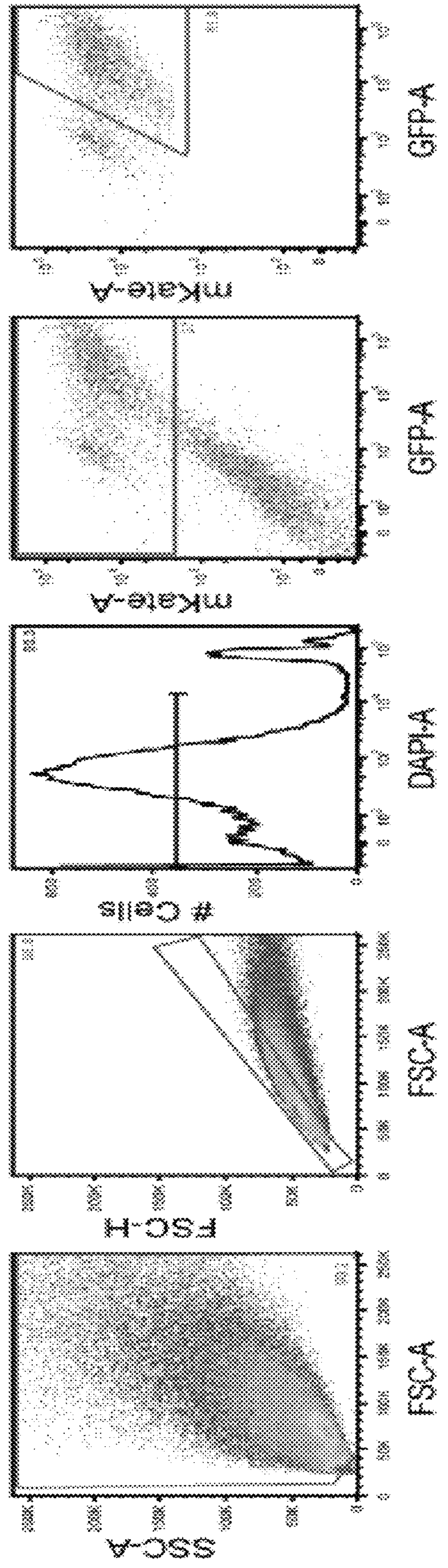

FIGS. 16C-16D show the in vivo shRNA competition assay gating strategy. FIG. 16C shows the strategy to determine initial shRNA (GFP+) percentage at injection. From left to right: cells were identified by forward and side scatter. Forward scatter area and forward scatter height used to discriminate doublets. Viable cells identified by negative DAPI staining. Percent GFP+ cells determined out of total mKate positive cells. FIG. 16D shows the strategy to determine final shRNA (GFP+) percentage after 3 weeks of tumor growth. From left to right: cells were identified by forward and side scatter. Forward scatter area and forward scatter height used to discriminate doublets. Viable cells identified by negative DAPI staining. Percent GFP+ cells determined out of total mKate positive cells.

Figure 16E:
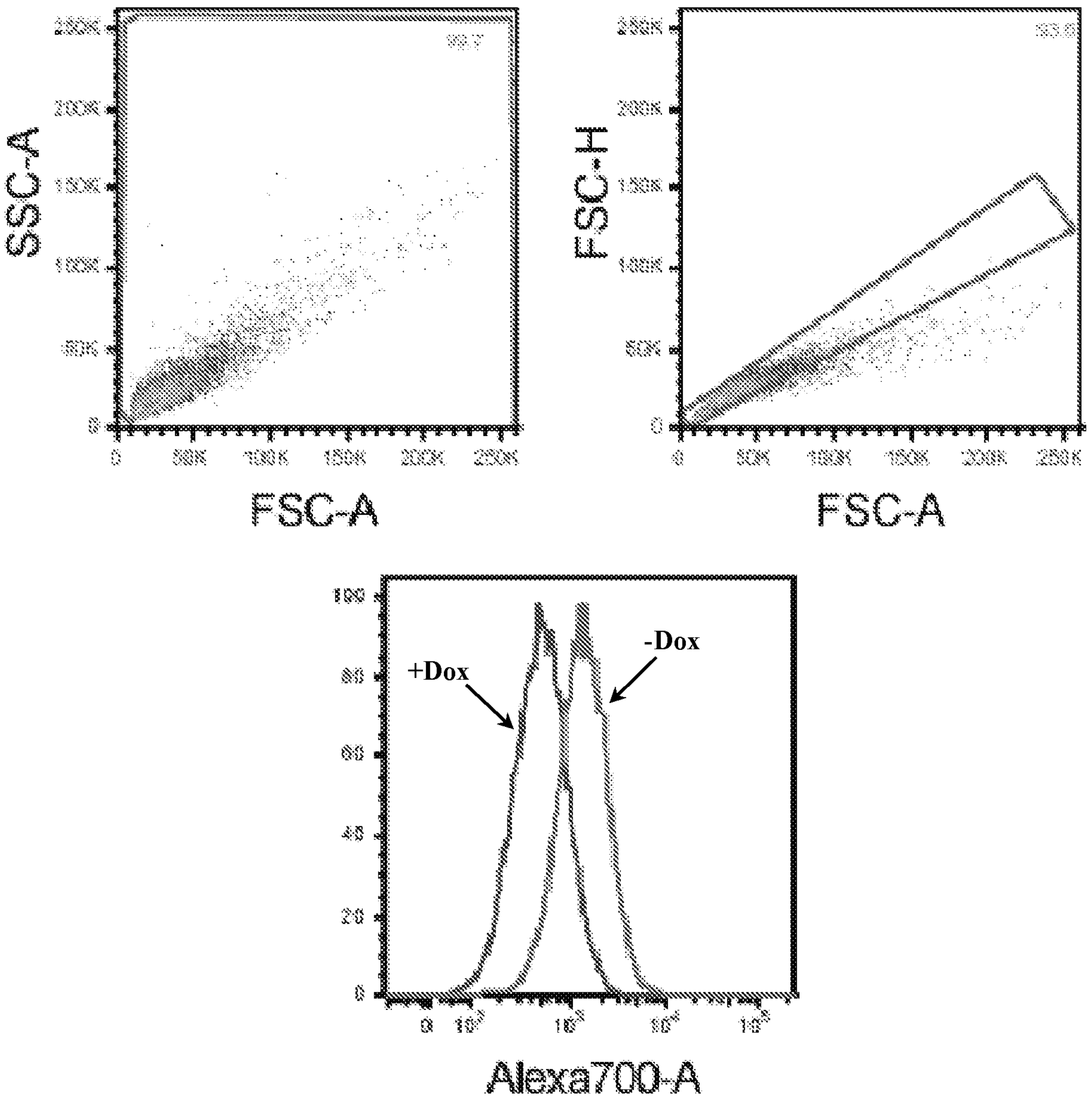

FIG. 16E shows the strategy to determine 5hmC median fluorescence intensity (MFI) in mouse and human PDAC cells. From left to right: cells were identified by forward and side scatter. Forward scatter area and forward scatter height used to discriminate doublets. 5hmC MFI was determined from resulting singlet histogram. Right panel, representative histograms of $KP^{sh}$ cells grown on or off dox for 8 days.

Figure 17A:
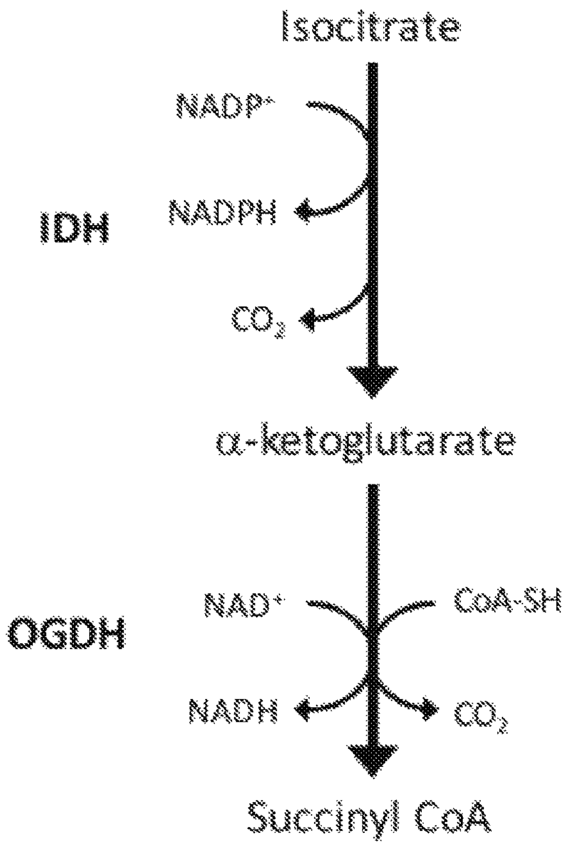

FIG. 17A shows the schematic of alpha-keto glutarate (αKG) metabolism.

Figure 17B:
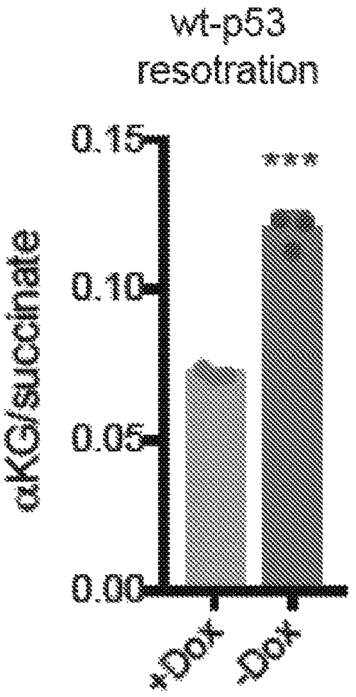
Figure 17C:
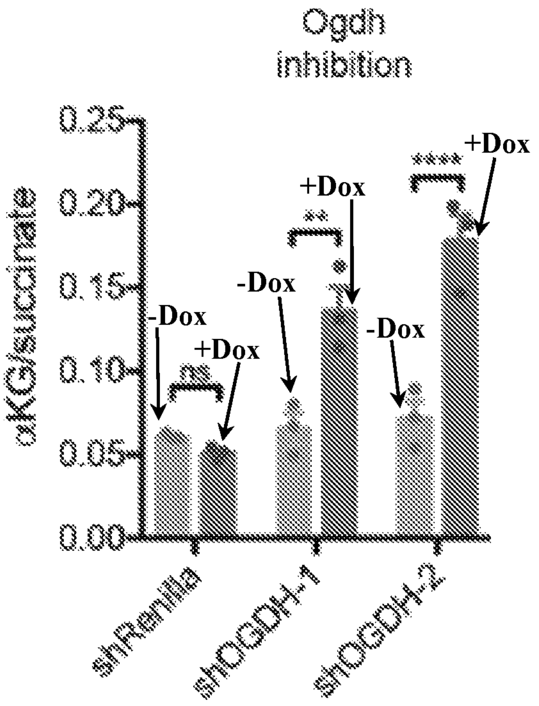

FIGS. 17B-17C shows the p53 restoration (FIG. 17B) or OGDH inhibition (FIG. 17C) increases the αKG:succinate ratio.

Figure 17D:
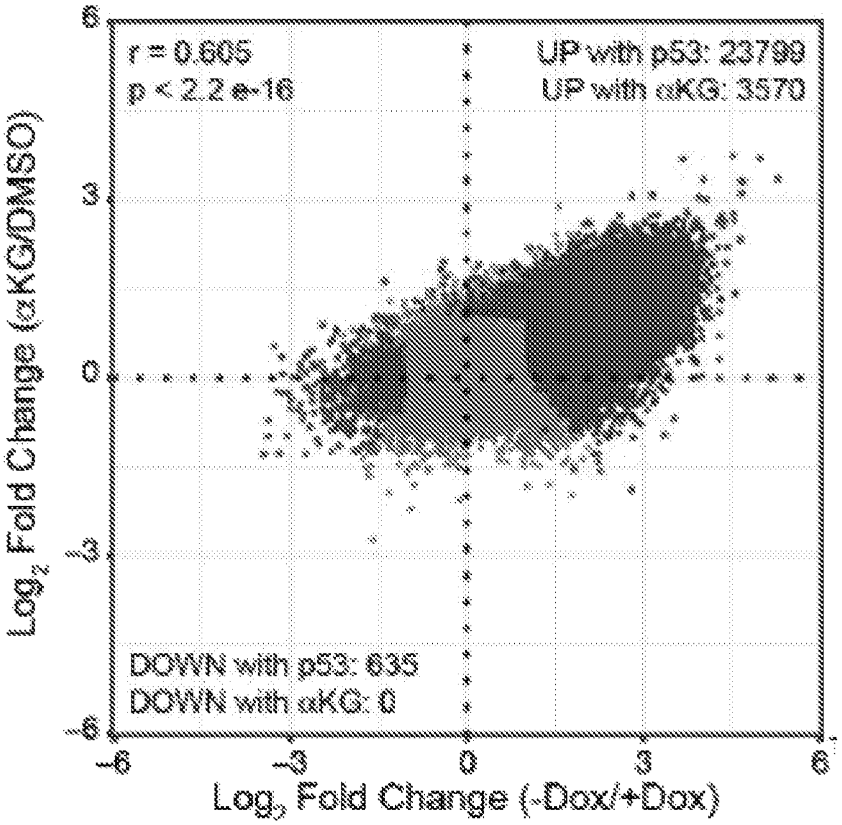

FIG. 17D shows the ATAC-seq of KPCsh cells following p53 restoration or αKG treatment.

Figure 17E:
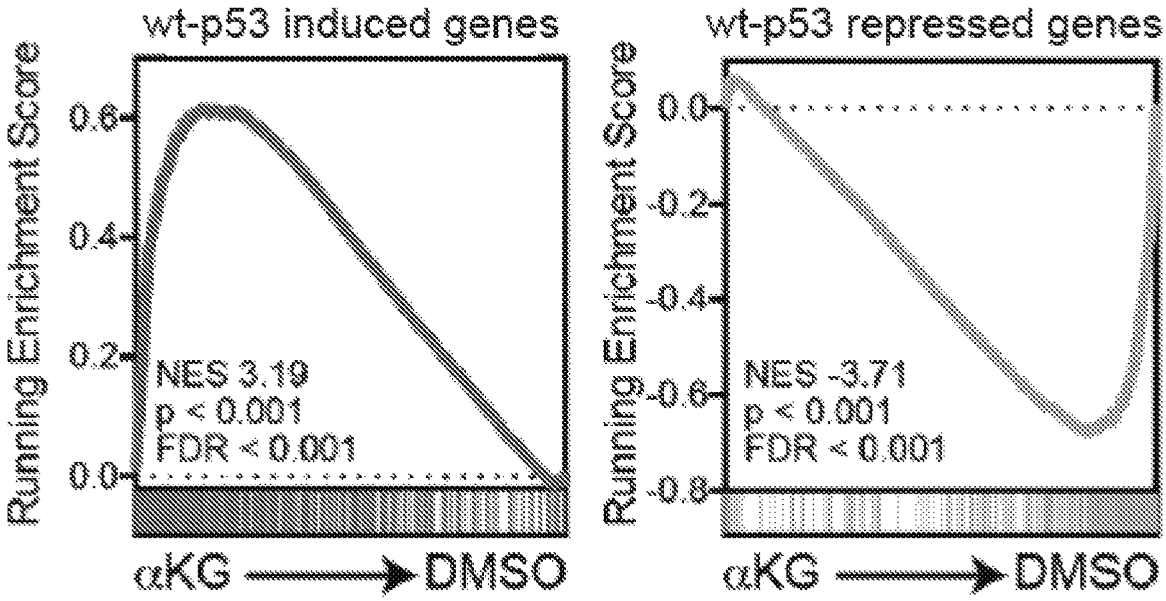

FIG. 17E shows the GSEA of p53 restoration induced gene signatures following αKG treatment.

Figure 18A:
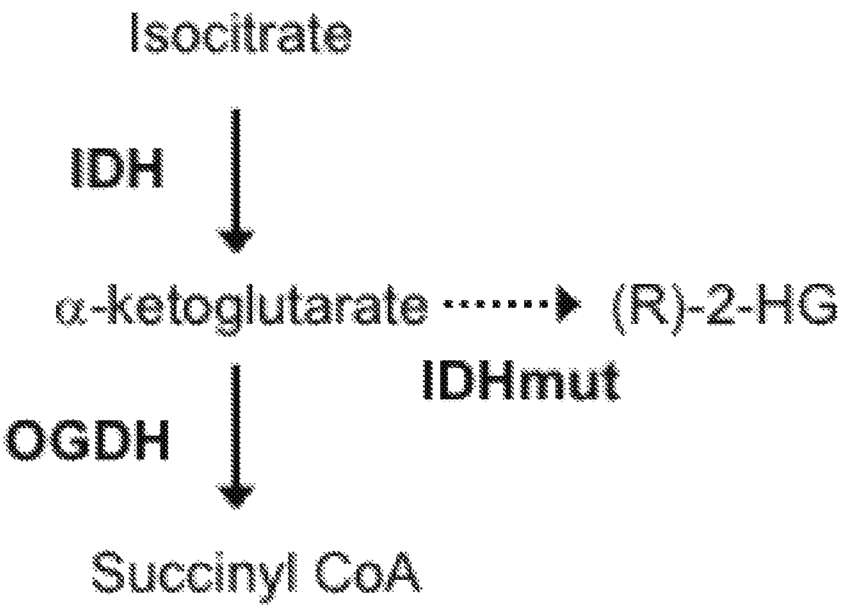

FIGS. 18A-18G show that the genetic inhibition of Ogdh drives a differentiation program. FIG. 18A shows a schematic of αKG metabolism in AML.

Figure 18B:
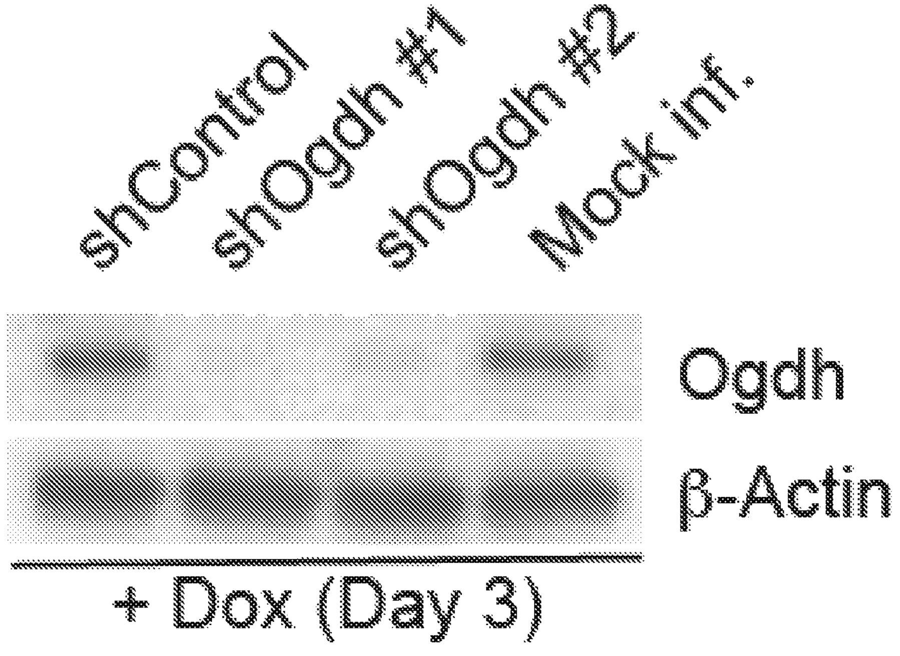

FIG. 18B shows the inducible knockdown of Ogdh in murine AML.

Figure 18C:
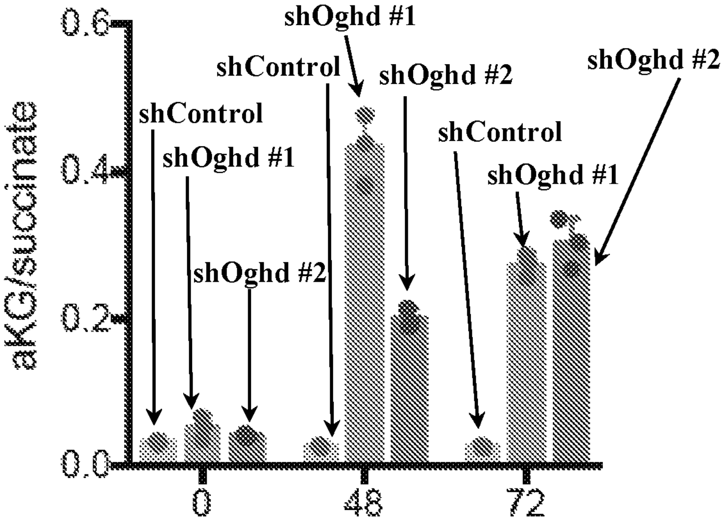

FIG. 18C shows that the Ogdh shRNA increased the cellular ratio of αKG:succinate.

Figure 18D:
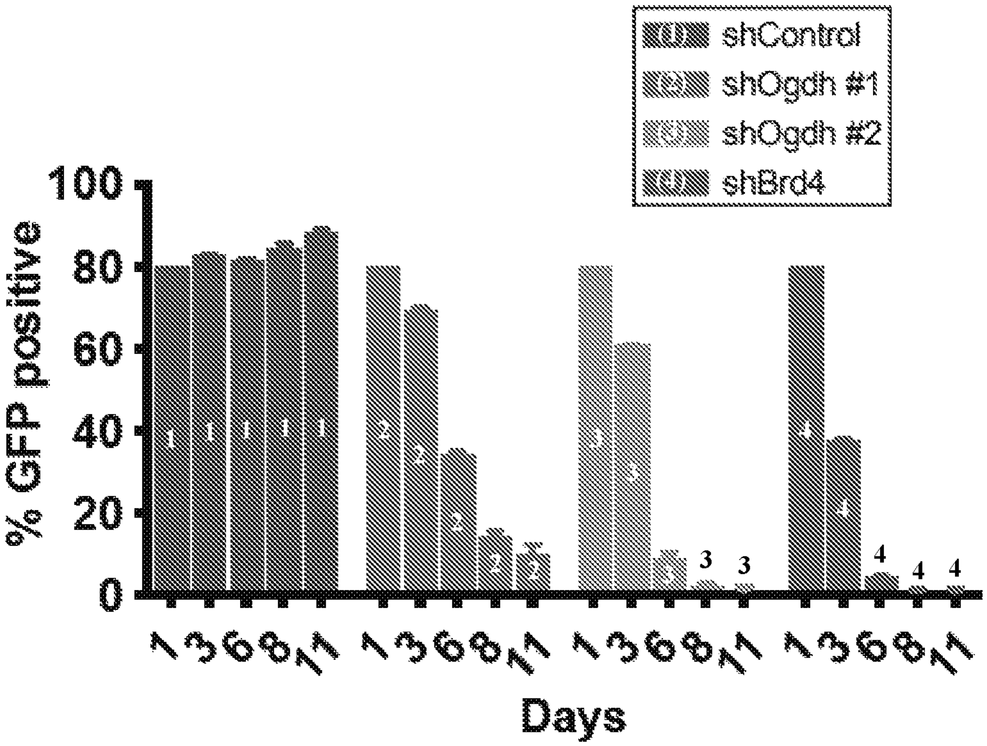

FIG. 18D shows that the Ogdh shRNA inhibited proliferation of murine AML. shBrd4 control is shown.

Figure 18E:
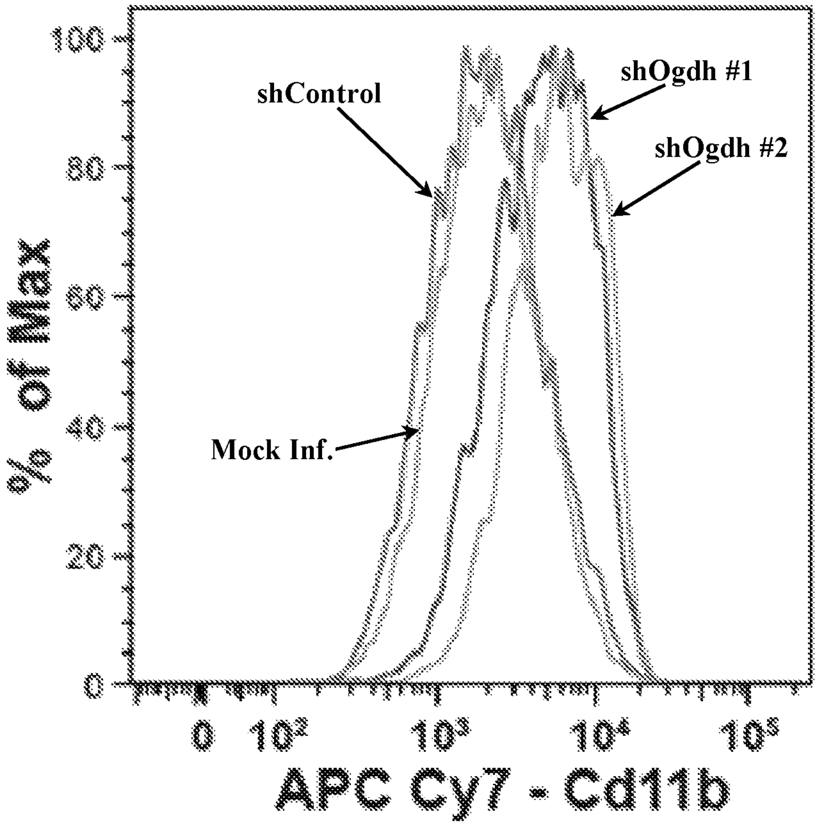
Figure 18E:
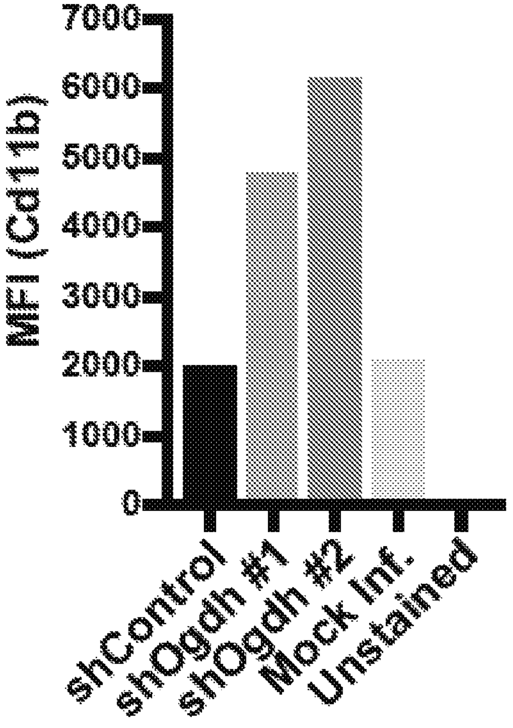

FIG. 18E shows that the OGDH inhibition induced cell surface expression of Cd11b (Day 4). Median fluorescence intensity (MFT) shown in right panel.

Figure 18F:
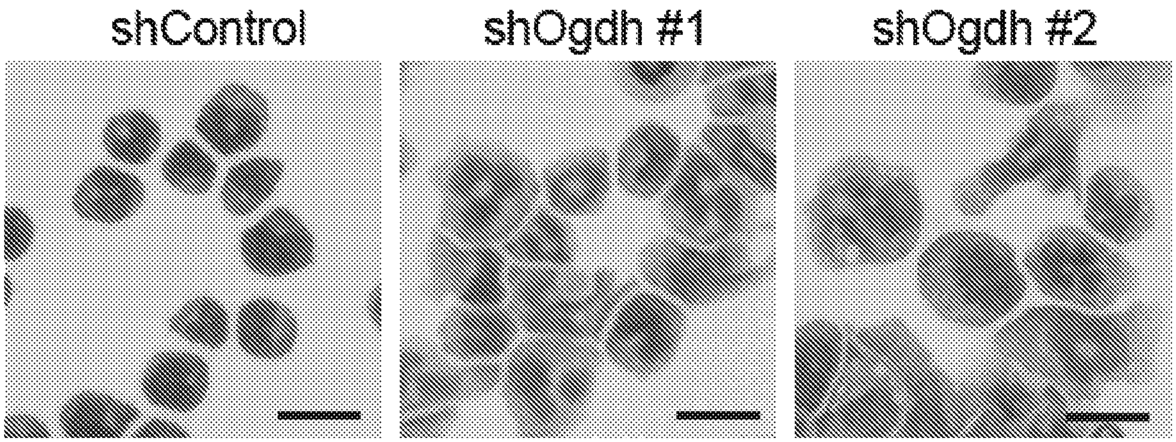

FIG. 18F shows the OGDH inhibition induced morphologic differentiation of murine AML (Day 4). 20× magnification shown. Scale bar=20 μm.

Figure 18G:
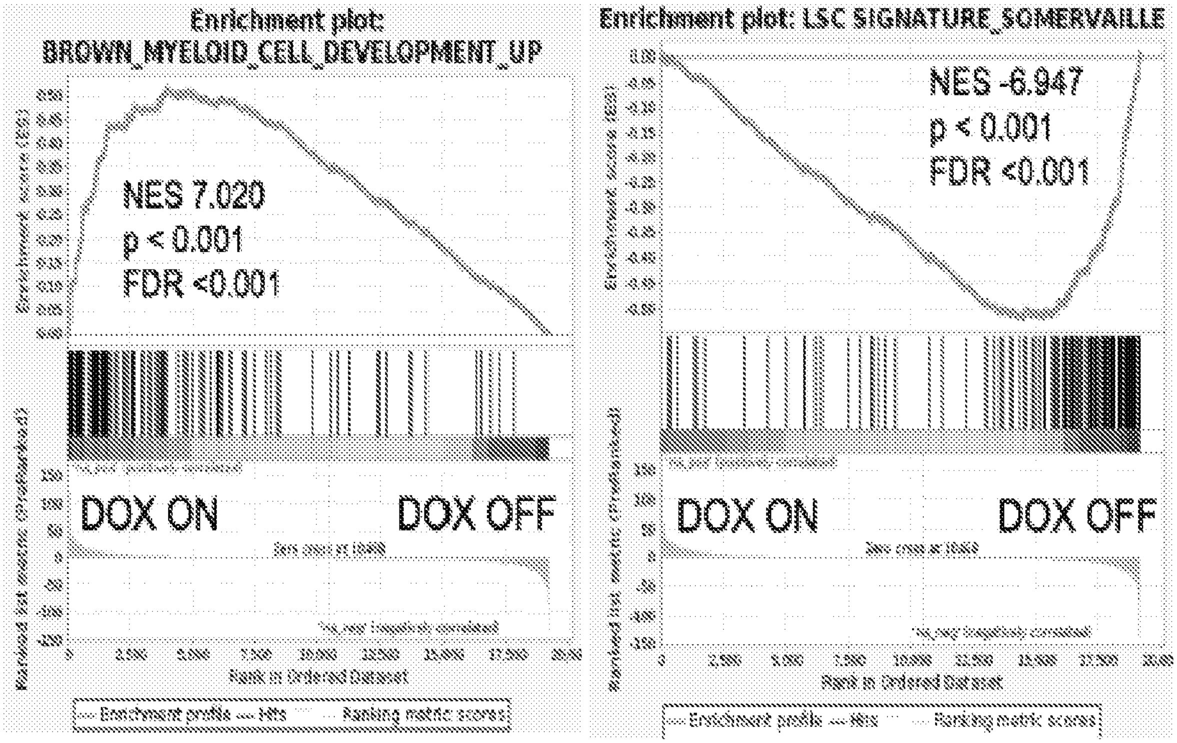

FIG. 18G shows the Gene Set Enrichment Analysis (GSEA) shows that Ogdh shRNA activated a myeloid gene signature (left panel) and suppressed an LSC gene signature (right panel).

Figure 19A:
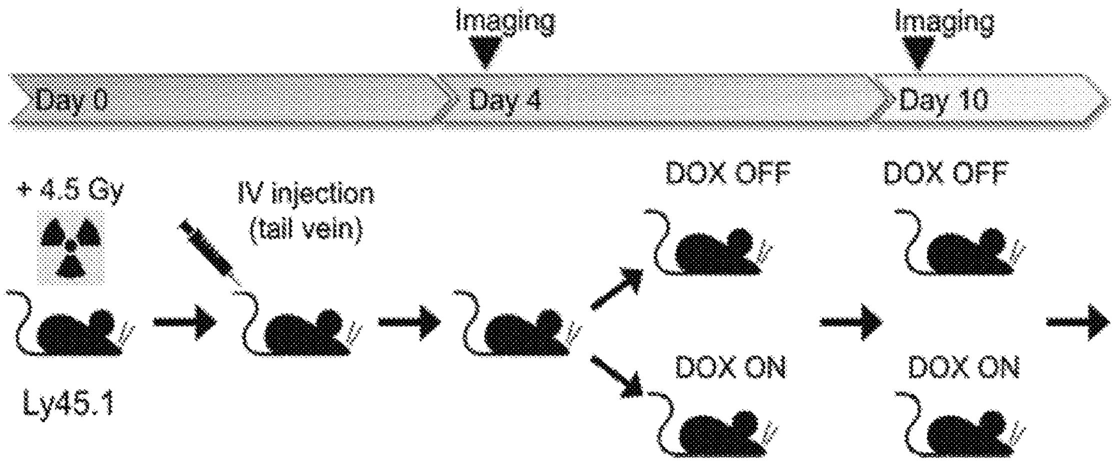

FIGS. 19A-19G show that OGDH is required for AML progression in vivo. FIG. 19A shows a schematic of intervention experiment using AML secondarily transplanted into sub-lethally irradiated recipient mice.

Figure 19B:
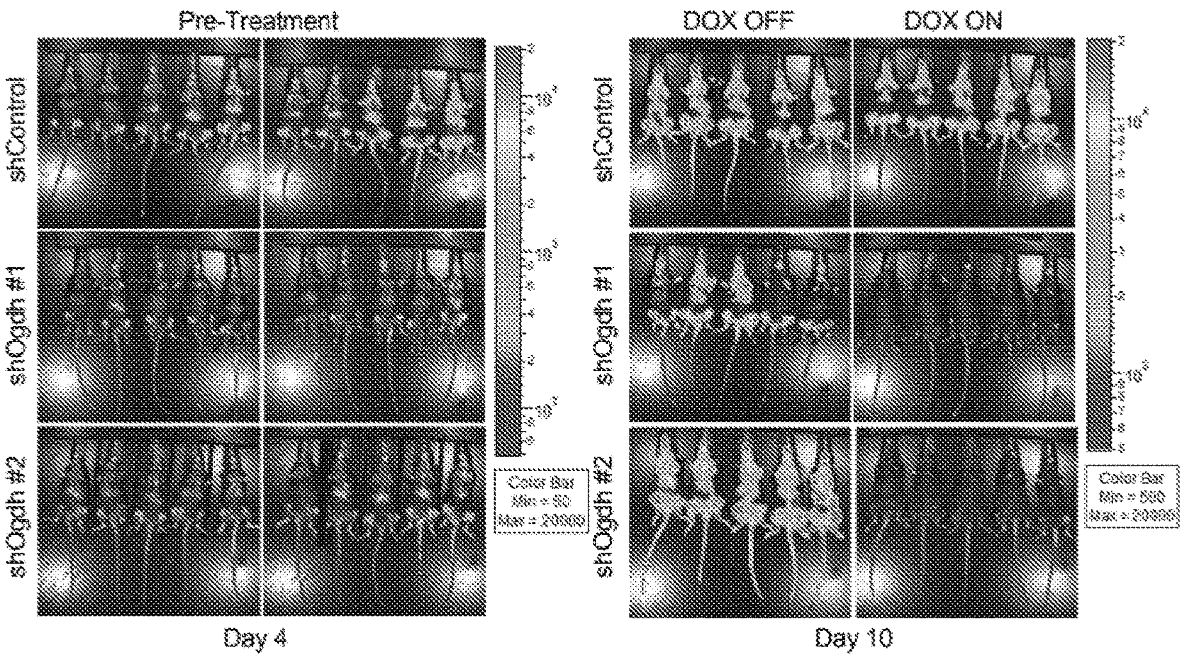

FIG. 19B shows that the doxycycline-inducible shOgdh inhibited AML progression in vivo. Transplant day +4 (pre-treatment) and day +10 (post-treatment) luminescence shown.

Figure 19C:
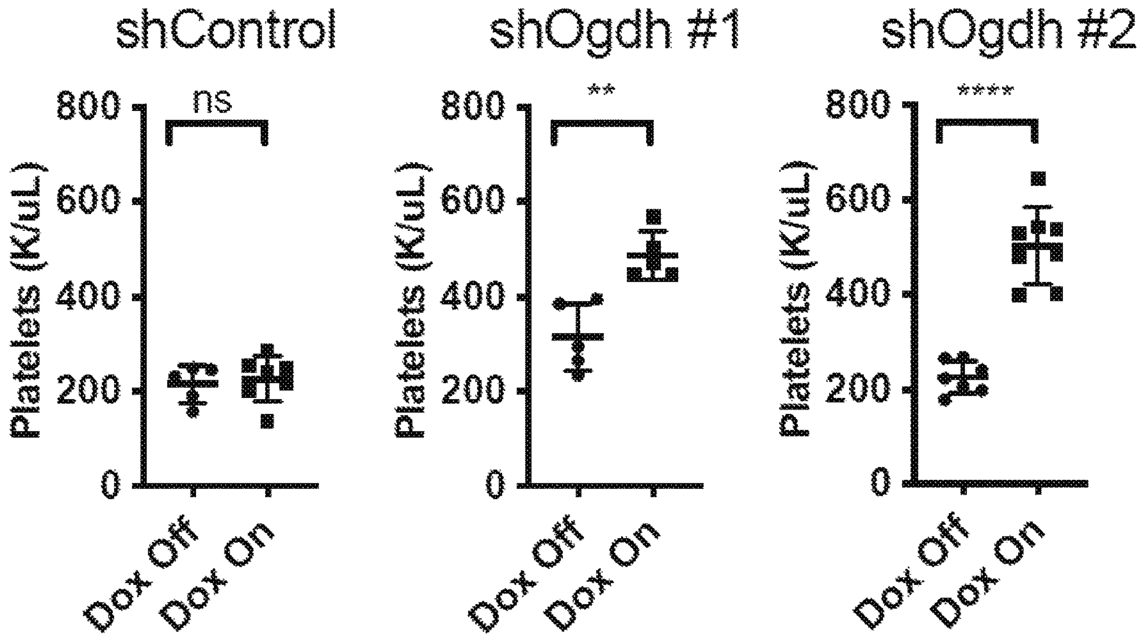

FIG. 19C shows that the OGDH depletion in transplanted AML resulted in normalization of platelets in recipient mice (p=0.0023, **p<0.0001; unpaired t-test; n=5-7/condition).

Figure 19D:
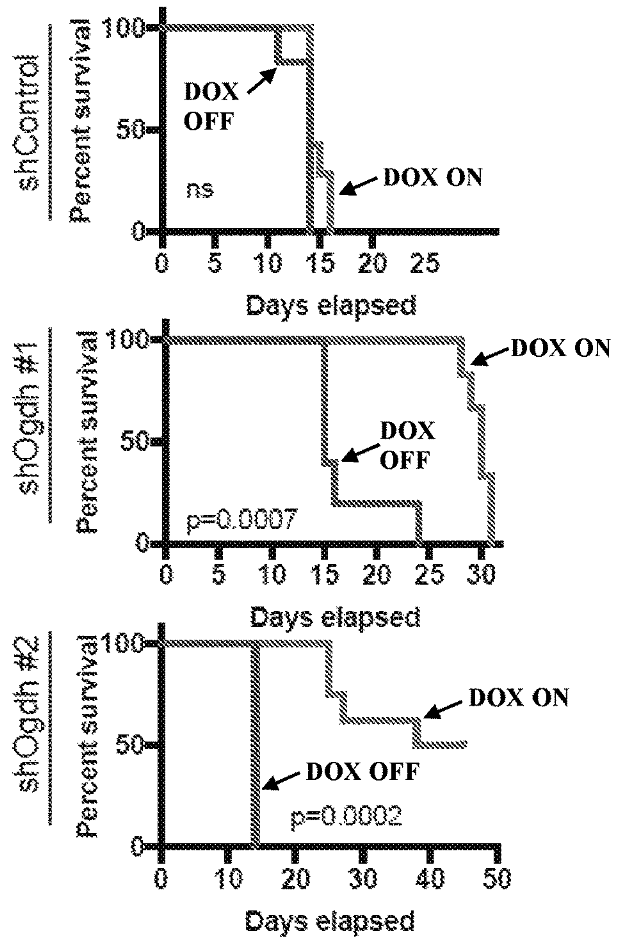

FIG. 19D shows that the OGDH depletion in transplanted AML conferred a significant survival benefit in recipient mice. p-values indicated (Log-rank test, n=5-7/condition).

Figure 19E:
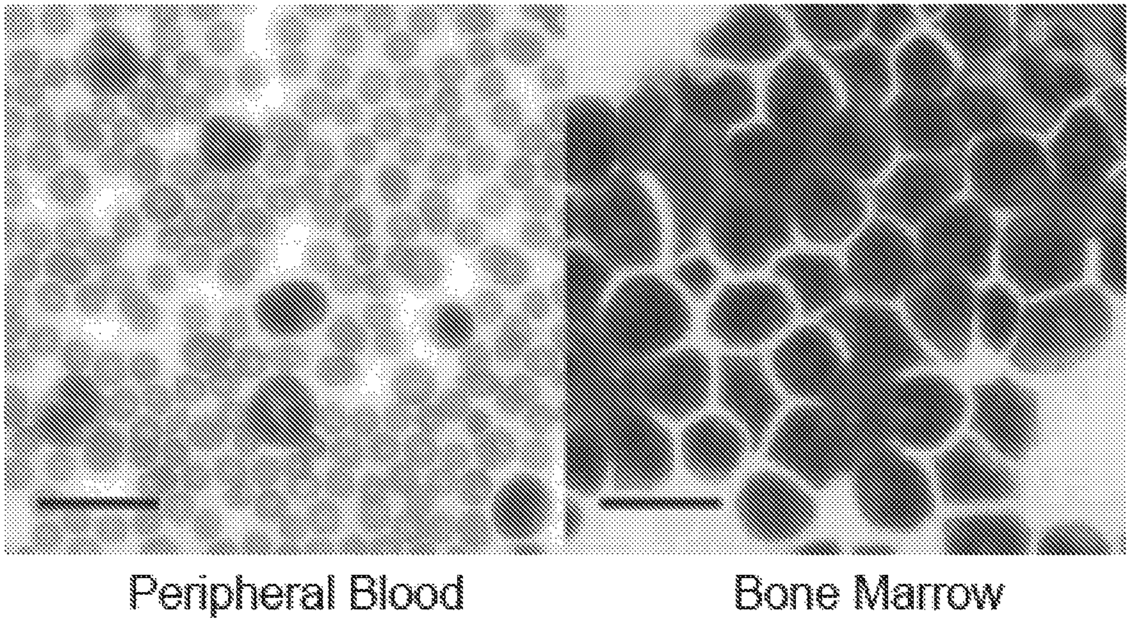

FIG. 19E shows that most doxycycline-treated AML recipient mice eventually succumbed to leukemia. Representative shOgdh #2 PB smear and BM aspirate shown. Scale bar=20 μm.

Figure 19F:
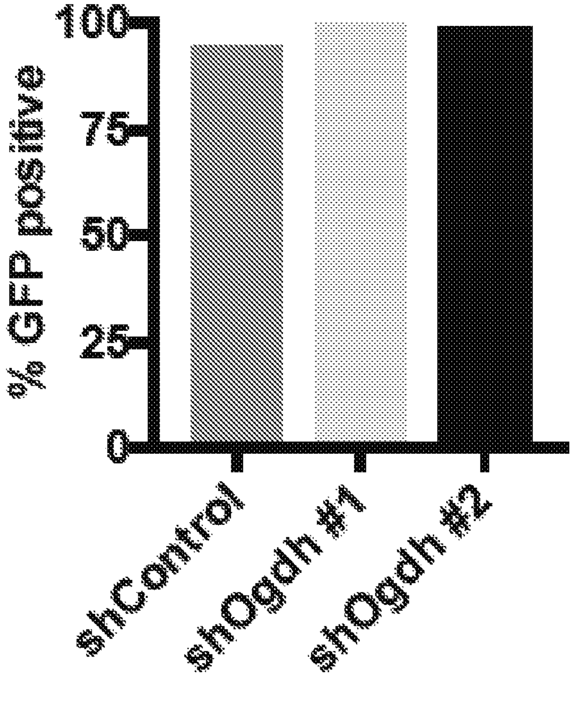

FIG. 19F shows that the doxycycline treatment induced GFP in >90% of AML cells harboring either shControl or shOgdh prior to transplant.

Figure 19G:
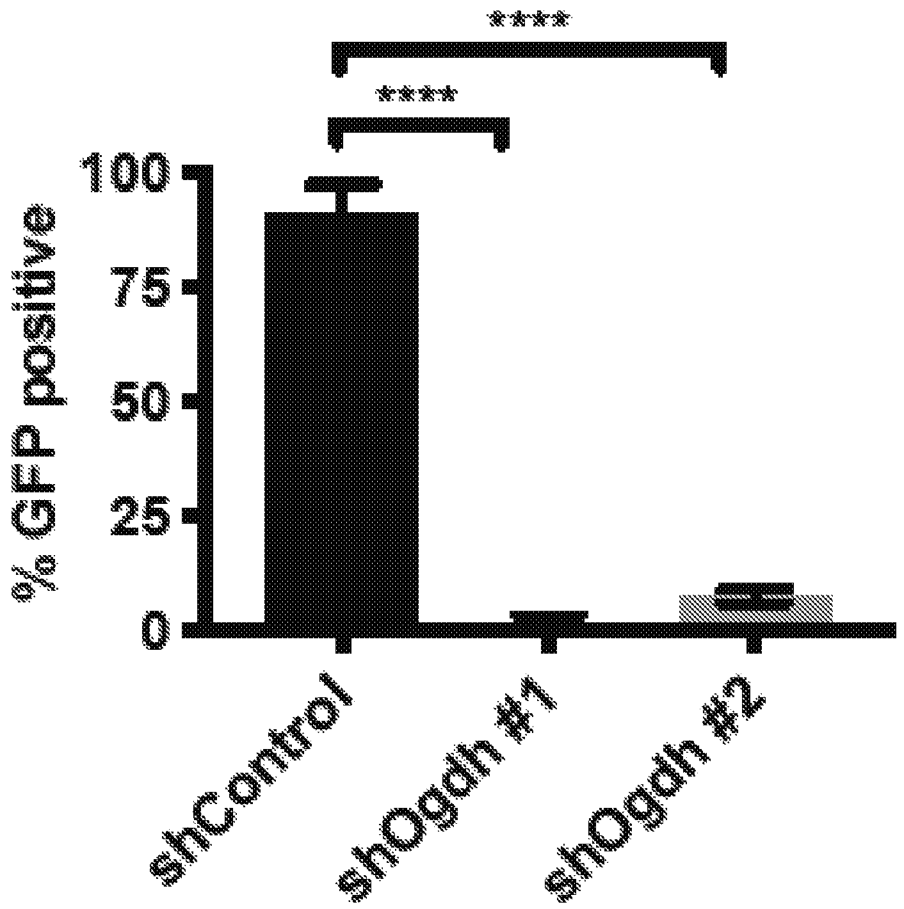

FIG. 19G shows that the bone marrow cells isolated from moribund doxycycline-treated shOgdh recipient mice lost GFP expression. (****p<0.0001; unpaired t-test; n=4-5/condition).

Figure 20A:
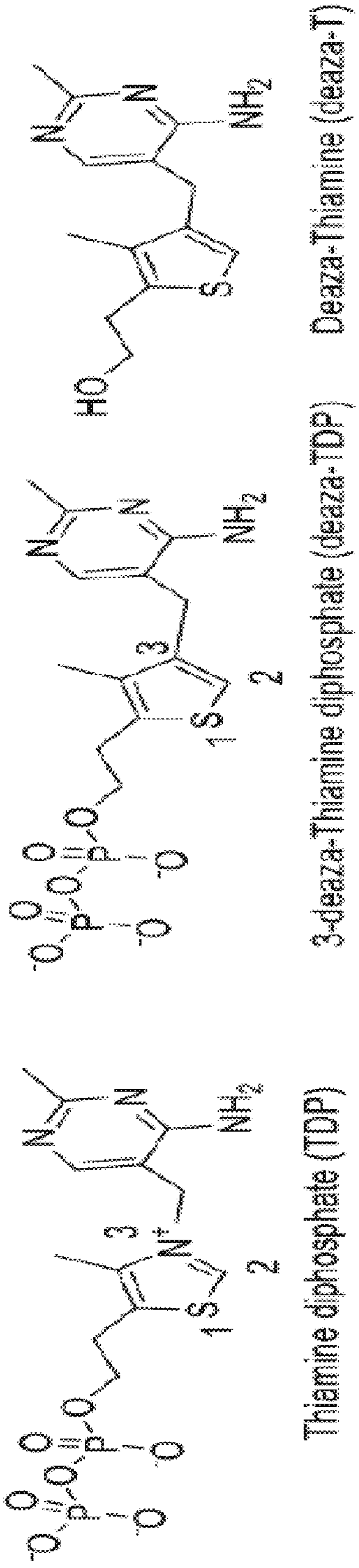

FIG. 20A-20F show the identification of putative OGDH inhibitors. FIG. 20A shows the chemical structure of the KGD/OGDH cofactor thiamine diphosphate (left panel) and derivative compounds 3-deazathiamine diphosphate (center panel) and 3-deazathiamine (right panel).

Figure 20B:
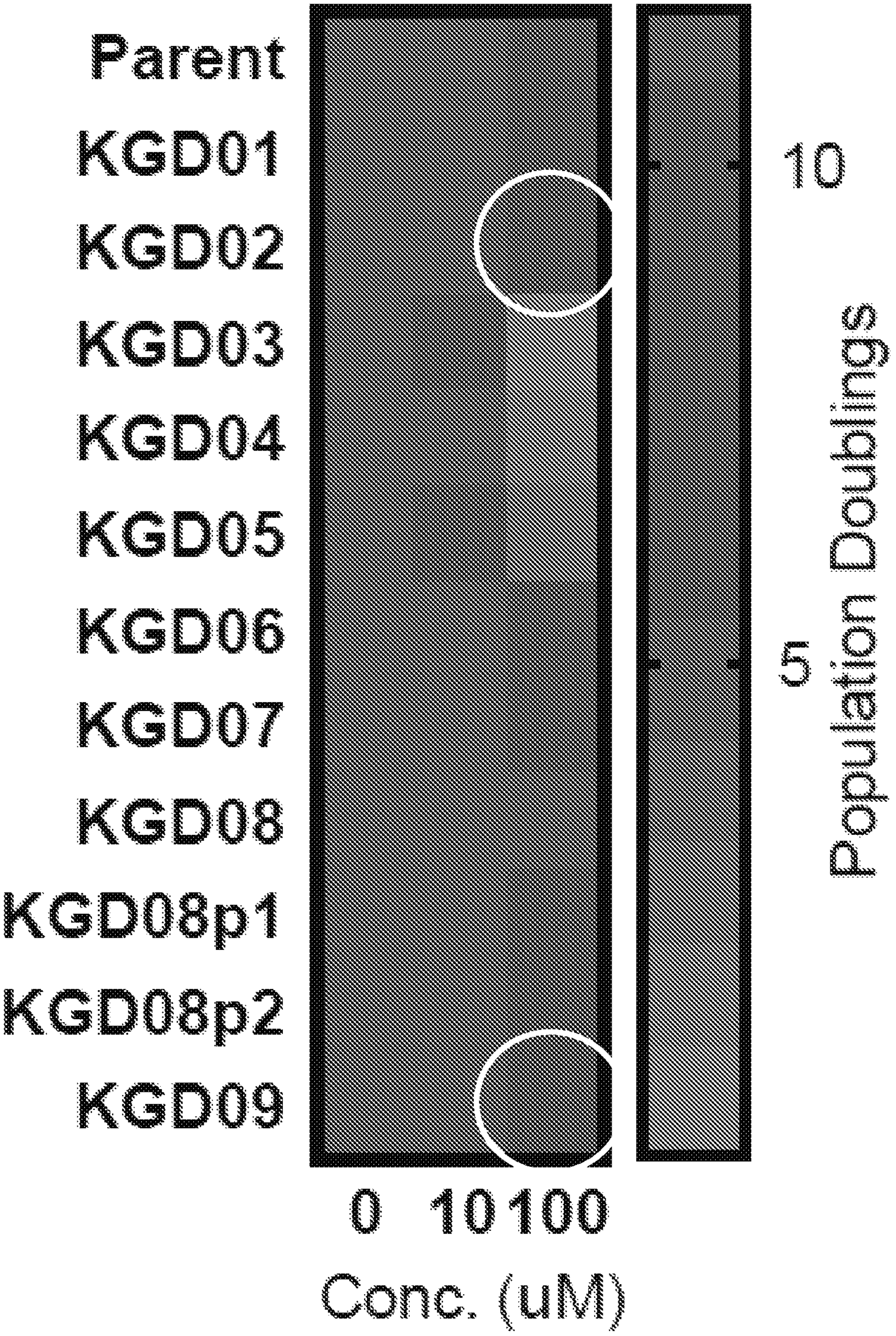

FIG. 20B shows that a pilot screen identified several anti-proliferative compounds.

Figure 20C:
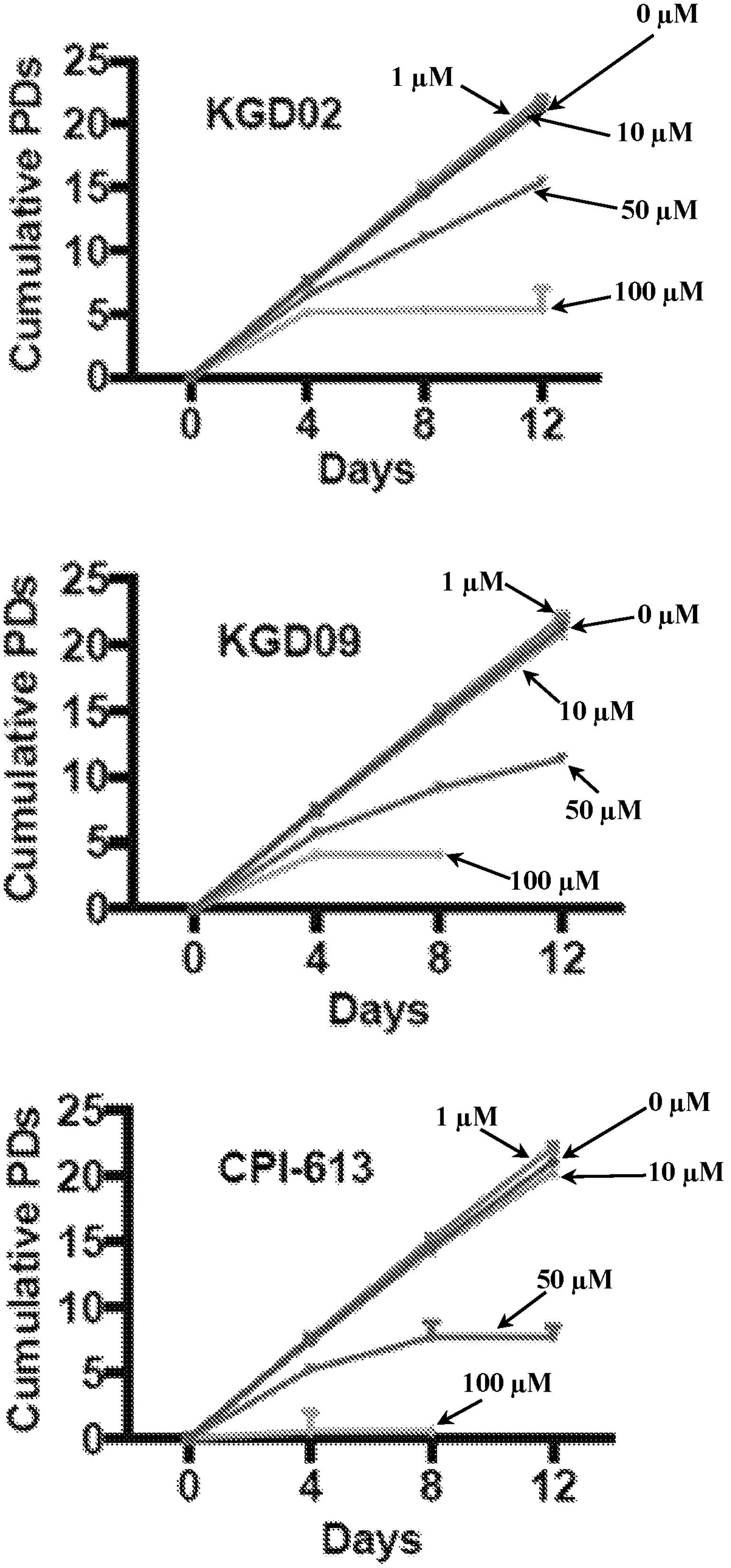

FIG. 20C shows the dose-dependent anti-proliferative efficacy of putative OGDH inhibitors.

Figure 20D:
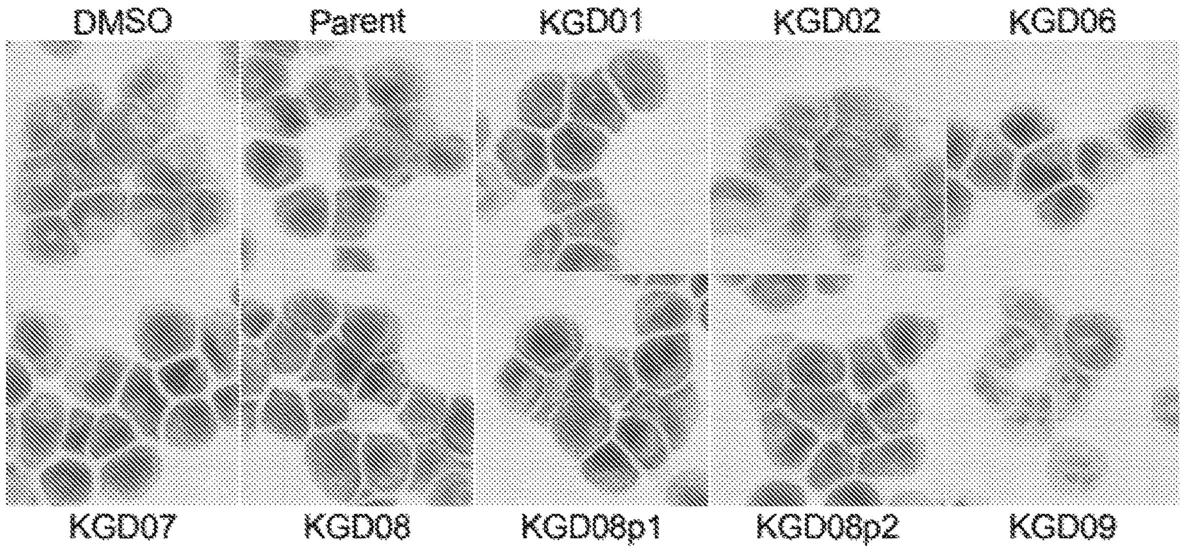

FIG. 20D shows that the select OGDH inhibitors induced morphologic differentiation of murine AML.

Figure 20E:
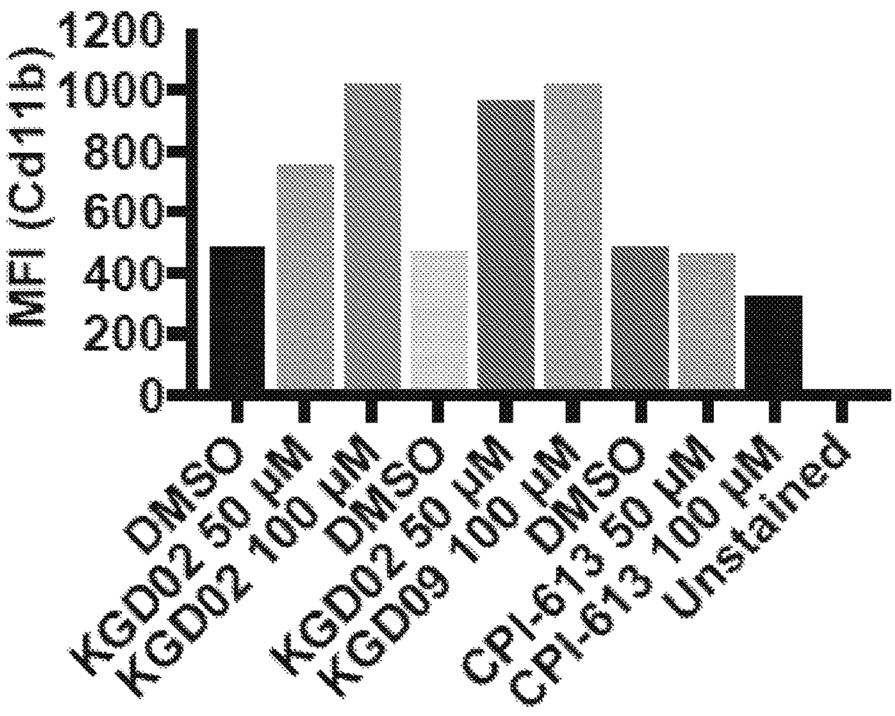

FIG. 20E shows that the select OGDH inhibitors upregulated cell surface expression of myeloid maturation markers.

Figure 20F:
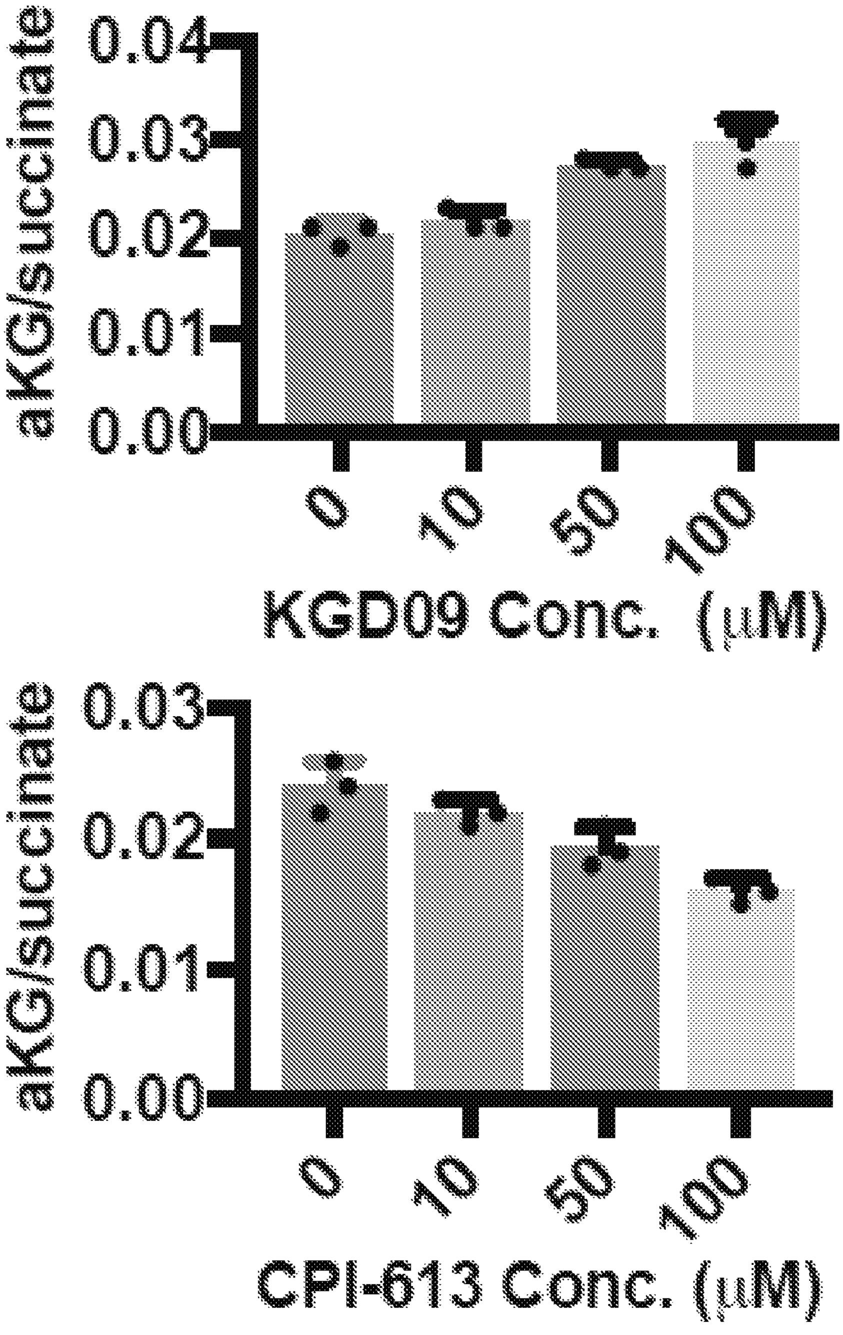

FIG. 20F shows that KGD09 (but not CPI-613) increased the cellular ratio of αKG:succinate in AML.

Figure 20G:
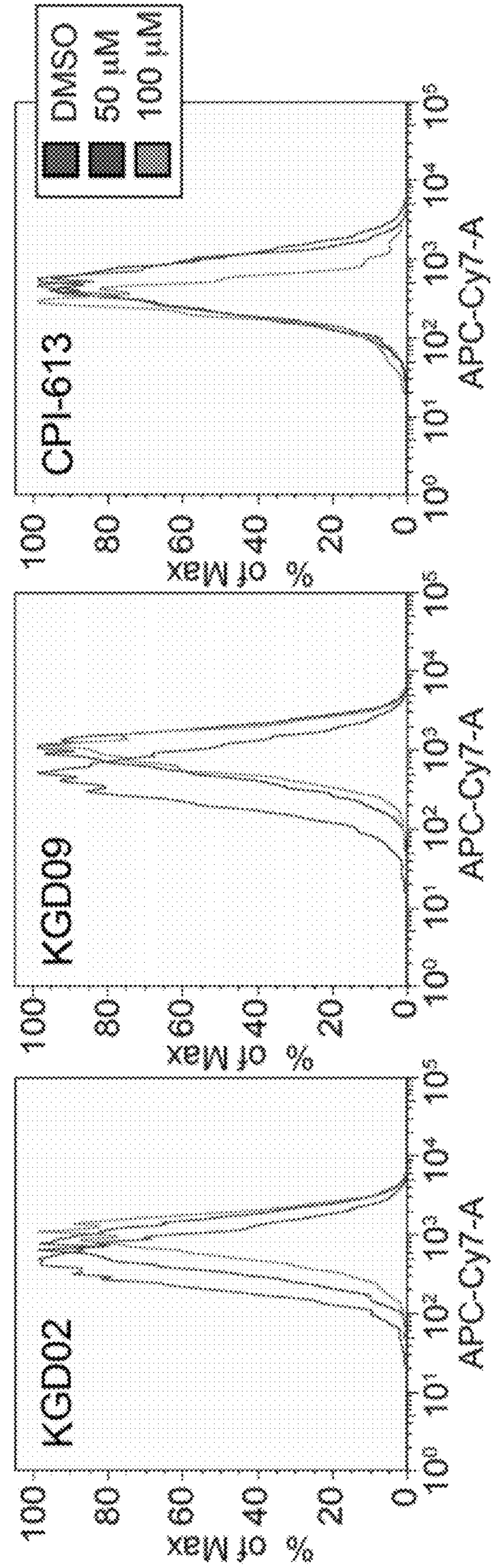

FIG. 20G shows OGDH inhibitors induce cell surface expression of Cd11b.

Figure 21:
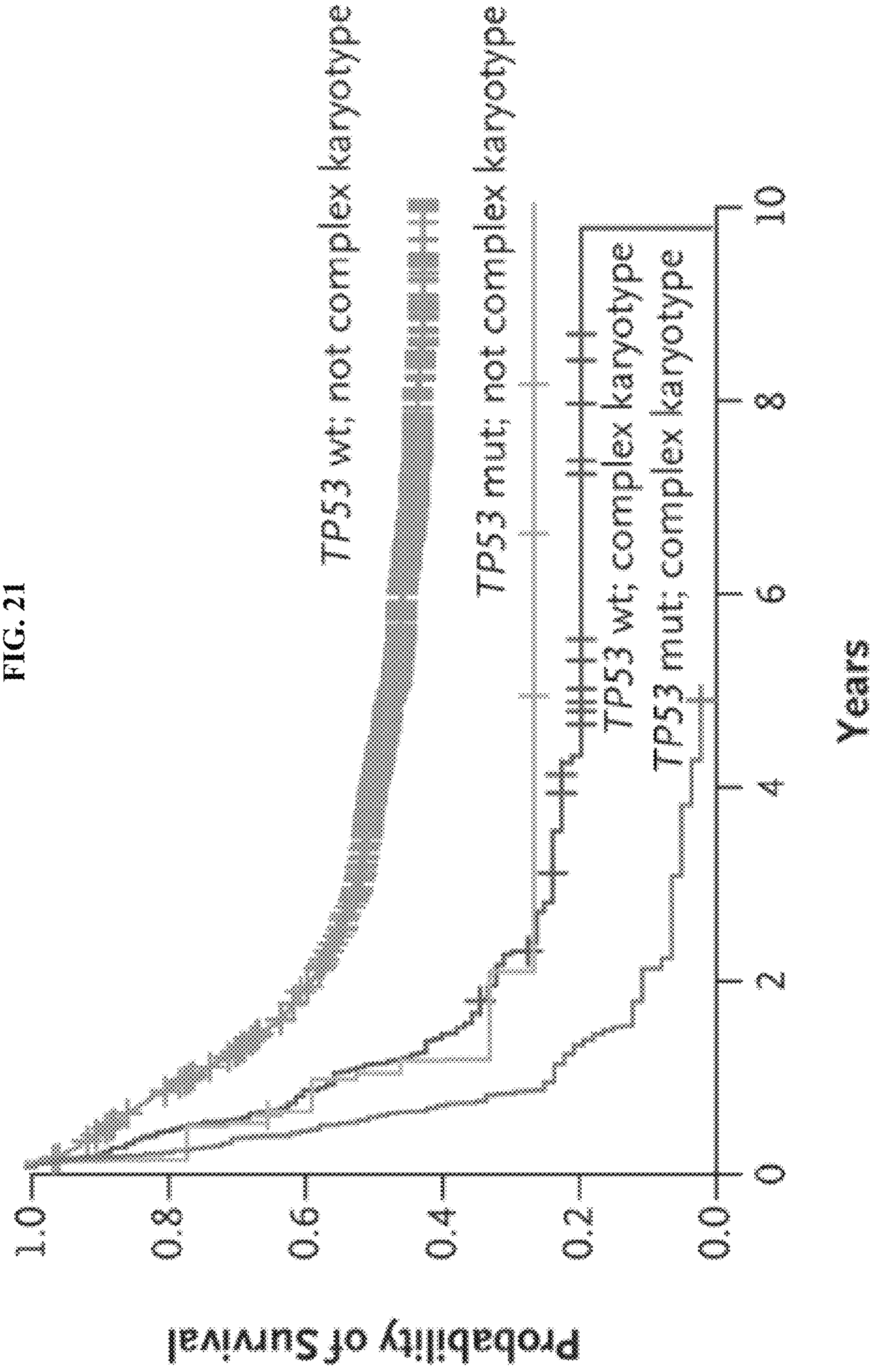

FIG. 21 shows that the CK and TP53 mutations are associated with poor prognosis. Kaplan-Meier curves demonstrating reduced OS in AML featuring CK and/or TP53 mutation. Source: Papaemmanuil et al., *N Engl J Med.* 374:2209-2221 (2016).

Figure 22A:
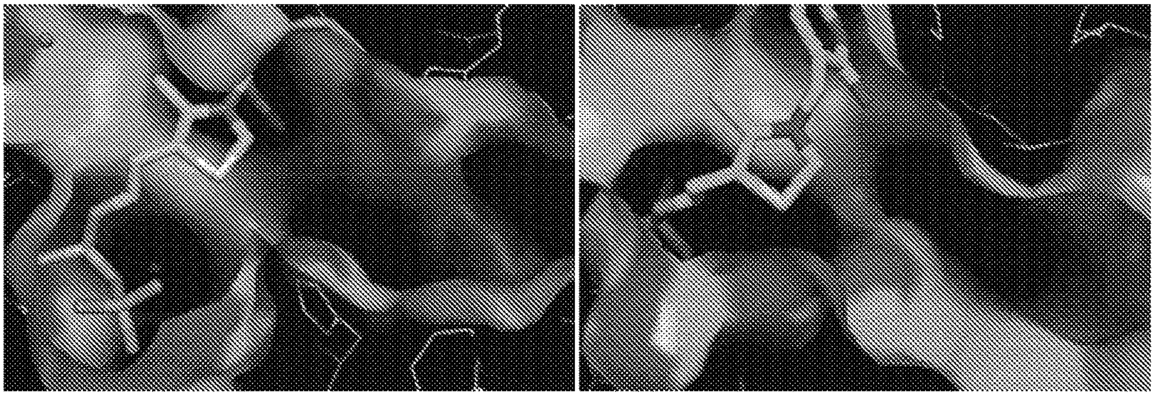
Figure 22B:
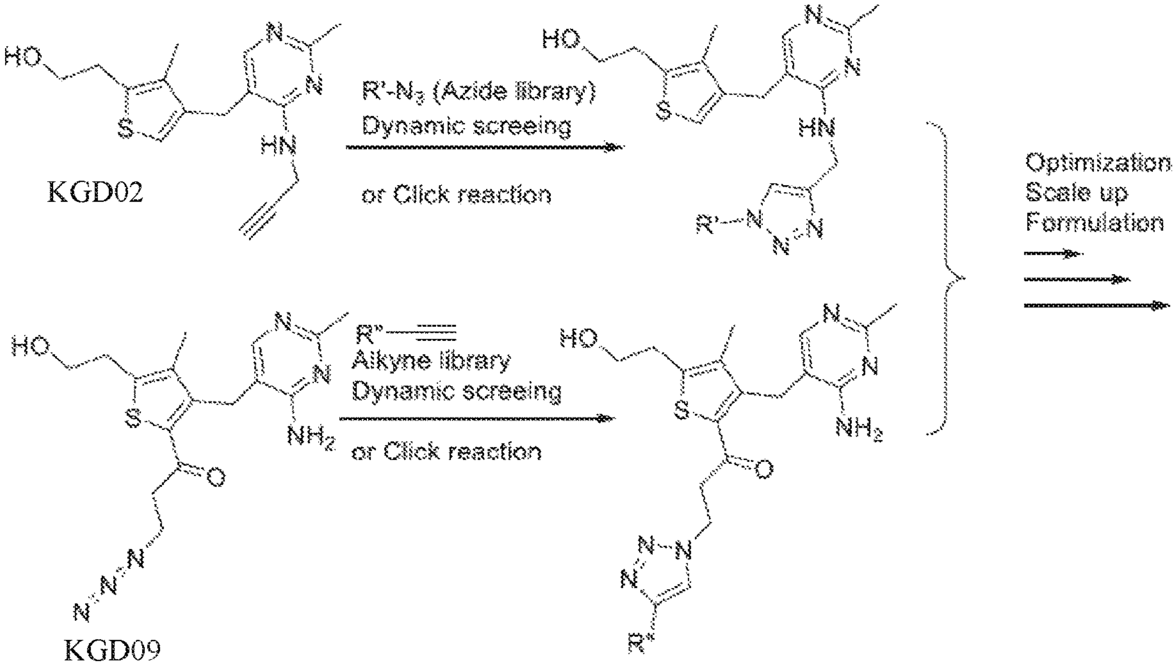

FIGS. 22A-22B show that putative OGDH inhibitors KGD09 and KGD02 are amenable to chemical optimization. FIG. 22A shows the virtual representation of thiamine diphosphate bound to the active site of *M. smegmatis* KGD reveals space for addition of chemical groups. Two views shown. Red indicates negative charge; blue indicates positive charge.

FIG. 22B shows a schematic of proposed azide-alkyne cycloaddition reactions for KGD02 (upper panel) and KGD09 (lower panel) either by dynamic screening or copper-catalyzed click chemistry.

DETAILED DESCRIPTION

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal*

*Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-S." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complementary sequence can also be an RNA sequence complementary to the DNA sequence or its complementary sequence, and can also be a cDNA.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff 60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al., 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

The term "OGDH inhibitor" as used herein refers to an agent that inhibits the expression and/or activity of alpha-ketoglutarate dehydrogenase, which is also known as 2-oxoglutarate dehydrogenase (OGDH). Examples of OGDH biological activity includes, but is not limited to, an enzymatic activity, a substrate binding activity, homo- or hereto-dimerization activity and/or binding activity to a cellular structure. The OGDH inhibitors of the present disclosure inhibit at least one biological activity of OGDH.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. The exact size of the oligonucleotide will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, prevention includes preventing or delaying the initiation of symptoms of a disease or condition described herein and/or preventing a recurrence of one or more signs or symptoms of a disease or condition described herein.

As used herein, the term "sample" refers to clinical samples obtained from a subject. Biological samples may include tissues, cells, protein or membrane extracts of cells, mucus, sputum, bone marrow, bronchial alveolar lavage (BAL), bronchial wash (BW), and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual," or "patient" are used interchangeably and refer to an individual organism, a vertebrate, a mammal, or a human. In certain embodiments, the individual, patient or subject is a human.

The term "specific" as used herein in reference to an oligonucleotide means that the nucleotide sequence of the oligonucleotide has at least 12 bases of sequence identity with a portion of a target nucleic acid when the oligonucleotide and the target nucleic acid are aligned. An oligonucleotide that is specific for a target nucleic acid is one that, under the stringent hybridization or washing conditions, is capable of hybridizing to the target nucleic acid of interest and not substantially hybridizing to nucleic acids which are not of interest. Higher levels of sequence identity are desirable and include at least 75%, at least 80%, at least 85%, at least 90%, at least 95% or at least 98% sequence identity.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "target sequence" and "target nucleic acid sequence" refer to a specific nucleic acid sequence to be modulated (e.g., inhibited or downregulated).

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

OGDH Inhibitors of the Present Technology

The present disclosure provides therapeutic agents that inhibit the activity or expression of OGDH. In some embodiments, the OGDH inhibitor is a small molecule, an inhibitory nucleic acid (e.g., siRNA, antisense nucleic acid, shRNA, sgRNA, ribozymes), or an antibody (e.g., a neutralizing antibody). Examples of small molecule OGDH inhibitors include, but are not limited to succinyl phosphonate, (S)-2-[(2,6-dichlorobenzoyl) amino] succinic acid (AA6), KGD09, KGD02, and derivatives (e.g., azide-alkyne cyclized derivatives) thereof.

Exemplary mRNA sequences of OGDH are provided below, represented by SEQ ID NOs: 4 and 90-92:

>NM_002541.4 *Homo sapiens* oxoglutarate dehydrogenase (OGDH), transcript variant 1, mRNA (SEQ ID NO: 90)

ATTCGGGTGGAGCTGAGCCGGAGACAGGCAGTTGTGAAAAACTTCAGGACAAAAATGTTTCATTTAAGGA

CTTGTGCTGCTAAGTTGAGGCCATTGACGGCTTCCCAGACTGTTAAGACATTTTCACAAAACAGACCAGC

AGCAGCTAGGACATTTCAACAGATTCGGTGCTATTCTGCACCTGTTGCTGCTGAGCCCTTTCTCAGTGGG

ACTAGTTCGAACTATGTGGAGGAGATGTACTGTGCTTGGCTGGAAAACCCCAAAAGTGTACATAAGTCAT

GGGACATTTTTTTTCGCAACACGAATGCCGGAGCCCCACCGGGCACTGCCTACCAGAGTCCCCTTCCCCT

GAGCCGAGGCTCCCTGGCTGCTGTGGCCCATGCACAGTCCCTGGTAGAAGCACAGCCCAACGTGGACAAG

CTCGTGGAGGACCACCTGGCAGTGCAGTCGCTCATCAGGGCATATCAGATACGAGGGCACCATGTAGCAC

AGCTGGACCCCCTGGGGATTTTGGATGCTGATCTGGACTCCTCCGTGCCCGCTGACATTATCTCATCCAC

AGACAAACTTGGGTTCTATGGCCTGGATGAGTCTGACCTCGACAAGGTCTTCCACTTGCCCACCACCACT

TTCATCGGGGGACAGGAATCAGCACTTCCTCTGCGGGAGATCATCCGTCGGCTGGAGATGGCCTACTGCC

AGCATATTGGGGTGGAGTTCATGTTCATCAATGACCTGGAGCAGTGCCAGTGGATCCGGCAGAAGTTTGA

GACCCCTGGGATCATGCAGTTCACAAATGAGGAGAAACGGACCCTGCTGGCCAGGCTTGTGCGGTCCACC

AGGTTTGAGGAGTTCCTACAGCGGAAGTGGTCCTCTGAGAAGCGCTTTGGTCTAGAAGGCTGCGAGGTAC

TGATCCCTGCCCTCAAGACCATCATTGACAAGTCTAGTGAGAATGGCGTGGACTACGTGATCATGGGCAT

GCCACACAGAGGGCGGCTGAACGTGCTTGCAAATGTCATCAGGAAGGAGCTGGAACAGATCTTCTGTCAA

-continued

TTCGATTCAAAGCTGGAGGCAGCTGATGAGGGCTCCGGAGATGTGAAGTACCACCTGGGCATGTATCACC

GCAGGATCAATCGTGTCACCGACAGGAACATTACCTTGTCCTTGGTGGCCAACCCTTCCCACCTTGAGGC

CGCTGACCCCGTGGTGATGGGCAAGACCAAAGCCGAACAGTTTTACTGTGGCGACACTGAAGGGAAAAAG

GTCATGTCCATCCTGTTGCATGGGGATGCTGCATTTGCTGGCCAGGGCATTGTGTACGAGACCTTCCACC

TCAGCGACCTGCCATCCTACACAACTCATGGCACCGTGCACGTGGTCGTCAACAACCAGATCGGCTTCAC

CACCGACCCTCGGATGGCCCGCTCCTCCCCCTACCCCACTGACGTGGCCCGAGTGGTGAATGCCCCCATT

TTCCACGTGAACTCAGATGACCCCGAGGCTGTCATGTACGTGTGCAAAGTGGCGGCCGAGTGGAGGAGCA

CCTTCCACAAGGACGTGGTTGTCGATTTGGTGTGTTACCGGCGCAACGGCCACAACGAGATGGATGAGCC

CATGTTCACGCAGCCGCTCATGTACAAGCAGATCCGCAAGCAGAAGCCTGTGTTACAGAAGTACGCTGAG

CTGCTGGTGTCGCAGGGTGTGGTCAACCAGCCTGAGTATGAGGAGGAAATTTCCAAGTATGATAAGATCT

GTGAGGAAGCTTTTGCCAGATCTAAAGATGAGAAGATCTTGCACATTAAGCACTGGCTGGACTCTCCCTG

GCCTGGCTTCTTCACCCTGGACGGGCAGCCCAGGAGCATGTCCTGCCCCTCCACGGGTCTGACGGAGGAT

ATTCTGACACACATCGGGAATGTGGCTAGTTCTGTGCCTGTGGAAAACTTTACTATTCATGGAGGGCTGA

GCCGGATCTTGAAGACTCGTGGGGAAATGGTGAAGAACCGGACTGTGGACTGGGCTCTAGCGGAGTACAT

GGCGTTTGGCTCGCTCCTGAAGGAGGGCATCCACATTCGGCTGAGCGGCCAGGACGTGGAGCGGGGCACA

TTCAGCCACCGCCACCATGTGCTCCATGACCAGAATGTGGACAAGAGAACCTGCATCCCCATGAACCATC

TCTGGCCCAATCAGGCCCCCTATACTGTGTGCAACAGCTCACTGTCTGAGTACGGCGTGCTGGGCTTTGA

GCTGGGCTTCGCCATGGCCAGTCCTAATGCCCTGGTCCTCTGGGAAGCCCAATTTGGTGACTTCCACAAC

ACGGCCCAGTGTATCATCGACCAGTTCATCTGCCCGGGACAAGCCAAGTGGGTGCGGCAGAATGGCATCG

TGTTGCTGCTGCCCCATGGCATGGAGGGCATGGGTCCAGAACATTCCTCCGCCCGCCCAGAGCGGTTCTT

GCAGATGTGCAACGATGACCCAGATGTCCTGCCAGACCTTAAAGAAGCCAACTTCGACATCAATCAGCTA

TATGACTGCAATTGGGTTGTTGTCAACTGCTCCACTCCTGGCAACTTCTTCCACGTGCTACGACGCCAGA

TCCTGCTGCCATTCCGGAAGCCGTTAATTATCTTCACCCCCAAATCCCTGTTGCGCCACCCCGAGGCCAG

ATCCAGCTTTGATGAGATGCTTCCAGGAACCCACTTCCAGCGGGTGATCCCAGAAGATGGCCCTGCAGCT

CAGAACCCAGAAAATGTCAAAAGGCTTCTCTTCTGCACCGGCAAAGTGTATTATGACCTCACCCGGGAGC

GCAAAGCACGCGACATGGTGGGGCAGGTGGCCATCACAAGGATTGAGCAGCTGTCGCCATTCCCCTTTGA

CCTCCTGCTGAAGGAGGTGCAGAAGTACCCCAATGCTGAGCTGGCCTGGTGCCAGGAGGAGCACAAGAAC

CAAGGCTACTATGACTACGTGAAGCCAAGACTTCGGACCACCATCAGCCGCGCCAAGCCCGTCTGGTATG

CCGGCCGGGACCCAGCGGCTGCTCCAGCCACCGGCAACAAGAAGACCCACCTGACGGAGCTGCAGCGCCT

CCTGGACACGGCCTTCGACCTGGACGTCTTCAAGAACTTCTCGTAGATGCTGCCTAGGGTTGCTTGGGCC

ACTGCCCTCTCCACACCCATGACTGCCCCTTGCTTCTCAACTAAAGAATAGTGCCTCAGCGCTGCCCACA

CCACCGCCCTCCTCGCTGTGCCACCACCCCTCCCTCTGCTCTCATAGGAGTTAGGCTGTCGTCCCCCTCC

AGTGCTTGGCTGCCCCACAGGCCACACGCTGCCCAGGCTCTGCTGACTTCTGAGCAGTTTTCCAGGAGGC

CGGGGGGAGCAGGAGGAGGAAAGGTAGCCCCCGAGGGATGTCCTTGGGGAGGGGTCAGCTCTGGCCACAA

TCCTCCCCACCAGTCTCACCCACTAGGATAGGAACTGGGCCTTGTGTGCTGGCTTCCGCTGTCACCCAGC

AAGGCACAGGCTCCTGTATTTGAGACTAGGATAGCTTCATCTTGAGCCTGAGCCTTAGAATCTGTAGAGG

AGCCTGGAGTCGGATCTAGCCATGGCTGGCAGAGGTTTCTAGGGTGGGCCCCAGCCGTGGCGTGAACTGA

GGATGACCCGGGGCAGCTGGCAGGAGAGAGCCTTGGCCTGACCTGGCACAGAAAGGGCAGCTTCAGTCTC

TGCAGTGTCCATTATCTGCTGTTCCTTCGAGGGTTCCAGGCTGTGTGTGGGGCCCAAGCATGCCCCACCC

ACCCCTCCTGGGCCCAGGCAGCACCTGGAGCCCACAGAGTCTGTGTGTAGCCAGGAAGCCCCGCTCAGGT

AGCCACCACCGGGGCACTGGCTGCTCTGTCTTGGTCCTGTTAACCCTCCACCTCCTCTCTTGGACTCCCT

-continued

CCCCACCCCAACCACTCTTTCTTTCTCCTTTAACCCAATGGAGACTTTCTGATGCATCGTTTTCTTTGCT

GTGCCAAAGCAGGTCAGAAGAGGGAGAGGAGGGGCTGGGGGTGAGGGGCCAGGCCATGGCCAAGGGGCCA

GCTGCCCCTCATTTATCACTCTGACCTTCACAGGGACAGATCTGATTTATTTATTTTGGTTAAAAAAAA

AAAAAGGAACAGAAACAACTTTGCATTGCATTGGCTTGACCCATAAACTAAGTTATATCCGTG

>NM_001003941.3 *Homo sapiens* oxoglutarate dehydrogenase (OGDH), transcript variant 2, mRNA (SEQ ID NO: 91)

ATTCGGGTGGAGCTGAGCCGGAGACAGGCAGTTGTGAAAAACTTCAGGACAAAAATGTTTCATTTAAGGA

CTTGTGCTGCTAAGTTGAGGCCATTGACGGCTTCCCAGACTGTTAAGACATTTTCACAAAACAGACCAGC

AGCAGCTAGGACATTTCAACAGATTCGGTGCTATTCTGCACCTGTTGCTGCTGAGCCCTTTCTCAGTGGG

ACTAGTTCGAACTATGTGGAGGAGATGTACTGTGCTTGGCTGGAAAACCCCAAAAGTGTACATAAGTCAT

GGGACATTTTTTTTCGCAACACGAATGCCGGAGCCCCACCGGGCACTGCCTACCAGAGTCCCCTTCCCCT

GAGCCGAGGCTCCCTGGCTGCTGTGGCCCATGCACAGTCCCTGGTAGAAGCACAGCCCAACGTGGACAAG

CTCGTGGAGGACCACCTGGCAGTGCAGTCGCTCATCAGGGCATATCAGATACGAGGGCACCATGTAGCAC

AGCTGGACCCCCTGGGGATTTTGGATGCTGATCTGGACTCCTCCGTGCCCGCTGACATTATCTCATCCAC

AGACAAACTTGGGTTCTATGGCCTGGATGAGTCTGACCTCGACAAGGTCTTCCACTTGCCCACCACCACT

TTCATCGGGGGACAGGAATCAGCACTTCCTCTGCGGGAGATCATCCGTCGGCTGGAGATGGCCTACTGCC

AGCATATTGGGGTGGAGTTCATGTTCATCAATGACCTGGAGCAGTGCCAGTGGATCCGGCAGAAGTTTGA

GACCCCTGGGATCATGCAGTTCACAAATGAGGAGAAACGGACCCTGCTGGCCAGGCTTGTGCGGTCCACC

AGGTTTGAGGAGTTCCTACAGCGGAAGTGGTCCTCTGAGAAGCGCTTTGGTCTAGAAGGCTGCGAGGTAC

TGATCCCTGCCCTCAAGACCATCATTGACAAGTCTAGTGAGAATGGCGTGGACTACGTGATCATGGGCAT

GCCACACAGAGGGCGGCTGAACGTGCTTGCAAATGTCATCAGGAAGGAGCTGGAACAGATCTTCTGTCAA

TTCGATTCAAAGCTGGAGGCAGCTGATGAGGGCTCCGGAGATGTGAAGTACCACCTGGGCATGTATCACC

GCAGGATCAATCGTGTCACCGACAGGAACATTACCTTGTCCTTGGTGGCCAACCCTTCCCACCTTGAGGC

CGCTGACCCCGTGGTGATGGGCAAGACCAAAGCCGAACAGTTTTACTGTGGCGACACTGAAGGGAAAAAG

GTAAGGCCCAGAGAGAGGCGTGCAAGGCAGATCGTCAAGGCCCCATGTTCCAGCATGGAGTTCCGCTCAC

CAACATAACCCAGAGCCCTGGGTGCATCTAGACTTTAAAAAAATATTTAAAGTCGGCCGGGCGCAGTGTC

TCACGCCTGTAATCCCAGCACTTTGGGAGGCCGAGGTGGGCAGATCACCTGAGTTCGGGAGTTGGAGACC

AGCCTGACCAACATGGAGAAACTCCATCTCTACTAAAAATACAAAATTAGCTGGGCGTGGTGGCGCGCGC

CTGTAATCCCAGCTACTCAGGAGGCTGAGGCAGGAGAATCGCTTGAACCCGGGAGGTGGAGGTTGCAGTG

AGCCGAGATTACGCCATTGCACTCCAGCCTGGGCCAACAAGAGCGAAACTCTGTCTCAAAGAAAAAAATA

AATAAATAAAAAA

>NM_001165036.2 *Homo sapiens* oxoglutarate dehydrogenase (OGDH), transcript variant 3, mRNA (SEQ ID NO: 92)

ATTCGGGTGGAGCTGAGCCGGAGACAGGCAGTTGTGAAAAACTTCAGGACAAAAATGTTTCATTTAAGGA

CTTGTGCTGCTAAGTTGAGGCCATTGACGGCTTCCCAGACTGTTAAGACATTTTCACAAAACAGACCAGC

AGCAGCTAGGACATTTCAACAGATTCGGTGCTATTCTGCACCTGTTGCTGCTGAGCCCTTTCTCAGTGGG

ACTAGTTCGAACTATGTGGAGGAGATGTACTGTGCTTGGCTGGAAAACCCCAAAAGTGTACATAAGTCAT

GGGACATTTTTTTTCGCAACACGAATGCCGGAGCCCCACCGGGCACTGCCTACCAGAGTCCCCTTCCCCT

GAGCCGAGGCTCCCTGGCTGCTGTGGCCCATGCACAGTCCCTGGTAGAAGCACAGCCCAACGTGGACAAG

CTCGTGGAGGACCACCTGGCAGTGCAGTCGCTCATCAGGGCATATCAGGTCAGGGGTCACCACATTGCAA

AACTTGATCCTCTCGGAATTAGTTGTGTAAATTTTGATGATGCTCCAGTAACTGTTTCTTCAAACGTGGG

-continued

```
GTTCTATGGCCTGGATGAGTCTGACCTCGACAAGGTCTTCCACTTGCCCACCACCACTTTCATCGGGGA

CAGGAATCAGCACTTCCTCTGCGGGAGATCATCCGTCGGCTGGAGATGGCCTACTGCCAGCATATTGGGG

TGGAGTTCATGTTCATCAATGACCTGGAGCAGTGCCAGTGGATCCGGCAGAAGTTTGAGACCCCTGGGAT

CATGCAGTTCACAAATGAGGAGAAACGGACCCTGCTGGCCAGGCTTGTGCGGTCCACCAGGTTTGAGGAG

TTCCTACAGCGGAAGTGGTCCTCTGAGAAGCGCTTTGGTCTAGAAGGCTGCGAGGTACTGATCCCTGCCC

TCAAGACCATCATTGACAAGTCTAGTGAGAATGGCGTGGACTACGTGATCATGGGCATGCCACACAGAGG

GCGGCTGAACGTGCTTGCAAATGTCATCAGGAAGGAGCTGGAACAGATCTTCTGTCAATTCGATTCAAAG

CTGGAGGCAGCTGATGAGGGCTCCGGAGATGTGAAGTACCACCTGGGCATGTATCACCGCAGGATCAATC

GTGTCACCGACAGGAACATTACCTTGTCCTTGGTGGCCAACCCTTCCCACCTTGAGGCCGCTGACCCCGT

GGTGATGGGCAAGACCAAAGCCGAACAGTTTTACTGTGGCGACACTGAAGGGAAAAAGGTCATGTCCATC

CTGTTGCATGGGGATGCTGCATTTGCTGGCCAGGGCATTGTGTACGAGACCTTCCACCTCAGCGACCTGC

CATCCTACACAACTCATGGCACCGTGCACGTGGTCGTCAACAACCAGATCGGCTTCACCACCGACCCTCG

GATGGCCCGCTCCTCCCCCTACCCCACTGACGTGGCCCGAGTGGTGAATGCCCCCATTTTCCACGTGAAC

TCAGATGACCCCGAGGCTGTCATGTACGTGTGCAAAGTGGCGGCCGAGTGGAGGAGCACCTTCCACAAGG

ACGTGGTTGTCGATTTGGTGTGTTACCGGCGCAACGGCCACAACGAGATGGATGAGCCCATGTTCACGCA

GCCGCTCATGTACAAGCAGATCCGCAAGCAGAAGCCTGTGTTACAGAAGTACGCTGAGCTGCTGGTGTCG

CAGGGTGTGGTCAACCAGCCTGAGTATGAGGAGGAAATTTCCAAGTATGATAAGATCTGTGAGGAAGCTT

TTGCCAGATCTAAAGATGAGAAGATCTTGCACATTAAGCACTGGCTGGACTCTCCCTGGCCTGGCTTCTT

CACCCTGGACGGGCAGCCCAGGAGCATGTCCTGCCCCTCCACGGGTCTGACGGAGGATATTCTGACACAC

ATCGGGAATGTGGCTAGTTCTGTGCCTGTGGAAAACTTTACTATTCATGGAGGGCTGAGCCGGATCTTGA

AGACTCGTGGGGAAATGGTGAAGAACCGGACTGTGGACTGGGCTCTAGCGGAGTACATGGCGTTTGGCTC

GCTCCTGAAGGAGGGCATCCACATTCGGCTGAGCGGCCAGGACGTGGAGCGGGGCACATTCAGCCACCGC

CACCATGTGCTCCATGACCAGAATGTGGACAAGAGAACCTGCATCCCCATGAACCATCTCTGGCCCAATC

AGGCCCCCTATACTGTGTGCAACAGCTCACTGTCTGAGTACGGCGTGCTGGGCTTTGAGCTGGGCTTCGC

CATGGCCAGTCCTAATGCCCTGGTCCTCTGGGAAGCCCAATTTGGTGACTTCCACAACACGGCCCAGTGT

ATCATCGACCAGTTCATCTGCCCGGGACAAGCCAAGTGGGTGCGGCAGAATGGCATCGTGTTGCTGCTGC

CCCATGGCATGGAGGGCATGGGTCCAGAACATTCCTCCGCCCGCCCAGAGCGGTTCTTGCAGATGTGCAA

CGATGACCCAGATGTCCTGCCAGACCTTAAAGAAGCCAACTTCGACATCAATCAGCTATATGACTGCAAT

TGGGTTGTTGTCAACTGCTCCACTCCTGGCAACTTCTTCCACGTGCTACGACGCCAGATCCTGCTGCCAT

TCCGGAAGCCGTTAATTATCTTCACCCCCAAATCCCTGTTGCGCCACCCCGAGGCCAGATCCAGCTTTGA

TGAGATGCTTCCAGGAACCCACTTCCAGCGGGTGATCCCAGAAGATGGCCCTGCAGCTCAGAACCCAGAA

AATGTCAAAAGGCTTCTCTTCTGCACCGGCAAAGTGTATTATGACCTCACCCGGGAGCGCAAAGCACGCG

ACATGGTGGGGCAGGTGGCCATCACAAGGATTGAGCAGCTGTCGCCATTCCCCTTTGACCTCCTGCTGAA

GGAGGTGCAGAAGTACCCCAATGCTGAGCTGGCCTGGTGCCAGGAGGAGCACAAGAACCAAGGCTACTAT

GACTACGTGAAGCCAAGACTTCGGACCACCATCAGCCGCGCCAAGCCCGTCTGGTATGCCGGCCGGGACC

CAGCGGCTGCTCCAGCCACCGGCAACAAGAAGACCCACCTGACGGAGCTGCAGCGCCTCCTGGACACGGC

CTTCGACCTGGACGTCTTCAAGAACTTCTCGTAGATGCTGCCTAGGGTTGCTTGGGCCACTGCCCTCTCC

ACACCCATGACTGCCCCTTGCTTCTCAACTAAAGAATAGTGCCTCAGCGCTGCCCACACCACCGCCCTCC

TCGCTGTGCCACCACCCCTCCCTCTGCTCTCATAGGAGTTAGGCTGTCGTCCCCCTCCAGTGCTTGGCTG

CCCCACAGGCCACACGCTGCCCAGGCTCTGCTGACTTCTGAGCAGTTTTCCAGGAGGCCGGGGGGAGCAG

GAGGAGGAAAGGTAGCCCCCGAGGGATGTCCTTGGGGAGGGGTCAGCTCTGGCCACAATCCTCCCCACCA
```

-continued

GTCTCACCCACTAGGATAGGAACTGGGCCTTGTGTGCTGGCTTCCGCTGTCACCCAGCAAGGCACAGGCT

CCTGTATTTGAGACTAGGATAGCTTCATCTTGAGCCTGAGCCTTAGAATCTGTAGAGGAGCCTGGAGTCG

GATCTAGCCATGGCTGGCAGAGGTTTCTAGGGTGGGCCCCAGCCGTGGCGTGAACTGAGGATGACCCGGG

GCAGCTGGCAGGAGAGAGCCTTGGCCTGACCTGGCACAGAAAGGGCAGCTTCAGTCTCTGCAGTGTCCAT

TATCTGCTGTTCCTTCGAGGGTTCCAGGCTGTGTGTGGGGCCCAAGCATGCCCCACCCACCCCTCCTGGG

CCCAGGCAGCACCTGGAGCCCACAGAGTCTGTGTGTAGCCAGGAAGCCCCGCTCAGGTAGCCACCACCGG

GGCACTGGCTGCTCTGTCTTGGTCCTGTTAACCCTCCACCTCCTCTCTTGGACTCCCTCCCCACCCCAAC

CACTCTTTCTTTCTCCTTTAACCCAATGGAGACTTTCTGATGCATCGTTTTCTTTGCTGTGCCAAAGCAG

GTCAGAAGAGGGAGAGGAGGGGCTGGGGGTGAGGGGCCAGGCCATGGCCAAGGGGCCAGCTGCCCCTCAT

TTATCACTCTGACCTTCACAGGGACAGATCTGATTTATTTATTTTGGTTAAAAAAAAAAAAAAAGGAACAG

AAACAACTTTGCATTGCATTGGCTTGACCCATAAACTAAGTTATATCCGTG

>NM_001363523.2 *Homo sapiens* oxoglutarate dehydrogenase (OGDH), transcript variant 4, mRNA (SEQ ID NO: 4)

ATTCGGGTGGAGCTGAGCCGGAGACAGGCAGTTGTGAAAAACTTCAGGACAAAAATGTTTCATTTAAGGA

CTTGTGCTGCTAAGTTGAGGCCATTGACGGCTTCCCAGACTGTTAAGACATTTTCACAAAACAGACCAGC

AGCAGCTAGGACATTTCAACAGATTCGGTGCTATTCTGCACCTGTTGCTGCTGAGCCCTTTCTCAGTGGG

ACTAGTTCGAACTATGTGGAGGAGATGTACTGTGCTTGGCTGGAAAACCCCAAAAGTGTACATAAGTCAT

GGGACATTTTTTTTCGCAACACGAATGCCGGAGCCCCACCGGGCACTGCCTACCAGAGTCCCCTTCCCCT

GAGCCGAGGCTCCCTGGCTGCTGTGGCCCATGCACAGTCCCTGGTAGAAGCACAGCCCAACGTGGACAAG

CTCGTGGAGGACCACCTGGCAGTGCAGTCGCTCATCAGGGCATATCAGGTCAGGGGTCACCACATTGCAA

AACTTGATCCTCTCGGAATTAGTTGTGTAAATTTTGATGATGCTCCAGTAACTGTTTCTTCAAACGTGGA

TCTTGCAGTTTTCAAGGAACGACTTCGAATGCTAACAGTAGGAGGGTTCTATGGCCTGGATGAGTCTGAC

CTCGACAAGGTCTTCCACTTGCCCACCACCACTTTCATCGGGGGACAGGAATCAGCACTTCCTCTGCGGG

AGATCATCCGTCGGCTGGAGATGGCCTACTGCCAGCATATTGGGGTGGAGTTCATGTTCATCAATGACCT

GGAGCAGTGCCAGTGGATCCGGCAGAAGTTTGAGACCCCTGGGATCATGCAGTTCACAAATGAGGAGAAA

CGGACCCTGCTGGCCAGGCTTGTGCGGTCCACCAGGTTTGAGGAGTTCCTACAGCGGAAGTGGTCCTCTG

AGAAGCGCTTTGGTCTAGAAGGCTGCGAGGTACTGATCCCTGCCCTCAAGACCATCATTGACAAGTCTAG

TGAGAATGGCGTGGACTACGTGATCATGGGCATGCCACACAGAGGGCGGCTGAACGTGCTTGCAAATGTC

ATCAGGAAGGAGCTGGAACAGATCTTCTGTCAATTCGATTCAAAGCTGGAGGCAGCTGATGAGGGCTCCG

GAGATGTGAAGTACCACCTGGGCATGTATCACCGCAGGATCAATCGTGTCACCGACAGGAACATTACCTT

GTCCTTGGTGGCCAACCCTTCCCACCTTGAGGCCGCTGACCCCGTGGTGATGGGCAAGACCAAAGCCGAA

CAGTTTTACTGTGGCGACACTGAAGGGAAAAAGGTCATGTCCATCCTGTTGCATGGGGATGCTGCATTTG

CTGGCCAGGGCATTGTGTACGAGACCTTCCACCTCAGCGACCTGCCATCCTACACAACTCATGGCACCGT

GCACGTGGTCGTCAACAACCAGATCGGCTTCACCACCGACCCTCGGATGGCCCGCTCCTCCCCCTACCCC

ACTGACGTGGCCCGAGTGGTGAATGCCCCCATTTTCCACGTGAACTCAGATGACCCCGAGGCTGTCATGT

ACGTGTGCAAAGTGGCGGCCGAGTGGAGGAGCACCTTCCACAAGGACGTGGTTGTCGATTTGGTGTGTTA

CCGGCGCAACGGCCACAACGAGATGGATGAGCCCATGTTCACGCAGCCGCTCATGTACAAGCAGATCCGC

AAGCAGAAGCCTGTGTTACAGAAGTACGCTGAGCTGCTGGTGTCGCAGGGTGTGGTCAACCAGCCTGAGT

ATGAGGAGGAAATTTCCAAGTATGATAAGATCTGTGAGGAAGCTTTTGCCAGATCTAAAGATGAGAAGAT

CTTGCACATTAAGCACTGGCTGGACTCTCCCTGGCCTGGCTTCTTCACCCTGGACGGGCAGCCCAGGAGC

ATGTCCTGCCCCTCCACGGGTCTGACGGAGGATATTCTGACACACATCGGGAATGTGGCTAGTTCTGTGC

-continued

```
CTGTGGAAAACTTTACTATTCATGGAGGGCTGAGCCGGATCTTGAAGACTCGTGGGGAAATGGTGAAGAA

CCGGACTGTGGACTGGGCTCTAGCGGAGTACATGGCGTTTGGCTCGCTCCTGAAGGAGGGCATCCACATT

CGGCTGAGCGGCCAGGACGTGGAGCGGGGCACATTCAGCCACCGCCACCATGTGCTCCATGACCAGAATG

TGGACAAGAGAACCTGCATCCCCATGAACCATCTCTGGCCCAATCAGGCCCCCTATACTGTGTGCAACAG

CTCACTGTCTGAGTACGGCGTGCTGGGCTTTGAGCTGGGCTTCGCCATGGCCAGTCCTAATGCCCTGGTC

CTCTGGGAAGCCCAATTTGGTGACTTCCACAACACGGCCCAGTGTATCATCGACCAGTTCATCTGCCCGG

GACAAGCCAAGTGGGTGCGGCAGAATGGCATCGTGTTGCTGCTGCCCCATGGCATGGAGGGCATGGGTCC

AGAACATTCCTCCGCCCGCCCAGAGCGGTTCTTGCAGATGTGCAACGATGACCCAGATGTCCTGCCAGAC

CTTAAAGAAGCCAACTTCGACATCAATCAGCTATATGACTGCAATTGGGTTGTTGTCAACTGCTCCACTC

CTGGCAACTTCTTCCACGTGCTACGACGCCAGATCCTGCTGCCATTCCGGAAGCCGTTAATTATCTTCAC

CCCCAAATCCCTGTTGCGCCACCCCGAGGCCAGATCCAGCTTTGATGAGATGCTTCCAGGAACCCACTTC

CAGCGGGTGATCCCAGAAGATGGCCCTGCAGCTCAGAACCCAGAAAATGTCAAAAGGCTTCTCTTCTGCA

CCGGCAAAGTGTATTATGACCTCACCCGGGAGCGCAAAGCACGCGACATGGTGGGGCAGGTGGCCATCAC

AAGGATTGAGCAGCTGTCGCCATTCCCCTTTGACCTCCTGCTGAAGGAGGTGCAGAAGTACCCCAATGCT

GAGCTGGCCTGGTGCCAGGAGGAGCACAAGAACCAAGGCTACTATGACTACGTGAAGCCAAGACTTCGGA

CCACCATCAGCCGCGCCAAGCCCGTCTGGTATGCCGGCCGGGACCCAGCGGCTGCTCCAGCCACCGGCAA

CAAGAAGACCCACCTGACGGAGCTGCAGCGCCTCCTGGACACGGCCTTCGACCTGGACGTCTTCAAGAAC

TTCTCGTAGATGCTGCCTAGGGTTGCTTGGGCCACTGCCCTCTCCACACCCATGACTGCCCCTTGCTTCT

CAACTAAAGAATAGTGCCTCAGCGCTGCCCACACCACCGCCCTCCTCGCTGTGCCACCACCCCTCCCTCT

GCTCTCATAGGAGTTAGGCTGTCGTCCCCCTCCAGTGCTTGGCTGCCCCACAGGCCACACGCTGCCCAGG

CTCTGCTGACTTCTGAGCAGTTTTCCAGGAGGCCGGGGGGAGCAGGAGGAGGAAAGGTAGCCCCCGAGGG

ATGTCCTTGGGGAGGGGTCAGCTCTGGCCACAATCCTCCCCACCAGTCTCACCCACTAGGATAGGAACTG

GGCCTTGTGTGCTGGCTTCCGCTGTCACCCAGCAAGGCACAGGCTCCTGTATTTGAGACTAGGATAGCTT

CATCTTGAGCCTGAGCCTTAGAATCTGTAGAGGAGCCTGGAGTCGGATCTAGCCATGGCTGGCAGAGGTT

TCTAGGGTGGGCCCCAGCCGTGGCGTGAACTGAGGATGACCCGGGGCAGCTGGCAGGAGAGAGCCTTGGC

CTGACCTGGCACAGAAAGGGCAGCTTCAGTCTCTGCAGTGTCCATTATCTGCTGTTCCTTCGAGGGTTCC

AGGCTGTGTGTGGGGCCCAAGCATGCCCCACCCACCCCTCCTGGGCCCAGGCAGCACCTGGAGCCCACAG

AGTCTGTGTGTAGCCAGGAAGCCCCGCTCAGGTAGCCACCACCGGGGCACTGGCTGCTCTGTCTTGGTCC

TGTTAACCCTCCACCTCCTCTCTTGGACTCCCTCCCCACCCCAACCACTCTTTCTTTCTCCTTTAACCCA

ATGGAGACTTTCTGATGCATCGTTTTCTTTGCTGTGCCAAAGCAGGTCAGAAGAGGGAGAGGAGGGGCTG

GGGGTGAGGGGCCAGGCCATGGCCAAGGGGCCAGCTGCCCCTCATTTATCACTCTGACCTTCACAGGGAC

AGATCTGATTTATTTATTTTGGTTAAAAAAAAAAAAAAGGAACAGAAACAACTTTGCATTGCATTGGCTT

GACCCATAAACTAAGTTATATCCGTG
```

In one aspect, the present disclosure provides OGDH-specific inhibitory nucleic acids comprising a nucleic acid molecule, which is complementary to a portion of an OGDH nucleic acid sequence selected from the group consisting of SEQ ID NOs: 4 and 90-92.

The present disclosure also provides an antisense nucleic acid comprising a nucleic acid sequence that is complementary to and specifically hybridizes with a portion of any one of SEQ ID NOs: 4 and 90-92 (OGDH mRNA), thereby reducing or inhibiting expression of OGDH. The antisense nucleic acid may be antisense RNA, or antisense DNA. Antisense nucleic acids based on the known OGDH gene sequence can be readily designed and engineered using methods known in the art. In some embodiments, the antisense nucleic acid comprises the nucleic acid sequence of any one of SEQ ID NOs: 13, 14, 43, 44 or a complement thereof.

Antisense nucleic acids are molecules which are complementary to a sense nucleic acid strand, e.g., complementary to the coding strand of a double-stranded DNA molecule (or cDNA) or complementary to an mRNA sequence. Accordingly, an antisense nucleic acid can form hydrogen bonds with a sense nucleic acid. The antisense nucleic acid can be complementary to an entire OGDH coding strand, or to a portion thereof, e.g., all or part of the protein coding region (or open reading frame). In some embodiments, the antisense nucleic acid is an oligonucleotide which is complementary to only a portion of the mRNA coding region of OGDH. In certain embodiments, an antisense nucleic acid molecule can be complementary to a noncoding region of the OGDH coding strand. In some embodiments, the noncoding region refers to the 5' and 3' untranslated regions that flank the coding region and are not translated into amino acids. For example, the antisense oligonucleotide can be complementary to the region surrounding the translation start site of OGDH. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or modified nucleotides designed to increase the biological stability of the molecules or to increase the physical stability of the duplex formed between the antisense and sense nucleic acids, e.g., phosphorothioate derivatives and acridine substituted nucleotides. Examples of modified nucleotides which can be used to generate the antisense nucleic acid include 5-fluorouracil, 5-bromouracil, 5-chlorouracil, 5-hodouracil, hypoxanthine, xanthine, 4-acetylcytosine, 5-(carboxyhydroxylmethyl)uracil, 5-carboxymethylaminomethyl-2-thouridine, 5-carboxymethylaminometh-yluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-metnylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutosine, pseudouracil, queosine, 2-thiocytosine, 5-methyl-2-thiouracil, 2-thlouracil, 4-thiouracil, 5-methyluracil, uracil-5-oxyacetic acid methylester, uracil-5-cxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules may be administered to a subject or generated in situ such that they hybridize with or bind to cellular mRNA and/or genomic DNA encoding the protein of interest to thereby inhibit expression of the protein, e.g., by inhibiting transcription and/or translation. The hybridization can occur via Watson-Crick base pairing to form a stable duplex, or in the case of an antisense nucleic acid molecule which binds to DNA duplexes, through specific interactions in the major groove of the double helix.

In some embodiments, the antisense nucleic acid molecules are modified such that they specifically bind to receptors or antigens expressed on a selected cell surface, e.g., by linking the antisense nucleic acid molecules to peptides or antibodies which bind to cell surface receptors or antigens. In some embodiments, the antisense nucleic acid molecule is an alpha-anomeric nucleic acid molecule. An alpha-anomeric nucleic acid molecule forms specific double-stranded hybrids with complementary RNA in which, contrary to the usual β-units, the strands run parallel to each other (Gaultier et al., *Nucleic Acids. Res.* 15:6625-6641(1987)). The antisense nucleic acid molecule can also comprise a 2'-O-methylribonucleotide (Inoue et al., *Nucleic Acids Res.* 15:6131-6148 (1987)) or a chimeric RNA-DNA analogue (Inoue et al., *FEBS Lett.* 215:327-330 (1987)).

The present disclosure also provides a short hairpin RNA (shRNA) or small interfering RNA (siRNA) comprising a nucleic acid sequence that is complementary to and specifically hybridizes with a portion of any one of SEQ ID NOs: 4 or 90-92 (mRNA of OGDH), thereby reducing or inhibiting expression of OGDH. In some embodiments, the shRNA or siRNA is about 18, 19, 20, 21, 22, 23, 24, 25, 26, 27, 28 or 29 base pairs in length. Double-stranded RNA (dsRNA) can induce sequence-specific post-transcriptional gene silencing (e.g., RNA interference (RNAi)) in many organisms such as *C. elegans, Drosophila*, plants, mammals, oocytes and early embryos. RNAi is a process that interferes with or significantly reduces the number of protein copies made by an mRNA. For example, a double-stranded siRNA or shRNA molecule is engineered to complement and hybridize to a mRNA of a target gene. Following intracellular delivery, the siRNA or shRNA molecule associates with an RNA-induced silencing complex (RISC), which then binds and degrades a complementary target mRNA (such as mRNA of OGDH). In some embodiments, the shRNA or siRNA comprises the nucleic acid sequence of any one of SEQ ID NOs: 13, 14, 43 or 44.

The present disclosure also provides a ribozyme comprising a nucleic acid sequence that is complementary to and specifically hybridizes with a portion of any one of SEQ ID NOs: 4 or 90-92 (OGDH mRNA), thereby reducing or inhibiting expression of OGDH. Ribozymes are catalytic RNA molecules with ribonuclease activity which are capable of cleaving a complementary single-stranded nucleic acid, such as an mRNA. Thus, ribozymes (e.g., hammerhead ribozymes (described in Haselhoff and Gerlach, *Nature* 334:585-591 (1988))) can be used to catalytically cleave OGDH transcripts, thereby inhibiting translation of OGDH.

A ribozyme having specificity for an OGDH-encoding nucleic acid can be designed based upon a nucleic acid sequence of OGDH. For example, a derivative of a Tetrahymena L-19 IVS RNA can be constructed in which the nucleotide sequence of the active site is complementary to the nucleotide sequence to be cleaved in an OGDH-encoding mRNA. See, e.g., U.S. Pat. Nos. 4,987,071 and 5,116,742. Alternatively, mRNA of an OGDH can be used to select a catalytic RNA having a specific ribonuclease activity from a pool of RNA molecules. See, e.g., Bartel and Szostak (1993) *Science* 261:1411-1418, incorporated herein by reference.

The present disclosure also provides a synthetic guide RNA (sgRNA) comprising a nucleic acid sequence that is complementary to and specifically hybridizes with a portion of any one of SEQ ID NOs: 4 or 90-92 (mRNA of OGDH). Guide RNAs for use in CRISPR-Cas systems are typically generated as a single guide RNA comprising a crRNA segment and a tracrRNA segment. The crRNA segment and a tracrRNA segment can also be generated as separate RNA molecules. The crRNA segment comprises the targeting sequence that binds to a portion of any one of SEQ ID NOs: 4 or 90-92, and a stem portion that hybridizes to a tracrRNA. The tracrRNA segment comprises a nucleotide sequence that is partially or completely complementary to the stem sequence of the crRNA and a nucleotide sequence that binds to the CRISPR enzyme. In some embodiments, the crRNA segment and the tracrRNA segment are provided as a single guide RNA. In some embodiments, the crRNA segment and the tracrRNA segment are provided as separate RNAs. The combination of the CRISPR enzyme with the crRNA and tracrRNA make up a functional CRISPR-Cas system. Exemplary CRISPR-Cas systems for targeting nucleic acids, are described, for example, in WO2015/089465.

In some embodiments, a synthetic guide RNA is a single RNA represented as comprising the following elements:

5'-X1-X2-Y-Z-3' where X1 and X2 represent the crRNA segment, where X1 is the targeting sequence that binds to a portion of any one of SEQ ID NOs: 4 or 90-92, X2 is a stem sequence the hybridizes to a tracrRNA, Z represents a tracrRNA segment comprising a nucleotide sequence that is partially or completely complementary to X2, and Y represents a linker sequence. In some embodiments, the linker sequence comprises two or more nucleotides and links the crRNA and tracrRNA segments. In some embodiments, the linker sequence comprises 2, 3, 4, 5, 6, 7, 8, 9, 10 or more nucleotides. In some embodiments, the linker is the loop of the hairpin structure formed when the stem sequence hybridized with the tracrRNA.

In some embodiments, a synthetic guide RNA is provided as two separate RNAs where one RNA represents a crRNA segment: 5'-X1-X2-3' where X1 is the targeting sequence that binds to a portion of any one of SEQ ID NOs: 4 or SEQ ID NOs: 90-92, X2 is a stem sequence the hybridizes to a tracrRNA, and one RNA represents a tracrRNA segment, Z, that is a separate RNA from the crRNA segment and comprises a nucleotide sequence that is partially or completely complementary to X2 of the crRNA.

Exemplary crRNA stem sequences and tracrRNA sequences are provided, for example, in WO/2015/089465, which is incorporated by reference herein. In general, a stem sequence includes any sequence that has sufficient complementarity with a complementary sequence in the tracrRNA to promote formation of a CRISPR complex at a target sequence, wherein the CRISPR complex comprises the stem sequence hybridized to the tracrRNA. In general, degree of complementarity is with reference to the optimal alignment of the stem and complementary sequence in the tracrRNA, along the length of the shorter of the two sequences. Optimal alignment may be determined by any suitable alignment algorithm, and may further account for secondary structures, such as self-complementarity within either the stem sequence or the complementary sequence in the tracrRNA. In some embodiments, the degree of complementarity between the stem sequence and the complementary sequence in the tracrRNA along the length of the shorter of the two when optimally aligned is about or more than about 25%, 30%, 40%, 50%, 60%, 70%, 80%, 90%, 95%, 97.5%, 99%, or higher. In some embodiments, the stem sequence is about or more than about 5, 6, 7, 8, 9, 10, 11, 12, 13, 14, 15, 16, 17, 18, 19, 20, 25, 30, 40, 50, or more nucleotides in length. In some embodiments, the stem sequence and complementary sequence in the tracrRNA are contained within a single RNA, such that hybridization between the two produces a transcript having a secondary structure, such as a hairpin. In some embodiments, the tracrRNA has additional complementary sequences that form hairpins. In some embodiments, the tracrRNA has at least two or more hairpins. In some embodiments, the tracrRNA has two, three, four or five hairpins. In some embodiments, the tracrRNA has at most five hairpins.

In a hairpin structure, the portion of the sequence 5' of the final "N" and upstream of the loop corresponds to the crRNA stem sequence, and the portion of the sequence 3' of the loop corresponds to the tracrRNA sequence. Further non-limiting examples of single polynucleotides comprising a guide sequence, a stem sequence, and a tracr sequence are as follows (listed 5' to 3'), where "N" represents a base of a guide sequence (e.g. a modified oligonucleotide provided herein), the first block of lower case letters represent stem sequence, and the second block of lower case letters represent the tracrRNA sequence, and the final poly-T sequence represents the transcription terminator:

```
(a)
                                          (SEQ ID NO: 93)
NNNNNNNNNNNNNNNNNNNNgttttgtactctcaagatttaGAAAt

aaatcttgcagaagctacaaagataaggcttcatgccgaaatcaaca

ccctgtcattttatggcagggtgttttcgttatttaaTTTTTT;

(b)
                                          (SEQ ID NO: 94)
NNNNNNNNNNNNNNNNNNNNgttttgtactctcaGAAAtgcagaag

ctacaaagataaggcttcatgccgaaatcaacaccctgtcattttat

ggcagggtgttttcgttatttaaTTTTTT;

(c)
                                          (SEQ ID NO: 95)
NNNNNNNNNNNNNNNNNNNNgttttgtactctcaGAAAtgcagaag

ctacaaagataaggcttcatgccgaaatcaacaccctgtcattttat

ggcagggtgtTTTTTT;

(d)
                                          (SEQ ID NO: 96)
NNNNNNNNNNNNNNNNNNNNgttttagagctaGAAAtagcaagttaa

aataaggctagtccgttatcaacttgaaaaagtggcaccgagtcggt

gcTTTTTT;

(e)
                                          (SEQ ID NO: 97)
NNNNNNNNNNNNNNNNNNNNgttttagagctaGAAATAGcaagttaa

aataaggctagtccgttatcaacttgaaaaagtgTTTTTTT;
and

(f)
                                          (SEQ ID NO: 98)
NNNNNNNNNNNNNNNNNNNNgttttagagctagAAATAGcaagttaa

aataaggctagtccgttatcaTTTTTTTT.
```

Selection of suitable oligonucleotides for use in as a targeting sequence in a CRISPR Cas system depends on several factors including the particular CRISPR enzyme to be used and the presence of corresponding proto-spacer adjacent motifs (PAMs) downstream of the target sequence in the target nucleic acid. The PAM sequences direct the cleavage of the target nucleic acid by the CRISPR enzyme. In some embodiments, a suitable PAM is 5'-NRG or 5'-NNGRR (where N is any Nucleotide) for SpCas9 or SaCas9 enzymes (or derived enzymes), respectively. Generally the PAM sequences should be present between about 1 to about 10 nucleotides of the target sequence to generate efficient cleavage of the target nucleic acid. Thus, when the guide RNA forms a complex with the CRISPR enzyme, the complex locates the target and PAM sequence, unwinds the DNA duplex, and the guide RNA anneals to the complementary sequence on the opposite strand. This enables the Cas9 nuclease to create a double-strand break.

A variety of CRISPR enzymes are available for use in conjunction with the disclosed guide RNAs of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any chimeras, mutants, homologs or orthologs. Non-limiting examples of Cas proteins include Cas1, Cas1B, Cast, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified variants thereof. In some embodiments, the CRISPR enzyme cleaves both strands of the target nucleic acid at the Protospacer Adjacent Motif (PAM) site. In some embodiments, the CRISPR enzyme is a nickase, which cleaves only one strand of the target nucleic acid.

Pharmaceutical Compositions

In one aspect, the present disclosure provides pharmaceutical compositions comprising an OGDH inhibitor.

The pharmaceutical compositions of the present disclosure may be prepared by any of the methods known in the pharmaceutical arts. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, the amount of active compound will be in the range of about 0.1 to 99 percent, more typically, about 5 to 70 percent, and more typically, about 10 to 30 percent.

In some embodiments, pharmaceutical compositions of the present technology may contain one or more pharmaceutically-acceptable carriers, which as used herein, generally refers to a pharmaceutically-acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body.

Examples of suitable aqueous and non-aqueous carriers that may be employed in the pharmaceutical compositions of the present technology include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

In some embodiments, the formulations may include one or more of sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; alginic acid; buffering agents, such as magnesium hydroxide and aluminum hydroxide; pyrogen-free water; isotonic saline; Ringer's solution; ethyl alcohol; pH buffered solutions; polyesters, polycarbonates and/or polyanhydrides; preservatives; glidants; fillers; and other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition of the present technology. Some examples of pharmaceutically-acceptable antioxidants include: water soluble antioxidants, such as ascorbic acid, cysteine hydrochloride, sodium bisulfate, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Therapeutic Methods

The following discussion is presented by way of example only, and is not intended to be limiting.

One aspect of the present technology includes methods of treating a disease or condition characterized by elevated expression levels and/or increased activity of OGDH. Additionally or alternatively, in some embodiments, the present technology includes methods of treating a p53-mutant cancer (e.g., pancreatic cancer, liver cancer, and AML). In some embodiments, the present technology includes methods of treating pancreatic cancer (e.g., PDAC), liver cancer, or AML. In one aspect, the present disclosure provides a method for inhibiting proliferation of a p53-mutant cancer (e.g., pancreatic cancer, liver cancer, or AML) in a subject in need thereof, comprising administering to the subject a therapeutically effective amount of at least one OGDH inhibitor, wherein the subject suffers from a disease or condition characterized by elevated expression levels and/or increased activity of OGDH. The OGDH inhibitor may be a small molecule (e.g., succinyl phosphonate, (S)-2-[(2,6-dichlorobenzoyl) amino] succinic acid (AA6), KGD09, KGD02), an inhibitory nucleic acid that targets OGDH (e.g., siRNA, antisense nucleic acid, shRNA, sgRNA, ribozymes), or an antibody (e.g., an anti-OGDH neutralizing antibody).

In some embodiments, the subject is diagnosed as having, suspected as having, or at risk of having a disease or condition characterized by elevated expression levels and/or increased activity of OGDH. Additionally or alternatively, in some embodiments, the subject is diagnosed as having a p53-mutant cancer (e.g., pancreatic cancer, liver cancer, or AML). In some embodiments, the subject is diagnosed as having pancreatic cancer, liver cancer, or AML.

In therapeutic applications, compositions or medicaments comprising an OGDH inhibitor disclosed herein are administered to a subject suspected of, or already suffering from such a disease or condition (such as, a subject diagnosed with a disease or condition characterized by elevated expression levels and/or increased activity of OGDH and/or a subject diagnosed with a p53-mutant cancer (e.g., pancreatic cancer, liver cancer, or AML) and/or a subject diagnosed with pancreatic cancer, liver cancer, or AML), in an amount sufficient to cure, or at least partially arrest, the symptoms of the disease, including its complications and intermediate pathological phenotypes in development of the disease.

Subjects suffering from a disease or condition characterized by elevated expression levels and/or increased activity of OGDH and/or a subject diagnosed with pancreatic cancer, liver cancer, or AML) can be identified by any or a combination of diagnostic or prognostic assays known in the art.

In some embodiments, subjects with a disease or condition characterized by elevated expression levels and/or increased activity of OGDH, and/or subjects suffering from an AML that are treated with the OGDH inhibitor will show amelioration or elimination of one or more of the following symptoms: leukemic cell proliferation, enlarged lymph nodes, anemia, neutropenia, leukopenia, leukostasis, chloroma, granulocytic sarcoma, myeloid sarcoma, fatigue, weakness, dizziness, chills, headaches, shortness of breath, thrombocytopenia, excess bruising and bleeding, frequent or severe nosebleeds, bleeding gums, gum pain and swelling, headache, weakness in one side of the body, slurred speech, confusion, sleepiness, blurry vision, vision loss, deep venous thrombosis (DVT), pulmonary embolism, bone or joint pain, swelling in the abdomen, seizures, vomiting, facial numbness, defects in balance, weight loss, fever, night sweats, and loss of appetite.

In some embodiments, subjects with a disease or condition characterized by elevated expression levels and/or increased activity of OGDH, and/or subjects suffering from a pancreatic cancer that are treated with the OGDH inhibitor will show amelioration or elimination of one or more of the following symptoms: pain in the upper abdomen that radiates to back, loss of appetite or unintended weight loss, depression, new-onset diabetes, blood clots, fatigue, yellowing of skin and the whites of eyes (jaundice), bloating, nausea, and vomiting.

In some embodiments, subjects with a disease or condition characterized by elevated expression levels and/or increased activity of OGDH, and/or subjects suffering from a pancreatic cancer that are treated with the OGDH inhibitor will show amelioration or elimination of one or more of the following symptoms: weight loss, loss of appetite, upper abdominal pain, nausea, vomiting, fatigue, abdominal swelling, jaundice, chalky stool, enlarged liver, and enlarged spleen.

In certain embodiments, subjects with a disease or condition characterized by elevated expression levels of OGDH and/or increased activity levels of OGDH, and/or subjects suffering from a p53-mutant cancer (e.g., pancreatic cancer, liver cancer, or AML), and/or subjects suffering from pancreatic cancer, liver cancer, or AML that are treated with the OGDH inhibitor will show reduced cancer proliferation and/or increased survival compared to untreated subjects suffering from the same disease or condition. Additionally or alternatively, in certain embodiments, subjects with a disease or condition characterized by elevated expression levels of OGDH and/or increased activity of OGDH, and/or subjects suffering from a p53-mutant cancer (e.g., pancreatic cancer, liver cancer, or AML), and/or subjects suffering from pancreatic cancer, liver cancer, or AML that are treated with the OGDH inhibitor will show reduced OGDH expression levels and/or reduced OGDH activity levels compared to untreated subjects suffering from the same disease or condition.

In one aspect, the present disclosure provides a method for monitoring the therapeutic efficacy of an OGDH inhibitor in a subject suffering from or diagnosed with a p53-mutant cancer (e.g., pancreatic cancer, liver cancer, or AML) comprising: (a) detecting OGDH expression levels in a test sample obtained from the subject after the subject has been administered the OGDH inhibitor; and (b) determining that the OGDH inhibitor is effective when the OGDH expression levels in the test sample are reduced compared to that observed in a control sample obtained from the subject prior to administration of the OGDH inhibitor. The OGDH inhibitor may be a small molecule (e.g., succinyl phosphonate, (S)-2-[(2,6-dichlorobenzoyl) amino] succinic acid (AA6), KGD09, KGD02), an inhibitory nucleic acid that targets OGDH (e.g., siRNA, antisense nucleic acid, shRNA, sgRNA, ribozymes), or an antibody (e.g., an anti-OGDH neutralizing antibody).

The test sample may be tissues, cells or biological fluids (blood, plasma, saliva, urine, serum, tumor, etc.) present within a subject. Alternatively, TP53 expression levels may be used to determine efficacy of the OGDH inhibitor in the subject (see Example 6 described herein). Accordingly, in certain embodiments, the method further comprises detecting expression levels of TP53 in the subject, wherein an increase in TP53 expression levels relative to those observed in the subject prior to treatment is indicative of the therapeutic efficacy of the OGDH inhibitor.

Additionally or alternatively, in some embodiments, the expression levels of OGDH and/or TP53 are detected via RT-PCR, Northern Blotting, RNA-Seq, microarray analysis, High-performance liquid chromatography (HPLC), mass spectrometry, immunohistochemistry (IHC), fluorescence in situ hybridization (FISH), Western Blotting, immunoprecipitation, flow cytometry, Immuno-electron microscopy, immunoelectrophoresis, enzyme-linked immunosorbent assays (ELISA), or multiplex ELISA antibody arrays.

Prophylactic Methods

In one aspect, the present technology provides a method for preventing or delaying the onset of a disease or condition characterized by elevated expression levels and/or increased activity of OGDH. Additionally or alternatively, in some aspects, the present technology provides a method for preventing or delaying the onset of a p53-mutant cancer (e.g., pancreatic cancer, liver cancer, or AML). The p53-mutant cancer may be pancreatic cancer (e.g., PDAC), liver cancer, or AML.

Subjects at risk or susceptible to a disease or condition characterized by elevated expression levels and/or increased activity of OGDH, and/or subjects at risk or susceptible to a p53-mutant cancer (e.g., pancreatic cancer, liver cancer, or AML), and/or subjects at risk or susceptible to a pancreatic cancer, liver cancer, or AML include those that exhibit one or more point mutations in p53. Alternatively, or additionally, the subjects may exhibit at least one mutation in one or more of a core set of twelve cellular signaling pathways and processes. Jones et al., *Science* 321(5897): 1801-1806 (2008). Such subjects can be identified by, e.g., any or a combination of diagnostic or prognostic assays known in the art.

In prophylactic applications, pharmaceutical compositions or medicaments comprising an OGDH inhibitor disclosed herein are administered to a subject susceptible to, or otherwise at risk of a disease or condition characterized by (a) elevated expression levels and/or increased activity of OGDH, and/or (b) a subject susceptible to, or otherwise at risk of a p53-mutant cancer (e.g., pancreatic cancer, liver cancer, or AML), and/or a subject susceptible to, or otherwise at risk of pancreatic cancer, liver cancer, or AML in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic OGDH inhibitor can occur prior to the manifestation of symptoms characteristic of the disease or disorder, such that the disease or disorder is prevented or, alternatively, delayed in its progression.

In some embodiments, treatment with the OGDH inhibitor will prevent or delay the onset of one or more of the following symptoms of liver cancer, pancreatic cancer, or AML. In certain embodiments, (a) subjects with a disease or condition characterized by elevated expression levels and/or increased activity of OGDH, and/or (b) subjects with a p53-mutant cancer (e.g., pancreatic cancer, liver cancer or AML), and/or subjects with pancreatic cancer, liver cancer, or AML that are treated with the OGDH inhibitor will show OGDH and/or p53 expression levels that resemble those observed in healthy control subjects.

For therapeutic and/or prophylactic applications, a composition comprising an OGDH inhibitor disclosed herein, is administered to the subject. In some embodiments, the OGDH inhibitor is administered one, two, three, four, or five times per day. In some embodiments, the OGDH inhibitor is administered more than five times per day. Additionally or alternatively, in some embodiments, the OGDH inhibitor is administered every day, every other day, every third day, every fourth day, every fifth day, or every sixth day. In some embodiments, the OGDH inhibitor is administered weekly, bi-weekly, tri-weekly, or monthly. In some embodiments, the OGDH inhibitor is administered for a period of one, two, three, four, or five weeks. In some embodiments, the OGDH inhibitor is administered for six weeks or more. In some embodiments, the OGDH inhibitor is administered for twelve weeks or more. In some embodiments, the OGDH inhibitor is administered for a period of less than one year. In some embodiments, the OGDH inhibitor is administered for a period of more than one year. In some embodiments, the OGDH inhibitor is administered throughout the subject's life.

In some embodiments of the methods of the present technology, the OGDH inhibitor is administered daily for 1 week or more. In some embodiments of the methods of the present technology, the OGDH inhibitor is administered daily for 2 weeks or more. In some embodiments of the methods of the present technology, the OGDH inhibitor is administered daily for 3 weeks or more. In some embodiments of the methods of the present technology, the OGDH inhibitor is administered daily for 4 weeks or more. In some embodiments of the methods of the present technology, the OGDH inhibitor is administered daily for 6 weeks or more. In some embodiments of the methods of the present technology, the OGDH inhibitor is administered daily for 12 weeks or more. In some embodiments, the OGDH inhibitor is administered daily throughout the subject's life.

Determination of the Biological Effect of OGDH Inhibitor

In various embodiments, suitable in vitro or in vivo assays are performed to determine the effect of a specific OGDH inhibitor and whether its administration is indicated for treatment. In various embodiments, in vitro assays can be performed with representative animal models, to determine if a given OGDH inhibitor exerts the desired effect on reducing or eliminating signs and/or symptoms of a p53-mutant cancer (e.g., pancreatic cancer, liver cancer, or AML). For example, for on-target evaluation, αKG/succinate ratios may be used (See Examples). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more OGDH-specific inhibitors. In some embodiments, in vitro or in vivo testing is directed to the biological function of OGDH protein and/or p53 protein.

Animal models of a p53-mutant cancer (e.g., pancreatic cancer, liver cancer, or AML), may be generated using techniques known in the art (see, e.g, Example 8 described herein). Such models may be used to demonstrate the biological effect of OGDH inhibitors in the prevention and treatment of conditions arising from disruption of a particular gene (e.g., p53), and for determining what comprises a therapeutically effective amount of the one or more OGDH inhibitors disclosed herein in a given context.

Modes of Administration and Effective Dosages

Any method known to those in the art for contacting a cell, organ or tissue with one or more OGDH inhibitors disclosed herein may be employed. Suitable methods include in vitro, ex vivo, or in vivo methods. In vivo methods typically include the administration of one or more OGDH inhibitors to a mammal, suitably a human. When used in vivo for therapy, the one or more OGDH inhibitors described herein are administered to the subject in effective amounts (i.e., amounts that have desired therapeutic effect). The dose and dosage regimen will depend upon the degree of the disease state of the subject, the characteristics of the particular OGDH inhibitor used, e.g., its therapeutic index, and the subject's history.

The effective amount may be determined during pre-clinical trials and clinical trials by methods familiar to physicians and clinicians. An effective amount of one or more OGDH inhibitors useful in the methods may be administered to a mammal in need thereof by any of a number of well-known methods for administering pharmaceutical compounds. The OGDH inhibitor may be administered systemically or locally.

The one or more OGDH inhibitors described herein can be incorporated into pharmaceutical compositions for administration, singly or in combination, to a subject for the treatment or prevention of a p53-mutant cancer, and/or a subject for the treatment or prevention of pancreatic cancer, liver cancer, or AML. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more OGDH inhibitors disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.,* 33:337-462 (1988); Anselem, et al., *Liposome Technology*, CRC Press (1993)). Liposomal formulations can delay clearance and increase cellular uptake (See Reddy, *Ann. Pharmacother.,* 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly $\alpha$-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more OGDH inhibitors disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more OGDH inhibitor concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more OGDH inhibitors may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy

In some embodiments, one or more of the OGDH inhibitor disclosed herein may be combined with one or more additional therapies for the prevention or treatment of a p53-mutant cancer. Additional therapeutic agents include, but are not limited to, Capecitabine, Erlotinib, Fluorouracil (5-FU), Gemcitabine, Irinotecan, Leucovorin, Nab-paclitaxel, Nanoliposomal irinotecan, Oxaliplatin, Larotrectinib, pembrolizumab, Cabozantinib-S-Malate, Ramucirumab, Lenvatinib Mesylate, Sorafenib Tosylate, Nivolumab, Ramucirumab, Regorafenib, Regorafenib, cisplatin, Doxorubicin, Mitoxantrone, Arsenic Trioxide, Daunorubicin, Cyclophosphamide, Cytarabine, Glasdegib Maleate, Dexamethasone, Doxorubicin, Enasidenib Mesylate, Gemtuzumab Ozogamicin, Gilteritinib Fumarate, Idarubicin, Ivosidenib, Midostaurin, Thioguanine, Venetoclax, Vincristine Sulfate, surgery, radiation, or any combination thereof.

Additionally or alternatively, in some embodiments, the one or more OGDH inhibitors disclosed herein may be separately, sequentially or simultaneously administered with at least one additional therapeutic agent selected from the group consisting of Capecitabine, Erlotinib, Fluorouracil (5-FU), Gemcitabine, Irinotecan, Leucovorin, Nab-paclitaxel, Nanoliposomal irinotecan, Oxaliplatin, Larotrectinib, pembrolizumab, Cabozantinib-S-Malate, Ramucirumab, Lenvatinib Mesylate, Sorafenib Tosylate, Nivolumab, Ramucirumab, Regorafenib, Regorafenib, cisplatin, Doxorubicin, Mitoxantrone, Arsenic Trioxide, Daunorubicin, Cyclophosphamide, Cytarabine, Glasdegib Maleate, Dexamethasone, Doxorubicin, Enasidenib Mesylate, Gemtuzumab Ozogamicin, Gilteritinib Fumarate, Idarubicin, Ivosidenib, Midostaurin, Thioguanine, Venetoclax, and Vincristine Sulfate.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Kits

The present disclosure also provides kits for the prevention and/or treatment of a p53-mutant cancer, comprising one or more OGDH inhibitors disclosed herein. Optionally, the above described components of the kits of the present technology are packed in suitable containers and labeled for the prevention and/or treatment of a p53-mutant cancer, pancreatic cancer, liver cancer, or AML.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology. The following Examples demonstrate the preparation, characterization, and use of illustrative compositions of the present technology that inhibit OGDH expression and/or activity.

Example 1: Experimental Materials and Methods

Mouse Strains. All animal experiments were performed in accordance with a protocol approved by the Memorial Sloan-Kettering Institutional Animal Care and Use Committee. All mouse strains have been previously described. Pdx1-Cre (Hingorani, et al., *Cancer Cell* 4: 437-450 (2003)), p48-Cre (Kawaguchi et al., *Nature Genetics* 32: 128-134 (2002)), p48-$Cre^{ER}$ (Pan et al., *Development* 140: 751-764 (2013)), LSL-$Kras^{G12D}$ (Jackson et al., *Genes & Development* 15: 3243-3248 (2001)), LSL-p53' (Olive et al., *Cell* 119: 847-860 (2004)), $p53^{flox}$ (Marino et al., *Genes & Development* 14: 994-1004 (2000)), *CHC* (Beard et al., Genesis 44: 23-28 (2006)), and CAGs-LSL-RIK strains (Saborowski et al., *Genes & Development* 28, 85-97 (2014); Dow et al., *PloS One* 9: e95236 (2014)) were interbred and maintained on mixed Bl6/129J backgrounds. Athymic nude mice (Envigo) were used for all transplant experiments.

Cell Lines and Cell Culture Treatments. $KP^{sh}$-1-3 cells were derived from PDAC that developed in three separate Pdx1-Cre; LSL-KrasG12D; Col1a1-TRE-shp53-shRenilla; Rosa26-CAGs-LSL-rtTA-IRES-mKate2 mice generated by blastocyst injection and maintained on doxycycline (dox) chow (625 mg/kg, Harlan Laboratories) 5 days from birth until sacrifice. Saborowski et al., *Genes & Development* 28, 85-97 (2014). Guide strands for Col1a1 targeted tandem shRNAs were: p53, TTACACATGTACTTGTAGTGG (SEQ ID NO: 1) and *Renilla*, TAGATAAGCATTATAATTCCT (SEQ ID NO: 2). $KP^{flox}$RIK cells were derived from PDAC that developed in a p48-Cre; LSL-KrasG12D;

$p53^{flox/+}$; Rosa26-CAGs-LSL-rtTA-IRES-mKate2 mouse generated by blastocyst injection. $KP^{R172H}$RIK cells were derived from tumors that developed in a $p48Cre^{ER}$; LSL-KrasG12D; LSL-$p53^{R172H/+}$; Rosa26-CAGs-LSL-rtTA-IRES-mKate2 mouse generated by blastocyst injection. This animal was treated with tamoxifen (1 mg dissolved in corn oil, 5 consecutive daily i.p. injections) at 4 weeks of age to induce Cre recombination. Tumors were diced with scissors and resulting pieces sequentially digested with 1 mg/ml collagenase V (Sigma) diluted in Hanks Buffered saline solution followed by 0.25% Trypsin. Digested suspensions were washed with complete DMEM (DMEM, 10% FBS (GIBCO), 1× Penicillin/Streptomycin) and propagated in complete DMEM on collagen-coated plates (PurCol, Advanced Biomatrix, 0.1 mg/ml). $KP^{sh}$ cells were grown in complete DMEM supplemented with 1 μg/ml doxycycline. $KP^{flox}$ cells (Weissmueller et al., *Cell* 157: 382-394 (2014)) were grown in complete DMEM on non-coated, tissue culture treated vessels. 1 μg/ml doxycycline was added to complete media to induce shRNA expression in $KP^{flox}$ $KP^{flox}$RIK and $KP^{R172H}$RIK cells infected with lentiviral or retroviral vectors encoding TRE-linked shRNAs. Where indicated, cells were treated with $H_2O$ (vehicle), DMSO (vehicle), 3 μNI Etoposide (Sigma), 25 nM Trametinib (Selleck Chemicals), 4 mM sodium acetate (Sigma), 4 mM dimethyl αKG (Sigma), or 4 mM diethyl αKG (Sigma).

Lentiviral and Retroviral Production and Infection. Lentivirus was generated by co-transfection of shRNA expressing viral vectors with packaging plasmids psPAX2 and pMD2.G (Addgene) into 293T cells. Retroviruses were generated by co-transfection of shRNA expressing viral vectors with pCMV-VSVG (Addgene) into 293GP cells. Viras-containing supernatants were cleared of cellular debris by 0.45 μNI filtration and mixed with 8 μg/ml polybrene. Target cells were exposed to viral supernatants for two 12 hour periods before being washed, grown for 24 h in fresh media, then subjected to antibiotic selection. Cells were maintained in antibiotic selection until used for experiments.

Lentiviral and Retroviral shRNA Vectors and Sequences. *Renilla* (TAGATAAGCATTATAATTCCT) (SEQ ID NO: 3); p19 (Ad) (ATGTTCACGAAAGCCAGAGCG) (SEQ ID NO: 5); p16/p19 (Cdkn2a) (AACACAAAGAGCACCCAGCGG) (SEQ ID NO: 6); p21 (Cdkn1a) (TTTAAGTTTGGAGACTGGGAG) (SEQ ID NO: 7); Sdha_1 (TTAATTGAAGGAACTTTATCTC) (SEQ ID NO: 8); Sdha_2 (TTCATAACCGATTCTTCTCCAG) (SEQ ID NO: 9); Sdha_3 (TCTGATGTTCTTATACTTCCAT) (SEQ ID NO: 10); Idh1_1 (TTCAATTGACTTATCCTGGTTG) (SEQ ID NO: 11), and Idh1_2 (TTGTATTTCTTTATAGCCTCTG) (SEQ ID NO: 12) shRNAs (only the guide strand sequences provided herein) were constitutively expressed in KPsh cells with retroviral LMNe-BFP, a modified version of LMP-GFP (Dickins et al., *Nature Genetics* 37: 1289-1295 (2005)) in which the mir30 context has been replaced by the optimized "mirE" context (Fellmann et al., *Cell Rep* 5: 1704-1713 (2013)), the puromycin resistance gene has been replaced by a neomycin resistance cassette, and GFP replaced by BFP, respectively. Cells infected with LMNe-BFP were selected in 1 mg/ml neomycin. *Renilla*; Ogdh_1 (TAAATGAAACATTTTGTCCTG) (SEQ ID NO: 13); Ogdh_2 (TAGCAATTCTGCATACTTCTG) (SEQ ID NO: 14); Sdha_1; Sdha_2, and Sdha_3 shRNAs (only the guide strand sequences provided herein) were introduced into KPflox cells to enable doxycycline (dox) inducible expression using lentiviral LT3GEPIR. Fellmann et al., *Cell Rep* 5: 1704-1713 (2013). Cells infected with LT3GEPIR were selected with 1 μg/ml puromycin. *Renilla*, Ogdh_1; Ogdh_2; Sdha_1; Sdha_2, and Sdha_3 shRNAs were introduced into $KP^{flox}$RIK and $KP^{R172H}$RIK cells to enable dox inducible expression using retroviral RT3GEN. Fellmann et al., *Cell Rep* 5: 1704-1713 (2013). Cells infected with RT3GEN were selected with 1 mg/ml neomycin. Wildtype (WT) p53 cDNA was obtained from Dharmacon and exchanged with the dsRED-shRNA cassette of RT3REVIN. Fellmann et al., *Cell Rep* 5: 1704-1713 (2013). Site directed mutagenesis was performed according to manufacturer's instructions to sequentially introduce mutations resulting in amino acid substitutions in the TAD1 and TAD2 regions of WT p53 (L25Q; W26S; F53Q; F54S) using a Q5 Site-Directed Mutagenesis kit (NEB, E0554) and a QuikChange II XL Site-Directed Mutagenesis Kit (Agilent 200522), respectively. $KP^{flox}$RIK cells were infected with virus generated from transfection of RT3-REVIN without cDNA (vector), RT3-REVIN-$p53^{WT}$, RT3-REVIN $p53^{TAD1/2M}$ as described above and selected with 1 mg/ml neomycin. Cas9 was constitutively expressed in $KP^{sh}$-2 cells via infection with lentiviral lentiCas9-Blast. Sanjana et al., *Nature Methods* 11: 783-784 (2014) (generous gift from Feng Zhang; Addgene plasmid #52962). LentiCas9-Blast cells were selected with 10 μg/ml blasticidin. sgRNAs targeting Tet1 (CCTACGGGAAGCGACCATAA (SEQ ID NO: 15); GACACCGGCGCCGAGTTTT (SEQ ID NO: 16)); Tet2 (GGGAGAAAGCAATATCTTCG (SEQ ID NO: 17); TGCGACGGCGGTGGACTGCG; (SEQ ID NO: 18)), and Tet3 (CTGGGATCAAGACCAGTGTC (SEQ ID NO: 19); CCGGGCCCCCTCATGGCCTG (SEQ ID NO: 20)) were constitutively introduced into stable $KP^{sh}$-2-Cas9 cells using a modified version of pUSEPB, a modified version of pUSEPR[42] in which the RFP cassette has been replaced with BFP. pUSEPB infected cells were selected with 4 μg/ml puromycin.

Growth Curves. Population doubling curves were generated from $KP^{sh}$ cells as follows: Cells were washed with PBS, trypsinized, and 50,000 cells were plated in triplicate in 6-well dishes with or without doxycycline (dox). Every 48 h cell number was recorded and ⅛ of the total cell number was replated. Population doublings for each 48 h period were calculated with the formula 3.32*(log(final cell number)−log(initial cell number)). Growth curves analysis for shOGDH expressing $KP^{flox}$RIK and $KP^{R172H}$RIK cells were performed by plating 10,000 cells on dox into 12-well dishes and counting the number of cells in triplicate every 24 h from day 1 to 4.

Senescence Associated Beta-Galactosidase (SA-β-Gal) Assay. SA-β-gal activity was detected as described previously. Aksoy et al., *Genes & Development* 26: 1546-1557 (2012). Briefly, cells were washed twice with PBS, fixed with 0.5% gluteraldehyde in phosphate-buffered saline (PBS) for 15 mM, washed with PBS supplemented with 1 mM $MgCl_2$, pH 5.5, and incubated overnight at 37° C. in PBS containing 1 mM $MgCl_2$, 1 mg/mL X-Gal (Roche), and 5 mM each potassium ferricyanide (Sigma) and potassium ferrocyanide (Sigma), pH 5.5. At least 200 cells were analyzed from triplicate wells at all conditions. Cells were plated for analysis 2 days before staining.

BrdU, Annexin-V, 5hmC Flow Cytometry Assays. BrdU (BD Pharmigen) and Annexin V (BDPharmigen) analysis was performed in triplicate in cells plated in 6-well dishes under indicated conditions via manufacturers' protocols. 5hmC flow was performed in triplicate in cells plated in 6-well dishes. Briefly, adherent cells were washed with PBS, collected by trypsinization, and fixed on ice for 15 minutes in fixation/permeabilization solution (BD Cat #554714). The cells were then washed with 1× perm/wash buffer (BD Cat #554714) supplemented with 0.1% Triton X, treated with 1× perm/wash buffer supplemented with 0.5% Triton X and 0.5% Nonidet P-40 substitute for 30 minutes. Then, the cells were washed with 1× perm/wash buffer supplemented with 0.1% Triton X, incubated overnight at 4° C. with rabbit anti-5hmC antibody diluted 1:100 in 1× perm/wash buffer supplemented with 0.1% Triton X, washed with 1× perm/wash buffer supplemented with 0.1% Triton X, and incubated for 1 hour at room temperature with goat anti-rabbit Alexa Fluor 700 diluted 1:200 in 1× perm/wash buffer supplemented with 0.1% Triton X. The cells were then washed with 1× perm/wash buffer supplemented with 0.1% Triton X, resuspended in 1× perm/wash buffer, and analyzed. Example gating strategies for all 3 assays are shown in FIG. 16.

Orthotopic Tumors. $KP^{sh}$ cells maintained on dox were washed, trypsinized, and counted. $5\times10^5$ cells in serum-free DMEM were mixed 1:1 with growth factor reduced matrigel (Corning) and injected into the exposed pancreas of athymic nude mice using a Hamilton syringe fitted with a 26 gauge needle. Recipient mice were enrolled on dox chow (625 mg/kg, Harlan Laboratories) 2 days before surgery and maintained on dox chow until mice were randomized for analysis. Tumor volume was measured by small animal ultrasound (Vevo 2100) 2 weeks post-transplant at which point 3 mice were maintained on dox chow and 6 mice were switched to dox-free chow. Tumor volume was measured 5, 10, and 18 days after randomization unless mice were sacrificed due to reaching IACUC approved humane endpoints for tumor burden. 3 mice were randomly censored for sacrifice and tissue analysis 10 days after being enrolled off dox. At sacrifice, epifluorescence for mKate2 and GFP were recorded with a fluorescent dissection scope (Nikon SMZ1500) before tissues were fixed for histological analysis. For shOGDH orthotopic tumor growth assay, $KP^{flox}$ cells were infected with LT3GEPIR lentiviral vectors expressing GFP linked shRNAs targeting *Renilla* luciferase or mouse Ogdh and subjected to antibiotic selection. Cells were treated with doxycycline 2 days before injection and transplanted into the pancreas of dox fed mice. Pancreata were removed 2 weeks after transplant and GFP epifluorescence was recorded before tissues were fixed for histological analysis.

Immunofluorescence. Tissues were fixed overnight at 4° C. in 10% formalin prior to paraffin embedding. Five-micron sections were deparaffinized and rehydrated with a histoclear/alcohol series and subjected to antigen retrieval by boiling in citrate antigen retrieval buffer (Vector). Slides were blocked in PBS with 5% BSA and primary antibody staining was performed in blocking buffer overnight at 4° C. The following primary antibodies were used: chicken anti-GFP (1:500, Abcam 13970), rabbit anti-mKate2/Turbo RFP (1:1000, Evrogen, AB233), mouse anti-p21 (1:1000, 556431, BD), mouse anti-Ki67 (1:500, BD, 550609), rat anti-CK19 (Troma III) (1:1000, Developmental Studies Hybridoma Bank, AB_2133570), rabbit anti-p53 (1:500, NCL-L-p53-CM5p, Leica Biosystems), rabbit anti-5hmC (1:500, Active Motif, 39769), mouse anti-5hmC (1:200, Abcam, 178771) and mouse anti-β-Catenin (1:200, BD, 610153). Primary antibodies were detected with the following fluorescently conjugated secondary antibodies: goat-anti-chicken AF488 (Life Technologies A-11039), goat anti-rabbit AF488 (Life Technologies A-32723), goat anti-rabbit AF594 (Life Technologies A-11037), goat anti-mouse AF488 (Life Technologies, A-32723), goat anti-mouse AF594 (Life Technologies, A-11032), goat anti-rat AF488 (Life Technologies, A-11006) and goat anti-rat 594 (Life Technologies, A-11007). All secondary antibodies were diluted in blocking buffer and incubated for 1 hour at room temperature. Subsequently, slides were washed and nuclei counterstained with PBS containing DAPI and mounted under cover slips with ProLong Gold (LifeTechnologies). Images were acquired with a Zeiss AxioImager microscope using Axiovision software.

In Vivo Competition Assay. $KP^{flox}$RIK and $KP^{R172H}$RIK cells were infected with RT3GEN retroviral vectors expressing GFP linked shRNAs targeting *Renilla* luciferase or mouse Ogdh and subjected to antibiotic selection. Cells were treated with doxycycline 2 days before injection, analyzed for GFP expression (Flow cytometry strategy, FIG. 9), and transplanted into the pancreas of dox fed mice. Tumors were removed 3 weeks after transplant, epifluorescence for mKate2 and GFP was recorded, and tumors prepared for flow cytometry as described. Morris et al., *PloS One* 9: e95486 (2014). Briefly, tumors were minced with scissors and sequentially incubated with collagenase V (1 mg/ml (Fisher) in Hanks buffered saline solution), trypsin (0.05%), and dispase (2 U/ml, Invitrogen). DNase1 (100 μg/ml, Sigma) was added during all enzyme incubations. Cells were washed with PBS between the collagenase and trypsin steps, and with FACs buffer (2% FBS, 10 mM EGTA, in PBS) between the trypsin and dispase steps. Suspensions were then filtered through 40 μNI mesh and resuspended in FACS buffer with 300 nM DAPI for flow analysis.

qRT-PCR. Total RNA was extracted in triplicate wells from indicated conditions using the RNAeasy Mini Kit (Qiagen) according to manufacturer protocols. cDNA was synthesized from 1 μg of RNA (AffinityScript QPCR cDNA synthesis kit, Agilent) and QPCR amplification performed with SYBR green (Perfecta SYBR green fast mix, QuantaBio) using the following primer pairs on a ViiA 7 Real-Time PCR System (Life technologies). 36B4 was utilized as endogenous control. Following primers were used for qRT-PCR:

```
Dynlt3:
Left:
                                    (SEQ ID NO: 21)
TGGACTGCAAGCATAGTGGAA,
and

Right:
                                    (SEQ ID NO: 22)
GTGAAATCCATACGGGCTCCT;

Kif3c:
Left:
                                    (SEQ ID NO: 23)
CAGGCCGACCTGTATGACG,
and

Right:
                                    (SEQ ID NO: 24)
GTCCCCTGCATGGTGTAGG;

Nat2:
Left:
                                    (SEQ ID NO: 25)
ACACTCCAGCCAATAAGTACAGC,
and

Right:
                                    (SEQ ID NO: 26)
GGTAGGAACGTCCAAACCCA;
```

-continued

Arrdc4:
Left:
(SEQ ID NO: 27)
CCCTGGTGCTAAAAGATTGATGC,
and

Right:
(SEQ ID NO: 28)
TGAACTGGCTTGCGACACTG;

Perp:
Left:
(SEQ ID NO: 29)
ATCGCCTTCGACATCATCGC,
and

Right:
(SEQ ID NO: 30)
CCCCATGCGTACTCCATGAG;

Ccng2:
Left:
(SEQ ID NO: 31)
AGGGGTTCAGCTTTTCGGATT,
and

Right:
(SEQ ID NO: 32)
AGTGTTATCATTCTCCGGGGTAG;

Cdkn1a:
Left:
(SEQ ID NO: 33)
CGGTGTCAGAGTCTAGGGGA,
and

Right:
(SEQ ID NO: 34)
ATCACCAGGATTGGACATGG;

tp53:
Left:
(SEQ ID NO: 35)
CTAGCATTCAGGCCCTCATC,
and

Right:
(SEQ ID NO: 36)
TCCGACTGTGACTCCTCCAT;

Mdm2:
Left:
(SEQ ID NO: 37)
TGTCTGTGTCTACCGAGGGTG,
and

Right:
(SEQ ID NO: 38)
TCCAACGGACTTTAACAACTTCA;

Idh1:
Left:
(SEQ ID NO: 39)
ATGCAAGGAGATGAAATGACACG,
and

Right:
(SEQ ID NO: 40)
GCATCACGATTCTCTATGCCTAA;

Pcx:
Left:
(SEQ ID NO: 41)
GGCCAAGGAAAATGGTGTAG,
and

Right:
(SEQ ID NO: 42)
CTTCCACCTTGTCTCCCATC;

-continued

Ogdh:
Left:
(SEQ ID NO: 43)
GGTGGAAGCACAACCTAACG,
and

Right:
(SEQ ID NO: 44)
CATGGTGCCCTCGTATCTGA;

Tet1:
Left:
(SEQ ID NO: 45)
GAAGCTGCACCCTGTGACTG,
and

Right:
(SEQ ID NO: 46)
GACAGCAGCCACACTTGGTC;

Tet2:
Left:
(SEQ ID NO: 47)
AAGCTGATGGAAAATGCAAGC,
and

Right:
(SEQ ID NO: 48)
GCTGAAGGTGCCTCTGGAGT;

Tet3:
Left:
(SEQ ID NO: 49)
TCACAGCCTGCATGGACTTC,
and

Right:
(SEQ ID NO: 50)
ACGCAGCGATTGTCTTCCTT;

36B4:
Left:
(SEQ ID NO: 51)
GCTCCAAGCAGATGCAGCA,
and

Right:
(SEQ ID NO: 52)
CCGGATGTGAGGCAGCAG.

Western Blotting. Cell lysates were extracted using RIPA buffer and protein concentration was determined by BCA assay. Samples were boiled for 5 minutes and 20 to 30 μg of protein were separated by SDS-PAGE, transferred to nitrocellulose membranes, blocked with 3% milk prepared in 1×TBS-Tween and probed with the relevant primary antibody overnight at 4° C. Membranes were then incubated with horseradish peroxide (HRP)-conjugated secondary antibodies at room temperature and proteins were detected using Pierce ECL Western Blotting Substrate (34095, Thermo Fisher Scientific). Blots were imaged using HyBlot CL Autoradiography Film (E3018, Denville Scientific) and Konica Medical Film Processor (Model SRX-101A). Antibodies were diluted as follows: p53 (CM5) (1:500, NCL-L-p53-CM5p, Leica Biosystems), p21 (F-5) (1:500, sc-6246, Santa Cruz Biotechnology), p19 (M-167) (1:500, sc-1063, Santa Cruz Biotechnology), Ogdh (1:1000, 15212-1-AP, ProteinTech), Idh1 (1:1000, 12332-1-AP, ProteinTech), Sdha [2E3GC12FB2AE2] (1:1000, ab14715, Abcam) and tubulin (1:10,000, T9026, Sigma-Aldrich).

Image Analysis. The tumors of three mice were stained for 5hmC and DAPI. These tumors were imaged at three randomly chosen 20× fields and these images were analyzed using custom-made Matlab® scripts. Briefly, a GFP mask was created to identify regions having cells of interest. Within these regions cell nuclei were located and segmented using the DAPI staining. Nuclear 5hmC levels were then quantified within $GFP^+$ cells. To account for differences in nuclear area, median 5hmC values were used, but similar results were obtained using mean or total 5hmc levels. To account for changes on DNA levels, 5hmC values per cell were normalized to corresponding DAPI levels. Different values than those determined the stringency of the GFP mask for the parameter were also tested and the results remained qualitatively the same.

sgRNA Editing Analysis. Target locus analysis was performed and analyzed as previously described[45]. Briefly, genomic DNA was extracted as described from $KP^{sh}$-2-Cas9 cells expressing sgRNAs targeting Tet1, Tet2, and Tet3 (listed above) and amplification of target regions was performed from 100 ng of genomic DNA using Herculase II Fusion DNA polymerase (Agilent 600675) per manufacturer instructions. Edited regions were amplified using the following primers:

```
Tet1 sg1:
Left:
                        (SEQ ID NO: 53)
CAAGCTGTCTGATCCTTCTCC,
and

Right:
                        (SEQ ID NO: 54)
ACAGAGGTGGCATCCAGAAC;

Tet1 sg2:
Left:
                        (SEQ ID NO: 55)
CCGGAAAACCGAAGCAATTA,
and

Right:
                        (SEQ ID NO: 56)
TCGCCAGCTAAGAGAGGTTC;

Tet2 sg1:
Left:
                        (SEQ ID NO: 57)
ACACCAAGTGGCAATCTTCC,
and

Right:
                        (SEQ ID NO: 58)
GCTGCTTTTACCGTGGTTTC;

Tet2 sg2:
Left:
                        (SEQ ID NO: 59)
GCAGAAGGAAGCAAGATGG,
and

Right:
                        (SEQ ID NO: 60)
AAGGCCGAGAGAAAGAGAGG;

Tet3 sg1:
Left:
                        (SEQ ID NO: 61)
GCCTCCTTCCCTACTTCCAC,
and

Right:
                        (SEQ ID NO: 62)
CCTGGACCTGGATTTCTTGA;
```

-continued

```
Tet3 sg2:
Left:
                        (SEQ ID NO: 63)
TTCAGGTCTCCCCAGTCCTA,
and

Right:
                        (SEQ ID NO: 64)
CCCAATAGCTGCTCCAGTTC.
```

PCR products were column purified (Qiagen) for MiSeq. DNA-library preparation and sequencing were performed at GENEWIZ. An NEB NextUltra DNA Library Preparation kit was used according to the manufacturer's recommendations (Illumina). Adaptor-ligated DNA was indexed and limited-cycle PCR used for enrichment. DNA libraries were validated via TapeStation (Agilent) and measured with a Qubit 2.0 fluorometer. Libraries were further quantified through real-time PCR (Applied Biosystems) and loaded on an Illumina MiSeq instrument according to the manufacturer's instructions (Illumina). Sequencing was performed with a 2×150 paired-end configuration. Image analysis and base calling were conducted in MiSeq Control Software on a MiSeq instrument. Raw Fastq data was first trimmed to remove low quality data using the sickle tool. The PAired-eND Assembler for DNA sequences (Pandaseq) was then used to merge read1 and read2. The merged reads were mapped to the reference sequence using the Burrows-Wheeler Aligner (BWA). Lastly, a variant detection analysis was performed using GENEWIZ's custom in-house developed scripts, which has been independently validated with a custom bioinformatic pipeline. Zafra et al., *Nature Biotechnology* 36: 888-893 (2018).

RNA-Seq. Total RNA was isolated from duplicate wells of indicated conditions. RNA integrity and concentration were assessed using a BioAnalyzer (Agilent). RNA sequencing libraries were generated using Illumina mRNA TruSeq kit with dual index barcoding. Multiplexed libraries were sequenced at the Cold Spring Harbor Labs core sequencing facility. Approximately 8 million paired-end 76 bp reads were sequenced per replicate on a HiSeq 2500 instrument on RAPID mode. After removing adaptor sequences with Trimmomatic (Bolger et al., *Bioinformatics* 30: 2114-2120 (2014)), RNA-Seq reads were aligned to GRCm38—mm10 with STAR. Dobin et al., *Bioinformatics* 29: 15-21 (2013). Genome wide transcript counting was performed by HTSeq or featureCounts to generate FPKM matrix. Liao et al., *Bioinformatics* 30: 923-930 (2014); and Anders et al., *Bioinformatics* 31: 166-169 (2015). Differential expression analysis was performed with DESeq2 package in R[50]. Genes with a real adjusted p value were used for downstream analyses.

Gene Set Enrichment Analysis. Gene set enrichment analysis (GSEA) was performed using ranked lists. Subramanian et al., *Proceedings of the National Academy of Sciences of the United States of America* 102: 15545-15550 (2005). Gene lists associated with p53 activity are found in the MSigDB (Subramanian et al., *Proceedings of the National Academy of Sciences of the United States of America* 102: 15545-15550 (2005)). GSEAPreranked version 4 was used with default parameters and data were exported and graphed in GraphPad Prism version 7.

Glucose, Glutamine and Lactate Measurements. Glucose, glutamine and lactate levels in culture medium were measured using a YSI 7100 multichannel biochemistry analyzer (YSI Life Sciences). $1\times10^6$ $KP^{sh}$ cells were washed with PBS and plated on and off dox 8 days before YSI analysis (−D8). Cells maintained on dox and off dox were passaged every 48 h and additional cells were grown off dox starting 4 days before YSI analysis (−D4). All cell groups (On dox, off dox 4 days, off dox 8 days) were split into 6-well plates in sextuplicate for collection 2 days before YSI analysis (−D2) in fresh media. 24 h before collection media was refreshed. Media were harvested on D0. Changes in metabolite concentrations were determined relative to media maintained on 6-well plates without cells under similar conditions to control for evaporation. Values were further normalized to protein content of 6 replicate wells. These experiments were performed independently at least two times.

Metabolite Profiling. For all metabolite experiments, cells were seeded 2 days before collection in 6-well plates such that cell density was ~75% confluent at time of analysis. Media was refreshed 16-18 h before metabolite collection. Metabolites were extracted with 1 mL ice-cold 80% methanol supplemented with 2 μNI deuterated 2-hydroxyglutarate (D-2-hydroxyglutaric-2,3,3,4,4-$d_5$ acid, d5-2HG) as an internal standard. Lysates were incubated overnight incubation at −80° C. and then harvested and centrifuged at 21,000 g for 20 minutes. Metabolite extracts were dried in an evaporator (Genevac EZ-2 Elite) and resuspended in 50 uL of 40 mg/mL methoxyamine hydrochloride in pyridine with incubation at 30° C. for 2 h. Metabolites were further derivatized by adding 80 μL of MSTFA+1% TCMS (Thermo Scientific) and 70 μl ethyl acetate (Sigma) with incubation at 37° C. for 30 min. Samples were analyzed using an Agilent 7890A GC coupled to Agilent 5975C mass selective detector. The GC was operated in splitless mode with helium gas flow at 1 mL/min. 1 μl of sample was injected onto an HP-5MS column and the GC oven temperature ramped from 60° C. to 290° C. over 25 min. Peaks representing compounds of interest were extracted and integrated using MassHunter software (Agilent Technologies) and peak area was normalized to the internal standard (d5-2HG) peak area and protein content of duplicate samples as determined by BCA protein assay (Thermo Scientific). Ions used for quantification of metabolite levels are as follows: d5-2HG m/z 354; citrate, m/z 465; αKG, m/z 304; aspartate, m/z 334; fumarate, m/z 245; malate, m/z 335 and succinate, m/z 247. All peaks were manually inspected and verified relative to known spectra for each metabolite. For isotope tracing studies, experiments were set up as described above. 4 h before metabolite collection, cells were washed and incubated with glucose- and glutamine-free DMEM media base supplemented with $^{12}$C-glucose (Sigma) and $^{12}$C-glutamine (Gibco) or the $^{13}$C versions of each metabolite, [U-$^{13}$C]glucose or [U-$^{13}$C]glutamine (Cambridge Isotope Labs). Enrichment of $^{13}$C was determined by quantifying the abundance of the following ions: citrate, 465-482; αKG, 304-315, aspartate, m/z 334-346; fumarate, m/z 245-254; glutamate, m/z 363-377 and malate, m/z 335-347. Correction for natural isotope abundance was performed using IsoCor software. All experiments were performed independently at least twice and a representative experiment is shown. Peak areas for all individual metabolites as well as the technical normalizations were performed.

Epigenomic Analysis. 1×10$^6$ KP$^{sh}$ cells were washed with PBS and plated on and off dox 8 days (−D8) before collecting cells for ATAC-Seq analysis. Cells maintained on dox and off dox were passaged every 48 h. Three days prior to harvest, dimethyl-α-ketoglutarate (DM-αKG) was added to cells grown on dox, while DMSO was added to cells maintained on dox and cells maintained off dox. All cell groups (On dox, DMSO; On dox, DM-αKG; Off dox, DMSO) were split into 6-well plates in duplicate in fresh media containing dox, DM-αKG, and DMSO as indicated two days prior to harvest. This medium was refreshed 24 h before collection. Upon harvest, cells were washed with PBS, trypsinized, and collected as a single cell suspension in complete DMEM. 50,000 cells of each group were sorted using a BD-FACS-ARIA into complete DMEM and washed with PBS. Sorted cells were processed for ATAC-Seq as described (Buenrostro et al., *Curr Protoc Mol Biol.* 109: 21.29.1-9 (2015)). Nuclei from washed pellets were extracted using lysis buffer (10 mM Tris-HCl, 10 mM NaCl, 3 mM $MgCl_2$, 0.1% IGEPAL CA-630) and transposition performed at 37° C. for 30 min using the Nextera DNA Library Prep Kit (Illumina). Transposed DNA was purified using the QIAgen MinElute PCR Purification kit and amplified for 12 cycles using the barcoded primers below. Libraries were purified and library assessment was performed using a spectrophotometer (Nanodrop) and automated capillary electrophoresis (Agilent Bioanalyzer). Barcoded libraries were pooled (2-4 samples/lane) and run on an Illumina HiSeq 2500 sequencer using 50 bp paired-end reads.

Primer sequences used for ATAC-SEQ sample barcoding (Buenrostro et al., *Nature Methods.* 10(12):1213-8 (2013)) were as follows:

```
Ad1_noMX
                                          (SEQ ID NO: 65)
AATGATACGGCGACCACCGAGATCTACACTCGTCGGCAGCGTCAGATGT

G;

Ad2.1_TAAGGCGA
                                          (SEQ ID NO: 66)
CAAGCAGAAGACGGCATACGAGATTCGCCTTAGTCTCGTGGGCTCGGAGA

TGT;

Ad2.2_CGTACTAG
                                          (SEQ ID NO: 67)
CAAGCAGAAGACGGCATACGAGATCTAGTACGGTCTCGTGGGCTCGGAGA

TGT;

Ad2.3_AGGCAGAA
                                          (SEQ ID NO: 68)
CAAGCAGAAGACGGCATACGAGATTTCTGCCTGTCTCGTGGGCTCGGAGA

TGT;

Ad2.4_TCCTGAGC
                                          (SEQ ID NO: 69)
CAAGCAGAAGACGGCATACGAGATGCTCAGGAGTCTCGTGGGCTCGGAGA

TGT;

Ad2.5_GGACTCCT
                                          (SEQ ID NO: 70)
CAAGCAGAAGACGGCATACGAGATAGGAGTCCGTCTCGTGGGCTCGGAGA

TGT;

Ad2.6_TAGGCATG
                                          (SEQ ID NO: 71)
CAAGCAGAAGACGGCATACGAGATCATGCCTAGTCTCGTGGGCTCGGAGA

TGT;

Ad2.7_CTCTCTAC
                                          (SEQ ID NO: 72)
CAAGCAGAAGACGGCATACGAGATGTAGAGAGGTCTCGTGGGCTCGGAGA

TGT;
```

-continued

Ad2.8_CAGAGAGG
(SEQ ID NO: 73)
CAAGCAGAAGACGGCATACGAGATCCTCTCTGGTCTCGTGGGCTCGGAGA
TGT;

Ad2.9_GCTACGCT
(SEQ ID NO: 74)
CAAGCAGAAGACGGCATACGAGATAGCGTAGCGTCTCGTGGGCTCGGAGA
TGT;

Ad2.10_CGAGGCTG
(SEQ ID NO: 75)
CAAGCAGAAGACGGCATACGAGATCAGCCTCGGTCTCGTGGGCTCGGAGA
TGT;

Ad2.11_AAGAGGCA
(SEQ ID NO: 76)
CAAGCAGAAGACGGCATACGAGATTGCCTCTTGTCTCGTGGGCTCGGAGA
TGT;

Ad2.12_GTAGAGGA
(SEQ ID NO: 77)
CAAGCAGAAGACGGCATACGAGATTCCTCTACGTCTCGTGGGCTCGGAGA
TGT;

Ad2.13_GTCGTGAT
(SEQ ID NO: 78)
CAAGCAGAAGACGGCATACGAGATATCACGACGTCTCGTGGGCTCGGAGA
TGT;

Ad2.14_ACCACTGT
(SEQ ID NO: 79)
CAAGCAGAAGACGGCATACGAGATACAGTGGTGTCTCGTGGGCTCGGAGA
TGT;

Ad2.15_TGGATCTG
(SEQ ID NO: 80)
CAAGCAGAAGACGGCATACGAGATCAGATCCAGTCTCGTGGGCTCGGAGA
TGT;

Ad2.16_CCGTTTGT
(SEQ ID NO: 81)
CAAGCAGAAGACGGCATACGAGATACAAACGGGTCTCGTGGGCTCGGAGA
TGT;

Ad2.17_TGCTGGGT
(SEQ ID NO: 82)
CAAGCAGAAGACGGCATACGAGATACCCAGCAGTCTCGTGGGCTCGGAGA
TGT;

Ad2.18_GAGGGGTT
(SEQ ID NO: 83)
CAAGCAGAAGACGGCATACGAGATAACCCCTCGTCTCGTGGGCTCGGAGA
TGT;

Ad2.19_AGGTTGGG
(SEQ ID NO: 84)
CAAGCAGAAGACGGCATACGAGATCCCAACCTGTCTCGTGGGCTCGGAGA
TGT;

Ad2.20_GTGTGGTG
(SEQ ID NO: 85)
CAAGCAGAAGACGGCATACGAGATCACCACACGTCTCGTGGGCTCGGAGA
TGT;

-continued

Ad2.21_TGGGTTTC
(SEQ ID NO: 86)
CAAGCAGAAGACGGCATACGAGATGAAACCCAGTCTCGTGGGCTCGGAGA
TGT;

Ad2.22_TGGTCACA
(SEQ ID NO: 87)
CAAGCAGAAGACGGCATACGAGATTGTGACCAGTCTCGTGGGCTCGGAGA
TGT;

Ad2.23_TTGACCCT
(SEQ ID NO: 88)
CAAGCAGAAGACGGCATACGAGATAGGGTCAAGTCTCGTGGGCTCGGAGA
TGT;

Ad2.24_CCACTCCT
(SEQ ID NO: 89)
CAAGCAGAAGACGGCATACGAGATAGGAGTGGGTCTCGTGGGCTCGGAGA
TGT.

For data analysis, quality and adapter filtering was applied to raw reads using 'trim_galore' before aligning to mouse assembly mm9 with bowtie2 using the default parameters. The Picard tool MarkDuplicates was used to remove reads with the same start site and orientation. The BEDTools suite was used to create read density profiles. Enriched regions were discovered using MACS2 and scored against matched input libraries (fold change >2 and FDR-adjusted p-value <0.1). A consensus peak atlas was then created by filtering out blacklisted regions and then merging all peaks within 500 bp. A raw count matrix was computed over this atlas using featureCounts with the '-p' option for fragment counting. The count matrix and all genome browser tracks were normalized to a sequencing depth of ten million mapped fragments. DESeq2 was used to classify differential peaks between two conditions using fold change >2 and FDR-adjusted p-value <0.1. Peak-gene associations were made using linear genomic distance to the nearest transcription start site with Homer. ChIP-seq data were processed in the same way as ATAC-seq data, except read density profiles for ChIP included a read extension equivalent to the average library fragment size. Kenzelmann Broz et al., *Genes & Development* 27: 1016-1031 (2013). Motif signatures for p53 were discovered using Homer's annotatePeaks.pl script using the default settings.

Statistics and Reproducibility. GraphPad PRISM 7 software was used for statistical analyses. Error bars, P values and statistical tests are reported in the figure<legends. Statistical tests include unpaired two-tailed Student's t-test, one-way analysis of variance (ANOVA), two-way ANOVA and Fisher's exact test. All experiments (except sequencing experiments, which were done once) were performed independently at least two times.

Data Availability. RNA-Seq and ATAC-Seq data that support the findings of this study have been deposited in the Gene Expression Omnibus under the accession codes GSE114263 and GSE114342.

Figure 5A:
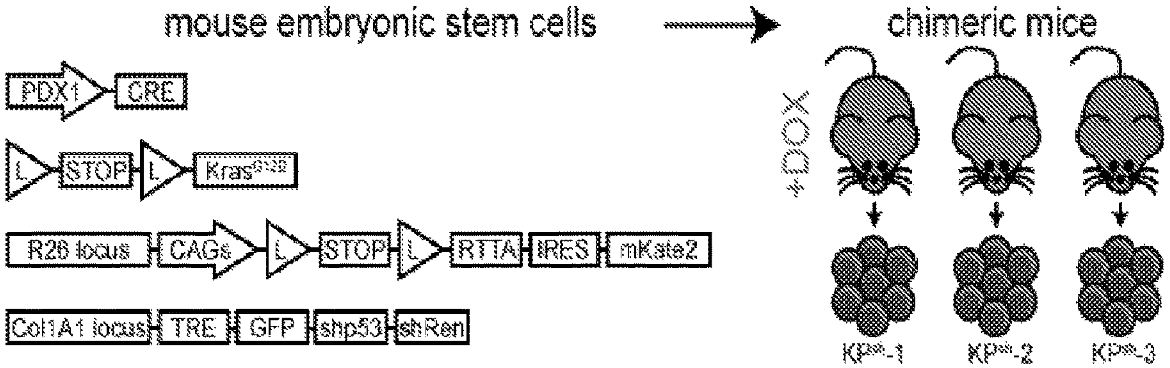
FIG. 5A shows a schematic of $KP^{sh}$ embryonic stem cell-based genetically engineered mouse model (ESC-GEMM) of pancreatic ductal adenocarcinoma (PDAC). Embryonic stem cells were derived from blastocysts expressing: Pdx1-Cre (transgenic allele, expression of Cre in pancreatic progenitors); LSL-$Kras^{G12D}$ (knock-in, conditional heterozygous expression of mutant Kras); RIK (knock in, conditional heterozygous expression of rtTA and fluorescent mKate2 from the Rosa26 locus); Col1a1-TRE-GFP-shp53-shRenilla (Col1a1 homing cassette (CHC) targeted with doxycycline inducible tandem shRNA expressing shp53 and shRenilla linked to GFP). $KP^{sh}$ mice were generated by blastocyst injection and mothers enrolled on dox chow at day 5. Cell lines were derived and maintained in dox-containing media from tumors arising in dox fed mice. All $KP^{sh}$ cells constitutively express mKate2 (Kate) and rtTA.
Figure 5B:
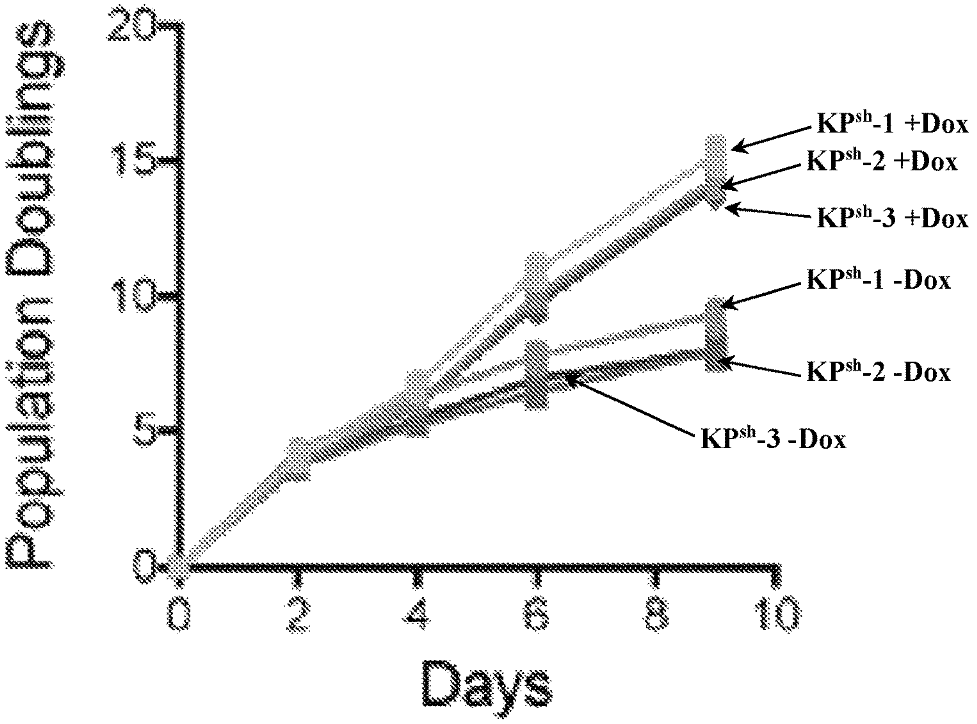
FIG. 5B shows the growth curves of $KP^{sh}$-1-3 cells cultured with or without dox.
Figure 5C:
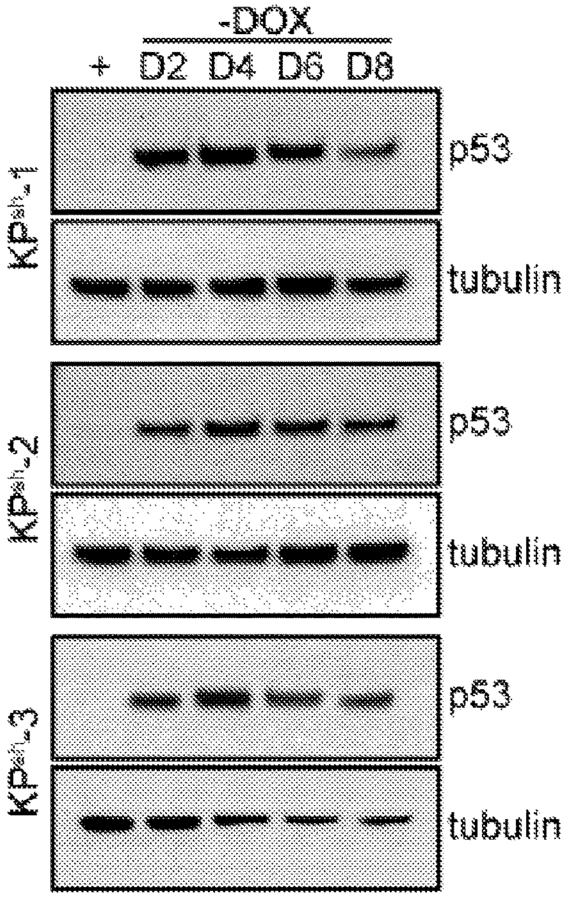
FIG. 5C shows Western blots showing the expression of p53 in $KP^{sh}$-1-3 cells cultured without dox for 2, 4, 6 or 8 days. Cells cultured with dox were used as a control. Tubulin was used to control loading of protein in each lane.
Figure 5D:
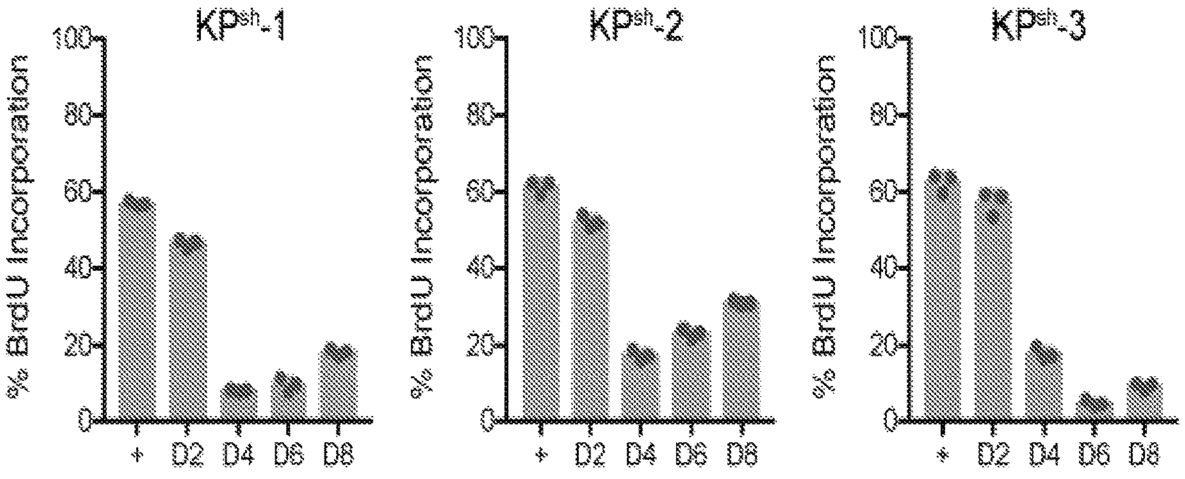
FIG. 5D shows the BrdU incorporation in $KP^{sh}$-1-3 cells cultured with dox or without dox for 2, 4, 6 or 8 days.
Figure 5E:
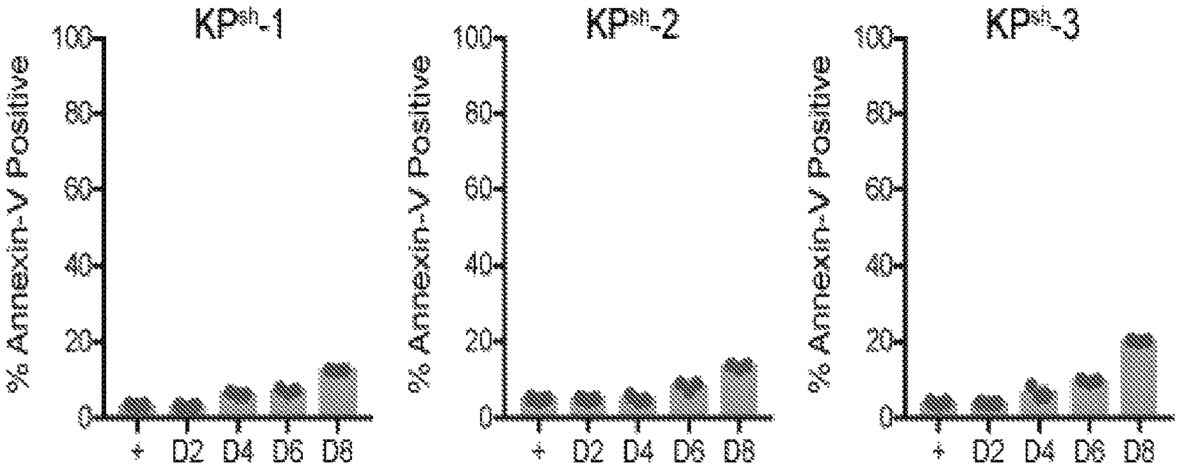
FIG. 5E shows the Annexin-V staining in $KP^{sh}$-1-3 cells cultured with dox or without dox for 2, 4, 6 or 8 days.
Figure 5F:
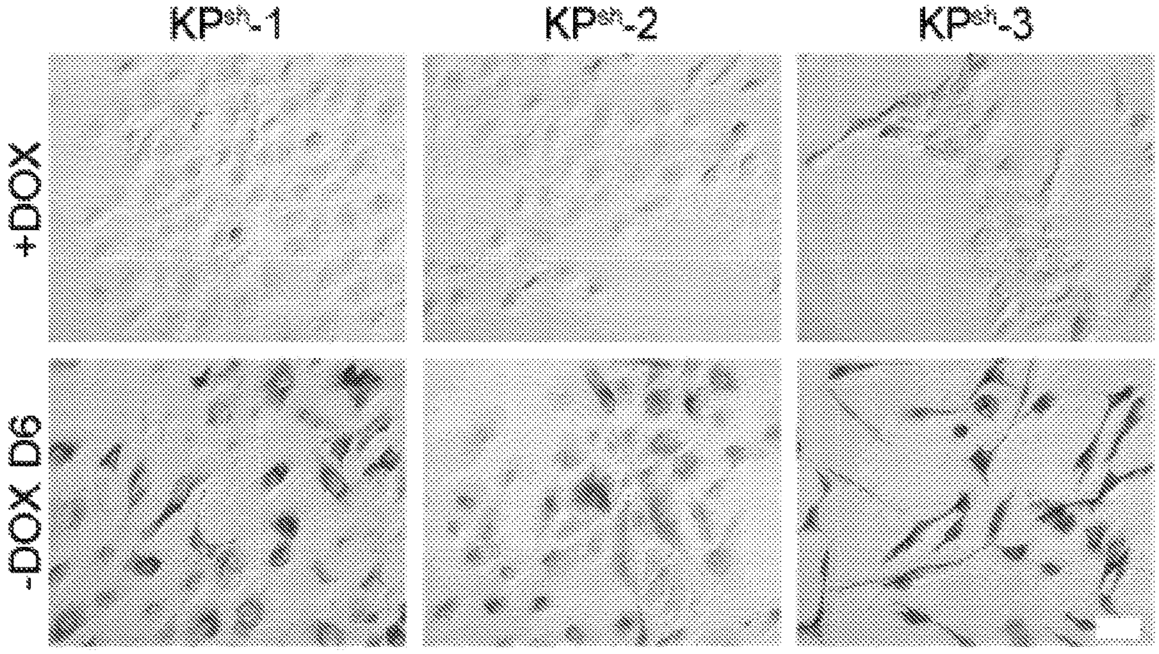
FIG. 5F shows the senescence-associated β-galactosidase (SA-β GAL) staining in $KP^{sh}$-1-3 cells cultured with dox or without dox for 6 days.
Figure 5G:
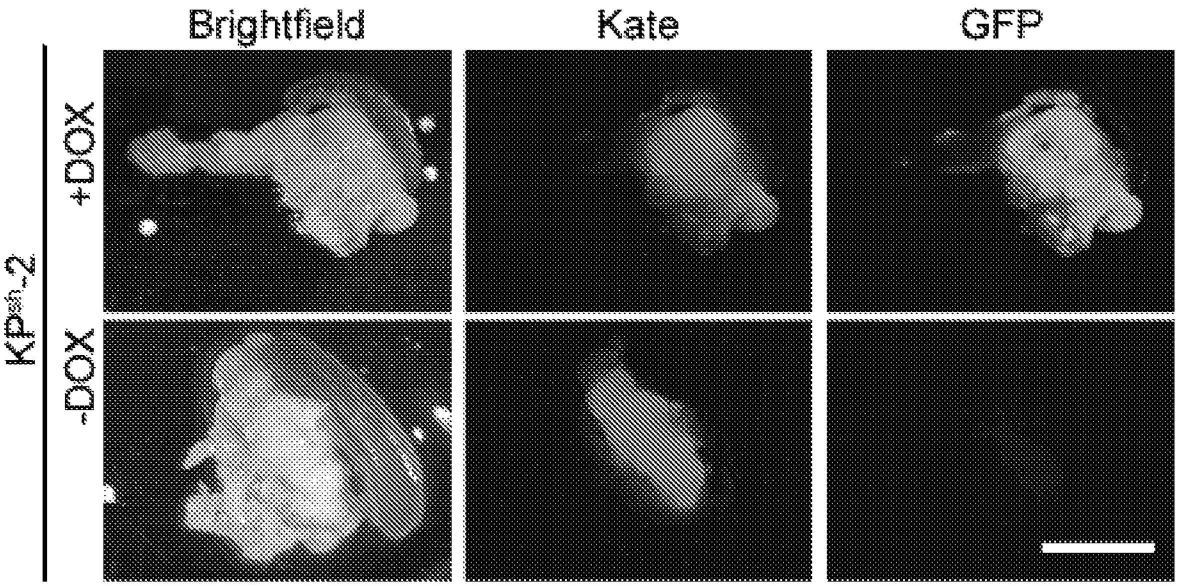
FIG. 5G shows the representative gross pathology and epifluorescence images of pancreatic tumors resulting from orthotopic transplant of $KP^{sh}$-2 cells into dox fed mice maintained on dox chow (top) or withdrawn from dox chow for 10 days (bottom). $KP^{sh}$ cells uniformly express Kate, while GFP expression indicates cell actively expressing the p53 shRNA. Scale bar for pathology 1 cm.
Figure 5H:
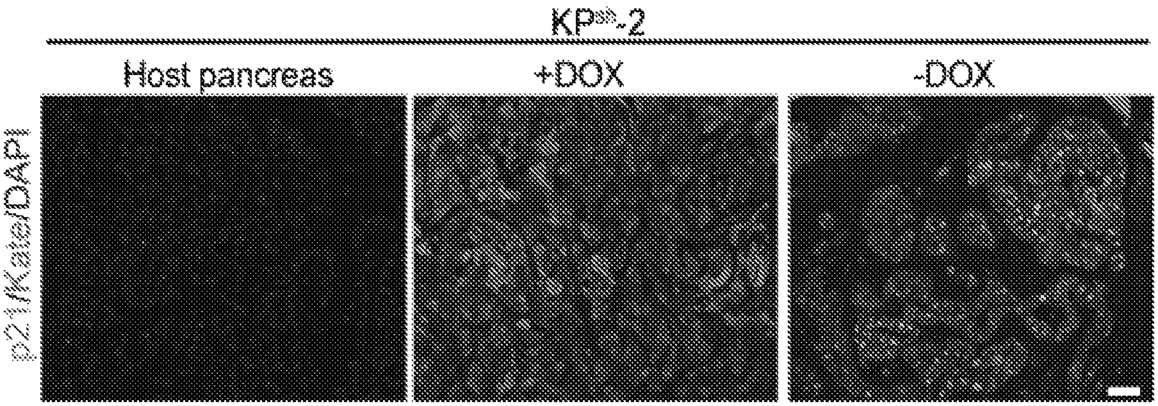
FIG. 5H shows the immunostaining of Cdkn1a/p21 in matched normal host pancreas, or in orthotopic $KP^{sh}$-2 tumors maintained on dox or 10 days following dox withdrawal. Kate indicates injected $KP^{sh}$-2 cells. Scale bar for immunostaining is 50 μM.
Figure 5I:
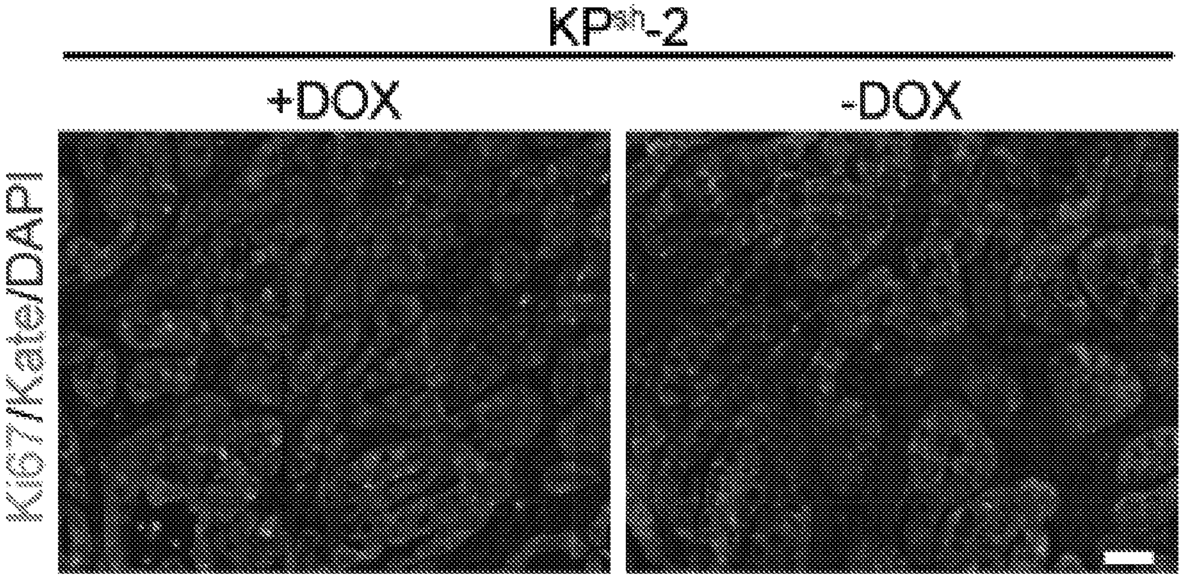
FIG. 5I shows the immunostaining of Ki67 in orthotopic $KP^{sh}$-2 tumors maintained on dox or 10 days following dox withdrawal. Kate indicates injected $KP^{sh}$-2 cells. Scale bar for immunostaining is 50 μM.
Figure 5J:
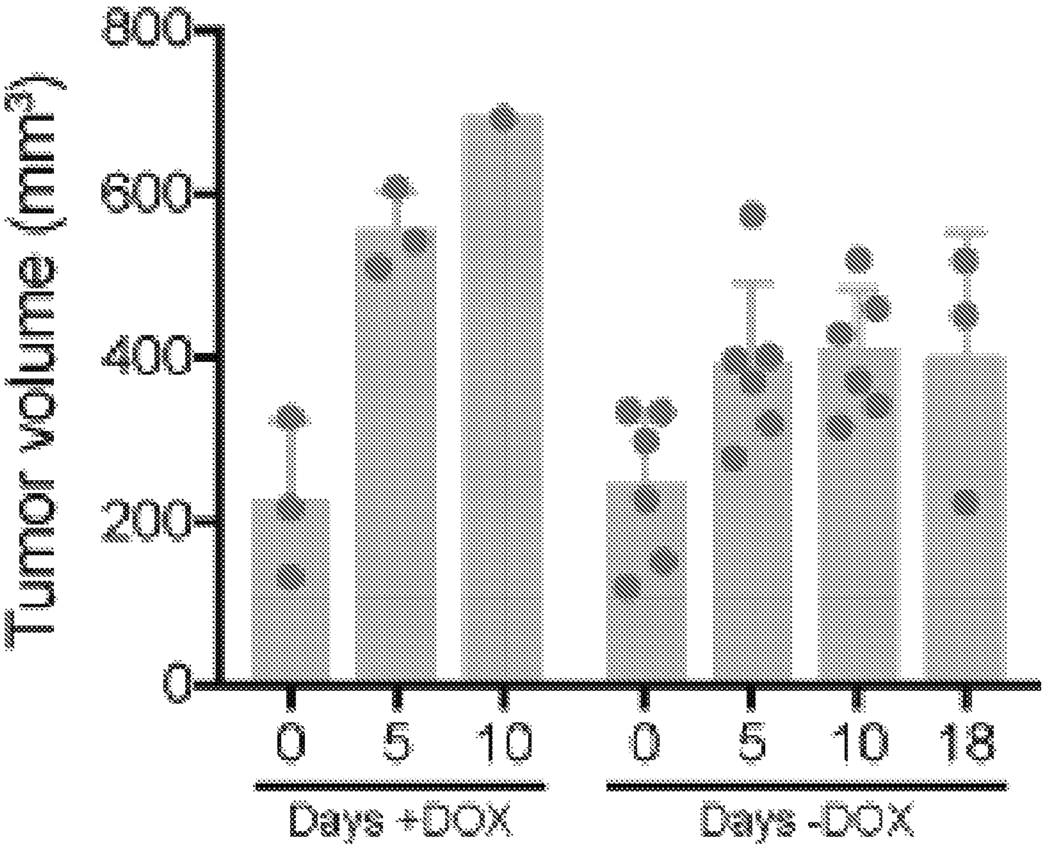
FIG. 5J shows the small animal ultrasound measurement of tumor volume. $KP^{sh}$-2 cells were injected into dox-fed mice and mice were maintained on dox diet for 2 weeks. After two weeks (D0), tumor size was measured and mice were randomized into off and on dox chow groups. Subsequent tumor size and mouse survival was monitored over time.
Figure 5K:
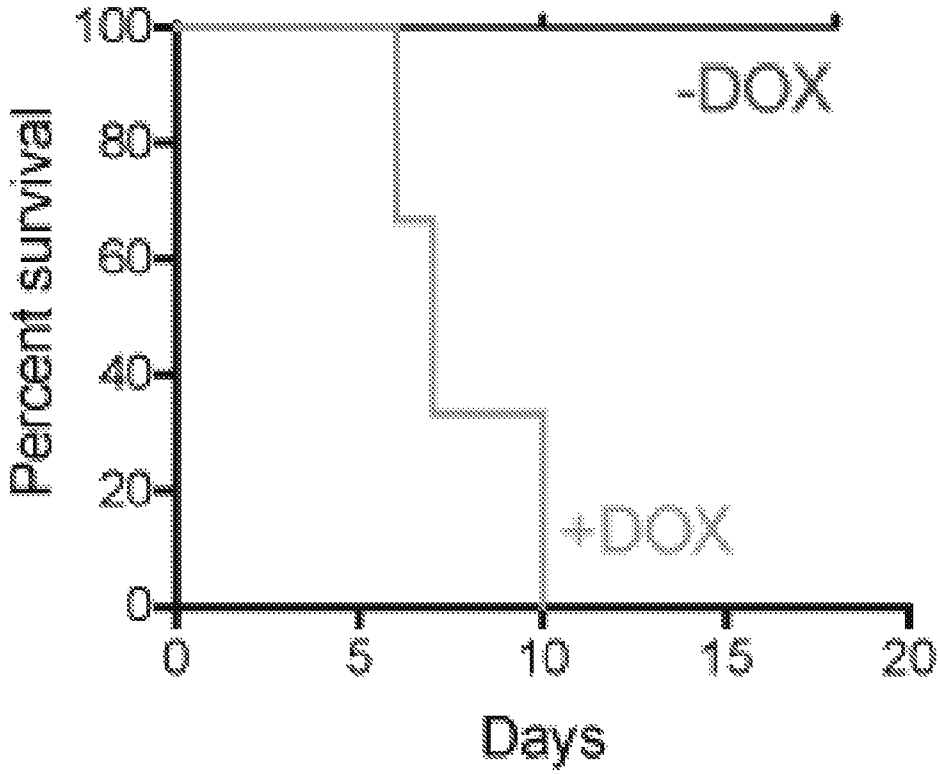
FIG. 5K shows the survival of mice shown in FIG. 5J after randomization into groups maintained on dox food or following dox withdrawal. Data are presented as mean SD of triplicate wells of a representative experiment with individual data points shown.

Example 2: p53 Restoration Increases the Cellular αKG/Succinate Ratio Independently of Changes in Proliferation In PDAC cell lines derived from p53-suppressed tumors arising in three independent dox fed mice (designated $KP^{sh}$-1-3, FIG. 5A), dox withdrawal resulted in robust p53 protein accumulation, induced expression of its downstream targets Cdkn1a/p21 and Mdm2, and triggered cellular senescence (FIGS. 1A-1B and FIGS. 5B-5E). Similarly, tumors produced following orthotopic injection of $KP^{sh}$ cells rapidly extinguished shp53 expression upon dox withdrawal, leading to sustained Cdkn1a/p21 induction, decreased tumor growth and enhanced animal survival (FIGS. 5F-5J). As shown in FIG. 5H, the levels of Cdkn1a/p21 induction following p53 reactivation in established tumors were substantially higher than those observed in surrounding normal cells suggesting that the oncogenic signaling produced by Kras contributes to p53 activation, as previously described. Thus, p53 inactivation is required to sustain tumorigenesis such that the accumulation of endogenously regulated levels of p53 produces a potent tumor suppressive response.

Figure 1A:
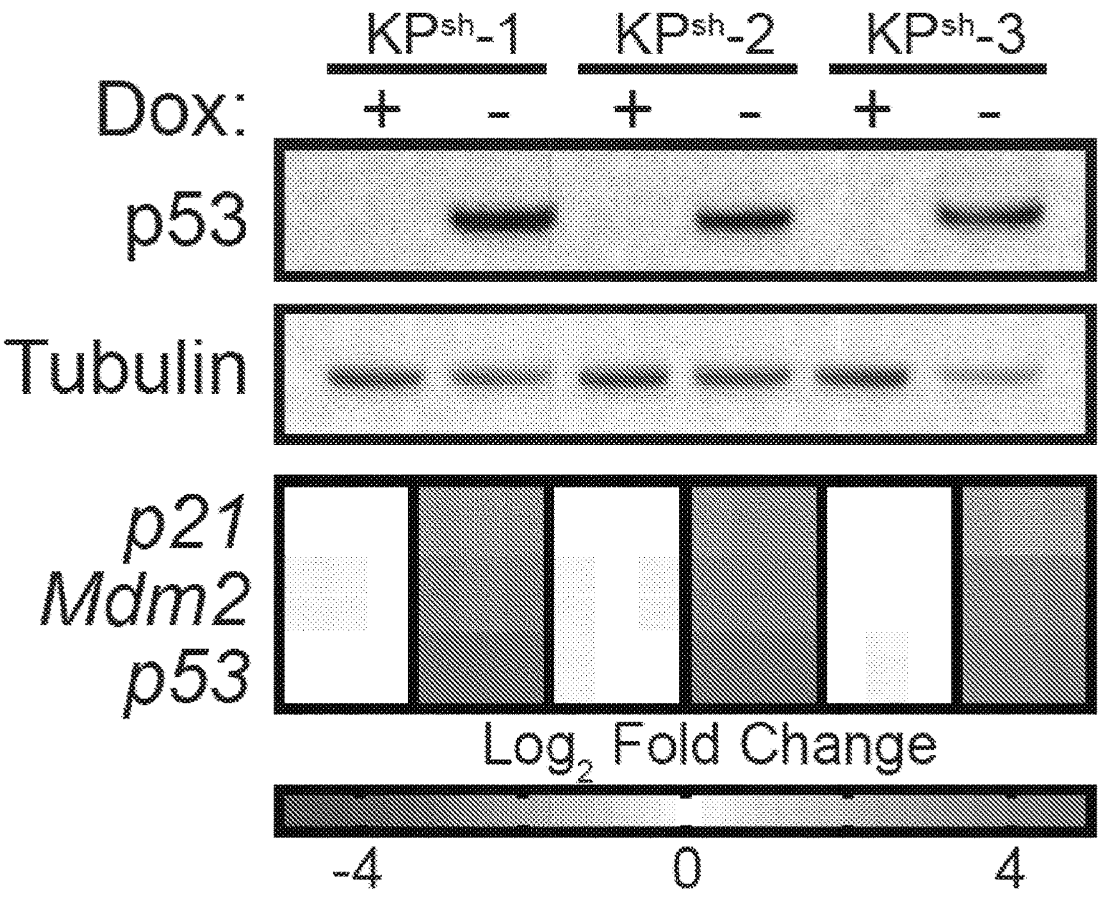
FIG. 1A shows a western blot (top) and a heat map showing results of qRT-PCR (bottom) of $KP^{sh}$-1-3 lines cultured with or without doxycycline (dox) for six days. Gene expression is represented as the $\log_2$ fold change relative to +dox controls for each line. As shown, dox withdrawal resulted in the induction of p53, Mdm2 and p21.
Figure 1B:
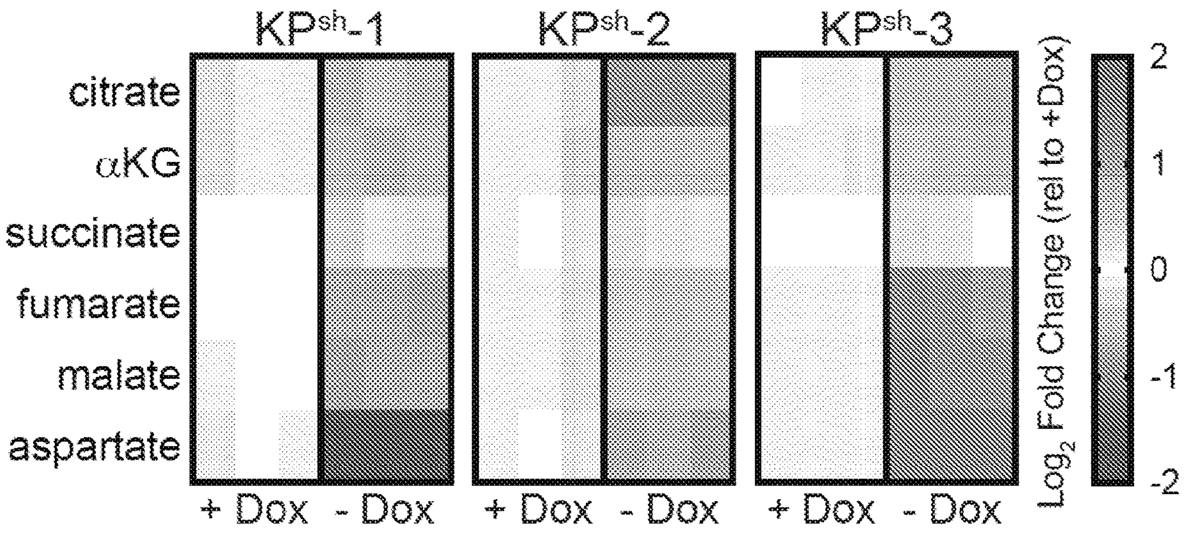
FIG. 1B shows the changes in the steady-state levels of TCA cycle metabolites in $KP^{sh}$-1-3 cells upon withdrawal of dox.
Figure 1C:
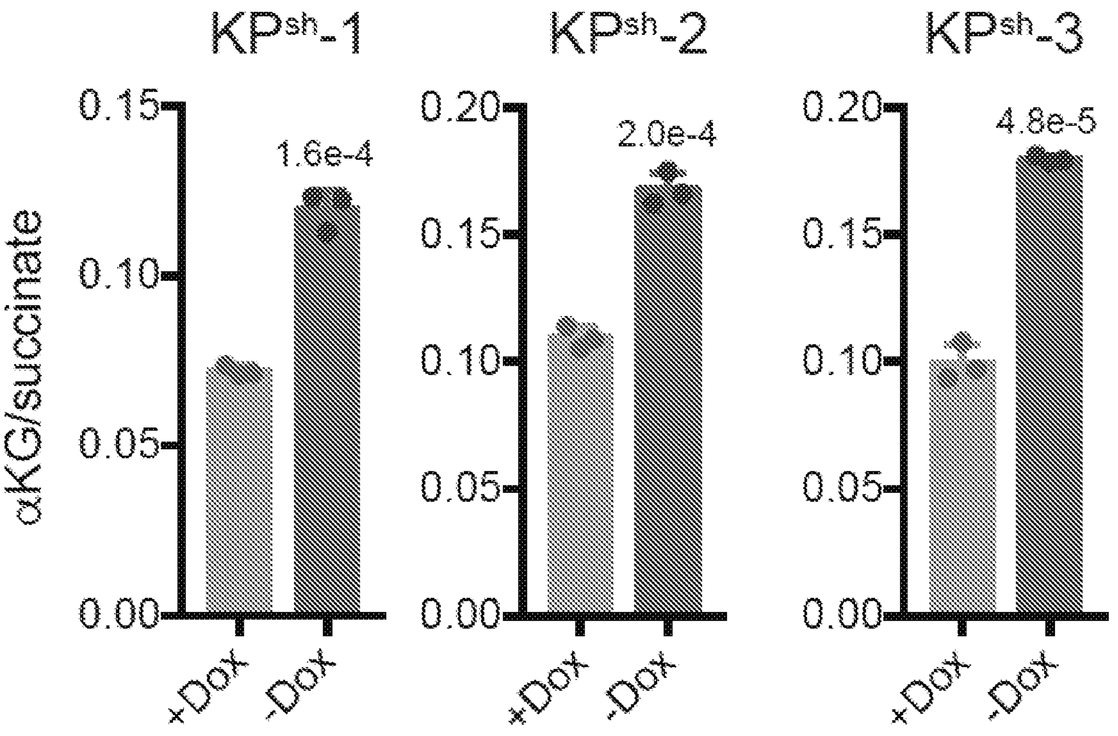
FIG. 1C shows the αKG/succinate ratio in $KP^{sh}$-1-3 cells cultured with or without dox for eight days. 1-way ANOVA with Tukey's post-test or 2-way ANOVA with Sidak's post-test
Figure 1D:
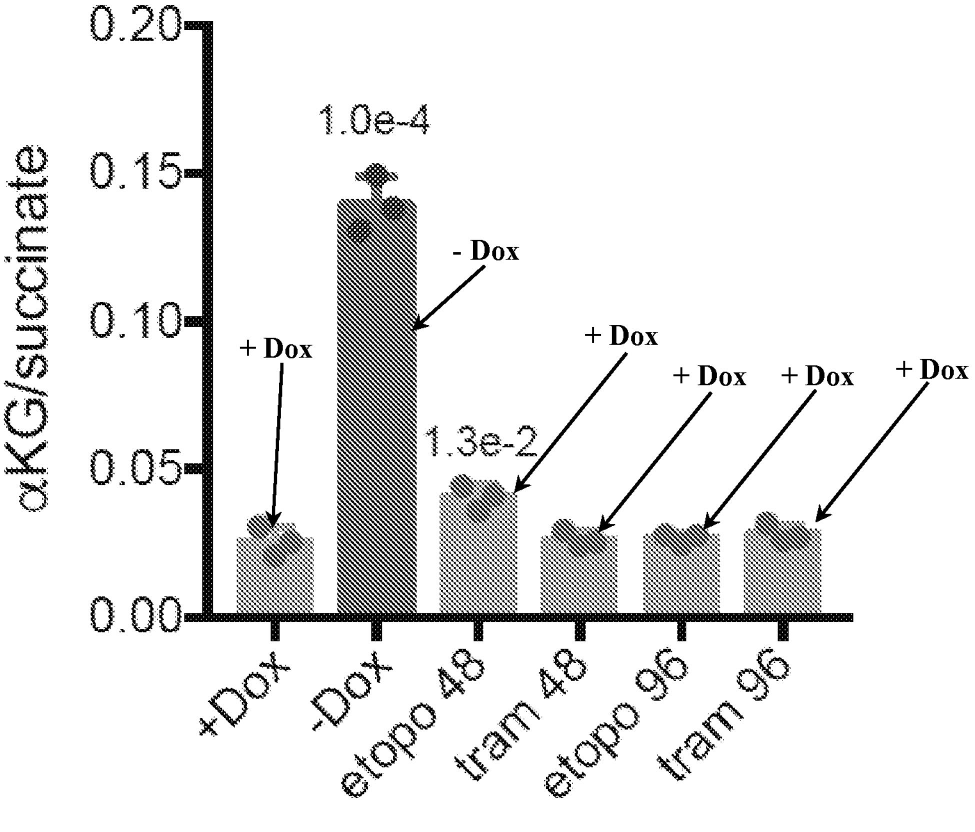
FIG. 1D shows the αKG/succinate ratio in $KP^{sh}$-1-3 cells cultured with dox and 25 nM trametinib or 3 μM etoposide for 48 or 96 hours. Cells cultured without dox for six days were included as a control.
Figure 6A:
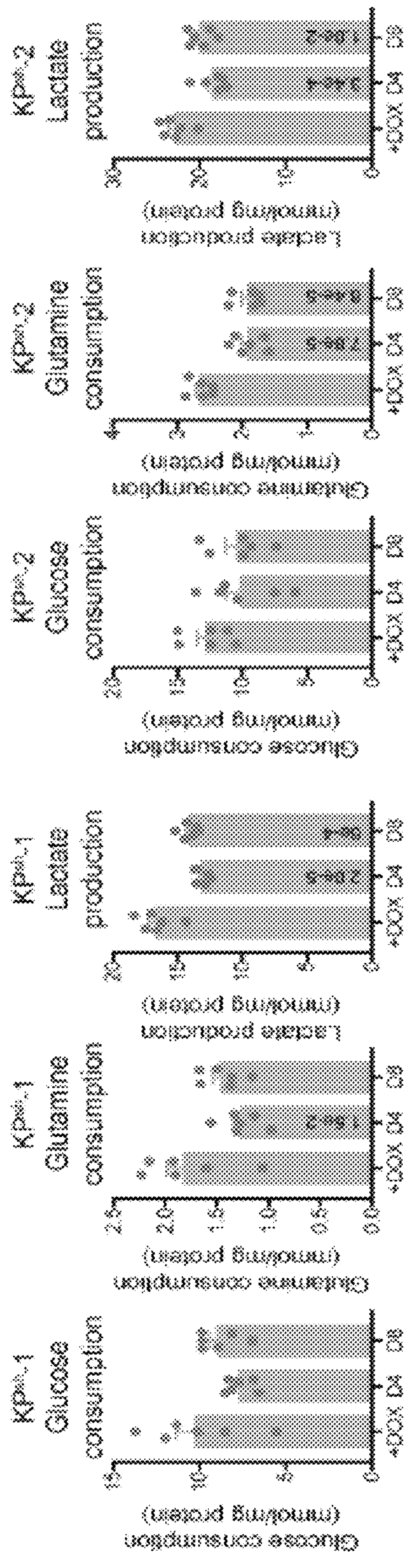
FIG. 6A shows the analysis of glucose consumption (left), glutamine consumption (middle) and lactate production (right) in two independent $KP^{sh}$ lines cultured with dox or without dox for 4 or 8 days (D, days).
Figure 6B:
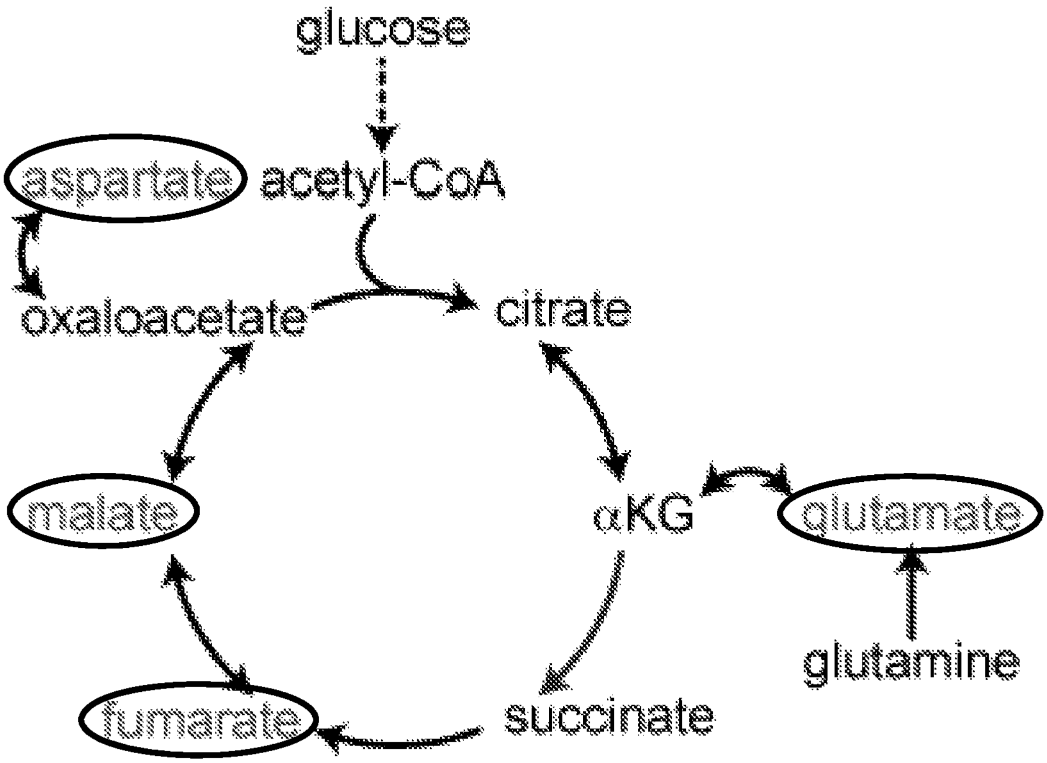
FIG. 6B shows a schematic of the TCA cycle that includes entry points for glucose- and glutamine-derived carbons. Metabolites in red (also bracketed in ovals) were assessed by isotope tracing experiments and were used to calculate the relative changes in TCA cycle metabolites.
Figure 6C:
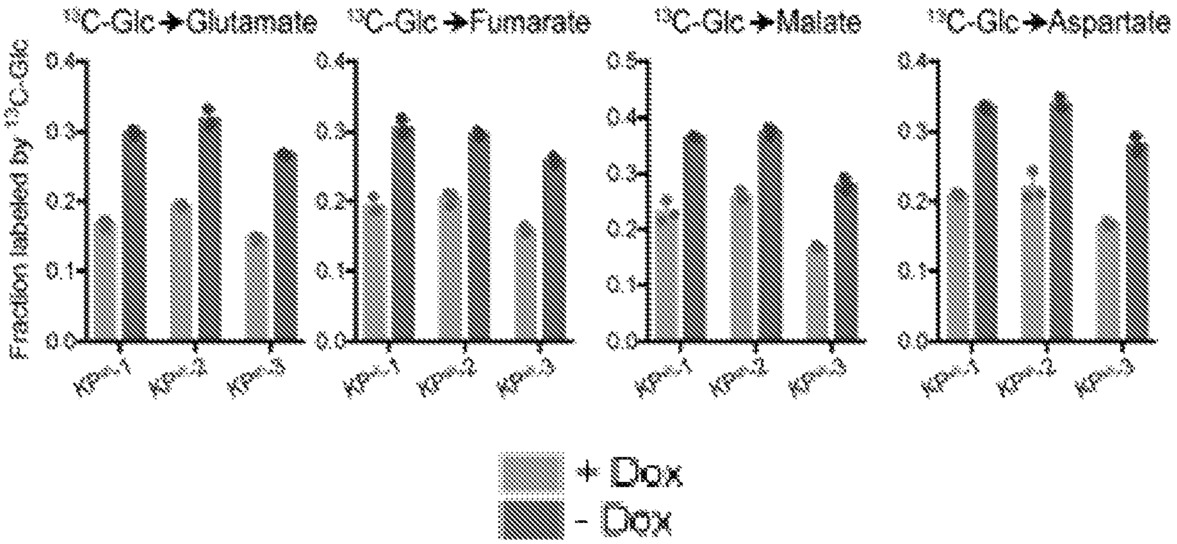
FIGS. 6C-6D show the fraction of metabolite containing $^{13}C$ derived from [U-$^{13}C$]glucose ($^{13}C$-Glc) (FIG. 6C), or derived from [U-$^{13}C$]glutamine ($^{13}C$-Gln) (FIG. 6D) after four hours of labeling in cells cultured with or without dox for six days.
Figure 6D:
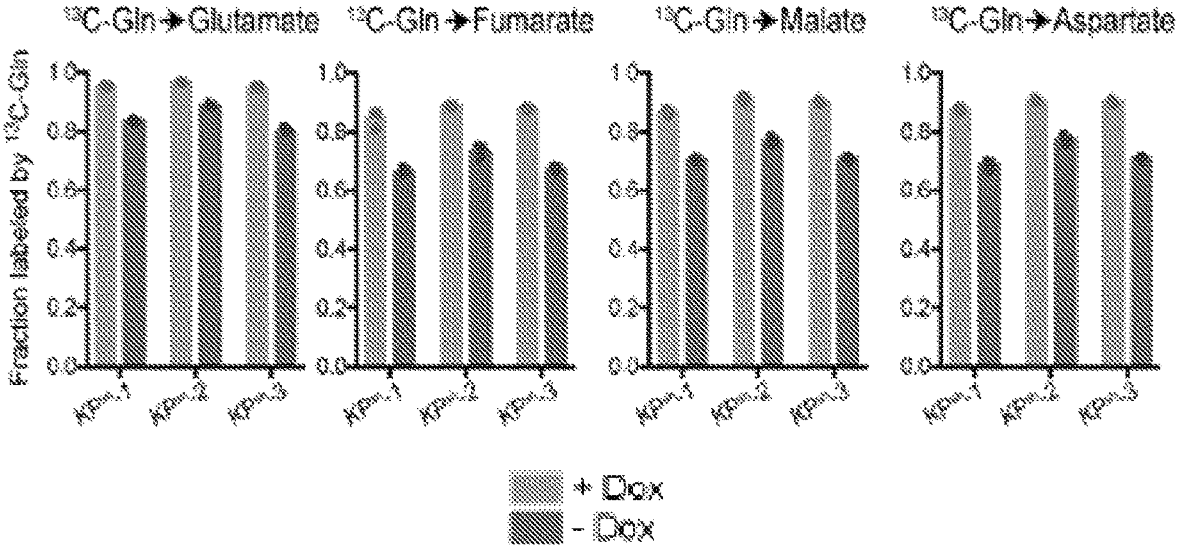
Figure 6E:
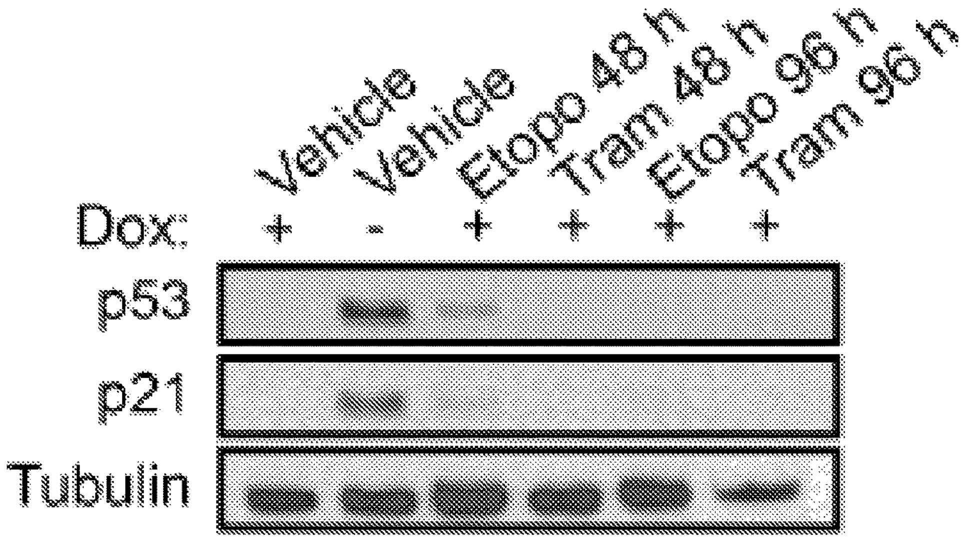
FIG. 6E shows a Western blot for p53 of $KP^{sh}$-2 cells grown with dox and treated with 3 μM etoposide (Etopo) or 25 nM trametinib (Tram) for 48 or 96 hours. Cells grown without dox for 6 days were included as positive control.

Taking advantage of the cell lines described above, the impact of restoring wild-type p53 on PDAC metabolism was studied. PDAC cells driven by oncogenic Kras and p53 disruption consume high amounts of glucose and glutamine, which provide the primary substrates that support anabolic proliferation in cultured cancer cells. Surprisingly, p53-restoration did not result in major changes in the consumption of glucose and glutamine, or the production of lactate, despite the induction of cell cycle arrest (FIG. 1B, FIGS. 5C-5D, and 2A). However, as shown in FIG. 1C, monitoring glucose and glutamine utilization via the mitochondrial tricarboxylic acid (TCA) cycle indicated that p53 triggered a metabolic switch marked by enhanced incorporation of glucose-derived carbons and reduced contribution of glutamine-derived carbons into TCA cycle intermediates despite sustained oncogene-associated levels of nutrient uptake (FIGS. 6B-6D). Accordingly, while citrate and αKG accumulated in response to p53, metabolites derived from glutamine oxidation including succinate, malate and aspartate were progressively decreased. This metabolic shift produced an increase in the αKG/succinate ratio (FIGS. 1C-1D), a metabolic change that is linked to cell fate decisions in some contexts.

Figure 6F:
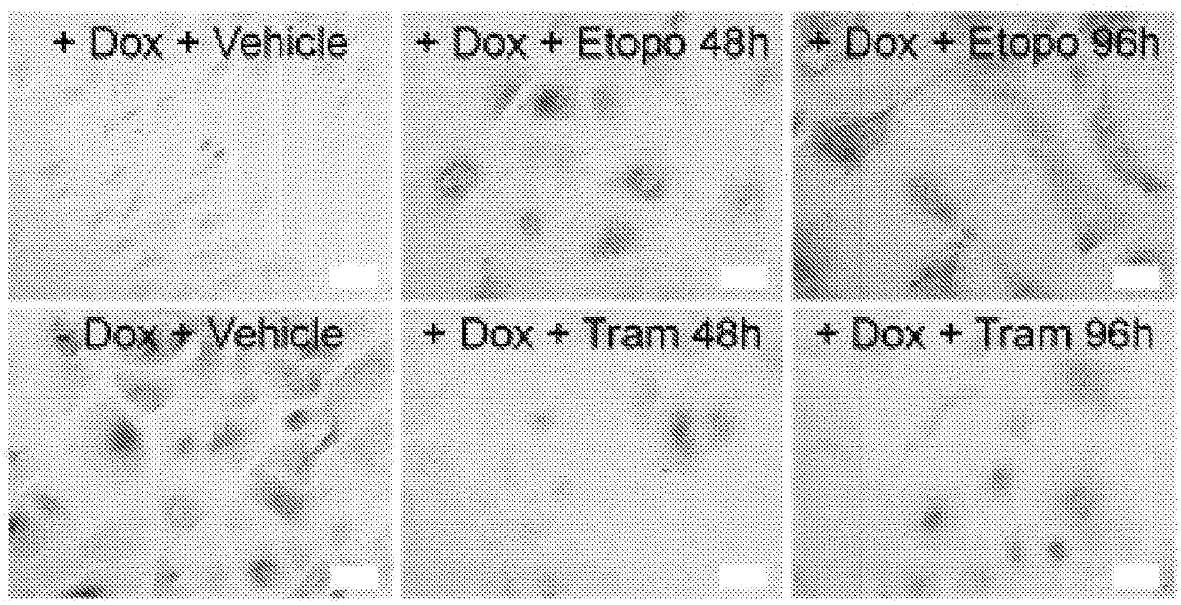
FIG. 6F shows the senescence-associated β-galactosidase (SA-β GAL) staining of $KP^{sh}$-2 cells grown on dox and treated with 3 μM etoposide (Etopo) or 25 nM trametinib (Tram) for 48 or 96 h. Cells grown in the absence of dox (−dox) for six days are included as a positive control.
Figure 6G:
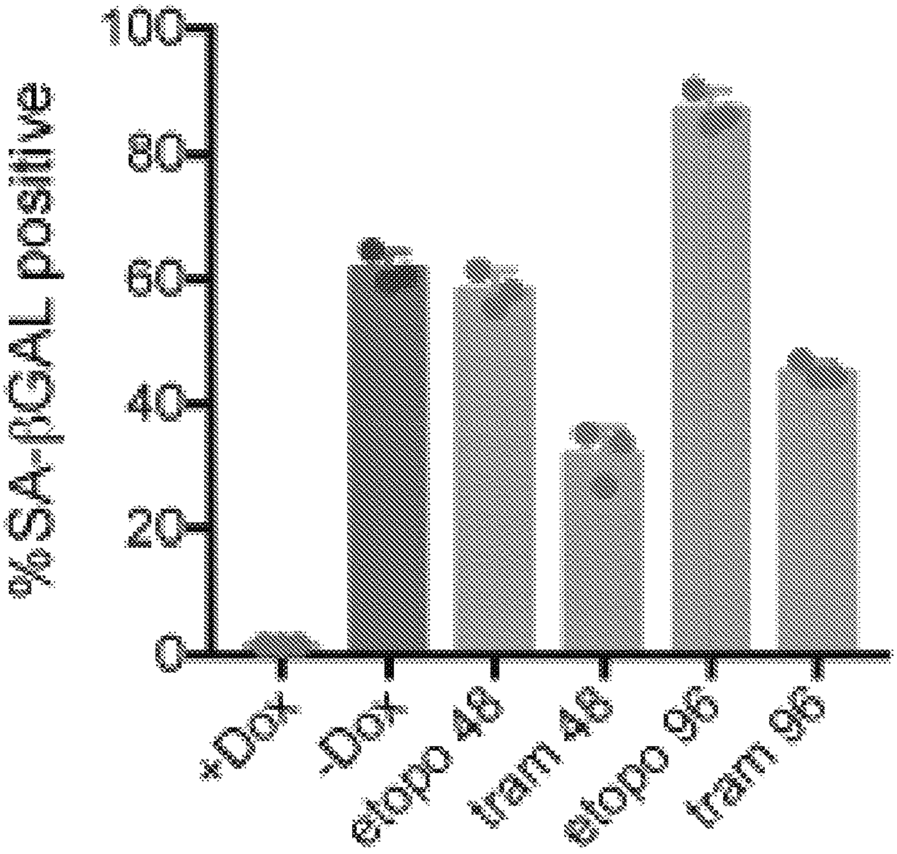
FIGS. 6G-6H show the quantification of the number of SA-13GAL positive (FIG. 6G) or BrdU positive (FIG. 6H) cells treated as described in FIG. 6E.
Figure 6H:
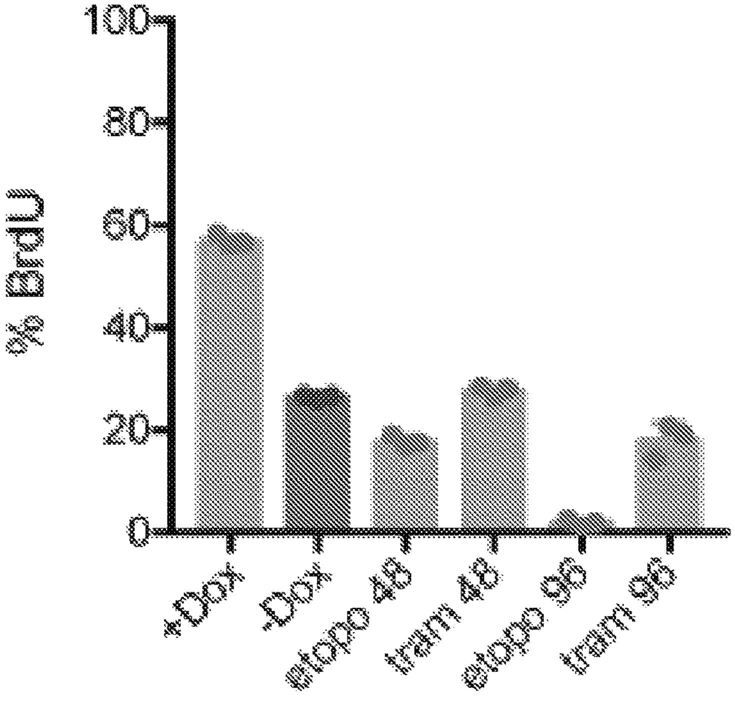
Figure 6I:
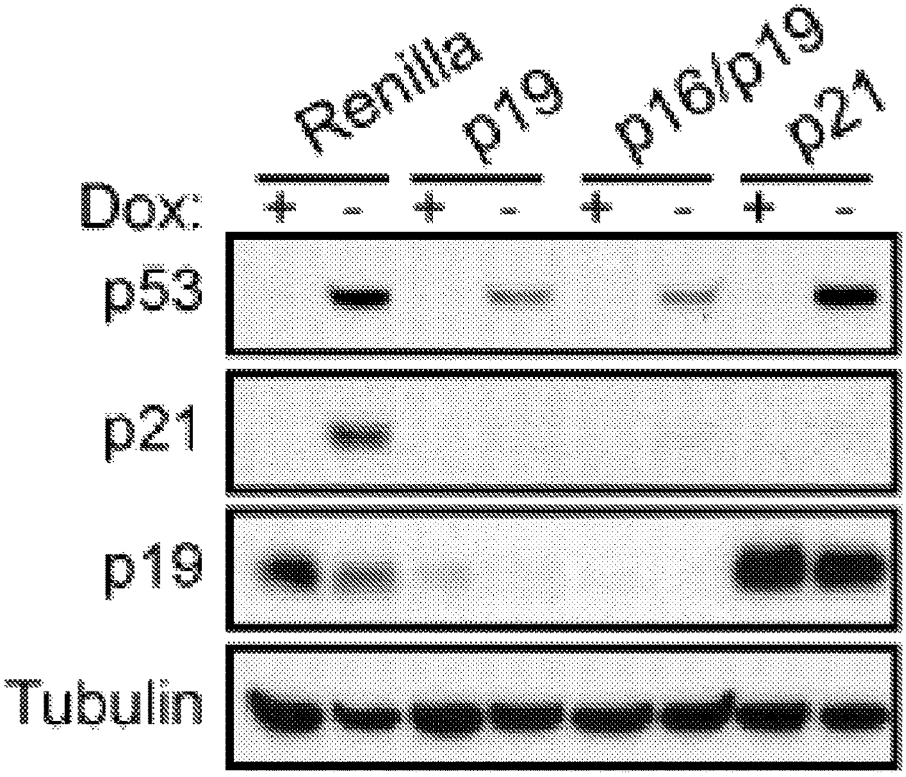
FIG. 6I shows the western blot analysis of cells expressing constitutive hairpins targeting *Renilla, p*19, p16/p19, or Cdkn1a/p21 (indicated on top) cultured with or without dox (to reactivate p53) for six days.
Figure 6J:
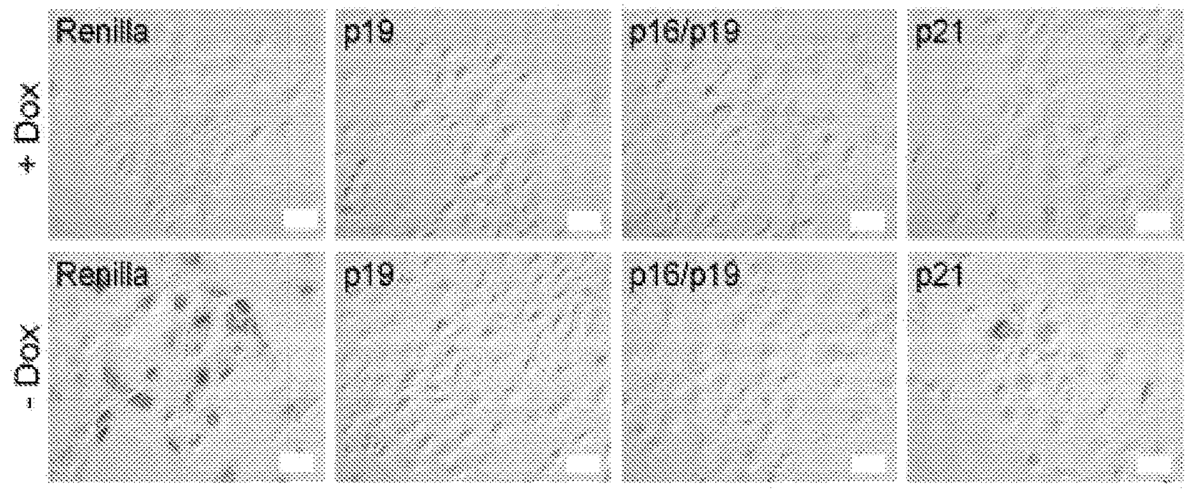
FIG. 6J shows the SA-13GAL staining of cells described in FIG. 6F.
Figure 6K:
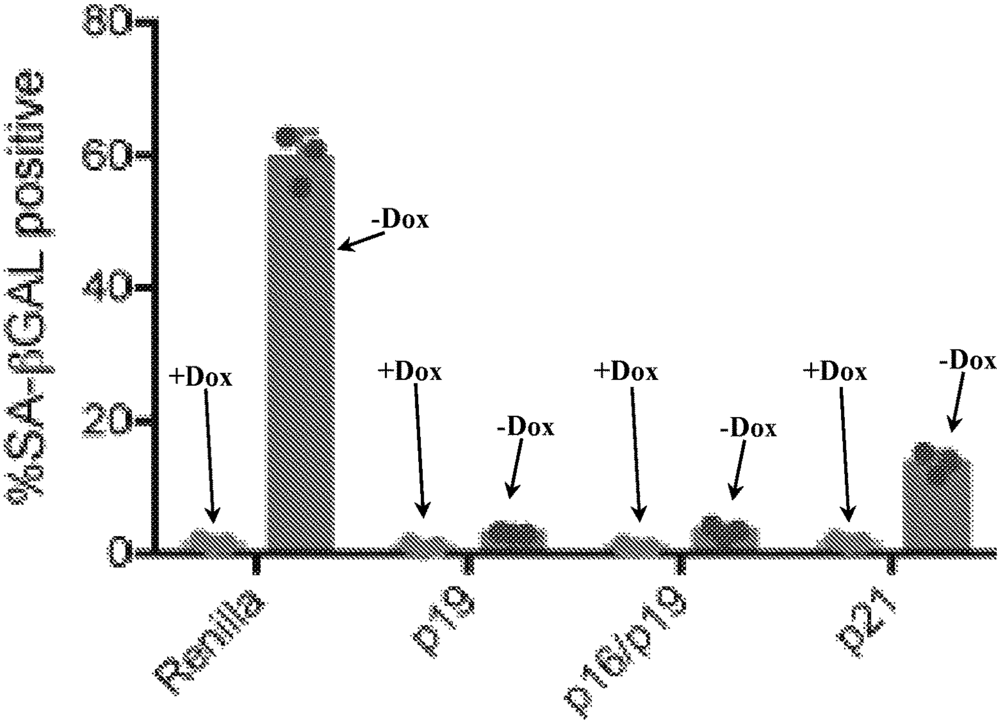
FIGS. 6K-6M show the quantification of the number of SA-13GAL positive cells (FIG. 6K) or BrdU positive cells (FIG. 6L), or αKG/succinate ratio (FIG. 6M) in cells treated as described in FIG. 6F. Data in FIGS. 6A-6M are presented as mean SEM (FIG. 6A) or SD of triplicate wells of a representative experiment with individual data points shown. Significance was assessed by 1-way ANOVA with Tukey's multiple comparison post-test. *, $p<0.05$; *, $p<0.0005$; **, $p<0.0001$. Scale bar 50 μM.
Figure 6L:
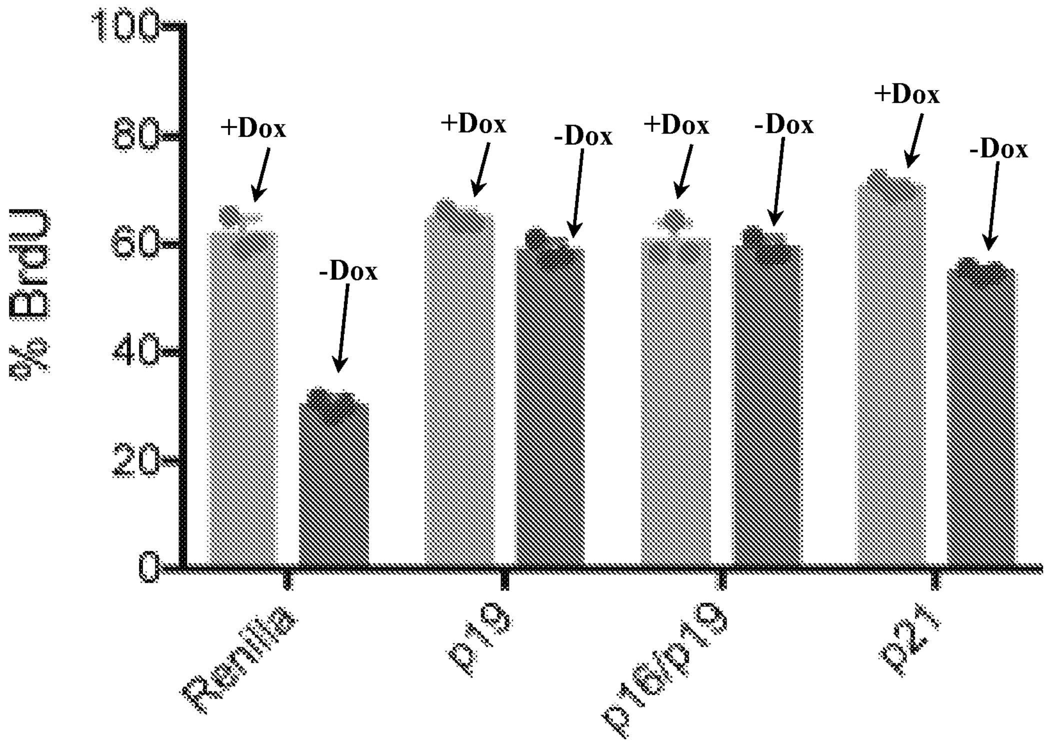
Figure 6M:
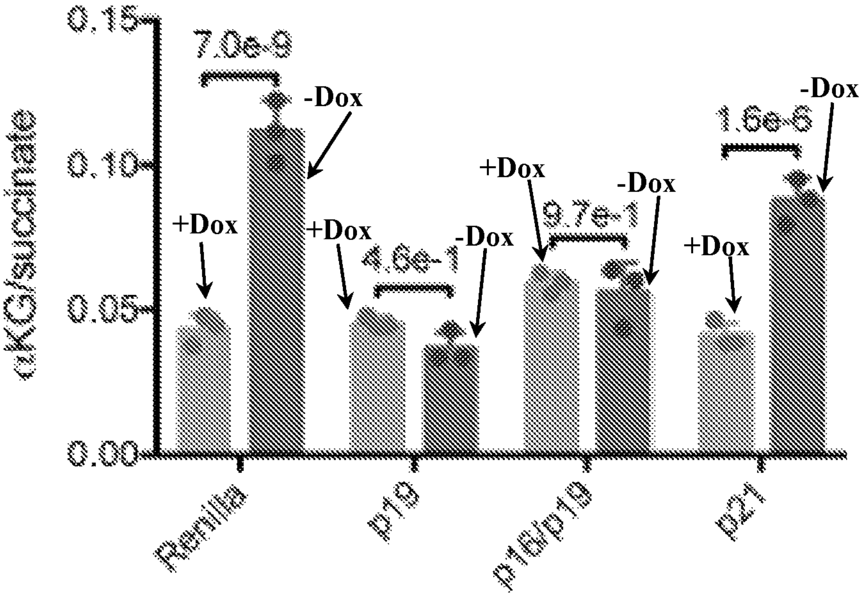
Figure 7A:
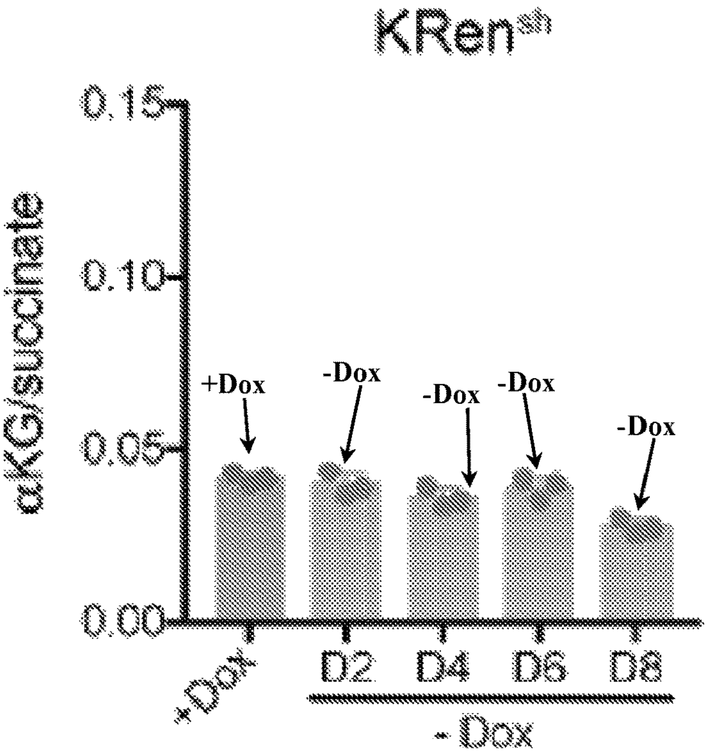
FIG. 7A shows the αKG/succinate ratio in $KP^{sh}$ cells cultured with or without dox for indicated number of days.
Figure 7B:
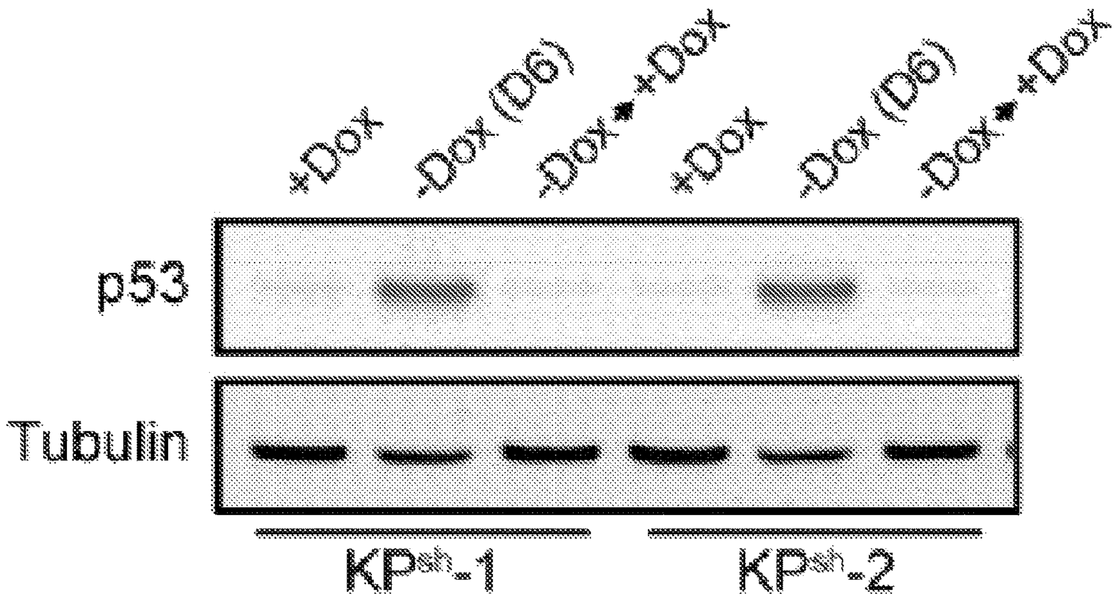
FIG. 7B shows the Western blot for p53 in 2 $KP^{sh}$ lines cultured with (+Dox) or without dox (−Dox) for 6 days or cultured without dox for 6 days, followed by 6 days of culture with dox (−Dox→+Dox).
Figure 7C:
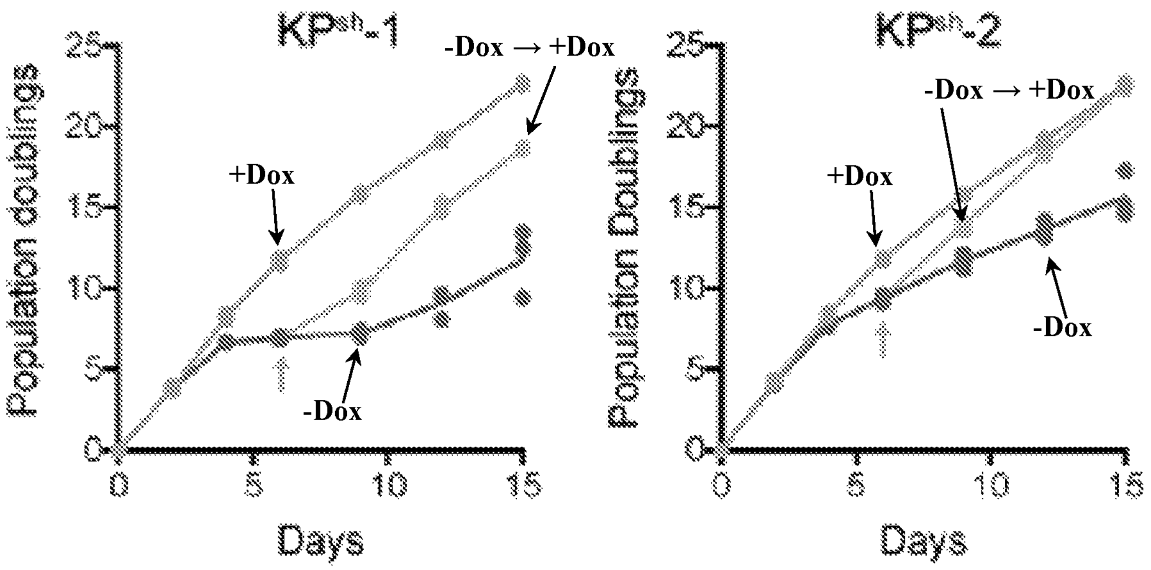
FIG. 7C shows the population doublings of $KP^{sh}$-1 and $KP^{sh}$-2 lines cultured with (+Dox) or without dox (−Dox) for 6 days, or cultured without dox for 6 days, followed by 6 days of culture with dox (−Dox→+Dox).
Figure 7D:
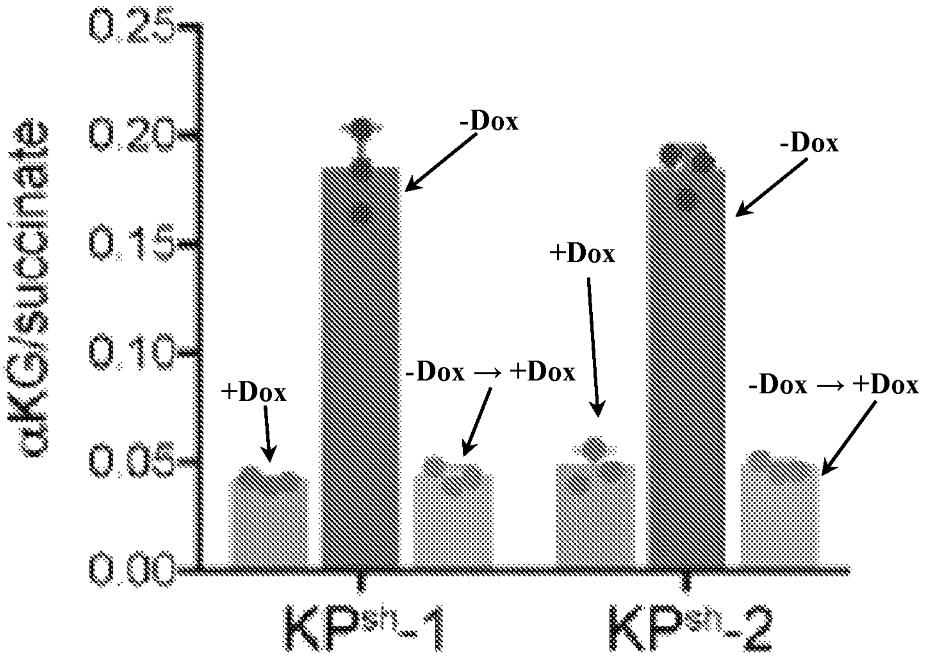
FIG. 7D shows the αKG/succinate ratio in $KP^{sh}$-1 and $KP^{sh}$-2 lines cultured with (+Dox) or without dox (−Dox) for 6 days, or cultured without dox for 6 days, followed by 6 days of culture with dox (−Dox→+Dox). Data are presented as mean SD of triplicate wells of a representative experiment with individual data points shown.

To test whether these metabolic changes are the result of p53 accumulation or are a secondary consequence of cell cycle arrest, pharmacologic and genetic experiments that uncoupled p53 accumulation from cellular proliferation were performed and assessed the effect of each on the αKG/succinate ratio. In one series of experiments, $KP^{sh}$ cells maintained on dox were treated with the chemotherapeutic drug etoposide or the MEK inhibitor trametinib. As shown in FIG. 1H, both treatments triggered cell cycle arrest and senescence but, in contrast to p53 induction, neither altered the αKG/succinate ratio (FIGS. 6B-E). In another set of experiments, $KP^{sh}$ cells were transduced with constitutive shRNAs targeting either Arf or Cdkn1a/p21, which can attenuate p53 accumulation or act downstream to circumvent cell cycle arrest, respectively (FIG. 6F). As shown in FIGS. 6G-6I, upon dox withdrawal, both cell populations failed to arrest or senesce to the same extent as control cells expressing a neutral shRNA targeting *Renilla* luciferase. As shown in FIGS. 6I and 6M, cells with silenced Arf accumulated less p53 than controls and showed no increase in the αKG/succinate ratio. By contrast, Cdkn1a/p21-silenced cells still accumulated p53 and increased the αKG/succinate ratio (FIGS. 6I and 6M). Therefore, the increase in the αKG/succinate ratio was not due to withdrawal of dox after long term exposure (FIG. 7A) and, moreover, was reversible upon p53 suppression following dox re-addition (FIG. 7B-7D). Collectively, these results demonstrate that p53 accumulation, rather than dox withdrawal or senescence, induces the αKG/succinate ratio in Kras-driven PDAC cells.

Figure 8A:
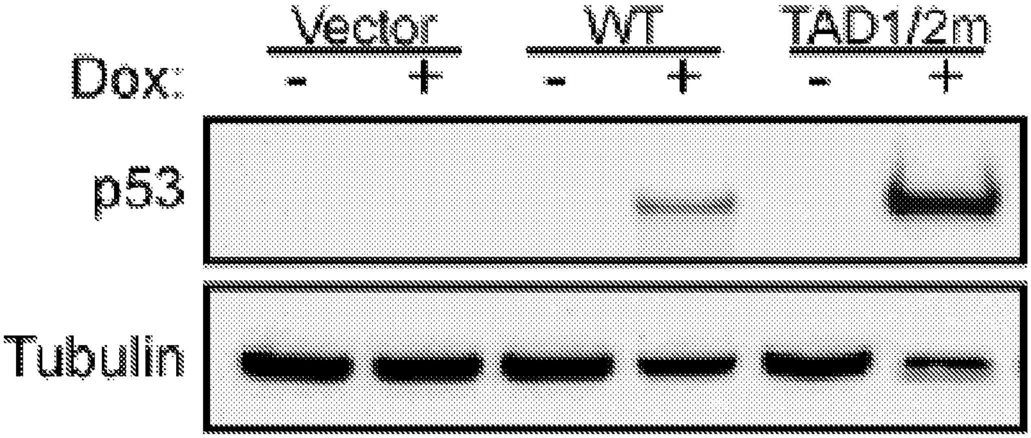
FIG. 8A shows the western blot analysis of p53 in $KP^{flox}$RIK-TRE-Empty (Vector), $KP^{flox}$RIK-TRE-$p53^{WT}$ (WT), and $KP^{flox}$RIK-TRE-$p53^{TAD1/2M}$(TAD1/2m) cells grown with dox for 2 days.
Figure 8B:
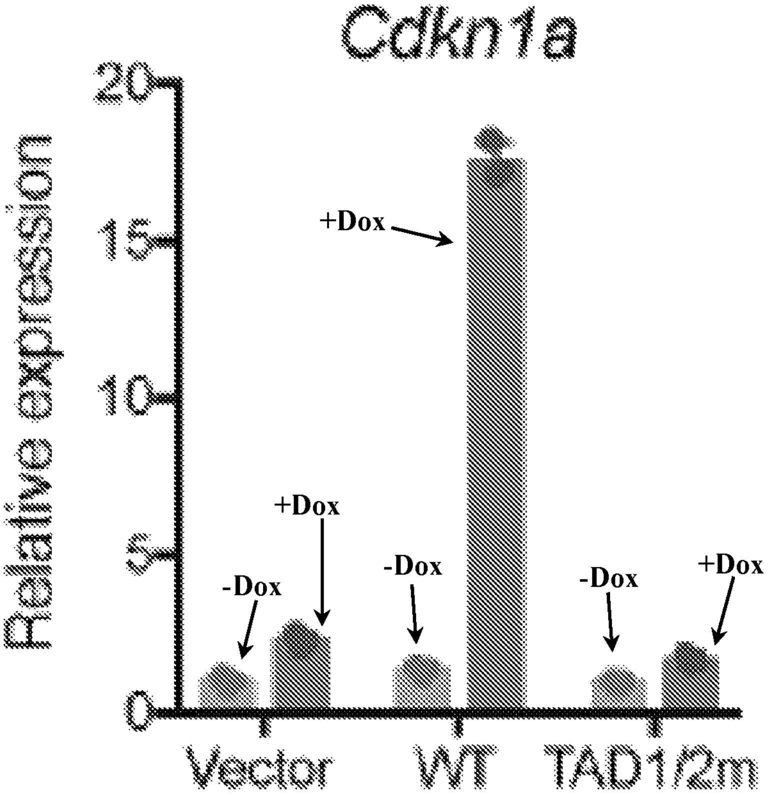
FIG. 8B shows the analysis of Cdkn1a/p21 expression evaluated by qRT-PCR in $KP^{flox}$RIK-TRE-Empty, $KP^{flox}$RIK-TRE-$p53^{WT}$, and $KP^{flox}$RIK-TRE-$p53^{TAD1/2M}$ cells grown with dox for 2 days.
Figure 8C:
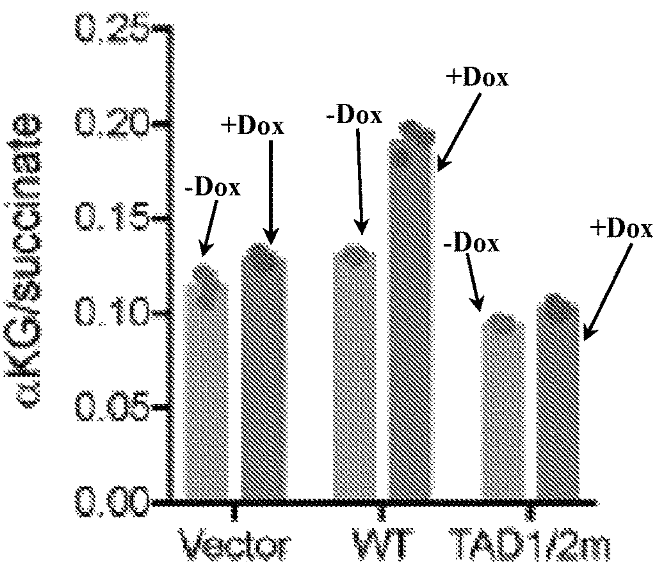
FIG. 8C shows the αKG/succinate ratio in $KP^{flox}$RIK-TRE-Empty, $KP^{flox}$RIK-TRE-$p53^{WT}$, and $KP^{flox}$RIK-TRE-$p53^{TAD1/2M}$ cells grown with dox for 2 days.
Figure 8D:
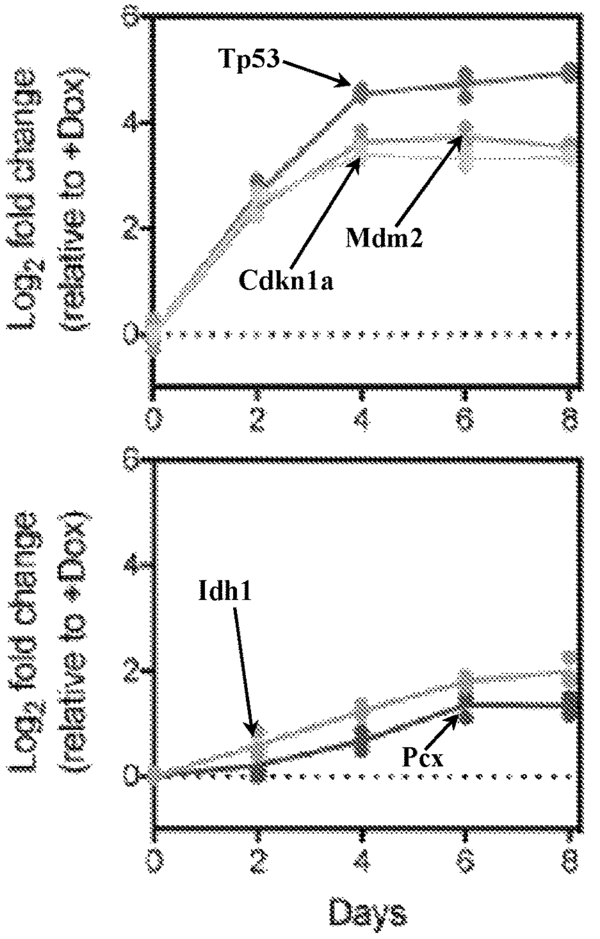
FIG. 8D shows the Cdkn1a/p21, Mdm2, p53 expression (top) and Idh1 and Pcx expression (bottom) evaluated by qRT-PCR in $KP^{sh}$-2 cells grown with or without dox for the indicated number of days. Expression values for Cdkn1a/p21, Mdm2, and p53 at day 6 are the same as displayed in FIG. 1A.
Figure 8E:
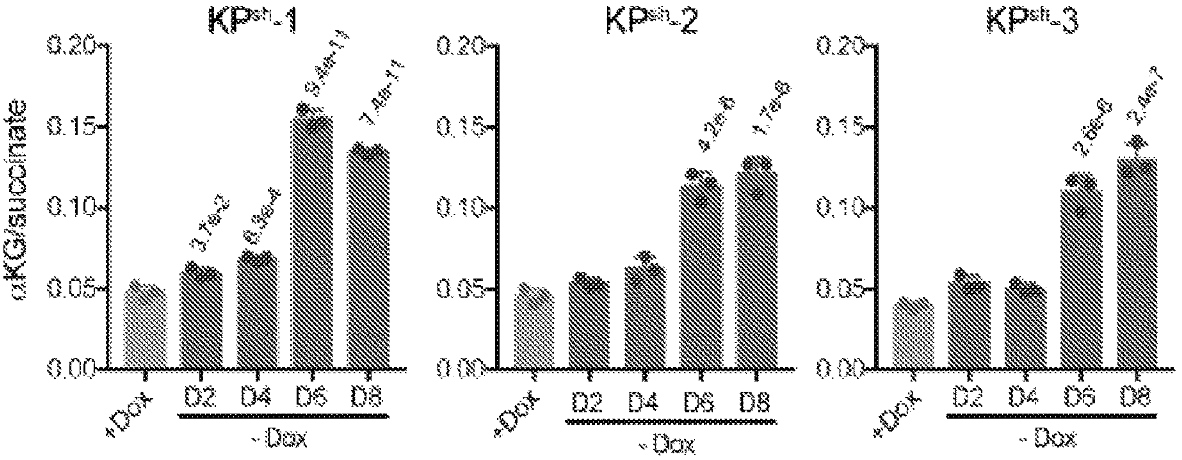
FIG. 8E shows the αKG/succinate ratio in $KP^{sh}$1-3 lines grown with or without dox for the indicated number of days.
Figure 8F:
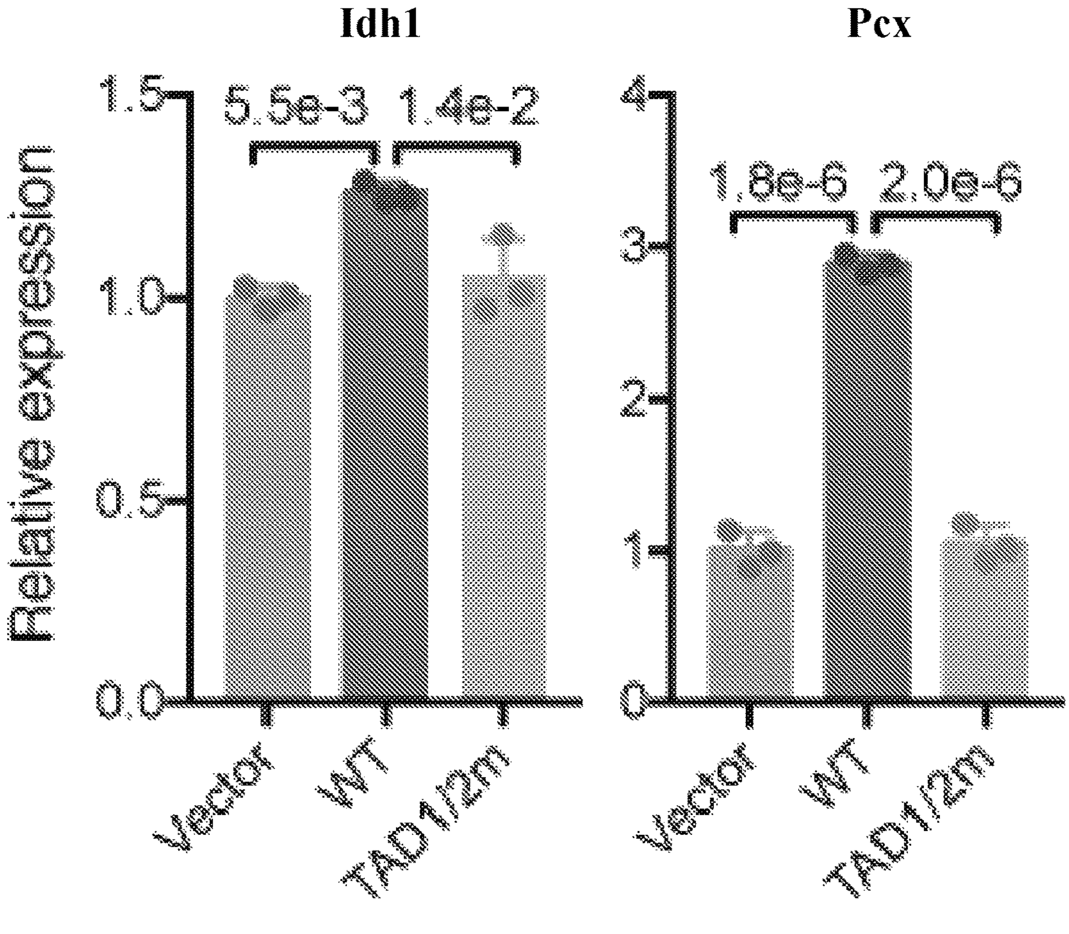
FIG. 8F shows the Idh1 and Pcx expression evaluated by qRT-PCR in $KP^{flox}$RIK-TRE-Empty, $KP^{flox}$RIK-TRE-$p53^{WT}$, and $KP^{flox}$RIK-TRE-$p53^{TAD1/2m}$ cells grown with dox for 2 days.
Figure 8G:
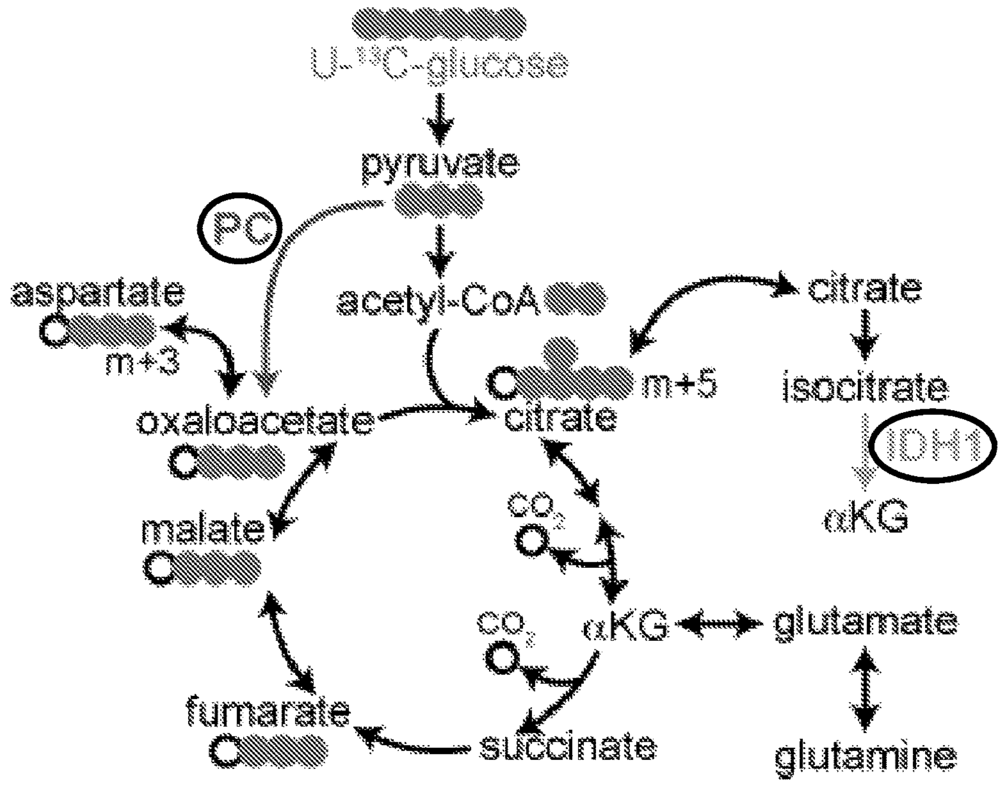
FIG. 8G shows a schematic of glucose labeling patterns associated with PC activity. Reactions dependent on IDH1 and PC activity are indicated with ovals.
Figure 8H:
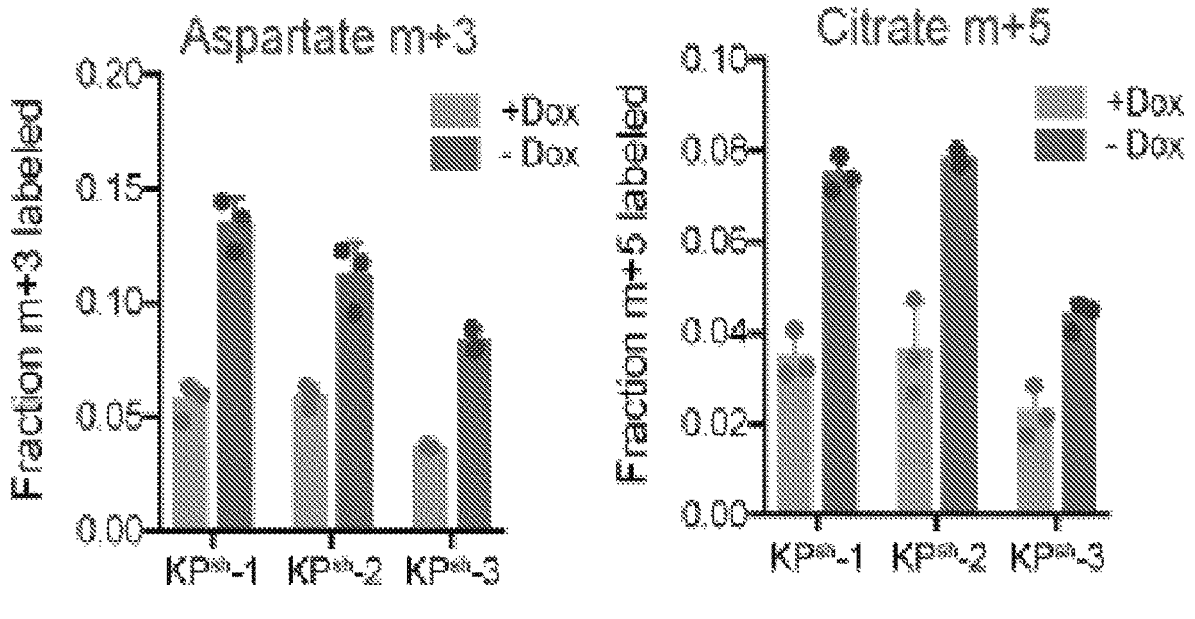
FIG. 8H shows the fractional m+3 (top) or m+5 (bottom) labeling of aspartate and citrate in cells cultured with or without dox for six days after four hours of culture in medium containing [U-$^{13}$C]glucose.
Figure 8I:
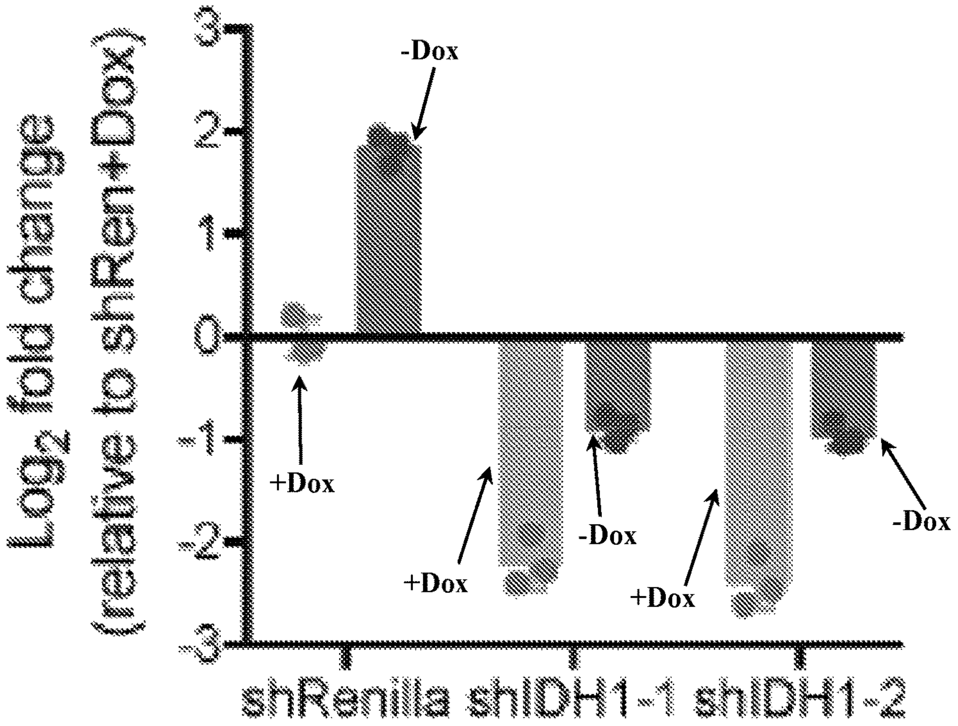
FIG. 8I shows the analysis of Idh1 expression as evaluated by qRT-PCR in $KP^{sh}$-2 cells expressing constitutive hairpins targeting *Renilla* or Idh1 grown with or without dox for 8 days.
Figure 8J:
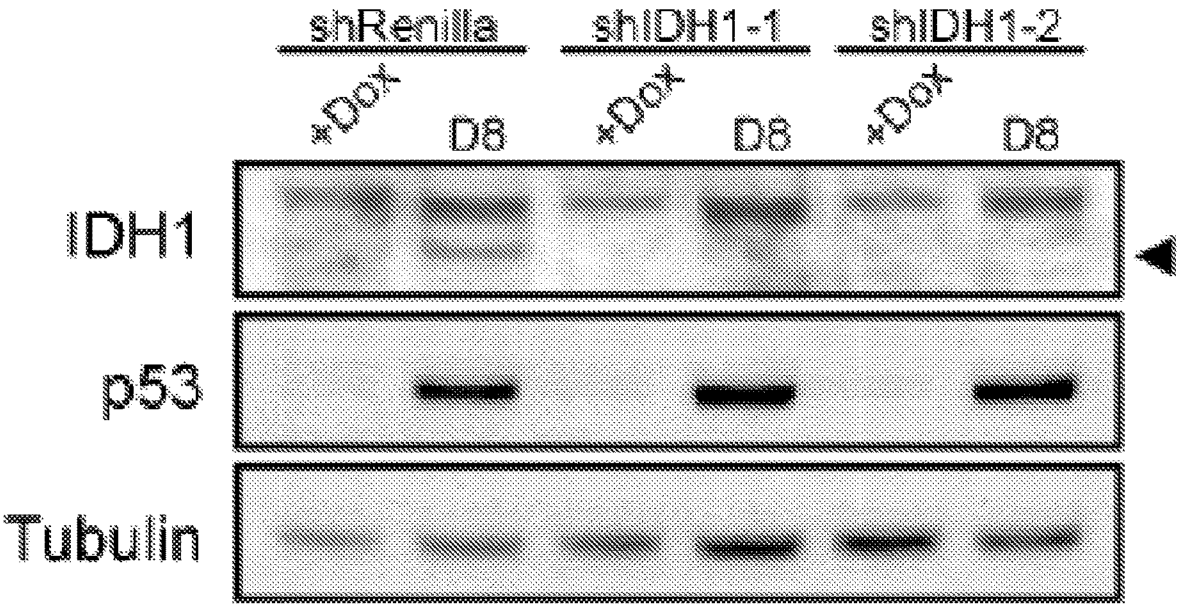
FIG. 8J shows the Idh1 and p53 western blot of $KP^{sh}$-2 cells expressing constitutive hairpins targeting *Renilla* or Idh1 grown with or without dox for 8 days. Arrowhead indicates specific Idh1 band.
Figure 8K:
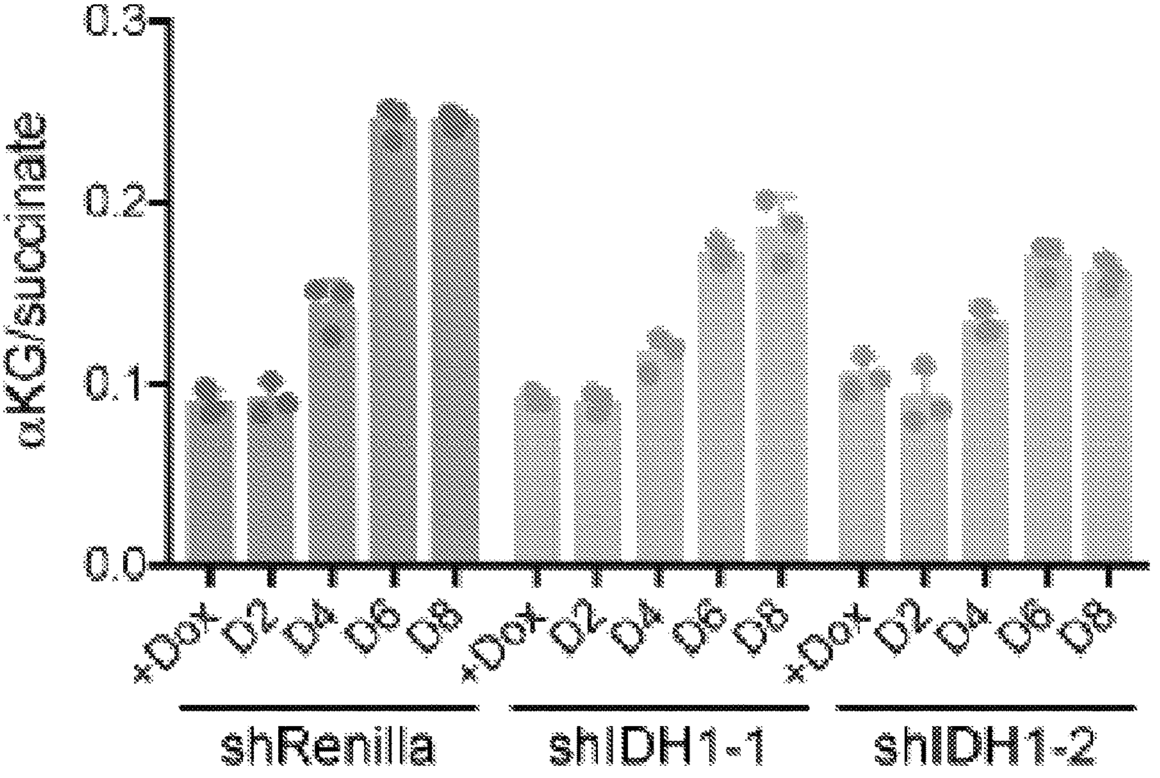
FIG. 8K shows the αKG/succinate ratio in $KP^{sh}$-2 cells expressing constitutive hairpins targeting *Renilla* or Idh1 grown with or without dox for the indicated number of days.
Figure 8L:
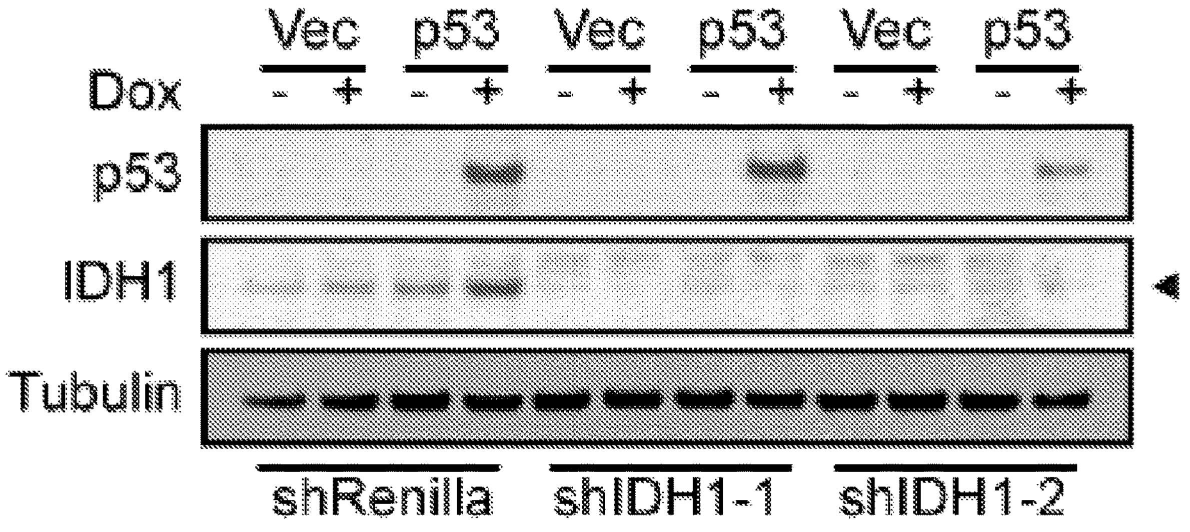
FIG. 8L shows the p53 and Idh1 western blot in $KP^{flox}$RIK-TRE-Empty and $KP^{flox}$RIK-TRE-$p53^{WT}$ cells expressing constitutive hairpins targeting *Renilla* or Idh1 grown with dox for 2 days.
Figure 8M:
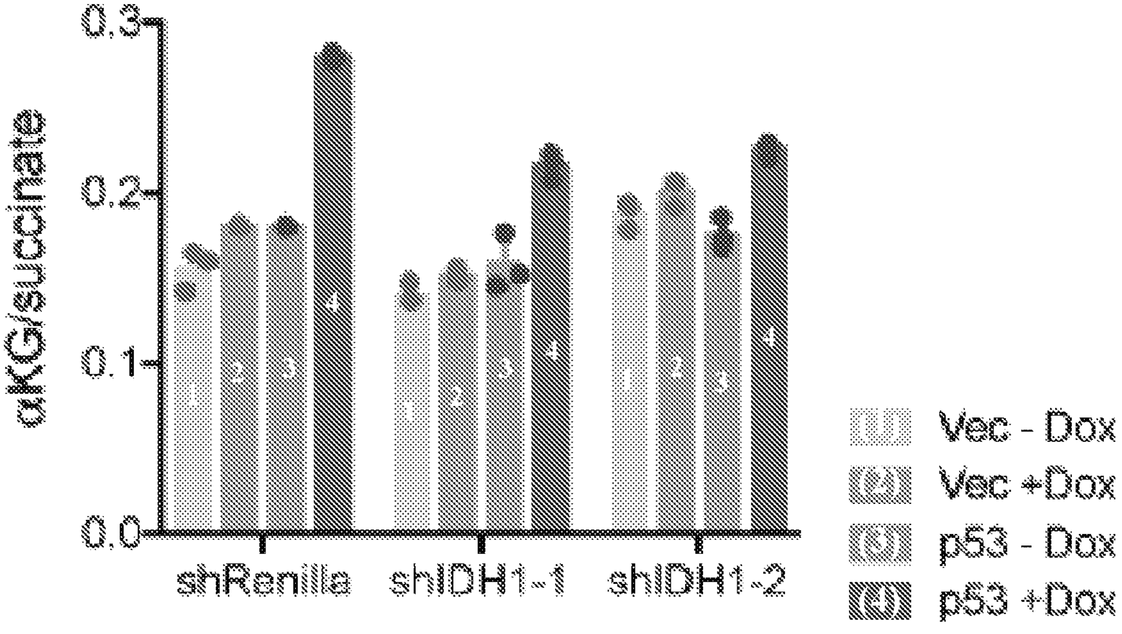
FIG. 8M shows the αKG/succinate ratio in $KP^{flox}$RIK-TRE-Empty, and $KP^{flox}$RIK-TRE-$p53^{WT}$ cells expressing constitutive hairpins targeting *Renilla* or Idh1 grown with dox for 2 days. Data are presented as mean SD of triplicate wells of a representative experiment with individual data points shown. Significance was assessed by 1-way ANOVA with Sidak's multiple comparisons post-test. *, p<0.05, , p<0.005; **, p<547 0.0001.
Figure 8N:
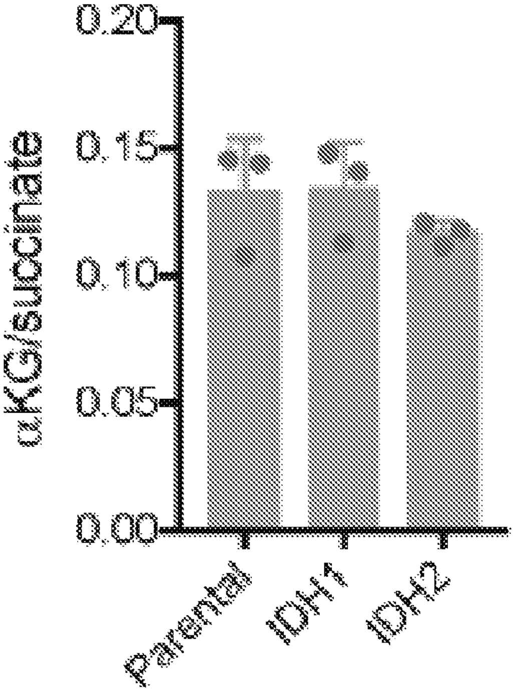
FIG. 8N shows the αKG/succinate ratio in parental KPsh-2 versus KPsh-2 expressing IDH1 or IDH2 cDNA grown on dox.
Figure 9A:
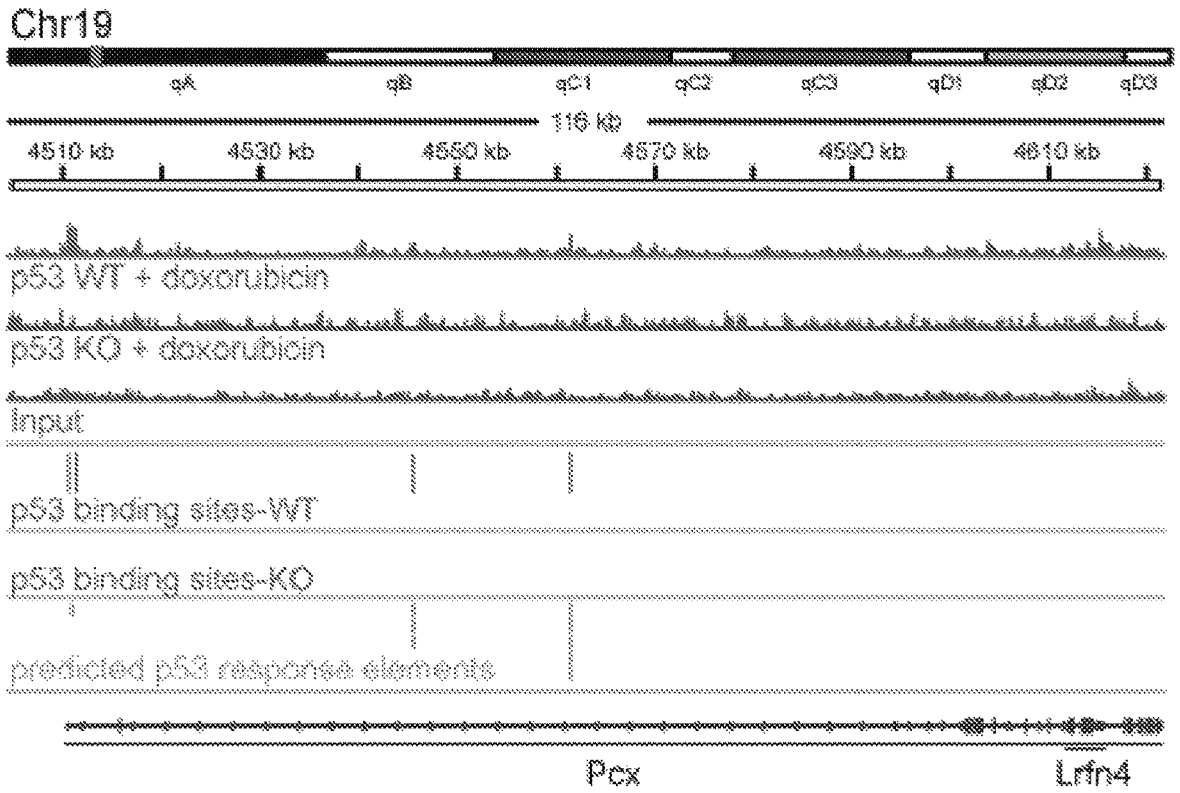
FIG. 9A shows the analysis of ChIP-Seq signal at the Pcx locus in primary $p53^{WT}$ and $p53^{null}$ (KO) mouse embryonic fibroblasts after treatment with doxorubicin.
Figure 9B:
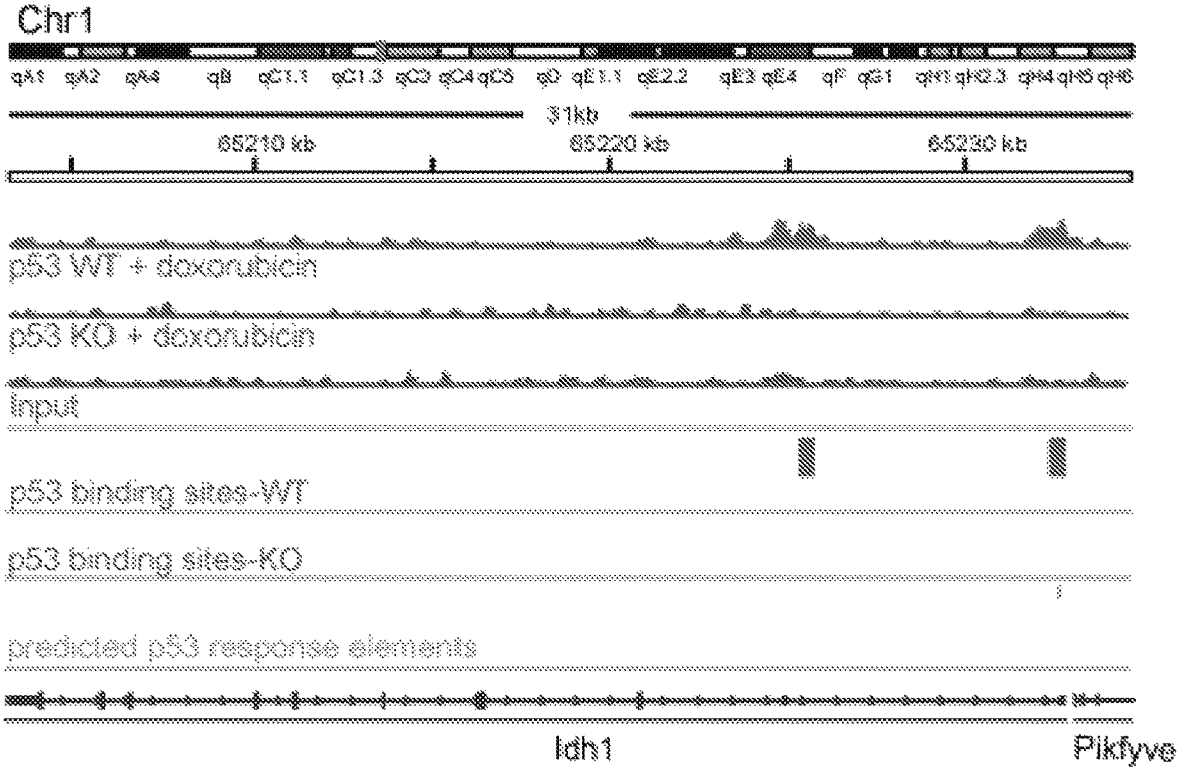
FIG. 9B shows the analysis of ChIP-Seq signal at the Idh1 locus in primary $p53^{WT}$ and $p53^{null}$ (KO) mouse embryonic fibroblasts after treatment with doxorubicin. p53 binding sites were predicted by MACs comparison of immunoprecipitation samples with input. Response elements predicted by Homer analysis as described in the methods disclosed herein. ChIP-Seq data from Kenzelmann Broz et al., *Genes & Development* 27: 1016-1031 (2013).

Example 3: Functional p53 Transactivation is Required to Increase the Cellular αKG/Succinate Ratio The tumor suppressor activity of p53 is most closely associated with its ability to transcriptionally activate downstream target genes. Accordingly, as shown in FIGS. 8A-8C, enforced expression of wild-type p53 but not a well characterized transactivation-defective p53 mutant was able to induce Cdkn1a/p21 and increase the αKG/succinate ratio in p53 null PDAC cells. As shown in FIGS. 8D-8F, transcriptional profiling following endogenous p53 restoration in $KP^{sh}$ cells revealed a significant increase in the TCA cycle enzymes pyruvate carboxylase (Pcx, PC) and isocitrate dehydrogenase 1 (Idh1) with kinetics similar to those of the increase in the αKG/succinate ratio and in a manner that was transactivation domain dependent. PC enables glucose-derived anaplerosis that can relieve the requirement for consumption of glutamine-derived αKG by the TCA cycle, while IDH1 generates cytosolic αKG from citrate, and so increased levels of either enzyme (or both) could lead to accumulation of αKG (FIG. 8G). Indeed, as shown in FIG. 8H, p53 activation was accompanied by an increase in glucose anaplerosis associated with PC activity and inhibition of p53-driven Idh1 expression blunted the p53-mediated increase in the αKG/succinate ratio (FIGS. 8I-8M). Although the precise mechanism whereby p53 influences PC and IDH1 levels remains to be determined, p53 was found to directly bind predicted p53 binding sites in the Pcx and Idh1 genes, as shown in FIGS. 9A-9B, suggesting that changes in TCA enzyme levels arising as a part of canonical p53 transcriptional functions including direct transactivation by p53 likely contribute to metabolic reprogramming driven by p53.

Figure 2A:
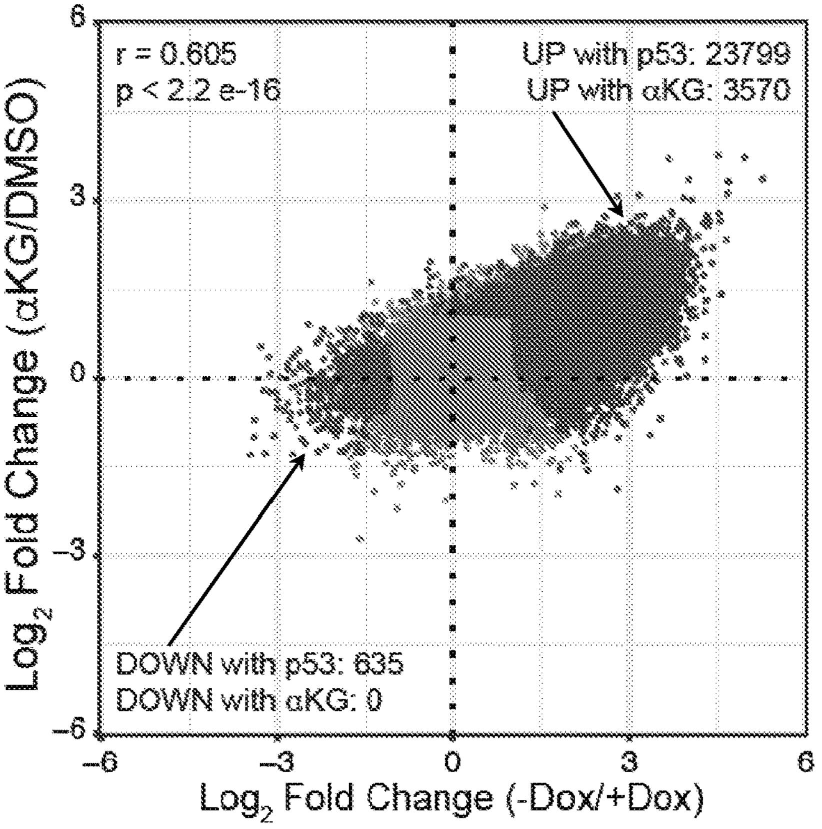
FIG. 2A shows a scatter plot depicting the $\log_2$ fold change of all ATAC-Seq peaks following p53 reactivation (−dox/+dox) or treatment with cell-permeable αKG (αKG/DMSO) in $KP^{sh}$-1 cells. All samples contained equivalent amounts of vehicle (DMSO). Pearson correlation r=0.605, p<2.2e-16. Number of peaks increased or decreased by at least two-fold with a false discovery rate <0.1 in each condition are shown. Peaks increased (red) or decreased (blue) by this threshold under either condition are highlighted.
Figure 2B:
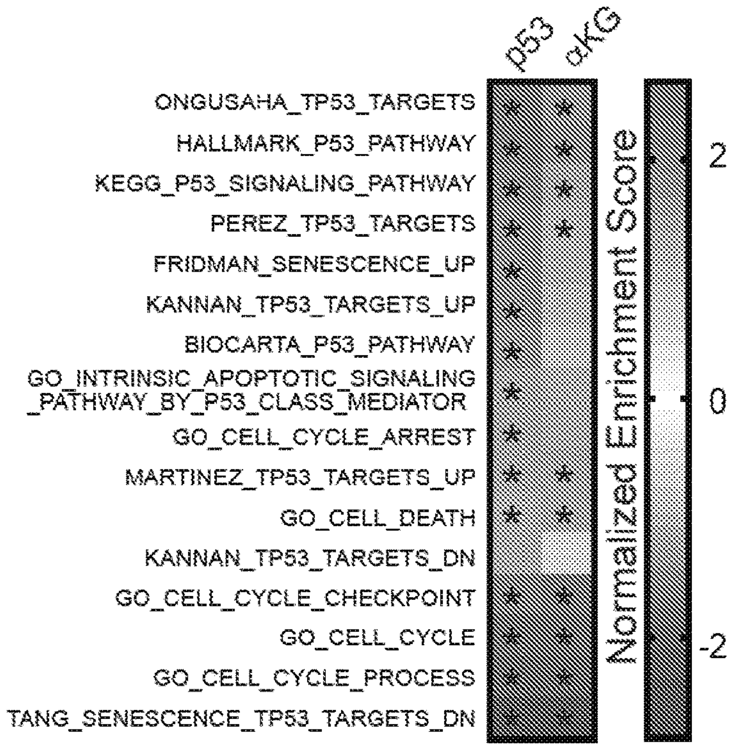
FIG. 2B shows a heat map depicting normalized gene enrichment score of published p53-associated gene sets using RNA-Seq analysis of $KP^{sh}$-1 cells. Genes were ranked by fold change with p53 restoration or αKG treatment, and gene set enrichment analysis (GSEA) was performed. Gene sets significantly (p<0.05) enriched (red) or depleted (blue) are marked with an asterisk.
Figure 2C:
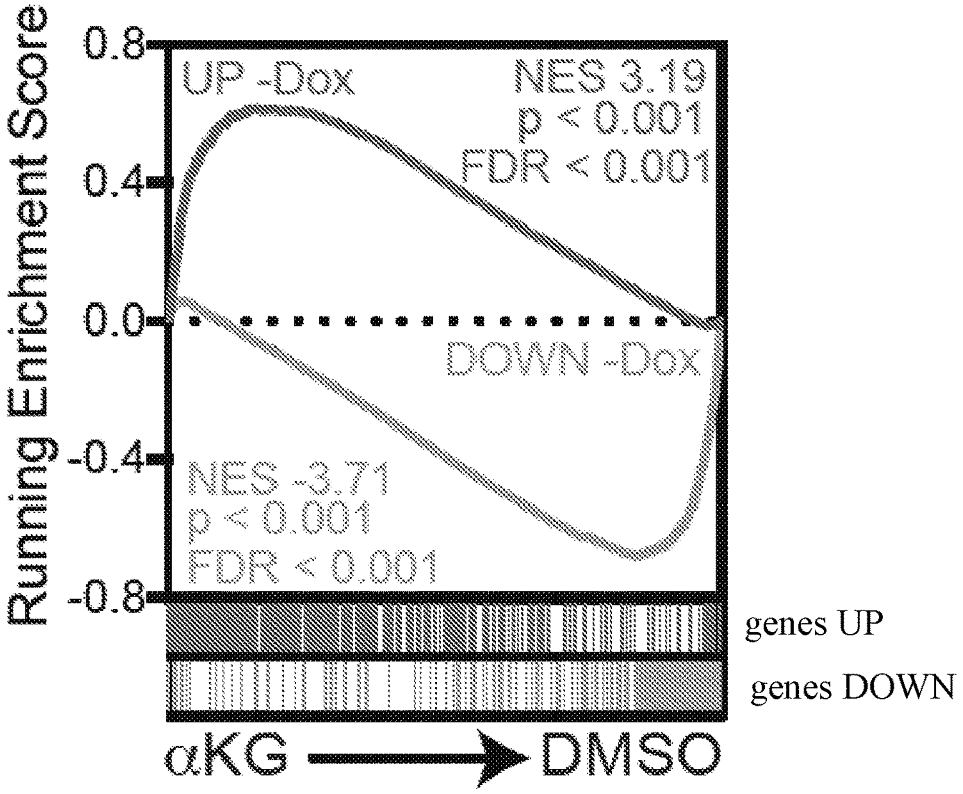
FIG. 2C shows the GSEA analyses of RNA-Seq data of $KP^{sh}$-1 cells treated with cell-permeable αKG showing enrichment of genes upregulated (genes UP) or downregulated (genes DOWN) at least 2-fold, padj<0.05 following p53 restoration.
Figure 10A:
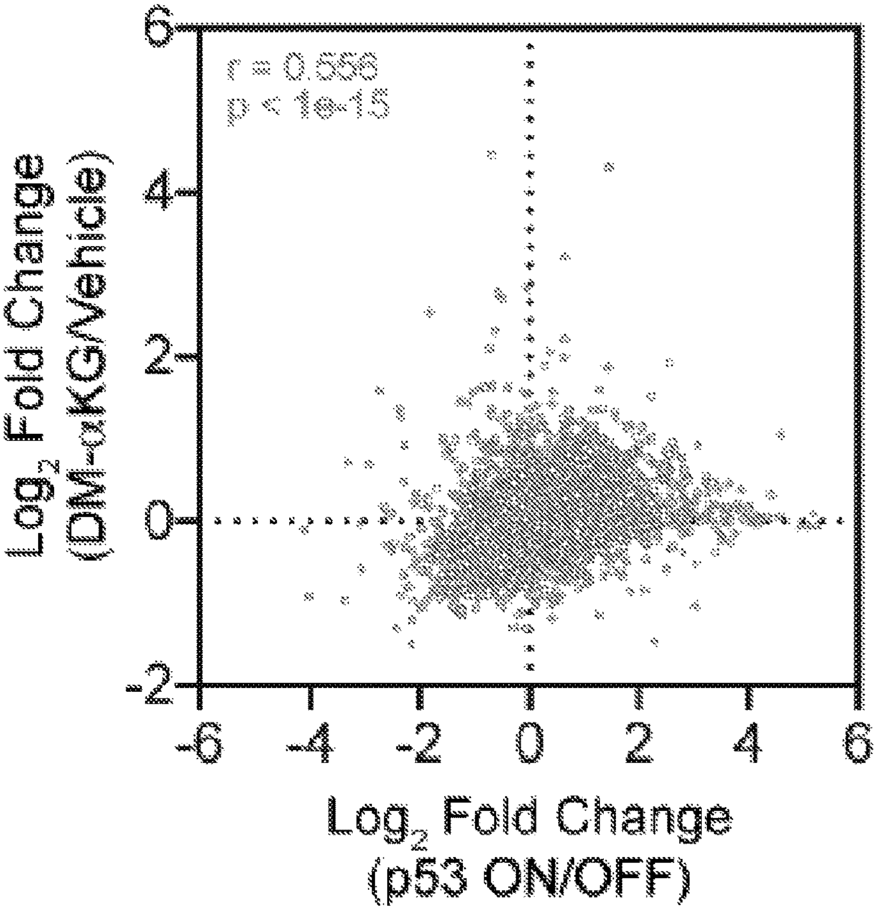
FIG. 10A shows a scatter plot depicting the $\log_2$ fold change calculated by Deseq2 of all genes following p53 reactivation (−dox/+dox) or treatment with cell-permeable αKG (αKG/DMSO) in $KP^{sh}$-1 cells. All samples contained equivalent amounts of vehicle (DMSO). Spearman correlation r=0.556, p<1e-15.

Example 4: αKG Recapitulates Gene Expression Changes Induced by p53 Restoration Alterations in the intracellular αKG/succinate ratio are associated with changes in the activity of αKG-dependent chromatin modifying enzymes that ultimately alter transcription. To determine the extent to which αKG alone could recapitulate the effects of p53 on global chromatin states and gene expression, ATAC-Seq was performed (which provides a global view of chromatin accessibility that can reflect changes in αKG-dependent enzyme function) and RNA-Seq on $KP^{sh}$ cells subjected either to dox withdrawal to trigger p53 reactivation or treatment with cell-permeable αKG in the presence of dox to maintain p53 suppression. As shown in FIG. 2A, both p53 and αKG produced a global increase in chromatin accessibility, with a strong correlation between those regions affected by p53 and αKG ($r=0.605$, $p<2.2e-16$). Moreover, as shown in FIG. 10A, there was a significant correlation between transcriptional profiles produced by p53 and αKG treatment ($r=0.556$; $p<1e-15$), with both treatments resulting in gene expression signatures previously linked to p53 action (FIG. 2B), and cell-permeable αKG recapitulating trends observed in the transcriptional response produced by p53 restoration in $KP^{sh}$ cells (FIG. 2C).

Figure 2D:
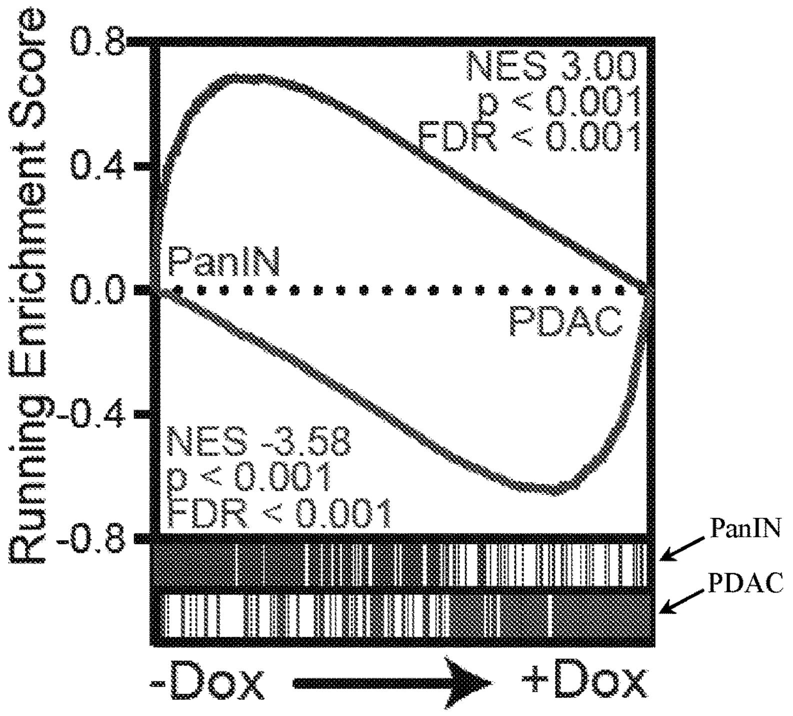
FIGS. 2D-2E show the GSEA analyses demonstrating that genes associated with PanIN-stage cells are enriched following p53 restoration (FIG. 2D) or αKG treatment (FIG. 2E) and genes associated with PDAC-stage cells are downregulated following p53 restoration (FIG. 2D) or αKG treatment (FIG. 2E).
Figure 2E:
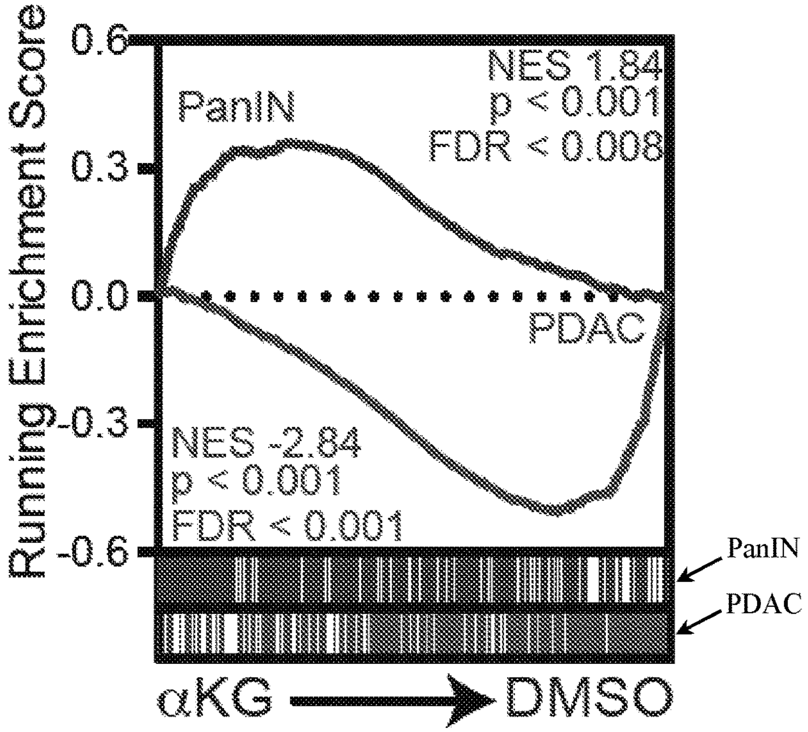
Figure 2F:
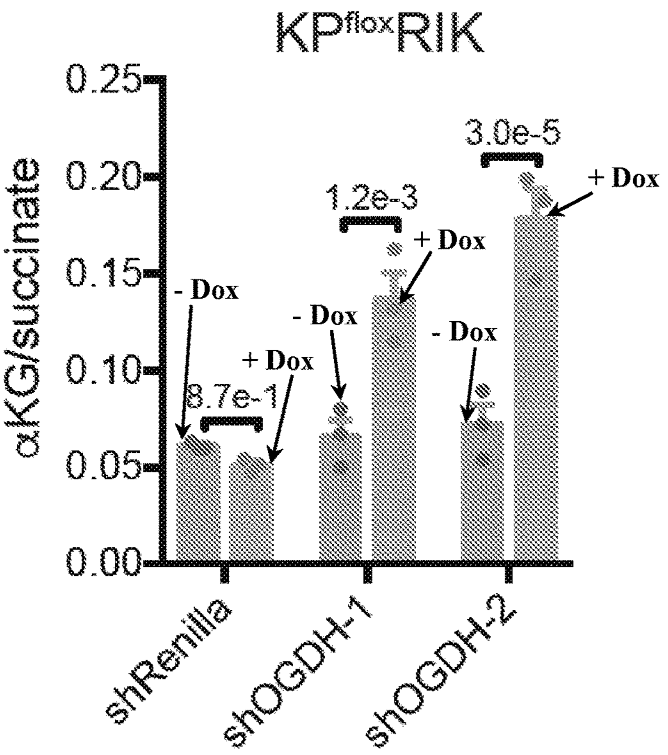
FIG. 2F shows the αKG/succinate ratio of p53 null ($KP^{flox}$RIK) cells expressing dox-inducible shRNAs targeting Ogdh or *Renilla* luciferase (control) grown 4 days with or without dox. Data are presented as mean SEM of triplicate wells of a representative experiment with individual data points shown. Significance was assessed by 2-way ANOVA with Sidak's multiple comparisons post-test. Expression is shown relative to shRenilla-expressing cells. p values are shown.
Figure 2G:
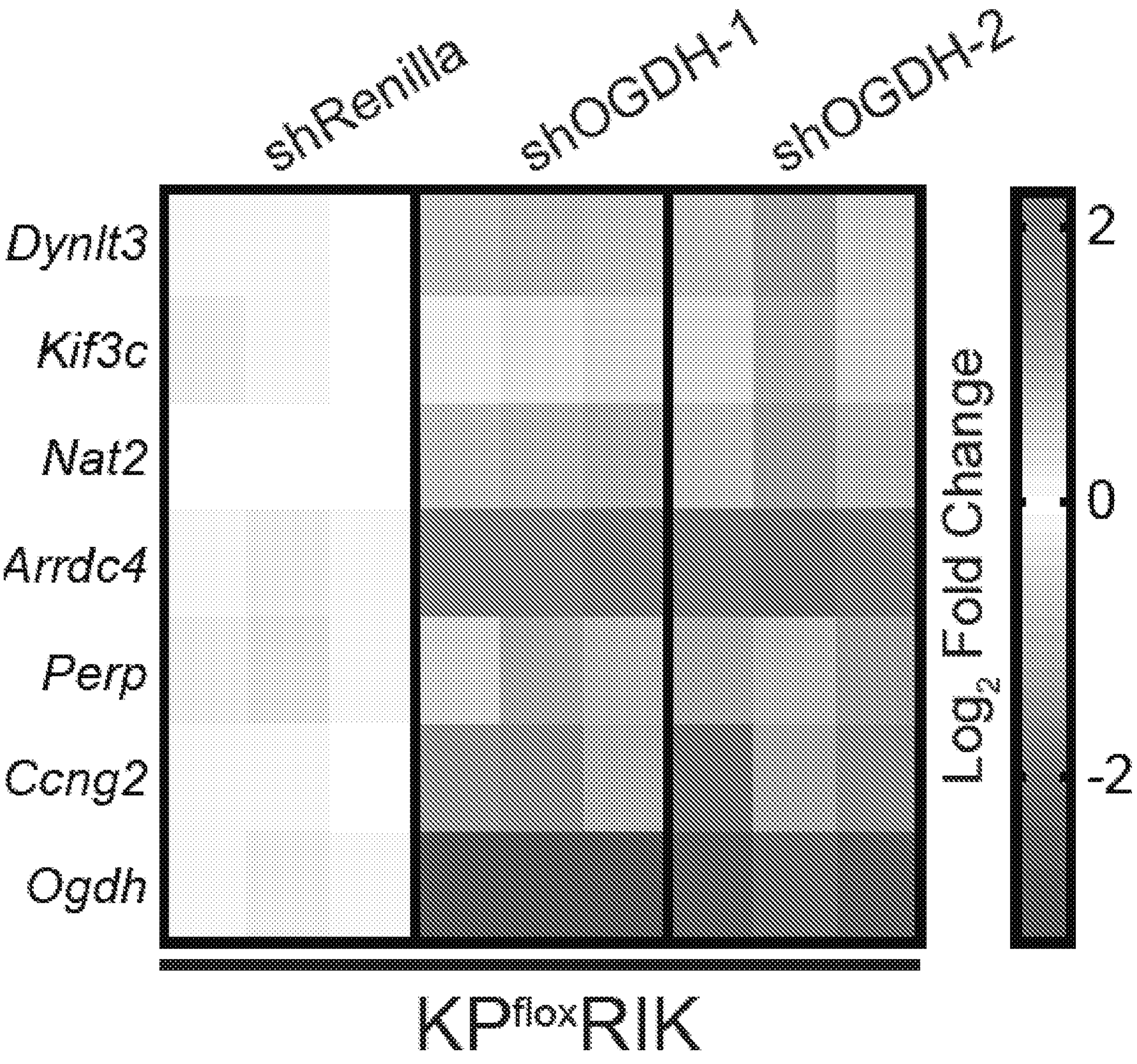
FIG. 2G shows that knockdown of Ogdh increased the αKG/succinate ratio to a similar degree as p53 and induced the expression of genes that could be induced by either p53 re-expression or αKG addition.
Figure 10B:
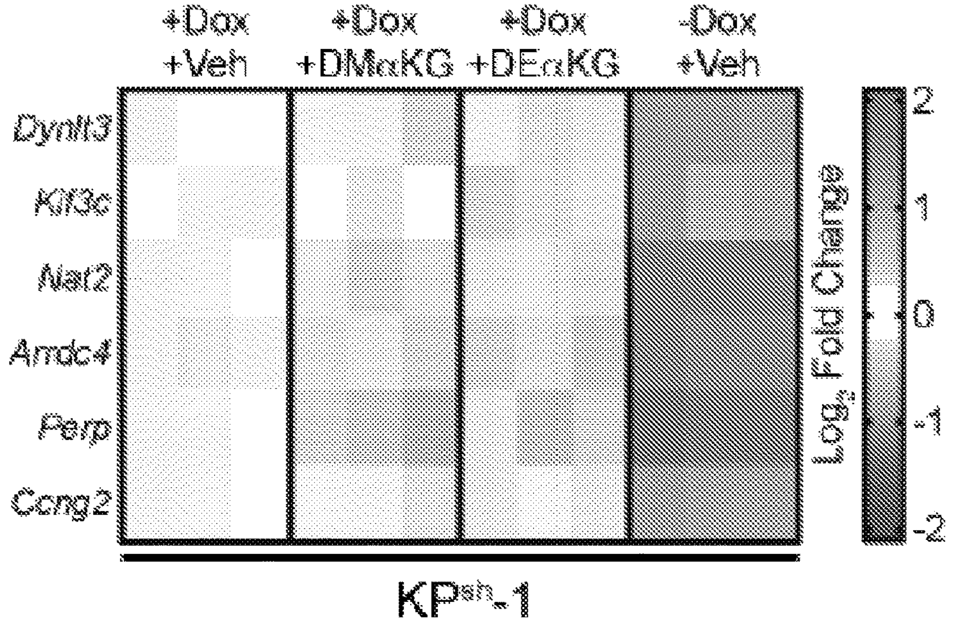
FIG. 10B shows the qRT-PCR analysis of genes upregulated with both p53 restoration and αKG treatment in $KP^{sh}$-1 cells treated for 72 h with vehicle, dimethyl-αKG (DM-αKG), diethyl-αKG (DE-αKG) or following p53 restoration (−dox 8 days).
Figure 10C:
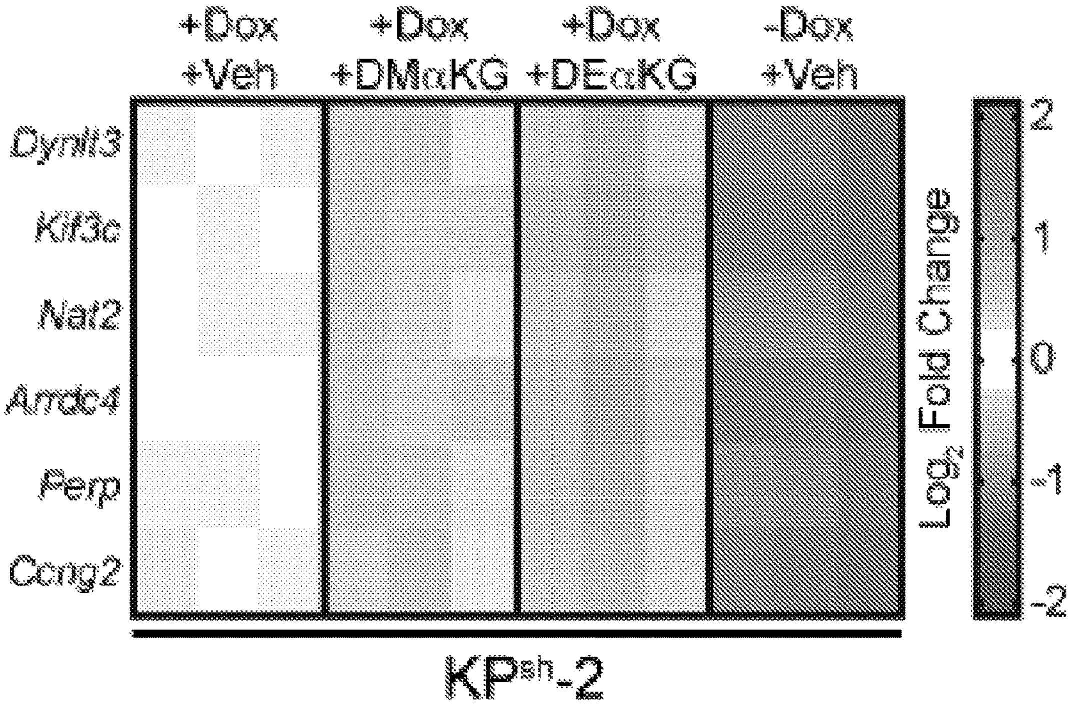
FIG. 10C shows the qRT-PCR analysis of genes upregulated with both p53 restoration and αKG treatment in $KP^{sh}$-2 cells treated for 72 h with vehicle, dimethyl-αKG (DM-αKG), diethyl-αKG (DE-αKG) or following p53 restoration (−dox 8 days).
Figure 10D:
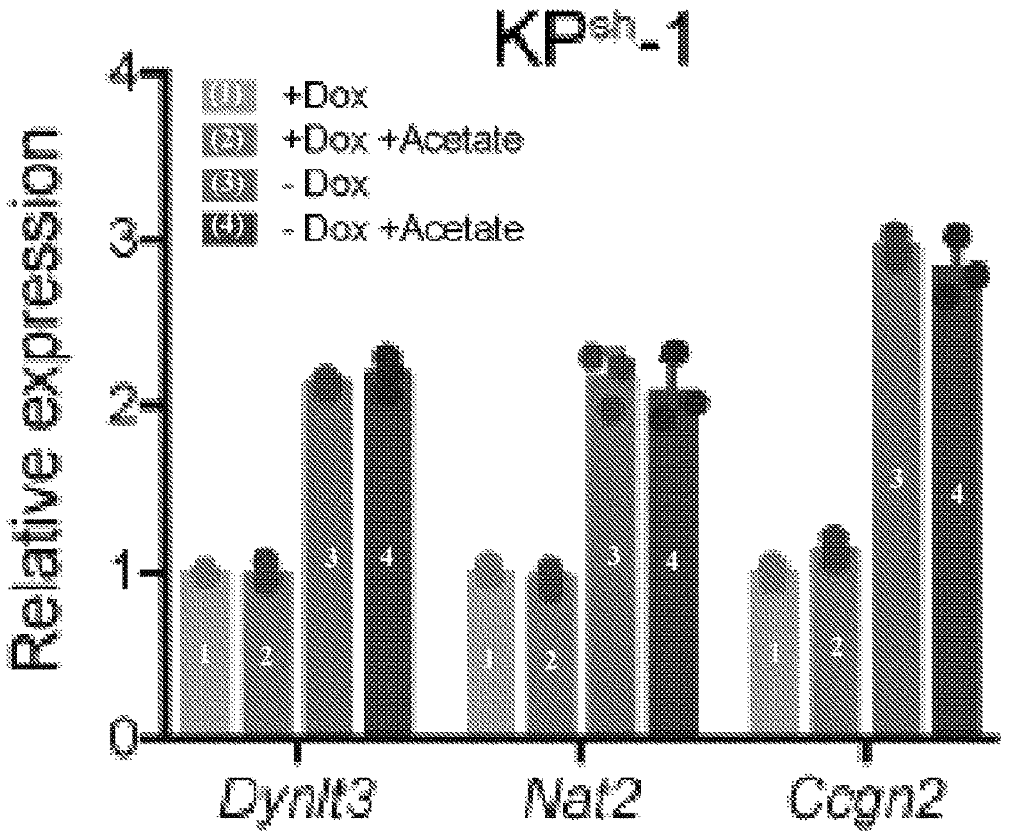
FIG. 10D shows the evaluation of PanIN associated genes by qRT-PCR in $KP^{sh}$-1 cells grown with or without dox and treated with 4 mM sodium acetate for 72 hours. Cells grown without dox are included as positive control.

As p53 inactivation is associated with malignant progression during pancreatic tumorigenesis, to evaluate whether gene expression programs regulated by p53 and αKG reflect defined stages of pancreatic cancer. Remarkably, as shown in FIGS. 2D-2E, both p53 and cell-permeable αKG triggered a robust increase in expression of genes selectively expressed in cells derived from premalignant PanIN lesions and concomitant downregulation of genes enriched in malignant PDAC cells. A similar induction in pre-malignant associated genes co-regulated by endogenous p53 and αKG was observed in cells treated with distinct forms of cell-permeable αKG, but not with acetate, a metabolite downstream of citrate that can regulate gene expression by contributing to histone acetylation (FIG. 2F and FIGS. 10B-10C).

Figure 10E:
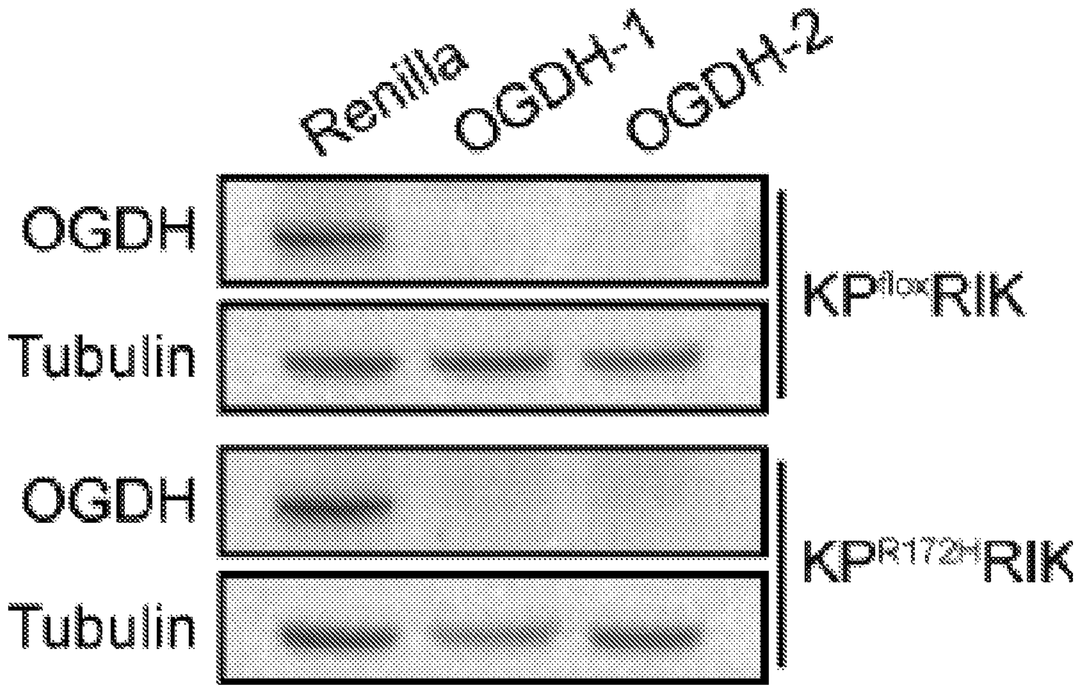
FIG. 10E shows a western blot assessing Ogdh protein levels in p53 null ($KP^{flox}$RIK) or p53 mutant ($KP^{R172H}$RIK) cells treated with dox for four days.
Figure 10F:
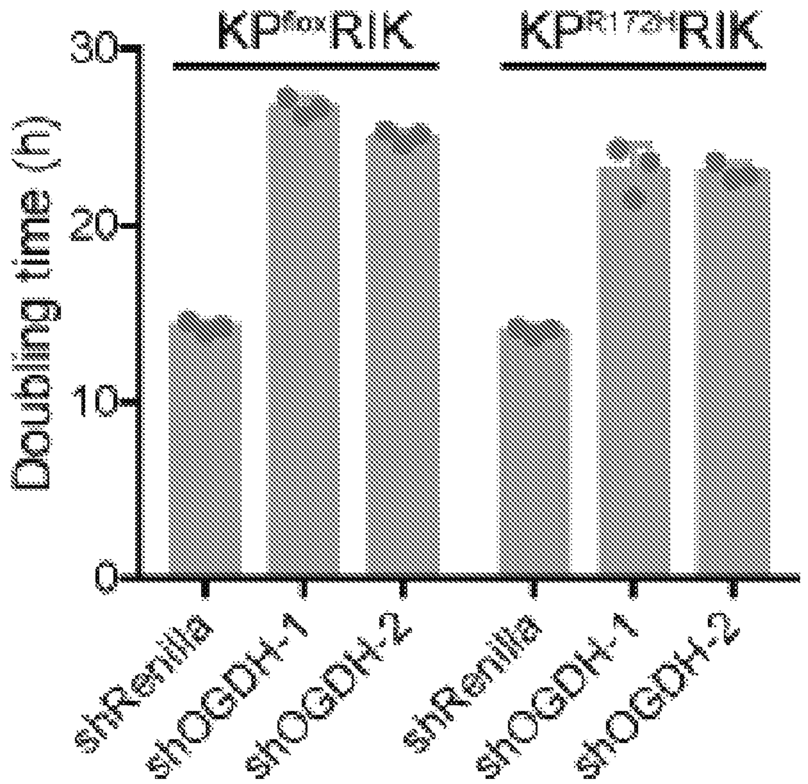
FIG. 10F shows the doubling time of $KP^{flox}$RIK and $KP^{R172H}$RIK cells expressing dox-inducible shRNAs targeting Ogdh or *Renilla* luciferase from day 1-4 following dox addition.
Figure 10G:
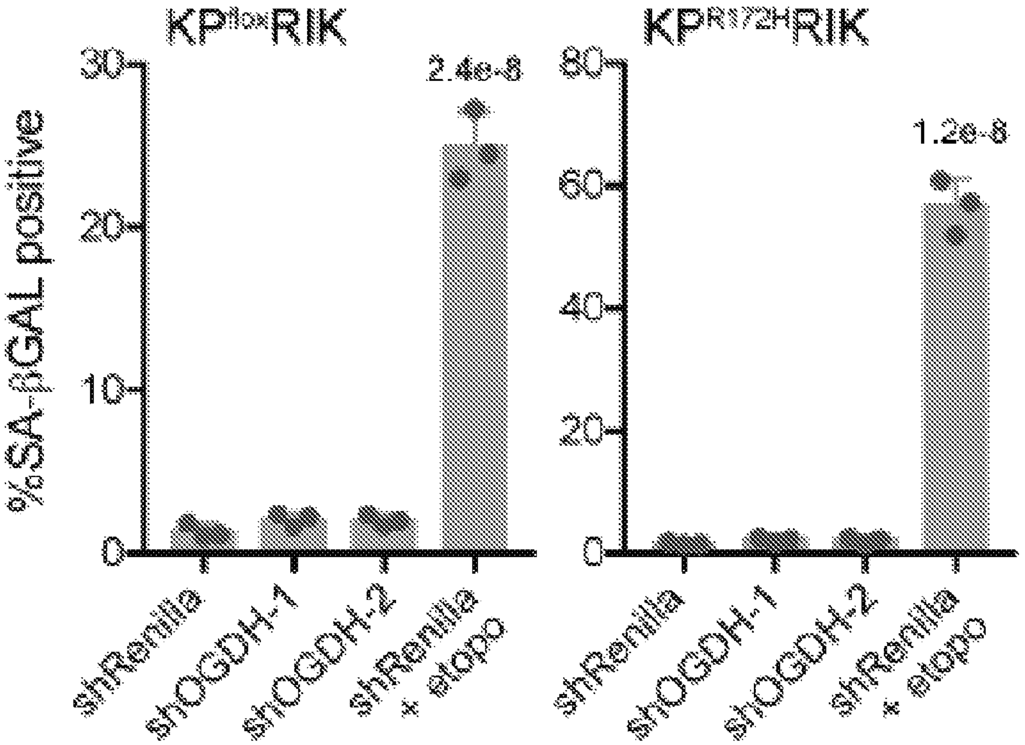
FIGS. 10G-10H show the number of SA-βGAL positive (FIG. 10G) or Annexin-V positive (FIG. 10H) $KP^{flox}$RIK and $KP^{R172H}$RIK cells expressing the indicated hairpins and treated with dox for 4 days. Cells treated with 3 μM etoposide (etopo) for 96 h are included as a positive control.
Figure 10H:
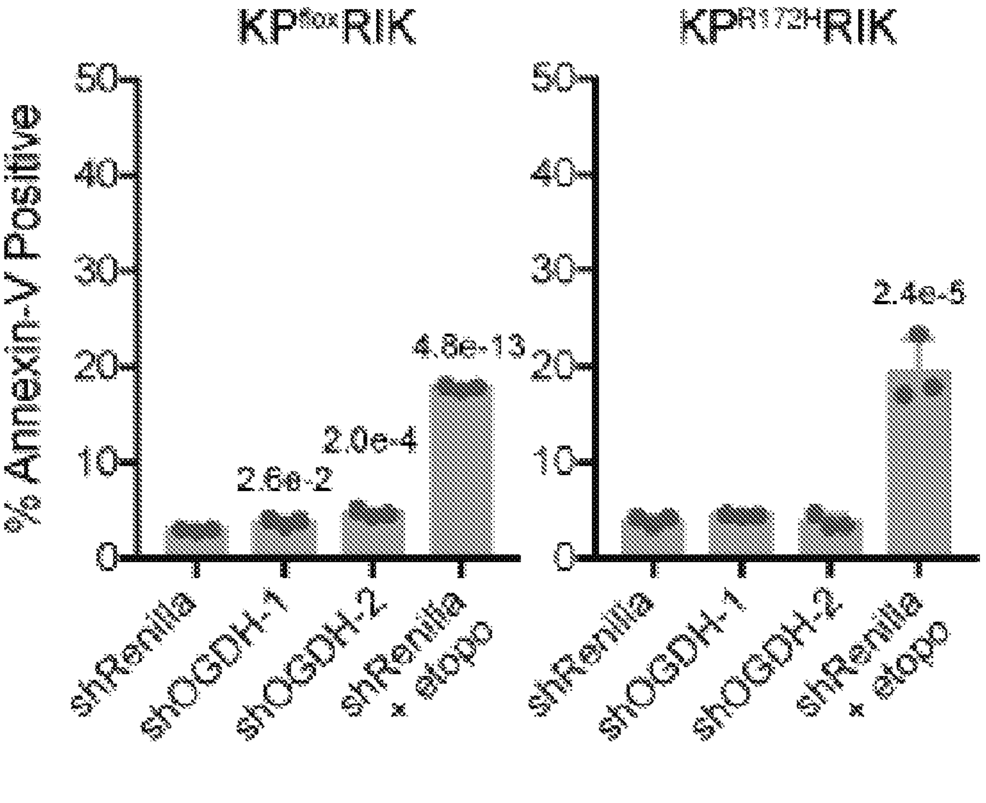
Figure 10I:
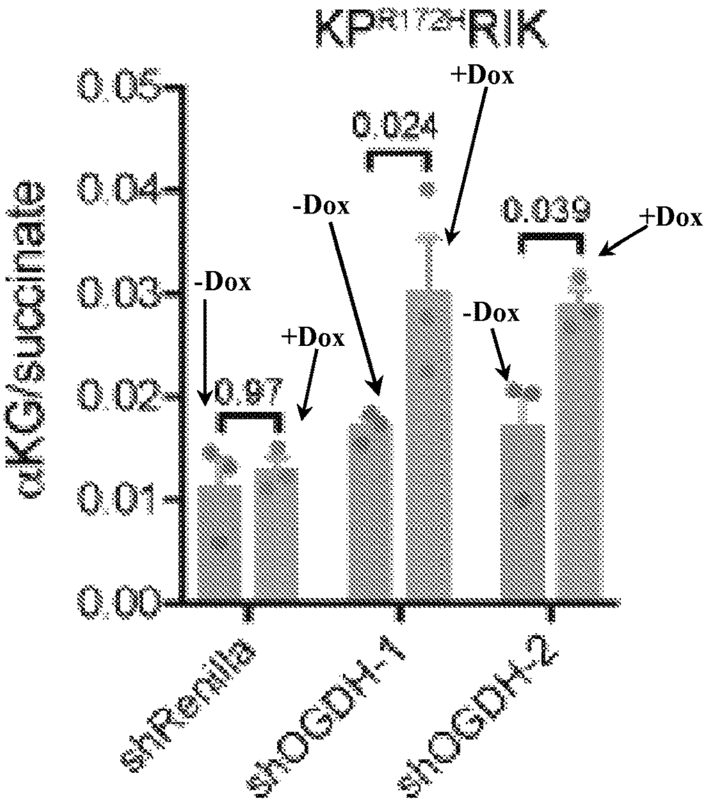
FIG. 10I shows the αKG/succinate ratio of $KPC^{R172H}$RIK cells expressing dox-inducible shRNAs targeting Ogdh or *Renilla* luciferase (control) grown 4 days with or without dox.
Figure 10J:
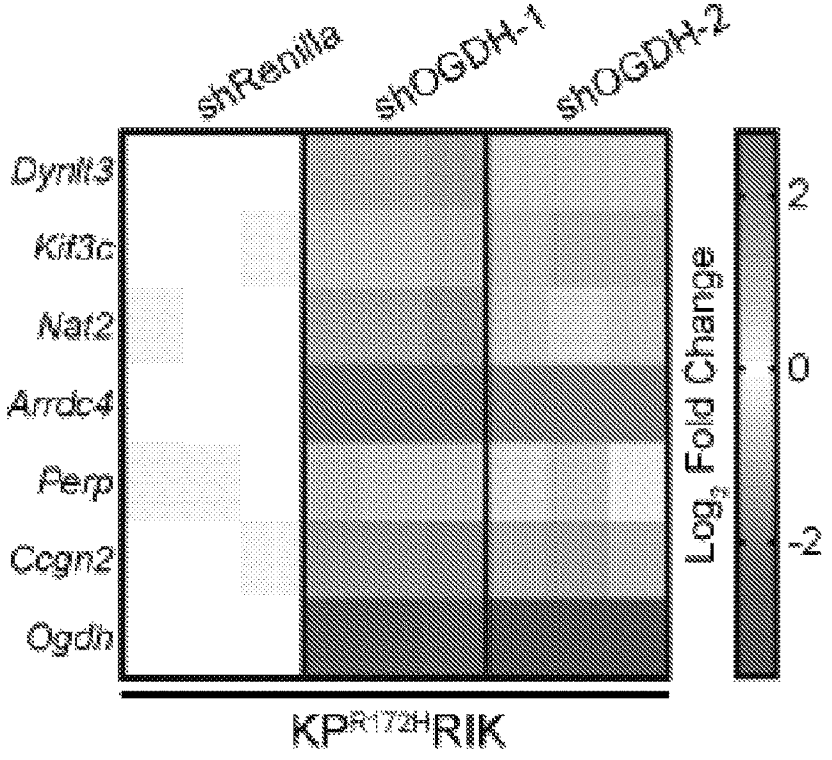
FIG. 10J shows the expression of p53/αKG co-regulated genes in $KP^{R172H}$RIK cells expressing the indicated hairpins was measured by qRT-PCR. All cells were grown with dox for four days and expression is shown relative to sh*Renilla*-expressing cells. Data are presented as mean±SEM (FIG. 10I) or ±SD of triplicate wells of a representative experiment with individual data points shown. Significance was assessed by 2-way ANOVA with Sidak's multiple comparison post test (FIG. 10F) or 1-way ANOVA with Tukey's multiple comparison post-test (FIGS. 10G-10H). *, p<0.05; *, p<0.0005; **, p<0.0001

These αKG-induced changes in gene expression were not merely due to supraphysiological concentrations, as manipulation of endogenous metabolic pathways to mimic the increase in the αKG/succinate ratio observed upon p53 reactivation recapitulated aspects p53 dependent gene expression in the absence of wild-type p53. rtTA-expressing cell lines derived from p53 null ($KP^{flox}$RIK) or p53 mutant ($KP^{R172H}$RIK) tumors were engineered to express dox-inducible hairpins against oxoglutarate dehydrogenase (Ogdh), a subunit of the oxoglutarate dehydrogenase complex that converts αKG to succinyl-CoA in the TCA cycle (FIG. 10E). As shown in FIGS. 10F-10G, while Ogdh knockdown slowed cell proliferation, no notable senescence or apoptosis was observed. Still, knockdown of Ogdh increased the αKG/succinate ratio to a similar degree as p53 and induced the expression of genes that could be induced by either p53 re-expression or αKG addition (FIGS. 2G-2H and FIGS. 10H-10I).

Figure 3A:
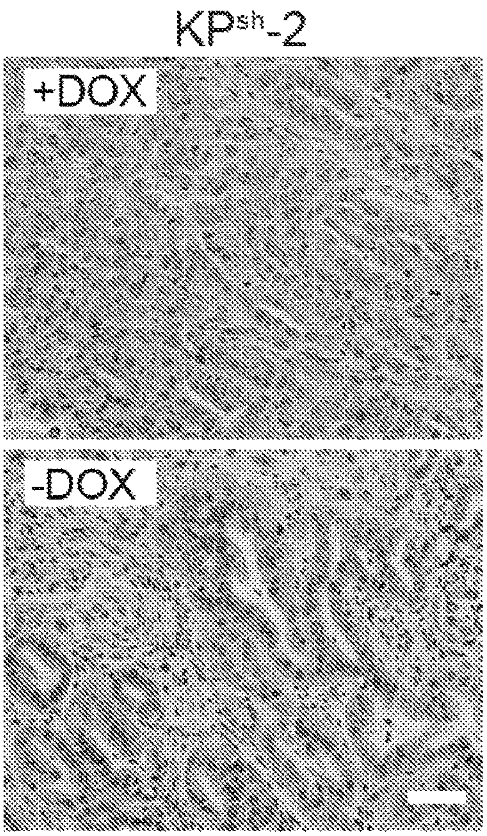
FIG. 3A shows the representative hematoxylin and eosin (H&E) staining of orthotopic tumors derived from $KP^{sh}$-2 cells grown in mice on dox-diet or ten days after dox withdrawal.
Figure 3B:
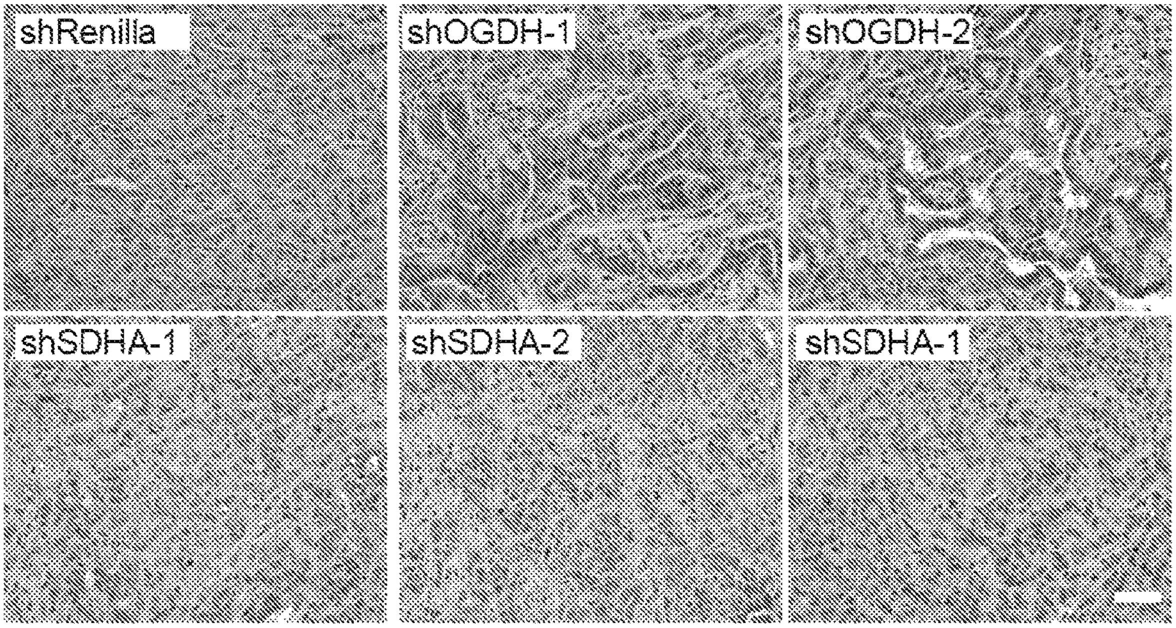
FIG. 3B shows the representative H&E staining of orthotopic tumors derived from $KP^{flox}$ cells expressing dox-inducible hairpins targeting *Renilla*, Ogdh, or Sdha two weeks after injection in mice maintained on dox.
Figure 11A:
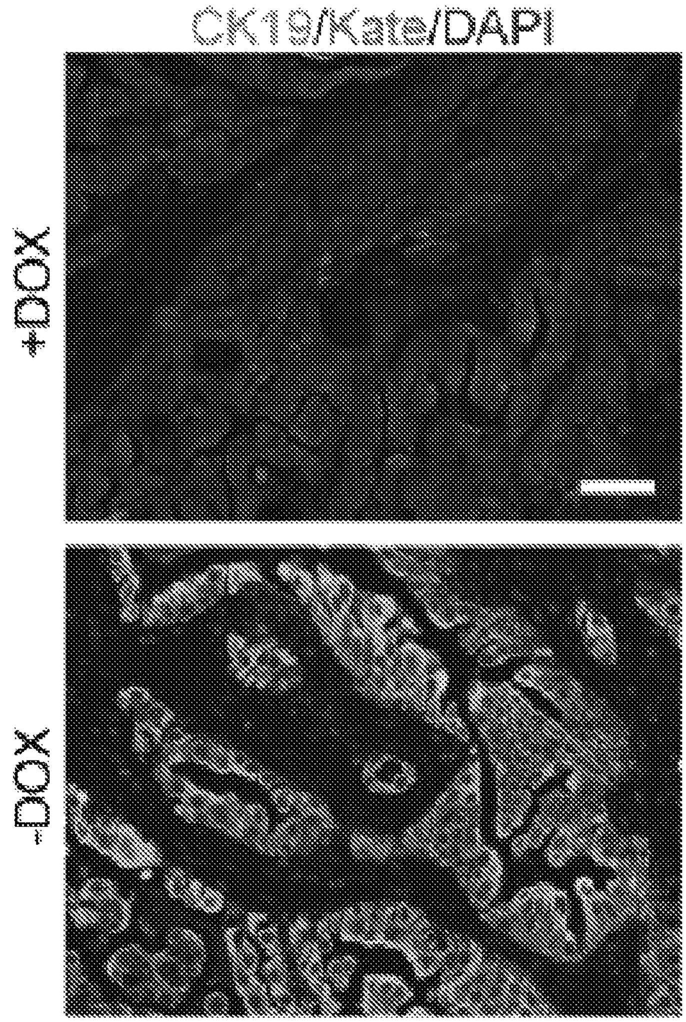
FIG. 11A shows the CK19 staining of orthotopic tumors derived from $KP^{sh}$-2 cells injected in mice on dox-diet or ten days after dox withdrawal. Kate marks injected $KP^{sh}$-2 cells.
Figure 11B:
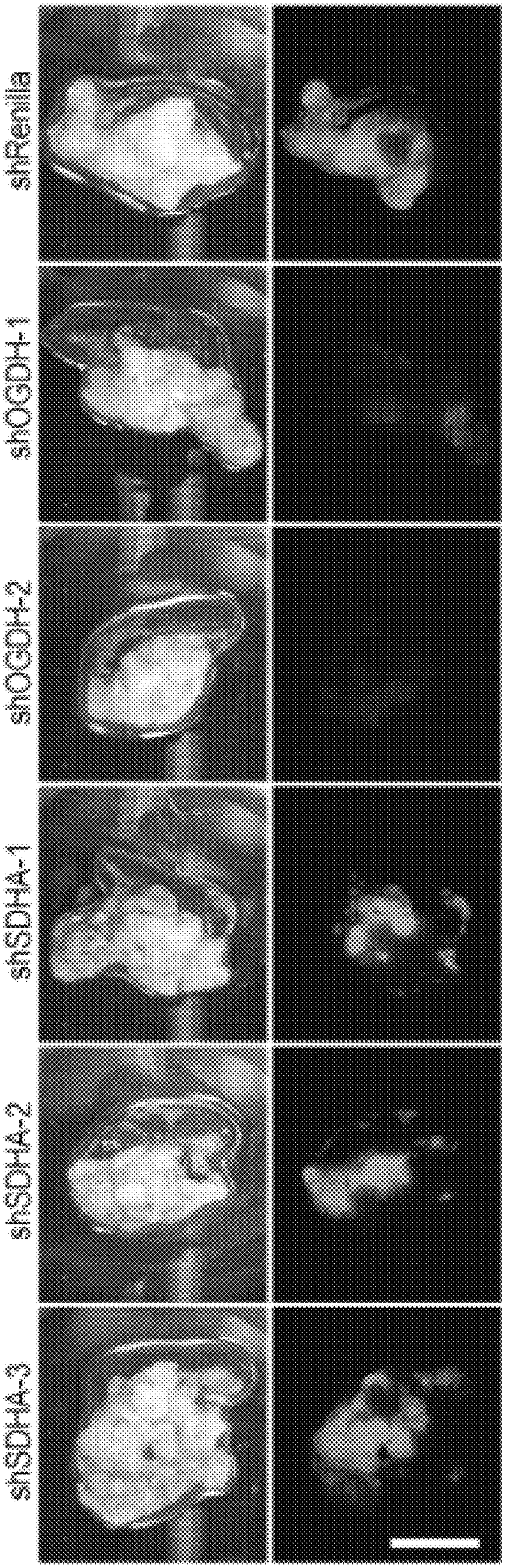
FIG. 11B shows gross images of pancreatic tumors arising in dox fed mice 12 days following orthotopic transplant of $KP^{flox}$ cells expressing lentiviral vectors encoding rtTA and GFP linked, dox inducible shRNAs targeting either *Renilla* luciferase, Ogdh, or Sdha. GFP indicates shRNA expressing cells. Scale bar for pathology 1 cm.
Figure 11C:
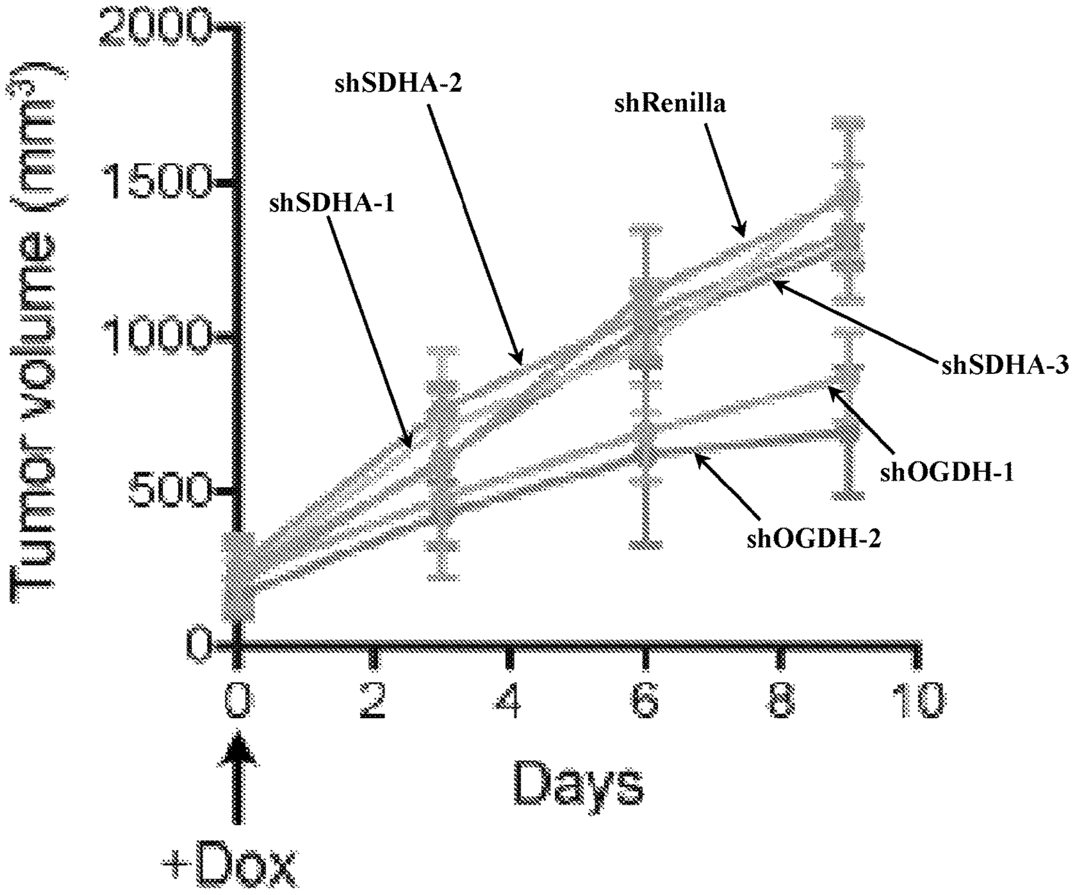
FIG. 11C shows the small animal ultrasound measurement of tumors derived from $KP^{flox}$ cells expressing dox-inducible hairpins targeting *Renilla*, Ogdh, or Sdha grown off dox and injected orthotopically into mice on normal chow. After two weeks (D0), tumor size was measured by small animal ultrasound and mice were changed to dox chow. Tumor size was monitored every 3 days after enrolling on dox. Data are presented as mean±SD. All other data are presented as mean±SD of triplicate wells of a representative experiment with individual data points shown.

Ogdh inhibition was next exploited to ask whether manipulating αKG levels in vivo could mimic phenotypes associated with p53-driven tumor suppression. Consistent with the ability of p53 to produce a premalignant gene expression profile in vitro, tumors with p53 activation displayed a more differentiated histopathology as defined by the emergence of clearly articulated glandular structures with cuboidal and columnar cellular morphology that were strongly positive for the epithelial cytokeratin CK19 (FIG. 3A and FIG. 11A). As shown in FIG. 11B, orthotopic tumors arising from p53 null cells expressing constitutive GFP-linked Ogdh shRNAs were much smaller than those produced from p53 null tumors expressing control shRNAs and had a notable decrease in the contribution of shRNA expressing cells to tumor areas. Similarly, induction of dox-inducible Ogdh shRNAs in established p53 null tumors also produced a reduction in tumor growth (FIG. 11C). Remarkably, in both the constitutive and inducible contexts, tumor cells expressing Ogdh shRNAs were characterized by abundant, well-differentiated, glandular structures with cuboidal/columnar cellular morphology and increased CK19 staining rarely observed in controls (FIGS. 3B-3C, FIGS. 11D-11F). Therefore, increases in the αKG/succinate ratio are sufficient to produce many of the tumor suppressive outputs of p53.

Figure 3C:
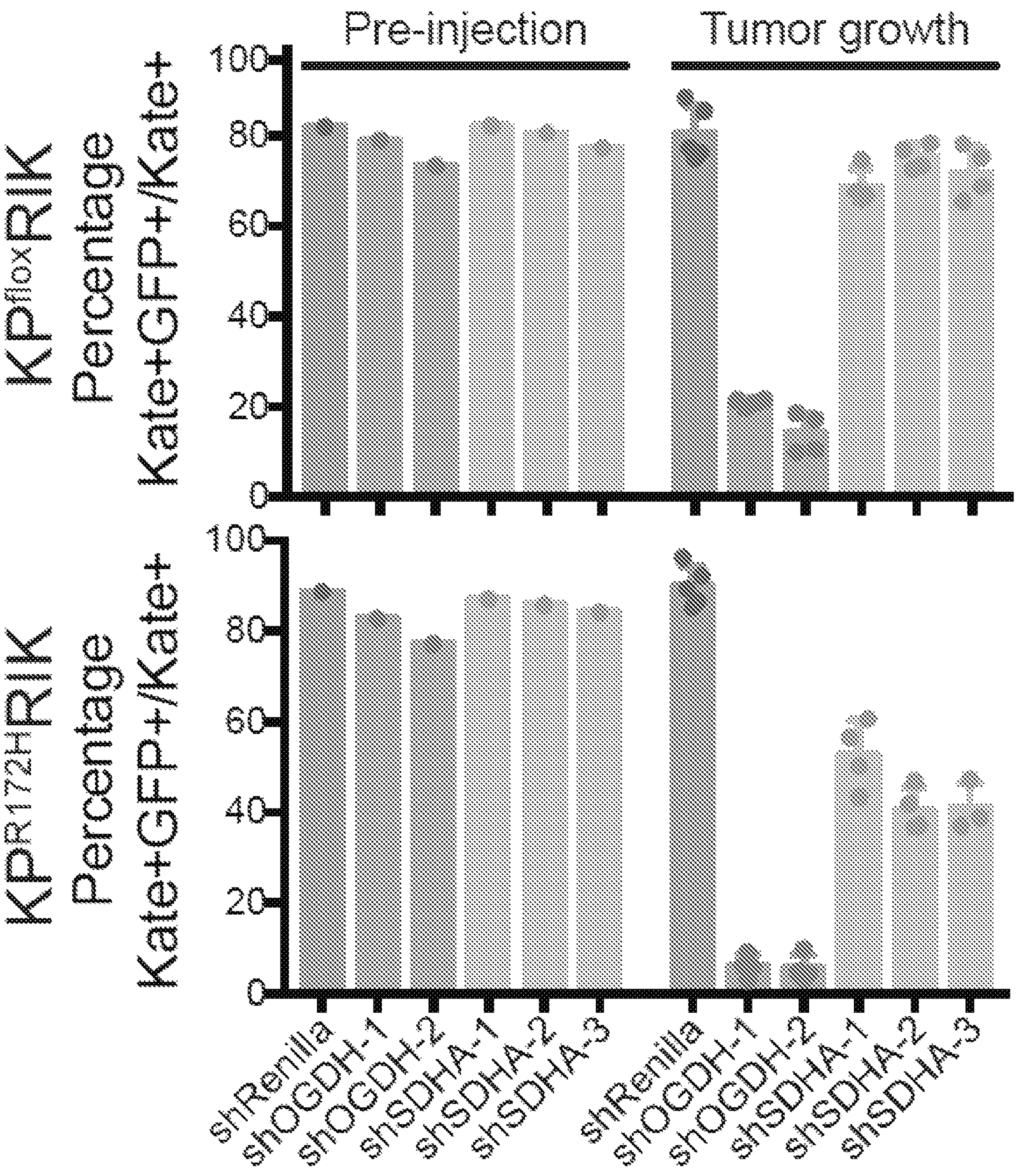
FIG. 3C shows the tumor mass of orthotopically injected $KP^{flox}$RIK (top) or $KP^{R172H}$RIK (bottom) cells expressing a mixture of shRNAs targeting *Renilla*, Ogdh, or Sdha and uninfected cells (80:20) three weeks after injection in dox-fed mice.
Figure 11D:
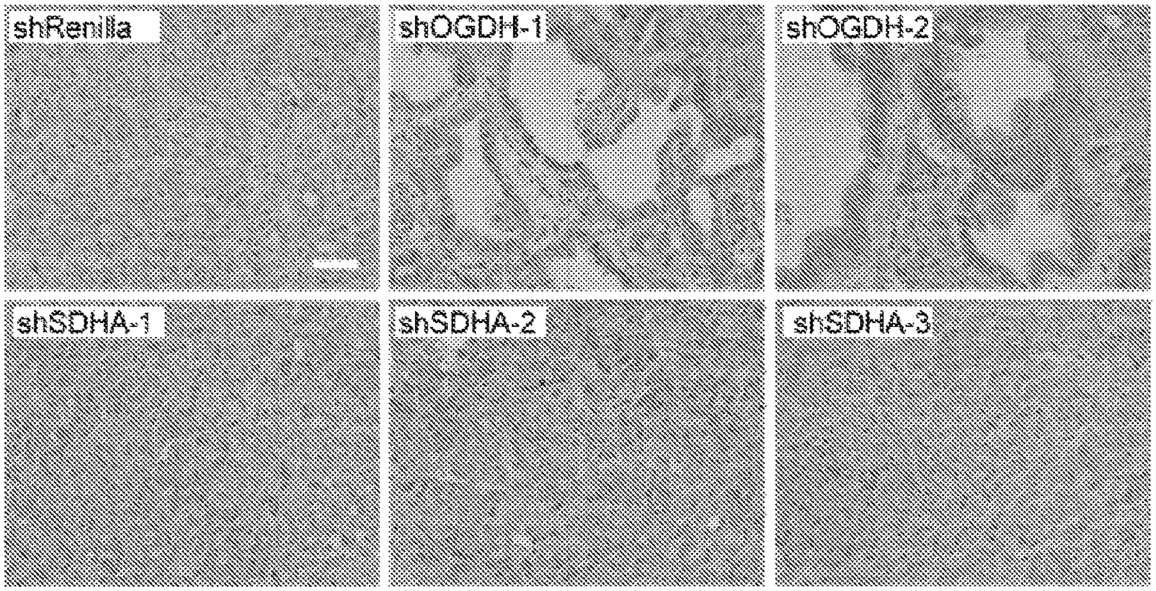
FIG. 11D shows the representative hematoxylin and eosin (H&E) staining of orthotopic tumors derived from $KP^{flox}$ cells expressing dox-inducible hairpins targeting *Renilla*, Ogdh, or Sdha two weeks after injection in mice maintained on dox.
Figure 11E:
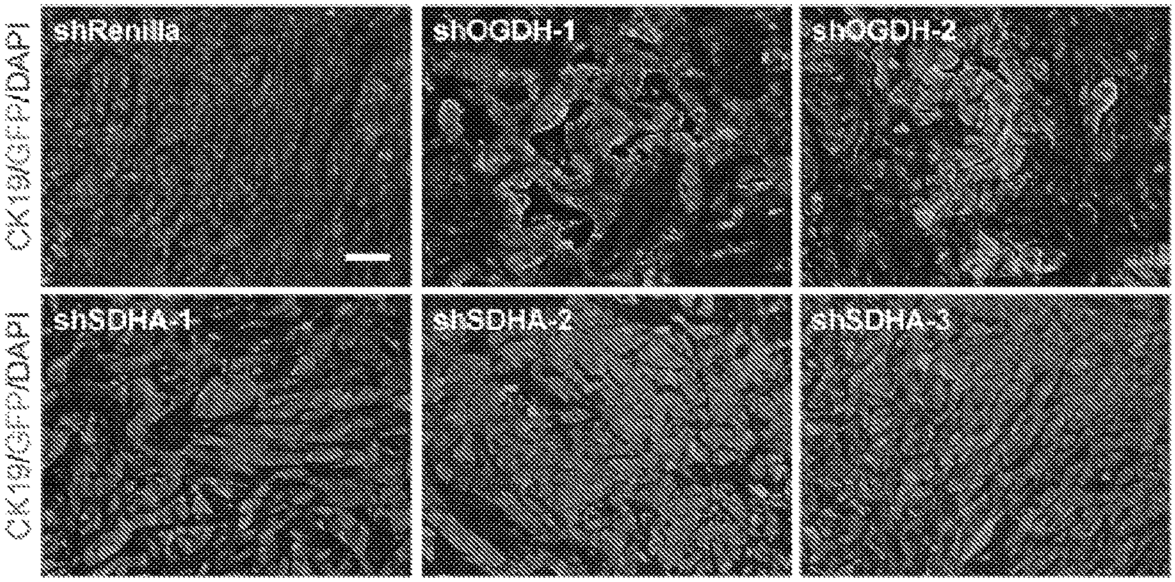
FIG. 11E shows the CK19 staining of orthotopic tumors derived from $KP^{flox}$ cells expressing dox-inducible hairpins targeting *Renilla*, Ogdh, or Sdha two weeks after injection in mice maintained on dox. GFP marks injected $KP^{flox}$ cells expressing indicated shRNA. Scale bar for immunostaining 50 μM.
Figure 11F:
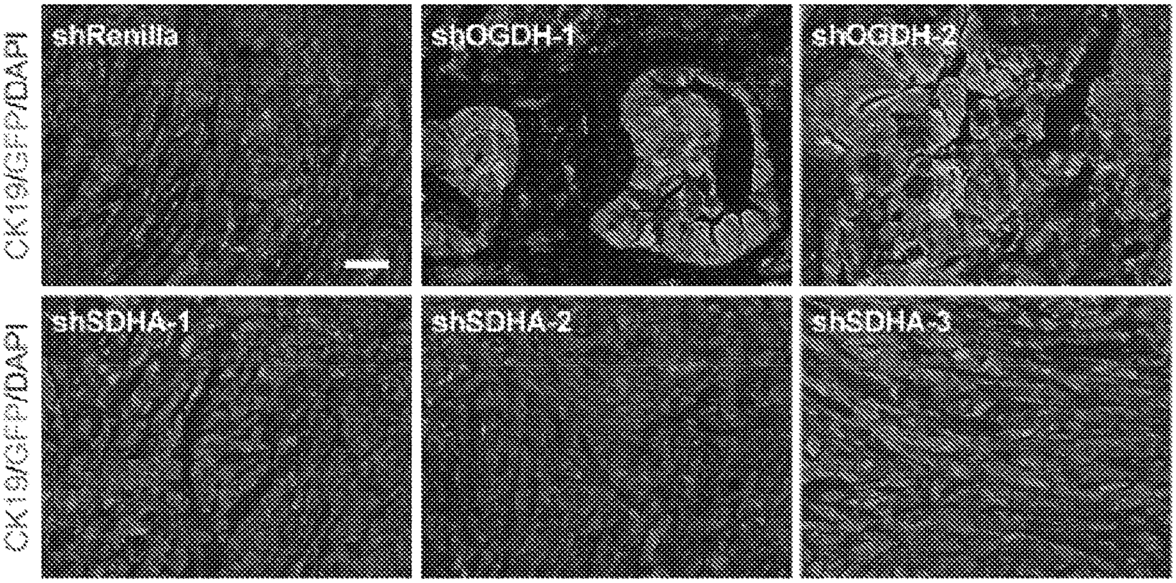
FIG. 11F shows the CK19 staining of orthotopic tumors derived from $KP^{flox}$ cells 9 days after expression of dox-inducible hairpins targeting *Renilla*, Ogdh, or Sdha in established tumors. GFP marks cells expressing indicated shRNA. Scale bar for immunostaining 50 μM.
Figure 11G:
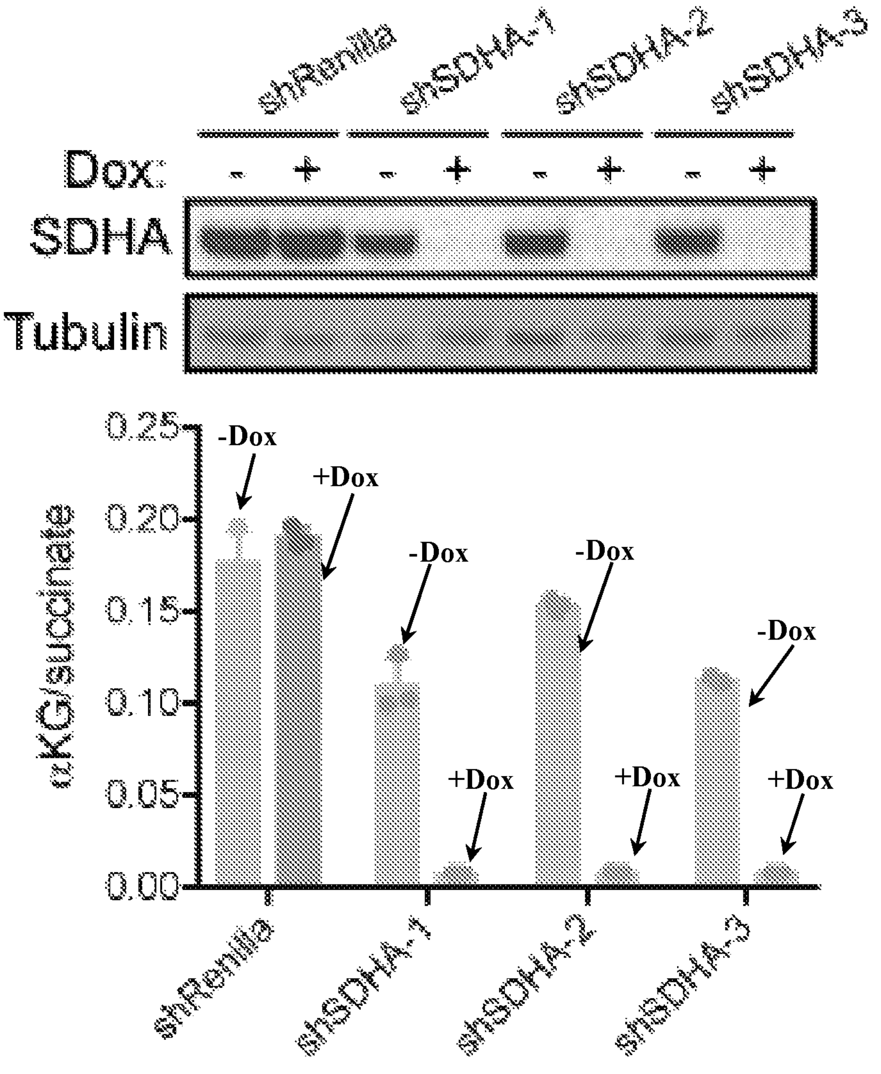
FIG. 11G shows the western blot (top) of Sdha in $KP^{flox}$ cells expressing dox-inducible hairpins targeting *Renilla* or Sdfha grown with dox for 4 days. αKG/succinate ratio (bottom) in in $KP^{flox}$ cells expressing dox-inducible hairpins targeting *Renilla* or Sdha grown with dox for 4 days.
Figure 12A:
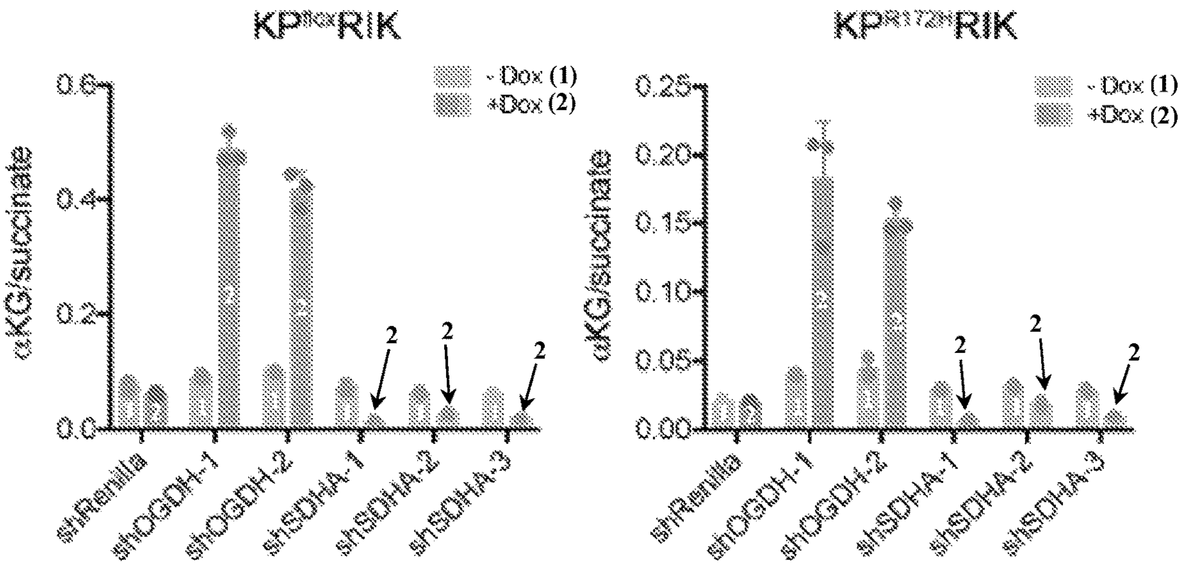
FIG. 12A shows the αKG/succinate ratio of $KPC^{flox}$RIK and $KPC^{R172H}$RIK cells expressing dox-inducible shRNAs targeting *Renilla*, Ogdh, and Sdha grown 4 days with or without dox.
Figure 12B:
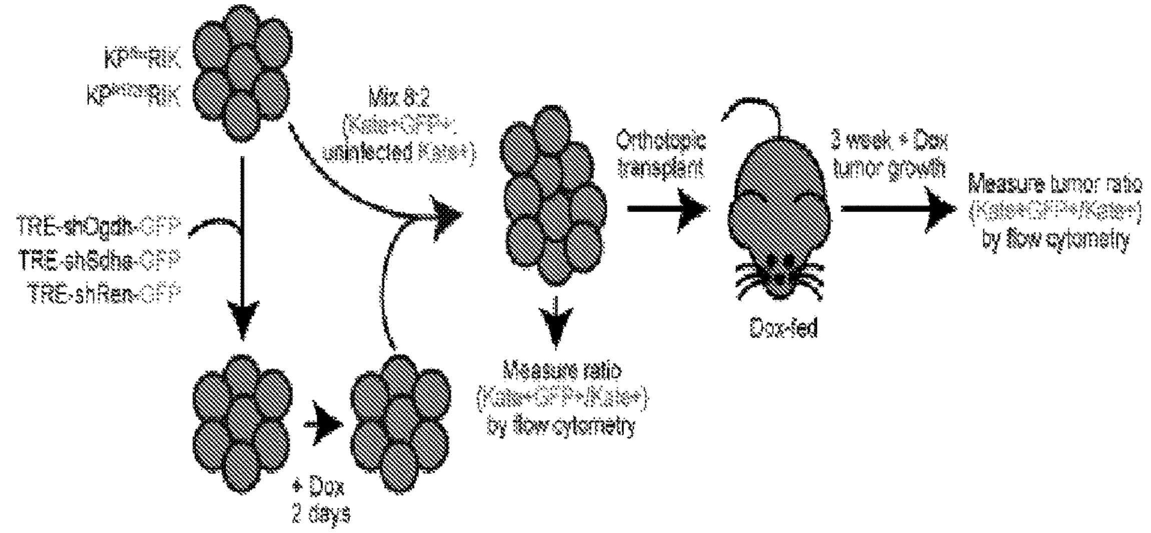
FIG. 12B shows the schematic of in vivo competition assay. Kate positive $KP^{flox}$RIK and $KP^{R172H}$RIK cells were infected with retroviruses encoding dox inducible, GFP linked shRNAs targeting *Renilla*, Ogdh, or Sdha. Cells were selected for viral integration, induced with dox for 2 days, mixed with uninfected parental cells at a ratio of 8:2 and analyzed by flow cytometry to determine initial ratio of shRNA expressing cells to uninfected cells. This cell mixture was injected orthotopically into dox fed recipient mice. After 3 weeks of tumor growth, pancreatic tumors were removed, weighed, dissociated, and analyzed by flow cytometry to measure final ratio of shRNA expressing to uninfected cells.
Figure 12C:
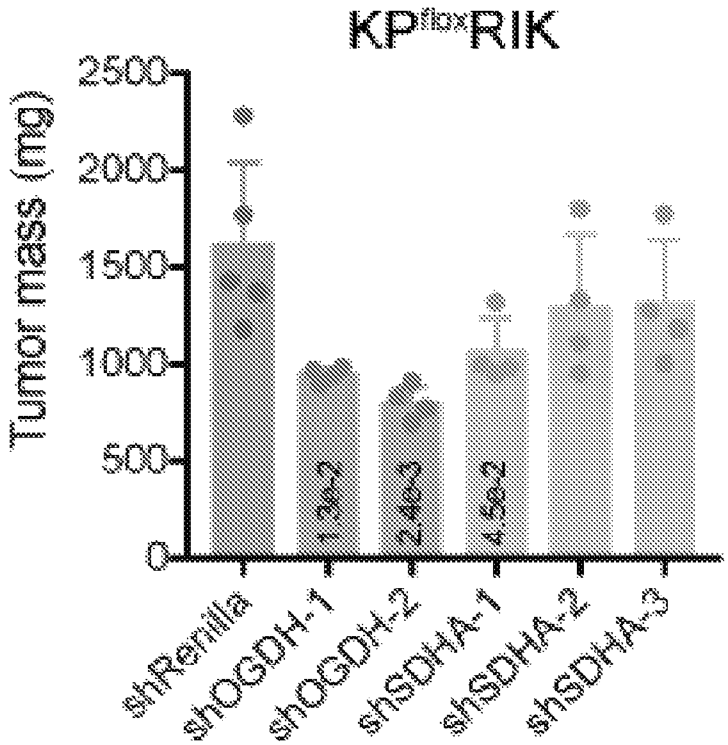
FIG. 12C shows the tumor mass of $KP^{flox}$RIK cells encoding dox inducible, GFP linked shRNAs targeting *Renilla*, Ogdh, or Sdha from the experiment described in FIG. 12B.
Figure 12D:
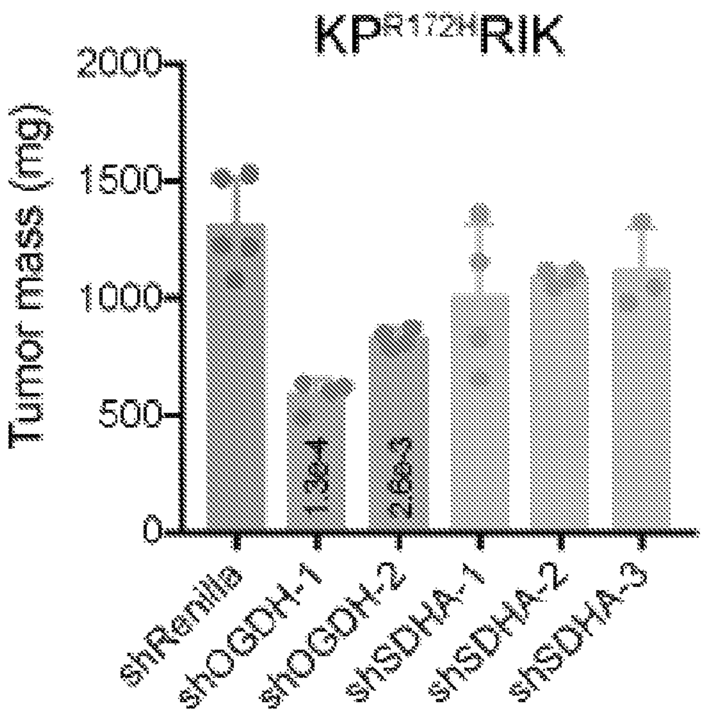
FIG. 12D shows the tumor mass of $KP^{R172H}$RIK cells encoding dox inducible, GFP linked shRNAs targeting *Renilla*, Ogdh, or Sdha from the experiment described in FIG. 12B.
Figure 12E:
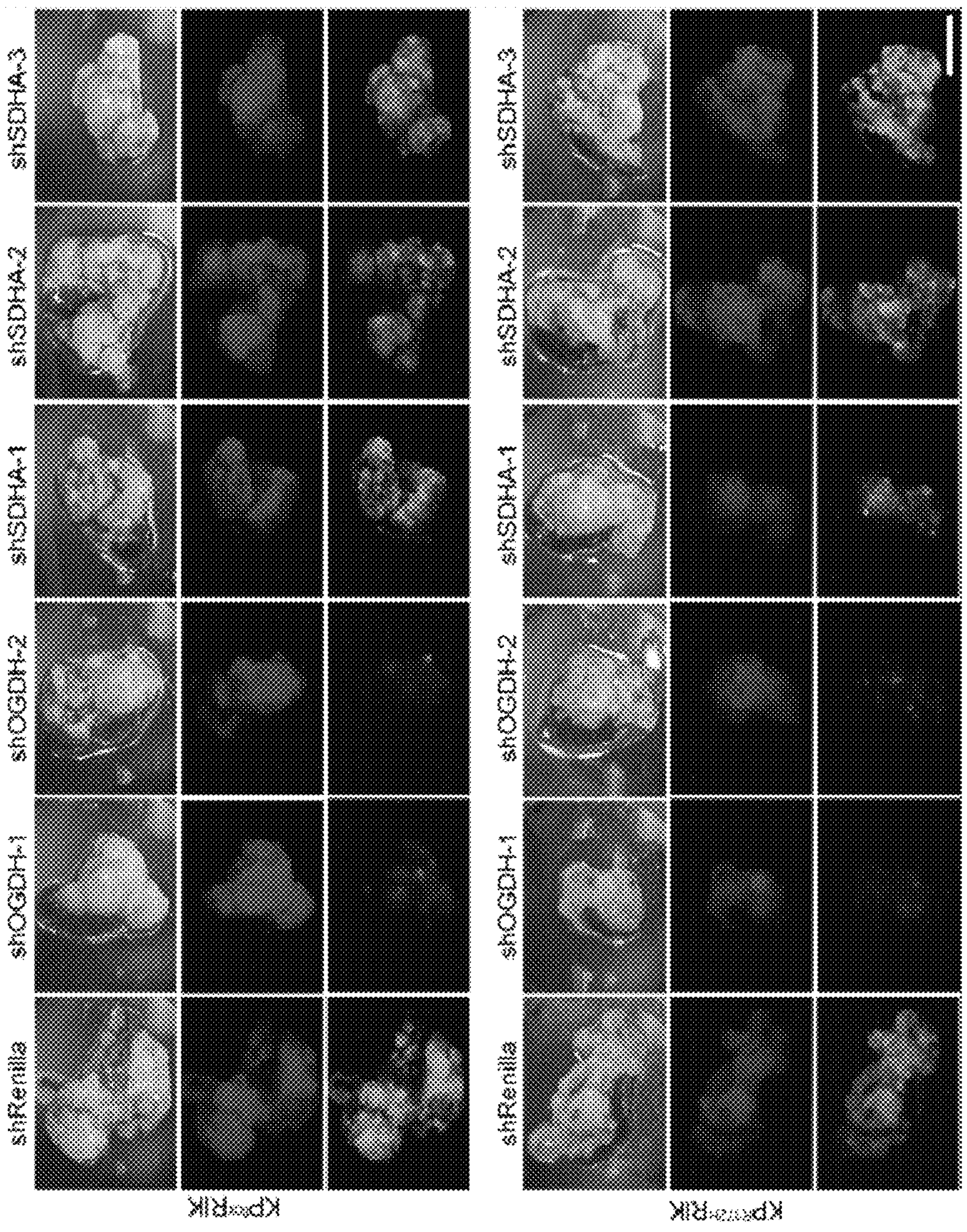
FIG. 12E shows the representative gross images of pancreatic tumors arising in dox fed mice 3 weeks days following orthotopic transplant of $KPC^{flox}$RIK (top) and $KPC^{R172H}$RIK (bottom) cells expressing dox-inducible shRNAs targeting *Renilla*, Ogdh, and Sdha mixed 8:2 with uninfected cells as described in FIG. 12B. Quantification of Kate+ and Kate+GFP+ cells shown. Data are presented as mean SD of triplicate wells of a representative experiment with individual data points shown. Scale bar 1 cm.

To rule out the possibility that the anti-tumor and pro-differentiation effects of Ogdh inhibition are a generic consequence of disrupting the TCA cycle, a parallel series of experiments were performed using shRNAs targeting succinate dehydrogenase subunit a (Sdha). Succinate dehydrogenase consumes succinate and, as expected, its inhibition in p53 null cells perturbed the TCA cycle without increasing the αKG/succinate ratio (FIG. 11G). shSdha-expressing cells more uniformly contributed to tumor areas (FIG. 11B) and did not display morphological features of differentiation or CK19 expression (FIG. 3B, FIGS. 11D-11F). Furthermore, induction of Sdha shRNAs in established tumors only modestly inhibited tumor growth and did not trigger differentiation (FIG. 3C and FIGS. 11C-11D). As shown in FIGS. 3D-3G and FIGS. 12A-12D, shOgdh specific anti-tumor effects on in vivo competitive fitness extended to both p53 null and p53 mutant PDAC cells. Collectively, these data support the notion that the p53-triggered increase in the αKG/succinate ratio results in specific tumor suppressive effects that are not a generalized response to the loss of TCA cycle function.

Example 5: p53 Status Predicts 5hmC Levels in PDAC

Figure 4A:
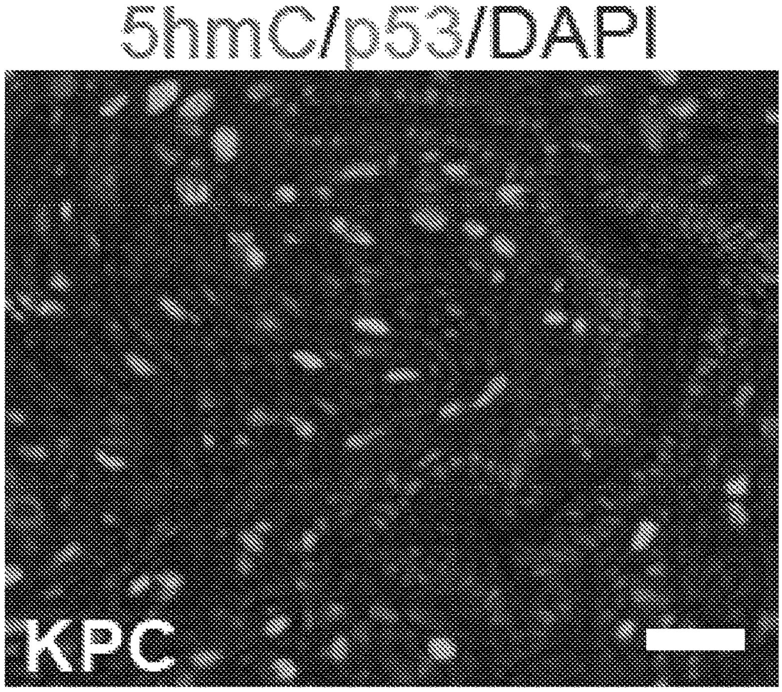
FIG. 4A shows the 5hmC and p53 staining in PDAC arising in KPC mice. Regions of high p53 staining denote malignant cells.
Figure 4B:
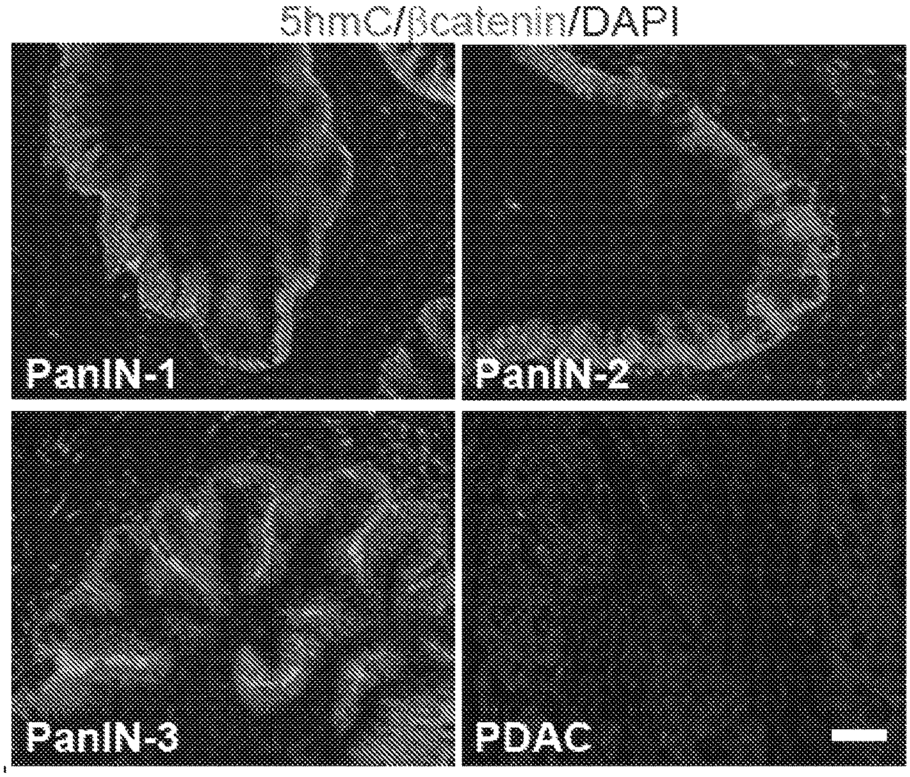
FIG. 4B shows the representative 5hmC staining in human PanIN 1-3 and PDAC samples. β-catenin is shown as a marker of tumor epithelium.
Figure 4C:
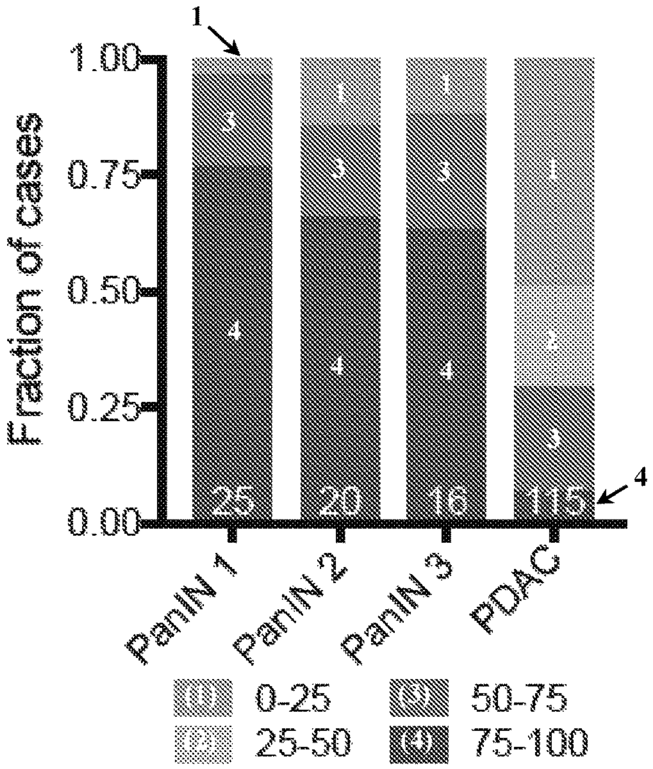
FIG. 4C shows the quantification of frequency of 5hmC-positive nuclei (binned into quartiles) in indicated numbers of human tumors.

These data implied that αKG-dependent processes induced by p53 during tumor suppression are involved in enforcing premalignant cell fate and are suppressed during malignant progression. One family of αKG-dependent enzymes relevant to gene regulation, cell fate decisions, and tumorigenesis is the ten eleven translocation (Tet) enzymes, which oxidize 5-methylcytosine (5mC) to 5-hydroxymethycytosine (5hmC)—a mark that is often lost in advanced tumors. To determine whether PDAC progression is associated with changes in 5hmC, 5hmC immunofluorescence was performed on mouse and human tissues at different stages of pancreatic cancer development. Of note, in the KPC mouse model, which is initially heterozygous for a missense $p53^{R172H}$ allele, loss of wild-type p53 precedes stabilization of the mutant p53 protein such that cells harboring high p53 staining are those with inactive p53. As shown in FIG. 4A, normal pancreatic epithelial cells and stromal cells, as well as premalignant cells with PanIN features, displayed low p53 (p53 wild-type) and high 5hmC staining. In contrast, malignant cells displaying high p53 levels (p53 mutant) showed very low 5hmC staining (FIG. 4A). Similarly, decreased 5hmC levels were observed during human PDAC progression, with the reduction in 5hmC coinciding with the transition from benign to malignant disease that is frequently characterized by acquisition of TP53 mutations (FIGS. 4B-4C).

Figure 4D:
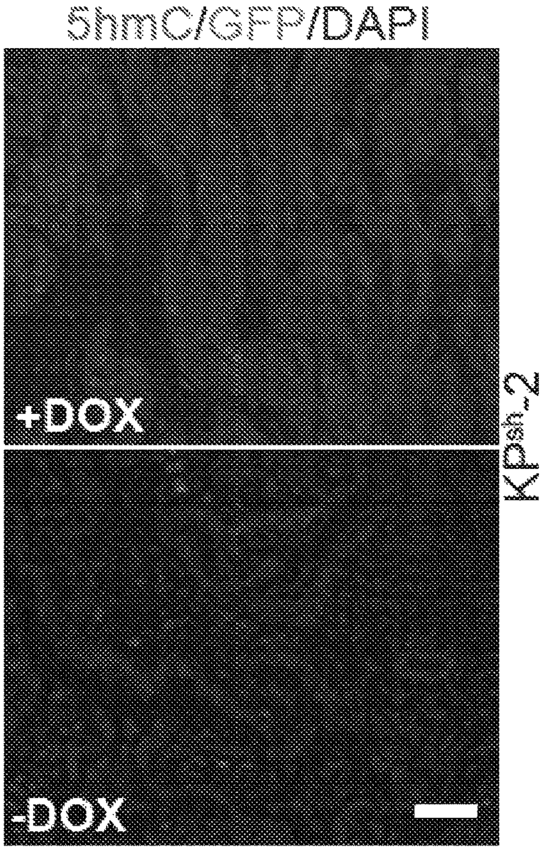
FIG. 4D shows the 5hmC staining in orthotopic tumors derived from $KP^{sh}$-2 cells in mice maintained on dox or ten days following dox withdrawal. GFP denotes cells expressing hairpin targeting p53. Scale bar 50 μm.
Figure 4E:
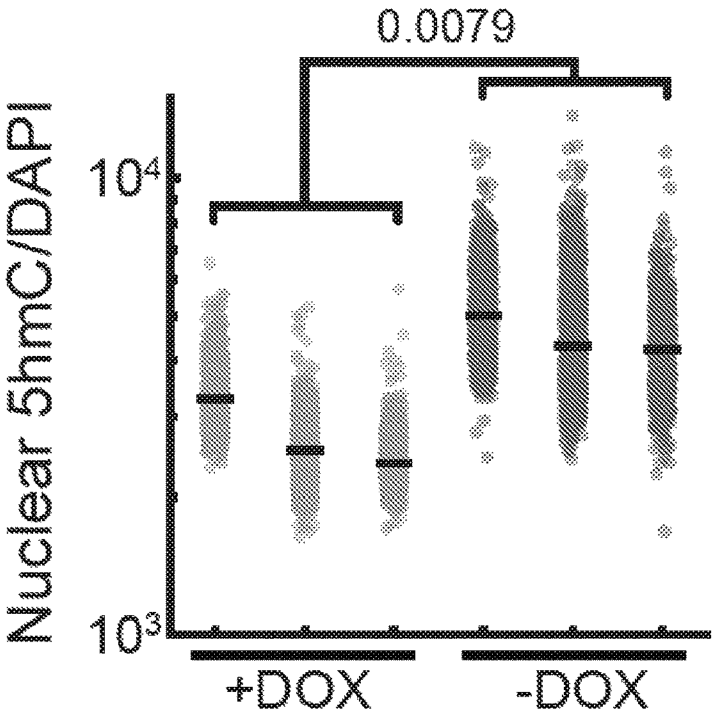
FIG. 4E shows the quantification of nuclear 5hmC intensity in lineage-traced (i.e., GFP high, +DOX; GFP low −DOX) tumor cells from three images each from three independent mice from FIG. 4D. Points represent total 5hmC levels of individual nuclei normalized to DAPI. Total number of quantified nuclei (left to right) are =1074, 1571, 1359, 1569, 1253, 781. These values were compared across different conditions using Students t-test.
Figure 4F:
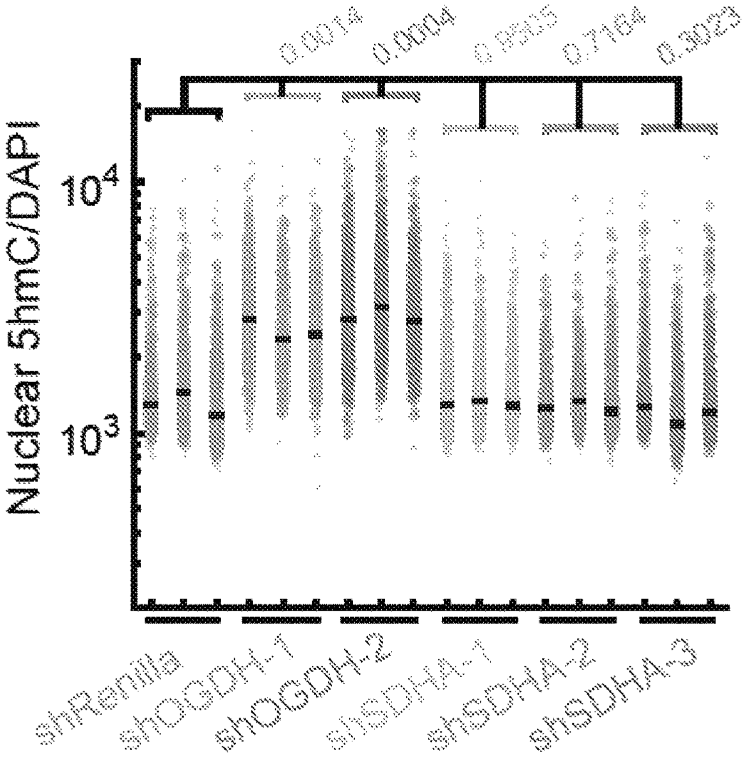
FIG. 4F shows the quantification of nuclear 5hmC intensity in lineage-traced tumor cells expressing shOGDH or shSDHA. Points represent total 5hmC levels of individual nuclei normalized to DAPI. These values were compared across different conditions using Students t-test.
Figure 4G:
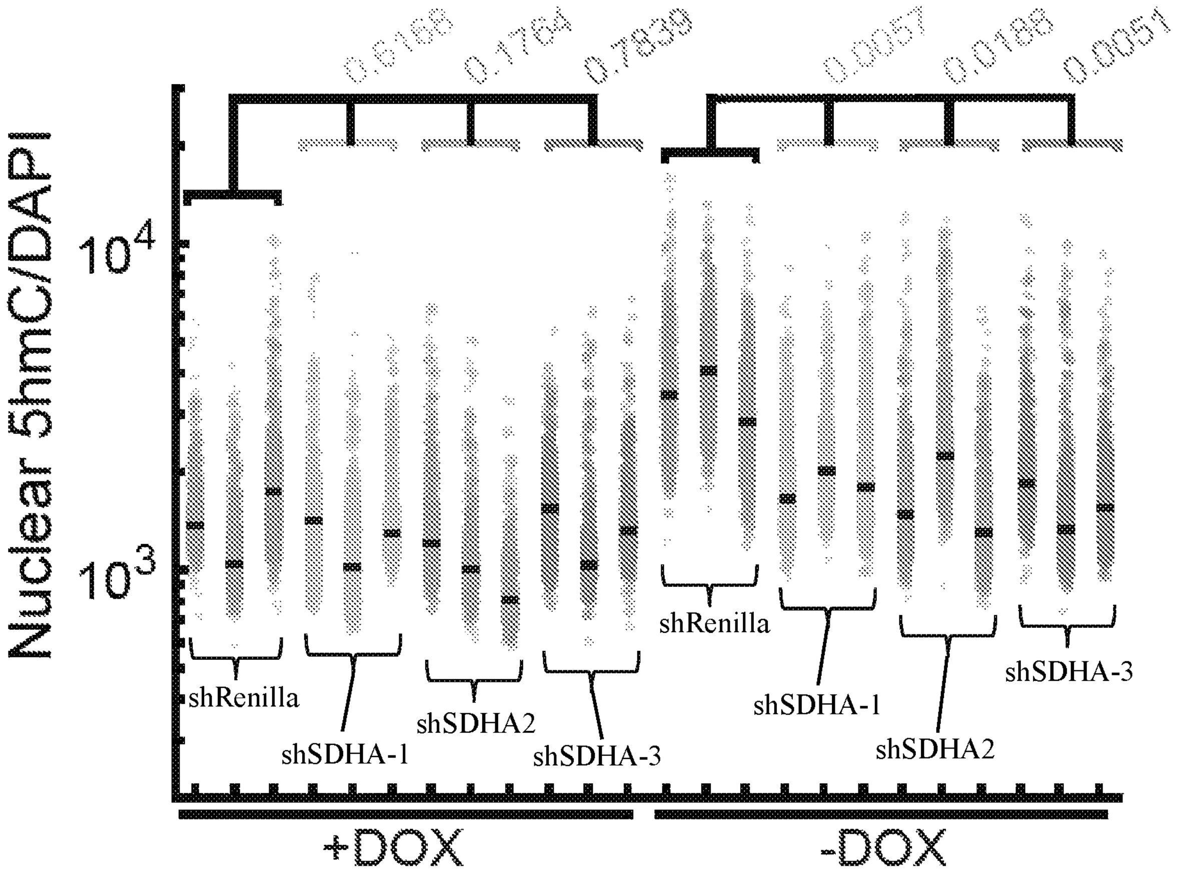
FIG. 4G shows quantification of nuclear 5hmC intensity in lineage-traced (i.e., GFP+) tumor cells from three images each from three independent mice from FIG. 4A. Total nuclei quantified per mouse (left to right) are n=1609, 1796, 1947, 1581, 1751, 1619, 1636, 1786, 1907, 1801, 1892, 1758, 1829, 2001, 1898, 1982, 1839, 1926. GFP denotes shRNA-expressing cells. Population medians were taken for each mouse. These values were compared across different conditions relative to shRenilla using Students t-test.
Figure 13A:
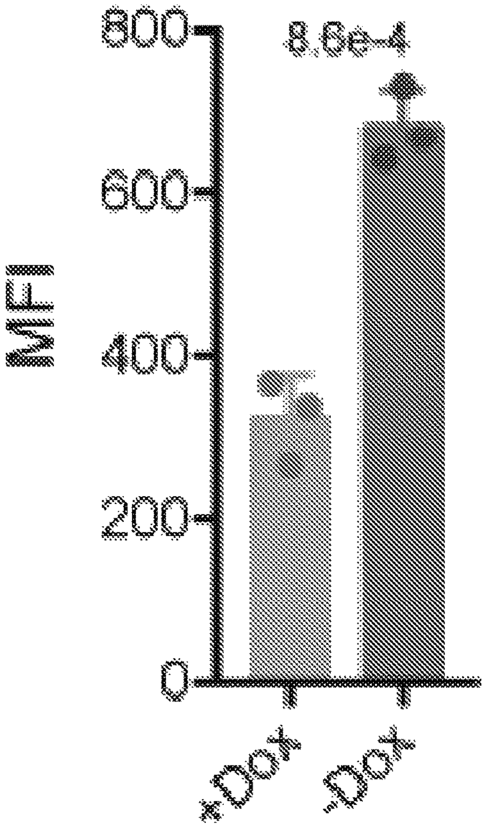
FIG. 13A shows the median fluorescence intensity of 5hmC in $KP^{sh}$-2 cells grown with or without dox for 8 days.
Figure 13B:
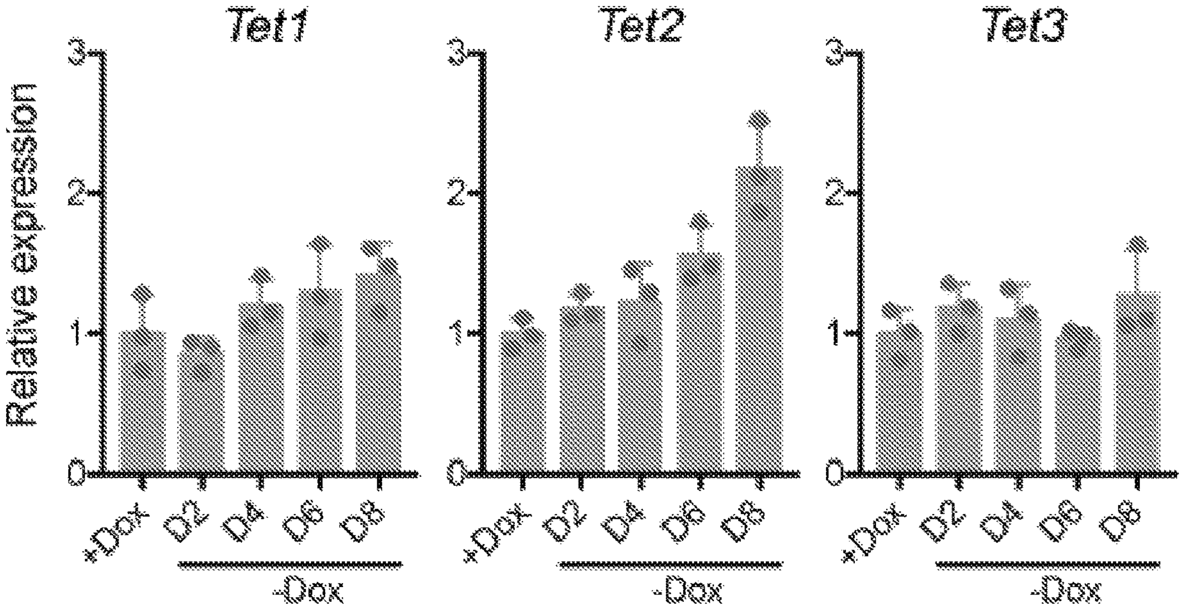
FIG. 13B shows the evaluation of Tet1, Tet2, and Tet3 expression by qRT-PCR in $KP^{sh}$-2 cells grown with or without dox for the indicated number of days.
Figure 13C:
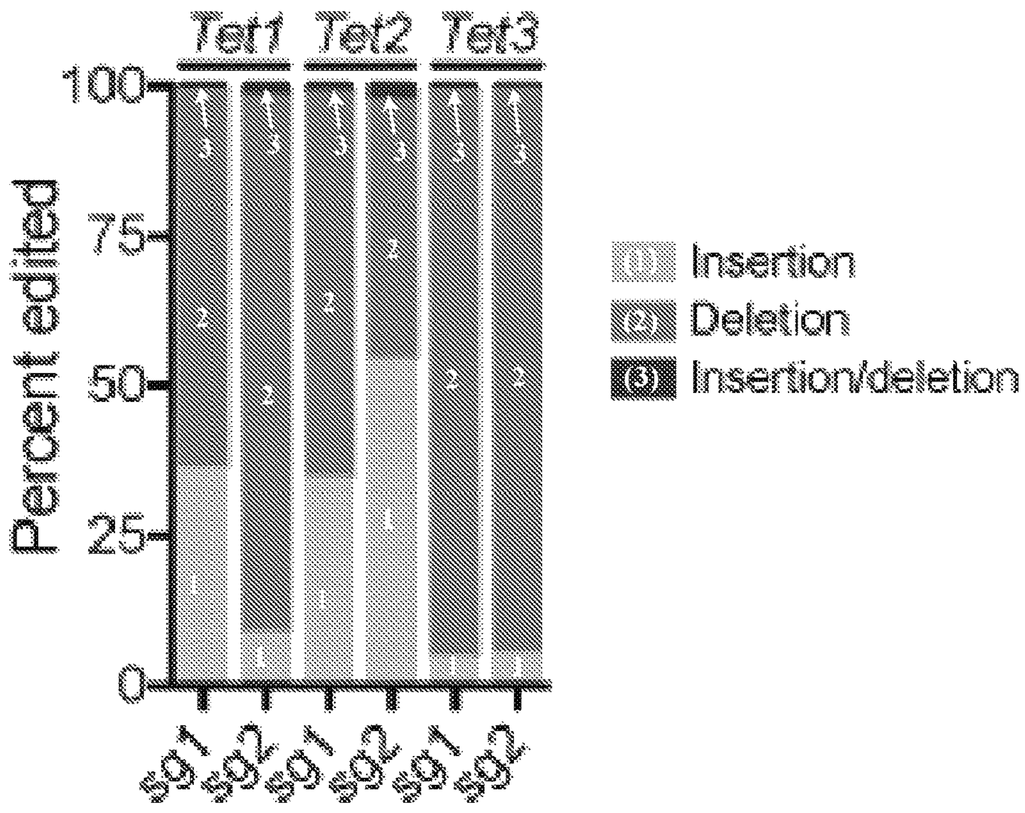
FIG. 13C shows the sequence analysis of CRISPR/Cas9 editing. Percentage of amplicons flanking sgRNA target sequence with indicated genotype amplified from $KP^{sh}$-2 cells expressing sgRNAs targeting Tet1, Tet2, and Tet3.
Figure 13D:
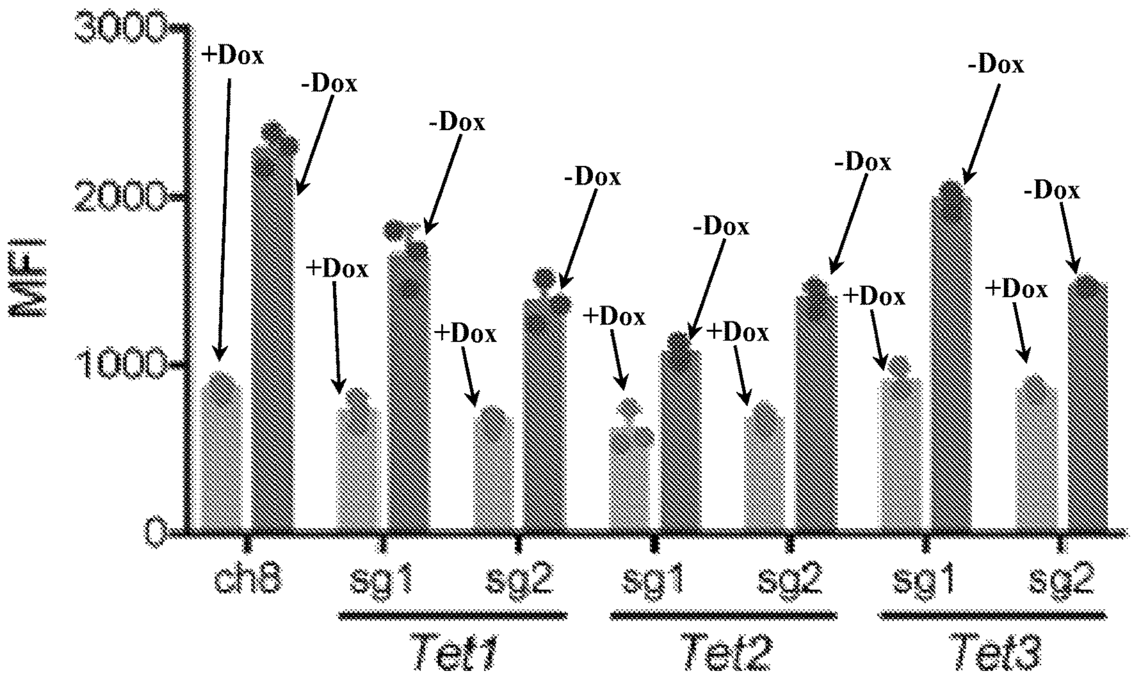
FIG. 13D shows the median fluorescence intensity of 5hmC in $KP^{sh}$-2 cells expressing sgRNAs targeting Tet1, Tet2, and Tet3 grown with or without dox for 8 days.
Figure 13E:
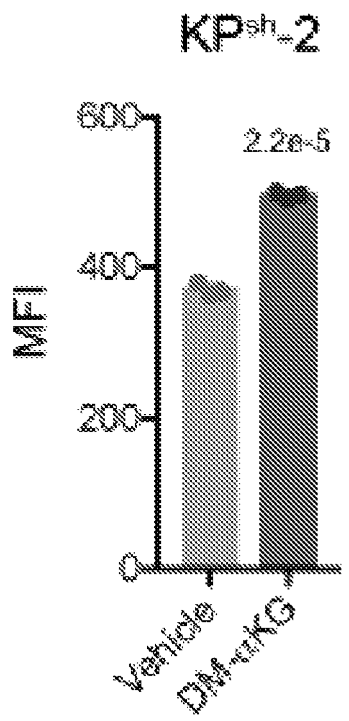
FIG. 13E shows the median fluorescence intensity of 5hmC in $KP^{sh}$-2 cells grown with 4 mM DM-αKG for 72 h.
Figure 13F:
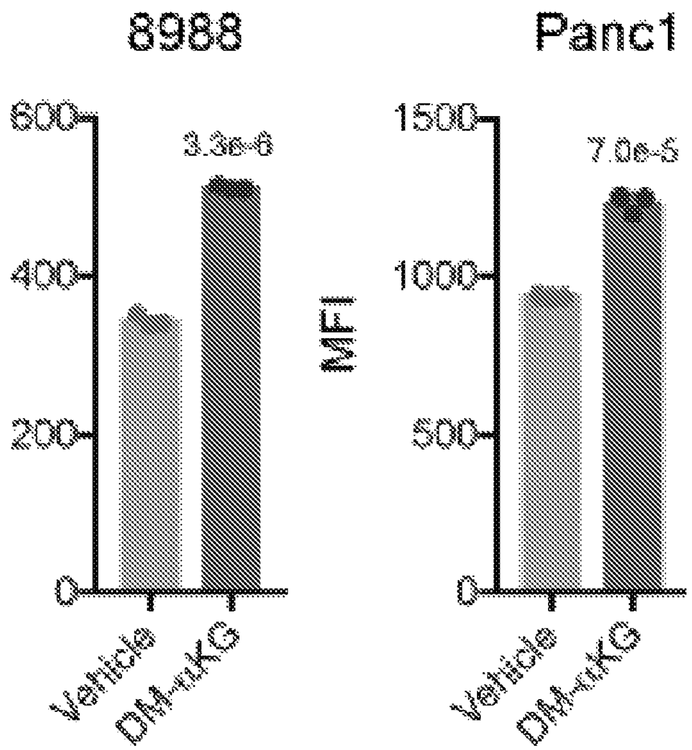
FIG. 13F shows the median fluorescence intensity of 5hmC in 8988 and Panel cells grown with 4 mM DM-αKG for 72 h.
Figure 13G:
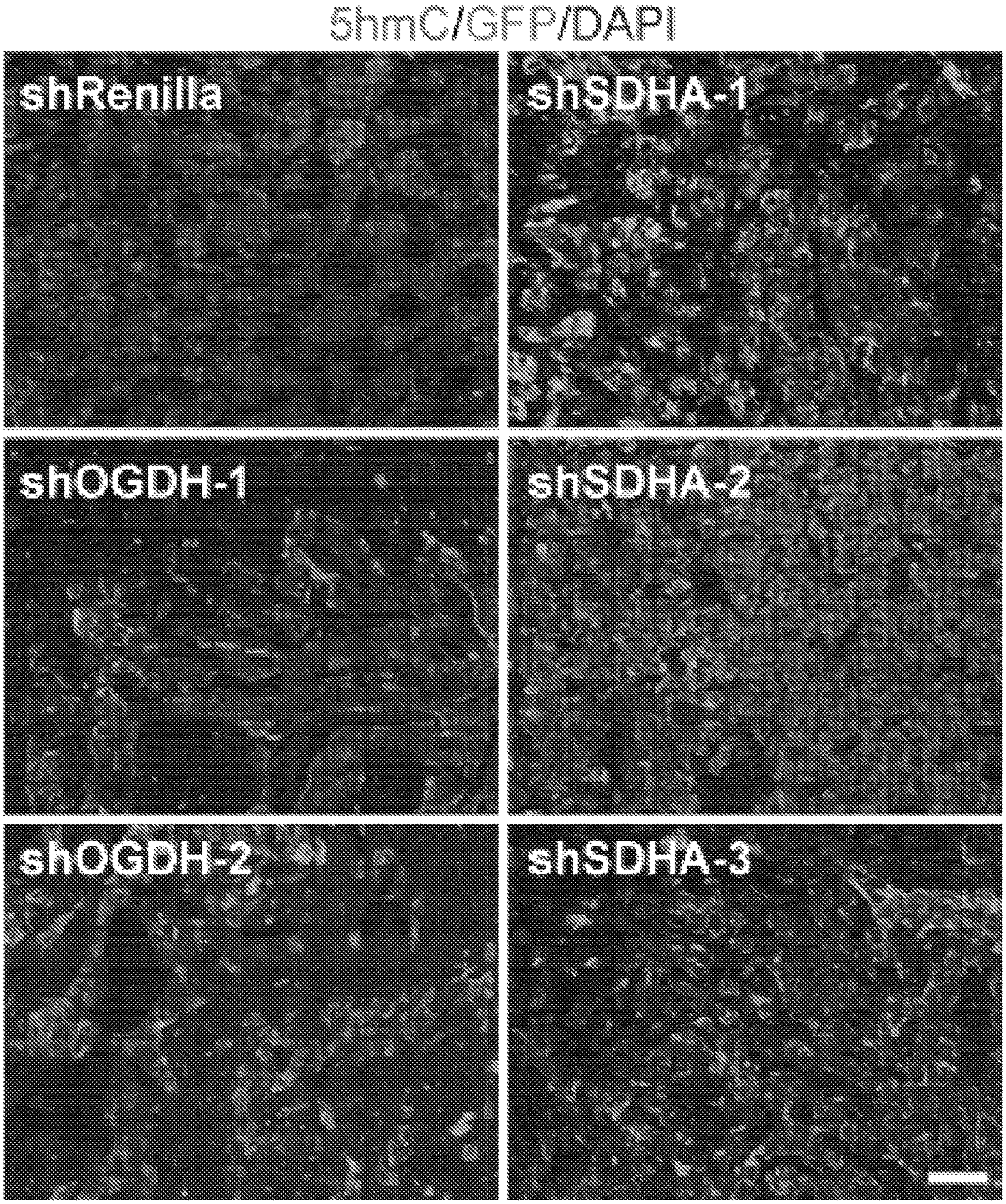
FIGS. 13G-13H shows the 5hmC staining of orthotopic tumors derived from $KP^{flox}$ cells 9 days after expression of dox-inducible hairpins targeting *Renilla*, Ogdh, or Sdha in established tumors. GFP marks cells expressing indicated shRNA. Scale bar 50 μM.
Figure 13H:
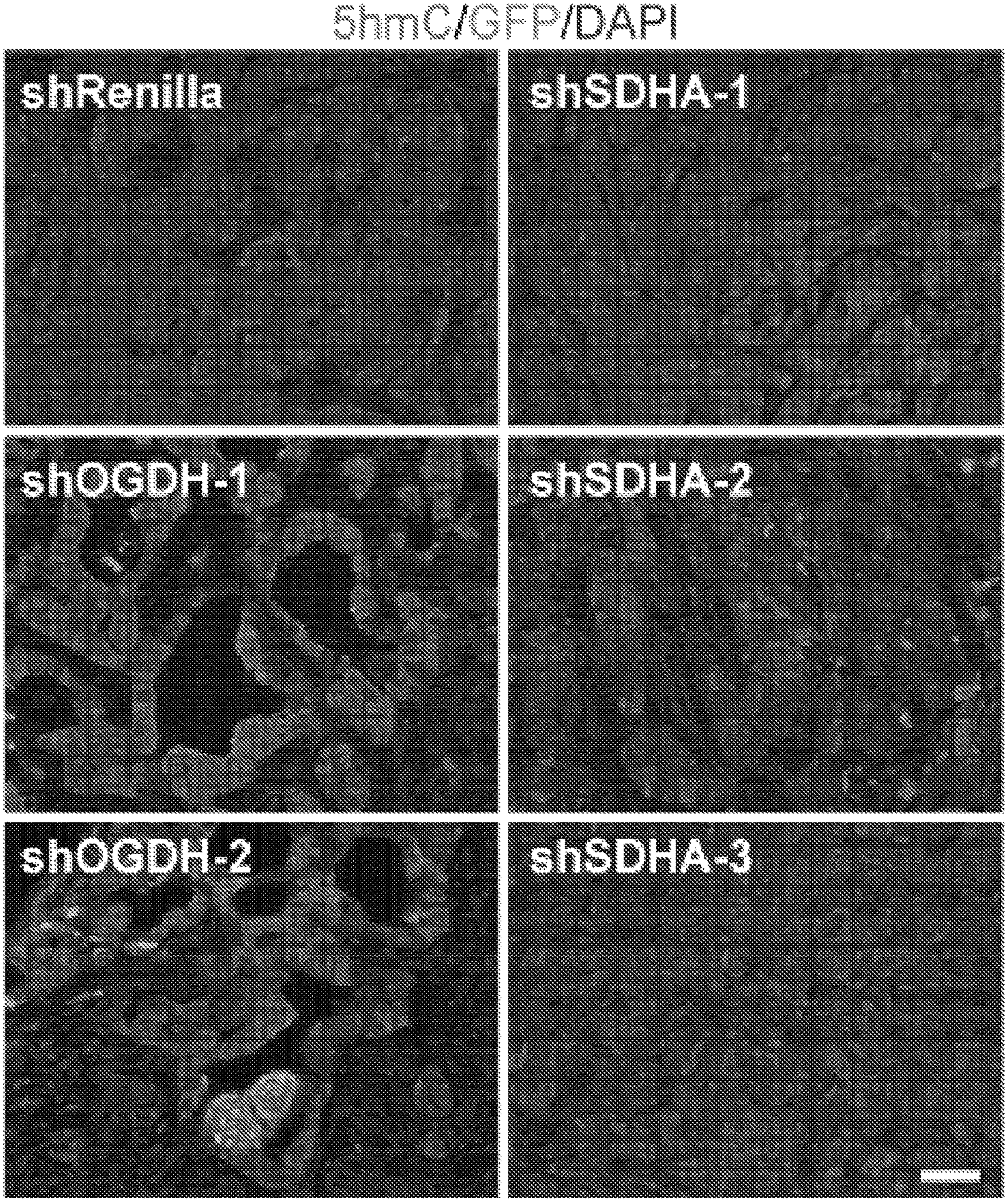
Figure 13I:
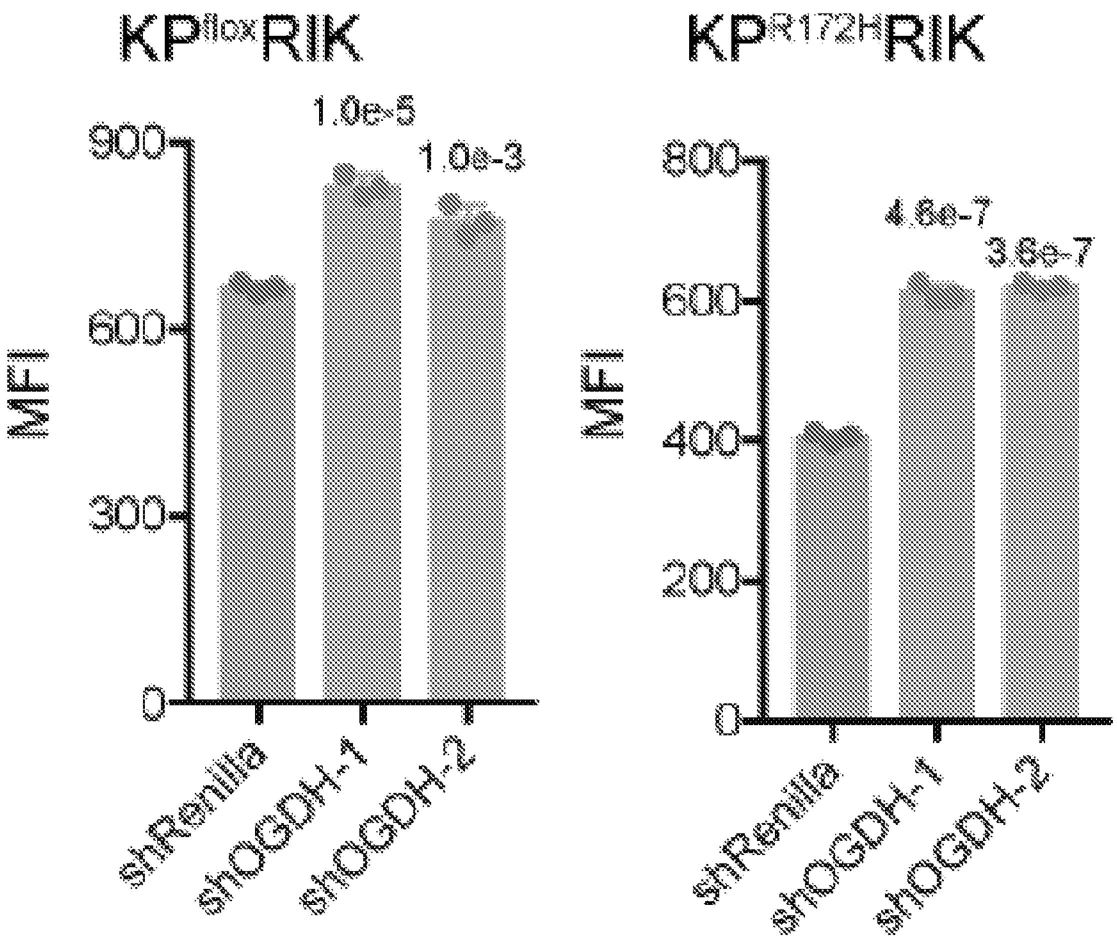
FIG. 13I shows 5hmC MFI in $KPC^{flox}$RIK and $KPC^{R172H}$RIK cells expressing dox-inducible shRNAs targeting *Renilla* or Ogdh grown 4 days with or without dox.

Given the link between loss of wild-type p53, malignant progression, and decreased 5hmC, it was explored whether 5hmC levels are sensitive to changes in p53 or αKG manipulation. Despite modest changes in expression of Tet enzymes, p53 reactivation was sufficient to induce 5hmC in $KP^{sh}$ cells in a Tet-dependent manner (FIGS. 13A-13D). Furthermore, cell-permeable αKG induced cellular 5hmC in dox-treated $KP^{sh}$ cells and p53 mutant human PDAC cells (FIGS. 13E-13F), while Ogdh inhibition increased 5hmC in p53 null and mutant mouse PDAC cells (FIG. 13G). Remarkably, both p53 restoration and Ogdh inhibition during tumor initiation or in established tumors led to increases in 5hmC in vivo that coincided with areas of increased glandular differentiation absent in the setting of Sdha suppression (FIGS. 4D-4E and FIG. 13H). Therefore, the decline in 5hmC associated with p53 loss during PDAC progression is specifically reversible by interventions that increase the αKG/succinate ratio and is associated with the reversion to a more pre-malignant like cell fate.

To test whether an increase in the αKG/succinate ratio was required for p53-mediated increases in 5hmC, we took advantage of the fact that Sdha silencing induces high levels of succinate, a competitive inhibitor of αKG-dependent dioxygenases. Constitutive suppression of Sdha in $KP^{sh}$ cells blocked p53-mediated induction of the αKG/succinate ratio despite abundant accumulation of p53 following dox withdrawal (FIGS. 14A-14B) and significantly reduced 5hmC levels in vitro and in vivo (FIG. 14C, FIG. 5B-5D). Furthermore, Sdha silencing resulted in sustained tumor growth and reduced survival following prolonged dox withdrawal (FIGS. 14D-14F), corresponding with an intermediate histological phenotype with reduction in the frequency of clearly articulated glandular structures (FIG. 14G). Therefore, an elevated αKG/succinate ratio appears necessary for the induction of chromatin marks characteristic of pre-malignant cell fate and functionally contributes to p53-driven tumor suppression. While additional αKG-dependent activities are affected by p53-driven metabolic reprogramming, these data suggest that 5hmC serves as a biomarker of p53-triggered, tumor suppressive changes in the αKG/succinate ratio.

These results identify a metabolic link between p53 function, chromatin regulation, and tumor cell fate. When responding to oncogenic signaling, p53 rewires glucose and glutamine metabolism to favor accumulation of αKG at the expense of succinate, thereby reinforcing the activity of αKG-dependent effectors and maintaining pre-malignant patterns of gene expression. Loss of p53 prevents these metabolic effects and enables transition to more aggressive and less differentiated carcinomas that display hallmarks of reduced αKG-dependent activity. Remarkably, αKG is sufficient to impose a p53-like chromatin and transcriptional profile in tumor cells lacking p53, thereby enabling cells to re-acquire a pre-malignant identity that can be recapitulated by genetic perturbations that increase αKG levels in vivo. Restoring p53 activity or enforcing p53 triggered metabolic reprogramming can specifically elevate levels of 5hmC, a Tet dependent chromatin mark that is frequently lost in advanced malignancy. These data suggest that αKG can play an active role in tumor suppression, a hypothesis that is strengthened by the observation that mutations in isocitrate dehydrogenase that produce 2-hydroxyglutarate—an antagonist of αKG-dependent enzymes—block differentiation and promote tumorigenesis[28]. Elucidating the context-specific and/or combinatorial roles of various αKG-dependent dioxygenases to the regulation of cell identity remains an important area of future investigation. Together, these results nominate therapeutic strategies to increase αKG levels as a mechanism to engage latent tumor suppressive pathways in p53-deficient tumors.

Example 6: Identification of "Metabolic Mimetics" of WT-p53

Evidence suggests that p53 can regulate metabolism, for example, by regulating nutrient uptake and directing metabolic flux to favor macromolecular synthesis, and that these effects may contribute to tumor suppression. Still, it has been unclear how these metabolic changes contribute to tumor suppression and whether or how the metabolic reprogramming produced by p53 inactivation sustains malignancy. Through the work in solid tumors described herein, it has been established that OGDH inhibition mimics metabolic and biological outputs of wt-p53 activity.

As shown in FIG. 17B, it was found that restoration of wt-p53 in cell lines derived from the KPCsh (Pdx1-Cre; LSL-KrasG12D; TRE-shp53; R26-LSL-rtta-IRES-Kate) model of pancreatic cancer increased the ratio of aKG:succinate as determined by gas chromatography/mass spectrometry (GC/MS), and as shown in FIG. 17C, a similar effect could be achieved by shRNA knockdown of OGDH. As shown in FIGS. 17D-17E, increase in the aKG:succinate ratio through restoration of wt-p53 induced changes in chromatin accessibility and gene transcription comparable with treatment with exogenous aKG, as determined by ATAC-seq and RNA-seq, respectively.

Beyond its role in central carbon metabolism, alpha-keto glutarate (αKG) also regulates a family of ~70 aKG-dependent dioxygenases, many of which influence gene expression and cell fate through chromatin modification. These enzymes require oxygen and aKG as co-substrates to perform oxidative reactions and are subject to feedback inhibition by succinate. Increased cellular ratio of aKG:succinate thus enhances dioxygenase activity, which include histone demethylation and conversion of 5-methylcytosine (5mC) to 5-hydroxymethylcytosine (5hmC), modifications that alter chromatin accessibility, gene expression, and cell fate. Relevant to AML, perturbations of this regulatory network are considered essential to the oncogenic action of IDH mutations and are reversed by mutant IDH inhibitors.

Example 7: Expanding p53 Mimicry into the AML System

In the pancreatic cancer models disclosed herein, increased aKG:succinate resulted in cell differentiation and tumor suppression. Given these solid tumor findings and similarities to the mechanisms by which IDH inhibitors function in IDH-mutant AML, it was explored whether perturbation in p53-aKG metabolic programs could promote differentiation in AML lacking oncogenic IDH mutations. FIGS. 17A and 18A show the reaction catalyzed by IDH and OGDH.

For these preliminary experiments, a Nras$^{G12D}$; Mll-Af9 driven model that is easy to manipulate and has been extensively studied was selected. Although TP53 itself is unaltered in this system, it appears dysfunctional. As shown in FIG. 18B, OGDH was depleted using retrovirally-expressed, doxycycline-inducible GFP-shRNAs. As shown in FIG. 18C, OGDH depletion led to increased aKG:succinate ratios. These OGDH-depleted GFP(+) cells were at a substantial proliferative disadvantage as shown by inhibition of proliferation of murine AML, compared to shControl (FIG. 18D). shBrd4 was used as a positive control. Further, as shown in FIG. 18E, OGDH inhibition induced cell surface expression of Cd11b (Day 4). These data demonstrate that knockdown of OGDH in AML cells causes cellular differentiation phenotype as demonstrated by an increase in the surface expression of the granulocytic maturation marker Cd11b. As shown in FIG. 18F, OGDH inhibition induced morphologic differentiation of murine AML (Day 4), as evident by cellular morphology. Further, as shown in FIG. 18G, the Gene Set Enrichment Analysis (GSEA) showed that shOgdh activated a myeloid gene signature (FIG. 18G, left panel) and suppressed an LSC gene signature (FIG. 18G, right panel).

Therefore, targeting OGDH genetically prohibits leukemic growth and stimulates differentiation, likely in an aKG-dependent manner. Accordingly, the OGDH inhibitors of the present technology are useful to treat AML.

Example 8: OGDH is Required for AML Progression

To test the anti-leukemic effects of OGDH blockade, sub-lethally irradiated recipient mice having AML transplantation were used. Nras$^{G12D}$; Mll-Af9 driven model cells, harboring shControl, or two different sequences of shOgdh, were described above were transplanted (FIG. 19A). Tumor burden was visualized using whole body scanning. As shown in FIG. 19B (left panel), the starting tumor burden in different animals was comparable. Mice were fed diets with or without doxycycline to induce shRNA. Doxycycline treatment induced GFP in >90% of AML cells harboring either shControl or shOgdh prior to transplant (FIG. 19F). As shown in FIG. 19B (right panel), the anti-leukemic effect of OGDH inhibition was evident when doxycycline-inducible shRNAs against Ogdh were turned on. OGDH depletion also resulted in normalization of platelets in recipient mice, and conferred a significant survival benefit (FIGS. 19C-19D). As shown in FIG. 19E, most doxycycline-treated AML recipient mice eventually succumbed to leukemia. As shown in FIG. 19G, the bone marrow cells isolated from moribund doxycycline-treated shOgdh recipient mice lost GFP expression.

Therefore, targeting OGDH genetically blocks AML growth. Accordingly, the OGDH inhibitors of the present technology are useful to treat AML.

Example 9: Developing Novel Metabolism-Based Therapeutics

The above results suggest that OGDH inhibitors would be useful therapeutic agents. As a first step towards identifying small molecule OGDH inhibitors, the advantage of a panel of small molecule inhibitors proprietary to MSKCC/WCM that were previously generated for the purpose of treating *Mycobacterium tuberculosis* was taken. These compounds are derivatives of 3-deazathiamine (FIG. 20A) and are intended to target the mycobacterial enzyme aKG decarboxylase (KGD), which shares structural homology with mammalian OGDH, by competing for a thiamine diphosphate pocket essential for enzyme function. A pilot screen of these compounds was conducted, assessing growth inhibitory effect and differentiation capacity in Nras$^{G12D}$; Mll-Af9 murine AML cells. Of 12 compounds initially tested, 5 inhibited AML proliferation (FIG. 20B). Of these 5 compounds, 3 were acutely toxic (KGD 03-05), and considered unlikely to be functioning through metabolic perturbation or differentiation programs. However, 2 compounds, KGD02 and KGD09, inhibited AML proliferation in a dose-dependent manner (FIG. 20C) and induced differentiation (FIGS. 20D-20E). Notably, treatment with KGD09 increased the aKG:succinate ratio as determined by GC/MS (FIG. 20F), indicating that this compound may act on-target.

It is worth noting that there are ongoing clinical trials in hematologic malignancies including AML for a compound designated CPI-613. This drug is an analog of lipoate, a catalytic co-factor and modulator of several metabolic enzymes, including the TCA enzymes pyruvate dehydrogenase (PDH) and OGDH. However, the compound is thought to elicit its anti-cancer effects through an indirect mechanism and may also target additional lipoate-dependent enzymes involved in amino acid catabolism. Preliminary studies and studies from Agios Pharmaceuticals Inc. suggest that CPI-613 lacks specificity for OGDH, inhibiting the enzyme only at high concentrations (>200 μM in vitro) and inducing metabolic changes irreflective of genetic suppression of OGDH (FIGS. 20C and 20F). Therefore, CPI-613 does not display properties of an OGDH inhibitor and as such is not a suitable tool to probe the therapeutic mechanism. Instead development of specific inhibitors of OGDH was initiated for the purpose of exploiting a known metabolic phenotype mimicking the wt-p53 tumor suppressive effect. These concepts and compounds will be tested in our models of CK AML.

These data demonstrate that the OGDH inhibitors of the present technology are useful to treat AML in subjects in need thereof.

Example 10: Optimization of KGD09 and KGD02 Hit Compounds

As described above, KGD09 and KGD02 demonstrate efficacy against murine AML cells in vitro. In order to advance these confirmed hits toward early lead status and therapeutic application, medical chemistry optimization of the hits will be performed, including but not limited to size/charge modification, stability enhancement, and cell permeability optimization. One opportunity for enhancing the activity of 3-deazathiamine derivatives is offered by the primary alcohol, which is naturally destined for intracellular bis-phosphorylation. However, from a bioavailability standpoint, such a negatively-charged entity may not be cell-permeable absent an active transporter. Non-charged bioisostere groups such a sulfonamides, carbamates and other suitable groups can be added to facilitate cell entry.

Any modified hit compounds generated will be assayed using Nras$^{G12D}$; Mll-Af9 murine AML cells. For on-target evaluation, αKG/succinate ratios will be assessed across a range of concentrations by GC/MS. For biological efficacy, screen will be optimized hits for: 1) cell proliferation, 2) immunophenotypic differentiation as determined by cell surface expression of Cd11b, Gr1, and Cd117, 3) morphological differentiation as determined by CytoSpin and Wright-Giemsa staining, and 4) global 5-hydroxymethylcytosine (5hmC) levels. These assays have been validated and will be performed using a multi-well high-throughput flow cytometer and spectrophotometer available. Lastly, as a biological readout of on-target specificity we will evaluate proliferation of Tet-deficient AML cells treated with the TDI-optimized hits. This genetic lesion should confer resistance if the compounds are on-target (i.e. inhibit OGDH and upregulate aKG).

The two best performing compounds with regard to biological effect and on-target potential will be subjected to in vivo rodent toxicity studies. Compounds will be formulated in 20% 2-hydroxypropyl-β-cyclodextrin and administered i.p. to C56BL6 mice at escalating doses (n=3 animals/dose), starting at 10 mg/kg, either 1 or 2 times daily for 14 days. Mice will subsequently be monitored daily for physical condition and mortality per IUCAC protocol. Full histopathological assessment of vital organs, including brain, heart, lungs, liver, kidneys, gastrointestinal tract, and bone marrow, will be performed. In vivo efficacy studies will involve the use of genetically-derived AML murine models as well as human patient-derived xenografts.

Example 11: Generation of New Hits for TDI Optimization Using the 3-Deazathiamine Scaffold The crystal structure of mammalian OGDH has not been solved, however, structures of mycobacterial KGD have been reported. Based on homology modeling, mycobacterial KGD and human OGDH demonstrate approximately 40% homology and 60% similarity. Examination of the structure of *Mycobacterium smegmatis* KGD in complex with thiamine diphosphate (FIG. 22A), clearly shows ample space available opposite both the amine and particularly the C2 carbon. This tunnel-shaped volume terminates with a reduction in diameter toward the exit, limiting the size of groups that can be added. Fortunately, the KGD09 and KGD02 compounds are amenable to exploitation of this space through a dynamic screening process using alkyne and azide click pairs (FIG. 22B).

Specifically, either KGD09 or KGD02 will be added to lysates from human cell lines with high level OGDH expression in 96-well format. To each reaction, an individual alkyne or azide fragment from an existing chemical library will be supplemented. During dynamic screening, the high activation energy necessary for the click-reaction to occur should be overcome by the fitting and binding energy within the target pocket.

Any azide-alkyne pair that achieves adequate fitting will undergo a spontaneous click reaction, the product of which can be easily characterized by mass spectrometry. Concise and protecting group-free synthesis of 3-deazathiamine has been developed. Compounds emanating from dynamic screening will be scaled up using traditional (i.e. copper-catalyzed) click chemistry approaches for use in the following downstream assays. Based on two initial hit compounds and a library of 400 alkyne or azide fragments, an output from dynamic screening of ~5 to 6 high-affinity compounds is estimated, which will be re-screened as discussed above. In the event that dynamic screening is unsuccessful, modified compounds will be generated in a parallel synthesis fashion, using copper-catalysis and the same library of alkyne fragments.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A method for treating a p53 mutant cancer in a subject in need thereof comprising administering to the subject an effective amount of an OGDH inhibitor, wherein the p53 mutant cancer is acute myeloid leukemia (AML), wherein the OGDH inhibitor is an OGDH-specific inhibitory nucleic acid, succinyl phosphonate, (S)-2-[(2,6-dichlorobenzoyl) amino] succinic acid (AA6), KGD09, or KGD02, and wherein the OGDH-specific inhibitory nucleic acid is an antisense oligonucleotide, or a sgRNA.

2. The method of claim 1, wherein the OGDH-specific inhibitory nucleic acid comprises a nucleic acid sequence of any one of SEQ ID NOs: 13, 14, 43, 44, or a complement thereof.

3. The method of claim 1, wherein the subject is human.

4. The method of claim 1, wherein the OGDH inhibitor is administered orally, topically, intranasally, systemically, intravenously, subcutaneously intraperitoneally, intradermally, intraocularly, iontophoretically, transmucosally, or intramuscularly.

5. The method of claim 1, further comprising separately, sequentially or simultaneously administering one or more additional therapeutic agents to the subject.

6. The method of claim 5, wherein the one or more additional therapeutic agents are selected from the group consisting of Capecitabine, Erlotinib, Fluorouracil (5-FU), Gemcitabine, Irinotecan, Leucovorin, Nab-paclitaxel, Nano-liposomal irinotecan, Oxaliplatin, Larotrectinib, pembrolizumab, Cabozantinib-S-Malate, Ramucirumab, Lenvatinib Mesylate, Sorafenib Tosylate, Nivolumab, Ramucirumab, Regorafenib, Regorafenib, cisplatin, Doxorubicin, Mitoxantrone, Arsenic Trioxide, Daunorubicin, Cyclophosphamide, Cytarabine, Glasdegib Maleate, Dexamethasone, Doxorubicin, Enasidenib Mesylate, Gemtuzumab Ozogamicin, Gilteritinib Fumarate, Idarubicin, Ivosidenib, Midostaurin, Thioguanine, Venetoclax, and Vincristine Sulfate.

* * * * *